US012698506B2

(12) United States Patent
Mathew et al.

(10) Patent No.: US 12,698,506 B2
(45) Date of Patent: Aug. 4, 2026

(54) METHODS AND COMPOSITIONS FOR IMPROVING YIELD CHARACTERISTICS IN PLANTS

(71) Applicants: Pairwise Plants Services, Inc., Durham, NC (US); Monsanto Technology LLC, St. Louis, MO (US)

(72) Inventors: Lolita George Mathew, Cary, NC (US); Graziana Taramino, St. Louis, MO (US); Thomas Louis Slewinski, St. Louis, MO (US)

(73) Assignees: Pairwise Plants Services, Inc., Durham, NC (US); Monsanto Technology LLC, St. Louis, MO (US)

( * ) Notice: Subject to any disclaimer, the term of this patent is extended or adjusted under 35 U.S.C. 154(b) by 148 days.

(21) Appl. No.: 18/667,314

(22) Filed: May 17, 2024

(65) Prior Publication Data

US 2024/0384280 A1     Nov. 21, 2024

Related U.S. Application Data

(60) Provisional application No. 63/502,987, filed on May 18, 2023.

(51) Int. Cl.
*C12N 15/82*         (2006.01)
*C12N 9/22*         (2006.01)

(52) U.S. Cl.
CPC ........... *C12N 15/8201* (2013.01); *C12N 9/22* (2013.01); *C12N 15/8261* (2013.01)

(58) Field of Classification Search
None
See application file for complete search history.

(56) References Cited

U.S. PATENT DOCUMENTS

| | | |
|---|---|---|
| 5,604,121 A | 2/1997 | Hilder et al. |
| 5,625,136 A | 4/1997 | Koziel et al. |
| 5,641,876 A | 6/1997 | McElroy et al. |
| 6,040,504 A | 3/2000 | Rice et al. |
| 6,468,747 B1 | 10/2002 | De Beuckeleer et al. |
| 6,855,533 B2 | 2/2005 | Kakefuda et al. |
| 7,141,424 B2 | 11/2006 | Shin et al. |
| 7,166,770 B2 | 1/2007 | Hohn et al. |
| 7,579,516 B2 | 8/2009 | Boudreau |
| 9,790,490 B2 | 10/2017 | Zhang et al. |
| 9,982,053 B2 | 5/2018 | Pantaleo et al. |
| 10,113,163 B2 | 10/2018 | Liu et al. |
| 10,167,457 B2 | 1/2019 | Liu et al. |
| 10,421,972 B2 | 9/2019 | Lira et al. |
| 2001/0029014 A1 | 10/2001 | Beuckeleer |
| 2002/0102582 A1 | 8/2002 | Levine |
| 2002/0120964 A1 | 8/2002 | Rangwala et al. |
| 2003/0097687 A1 | 5/2003 | Trolinder et al. |
| 2003/0126634 A1 | 7/2003 | Spencer et al. |
| 2003/0188347 A1 | 10/2003 | Both et al. |
| 2004/0172669 A1 | 9/2004 | Kraus et al. |

| | | |
|---|---|---|
| 2004/0250317 A1 | 12/2004 | Huber et al. |
| 2005/0039226 A1 | 2/2005 | Barbour et al. |
| 2005/0086719 A1 | 4/2005 | Spencer et al. |
| 2005/0188434 A1 | 8/2005 | Spencer et al. |
| 2005/0216969 A1 | 9/2005 | Song et al. |
| 2006/0059581 A1 | 3/2006 | Spencer et al. |
| 2006/0059590 A1 | 3/2006 | Cerny et al. |
| 2006/0070139 A1 | 3/2006 | Bing et al. |
| 2006/0095986 A1 | 5/2006 | Cavato et al. |
| 2006/0130175 A1 | 6/2006 | Ellis et al. |
| 2006/0162007 A1 | 7/2006 | Guo et al. |
| 2006/0230473 A1 | 10/2006 | Johnson et al. |
| 2006/0282915 A1 | 12/2006 | Malven et al. |
| 2007/0028322 A1 | 2/2007 | Dizigan et al. |
| 2007/0067868 A1 | 3/2007 | Negrotto et al. |
| 2007/0143876 A1 | 6/2007 | Song et al. |
| 2007/0292854 A1 | 12/2007 | Behr et al. |
| 2008/0028482 A1 | 1/2008 | Beazley et al. |
| 2008/0064032 A1 | 3/2008 | Townshend et al. |
| 2008/0070260 A1 | 3/2008 | Krieb et al. |
| 2008/0167456 A1 | 7/2008 | Steiner et al. |
| 2008/0196127 A1 | 8/2008 | De Beuckeleer |
| 2008/0260932 A1 | 10/2008 | Anderson et al. |
| 2008/0312082 A1 | 12/2008 | Kinney et al. |
| 2008/0320616 A1 | 12/2008 | De Beuckeleer |
| 2009/0130071 A1 | 5/2009 | Gao et al. |
| 2009/0137395 A1 | 5/2009 | Chicoine et al. |
| 2009/0210970 A1 | 8/2009 | Hondred et al. |
| 2009/0217423 A1 | 8/2009 | Cayley et al. |
| 2009/0265817 A1 | 10/2009 | Weyens et al. |

(Continued)

FOREIGN PATENT DOCUMENTS

| | | |
|---|---|---|
| EP | 0255378 A2 | 2/1988 |
| EP | 0342926 A2 | 11/1989 |

(Continued)

OTHER PUBLICATIONS

Marcon et al 2020 (Plant Physiology 184: p. 620-631) (Year: 2020).*
Kim et al 2018 (New Phytologist 220: p. 609-623) (Year: 2018).*
International Search Report and the Written Opinion of the International Searching Authority corresponding to International Patent Application No. PCT/US2024/029896 (18 pages) (mailed Sep. 25, 2024).
UniProt Accession No. A0A1D6H1K9 "PLATZ transcription factor family protein" uniprot.org (1 page) (Nov. 30, 2016).

(Continued)

*Primary Examiner* — Matthew R Keogh

(74) *Attorney, Agent, or Firm* — Myers Bigel, P.A.

(57)     ABSTRACT

This invention relates to compositions and methods for modifying a Plant AT-rich sequence- and Zinc-binding protein 8 (PLATZ8) gene in plants to improve yield traits. The invention further relates to plants and plant parts produced using the methods and compositions of the invention.

15 Claims, No Drawings

Specification includes a Sequence Listing.

(56)         References Cited

U.S. PATENT DOCUMENTS

| 2009/0300784 | A1 | 12/2009 | Long et al. |
| 2010/0024077 | A1 | 1/2010 | Cayley et al. |
| 2010/0050282 | A1 | 2/2010 | Trolinder et al. |
| 2010/0077501 | A1 | 3/2010 | Trolinder et al. |
| 2010/0080887 | A1 | 4/2010 | Wagner et al. |
| 2010/0184079 | A1 | 7/2010 | Cressman et al. |
| 2011/0067141 | A1 | 3/2011 | Froman et al. |
| 2011/0138504 | A1 | 6/2011 | Beazley et al. |
| 2012/0131692 | A1 | 5/2012 | Charne et al. |
| 2017/0219596 | A1 | 8/2017 | Tanenbaum et al. |

FOREIGN PATENT DOCUMENTS

| EP | 0452269 | A2 | 10/1991 |
| WO | 9307278 | A1 | 4/1993 |
| WO | 9717432 | A1 | 5/1997 |
| WO | 9808932 | A1 | 3/1998 |
| WO | 9844140 | A1 | 10/1998 |
| WO | 9850427 | A1 | 11/1998 |
| WO | 9942587 | A1 | 8/1999 |
| WO | 0026345 | A1 | 5/2000 |
| WO | 0026356 | A1 | 5/2000 |
| WO | 0131042 | A2 | 5/2001 |
| WO | 0141558 | A1 | 6/2001 |
| WO | 0147952 | A2 | 7/2001 |
| WO | 0151654 | A2 | 7/2001 |
| WO | 0173087 | A1 | 10/2001 |
| WO | 0227004 | A2 | 4/2002 |
| WO | 0234946 | A2 | 5/2002 |
| WO | 0236831 | A2 | 5/2002 |
| WO | 0240677 | A2 | 5/2002 |
| WO | 0244407 | A2 | 6/2002 |
| WO | 02100163 | A2 | 12/2002 |
| WO | 03013224 | A2 | 2/2003 |
| WO | 03052073 | A2 | 6/2003 |
| WO | 2004011601 | A2 | 2/2004 |
| WO | 2004039986 | A1 | 5/2004 |
| WO | 2004053062 | A2 | 6/2004 |
| WO | 2004072235 | A2 | 8/2004 |
| WO | 2004074492 | A1 | 9/2004 |
| WO | 2004099447 | A2 | 11/2004 |
| WO | 2005054479 | A1 | 6/2005 |
| WO | 2005054480 | A2 | 6/2005 |
| WO | 2005059103 | A2 | 6/2005 |
| WO | 2005061720 | A2 | 7/2005 |
| WO | 2005074671 | A1 | 8/2005 |
| WO | 2005103266 | A1 | 11/2005 |
| WO | 2005103301 | A1 | 11/2005 |
| WO | 2006098952 | A2 | 9/2006 |
| WO | 2006108674 | A2 | 10/2006 |
| WO | 2006108675 | A2 | 10/2006 |
| WO | 2006128568 | A2 | 12/2006 |
| WO | 2006128569 | A2 | 12/2006 |
| WO | 2006128570 | A1 | 12/2006 |
| WO | 2006128571 | A2 | 12/2006 |
| WO | 2006128572 | A1 | 12/2006 |
| WO | 2006128573 | A2 | 12/2006 |
| WO | 2006130436 | A2 | 12/2006 |
| WO | 2007017186 | A1 | 2/2007 |
| WO | 2007024782 | A2 | 3/2007 |
| WO | 2007091277 | A2 | 8/2007 |
| WO | 2007140256 | A1 | 12/2007 |
| WO | 2007142840 | A2 | 12/2007 |
| WO | 2008002872 | A2 | 1/2008 |
| WO | 2008054747 | A2 | 5/2008 |
| WO | 2008112019 | A2 | 9/2008 |
| WO | 2008114282 | A2 | 9/2008 |
| WO | 2008122406 | A1 | 10/2008 |
| WO | 2008151780 | A1 | 12/2008 |
| WO | 2009064652 | A1 | 5/2009 |
| WO | 2009100188 | A2 | 8/2009 |
| WO | 2009102873 | A1 | 8/2009 |
| WO | 2009103049 | A2 | 8/2009 |
| WO | 2009111263 | A1 | 9/2009 |
| WO | 2009152359 | A2 | 12/2009 |
| WO | 2010024976 | A1 | 3/2010 |
| WO | 2010037016 | A1 | 4/2010 |
| WO | 2010076212 | A1 | 7/2010 |
| WO | 2010077816 | A1 | 7/2010 |
| WO | 2010080829 | A1 | 7/2010 |
| WO | 2010117735 | A1 | 10/2010 |
| WO | 2010117737 | A1 | 10/2010 |
| WO | 2011006717 | A2 | 1/2011 |
| WO | 2011022469 | A2 | 2/2011 |
| WO | 2011034704 | A1 | 3/2011 |
| WO | 2011051199 | A2 | 5/2011 |
| WO | 2011062904 | A1 | 5/2011 |
| WO | 2011063413 | A2 | 5/2011 |
| WO | 2011066360 | A1 | 6/2011 |
| WO | 2011066384 | A1 | 6/2011 |
| WO | 2011075593 | A1 | 6/2011 |
| WO | 2011075595 | A1 | 6/2011 |
| WO | 2011084621 | A1 | 7/2011 |
| WO | 2011084632 | A1 | 7/2011 |
| WO | 2011153186 | A1 | 12/2011 |
| WO | 2012033794 | A2 | 3/2012 |
| WO | 2012051199 | A2 | 4/2012 |
| WO | 2012071039 | A1 | 5/2012 |
| WO | 2012075426 | A1 | 6/2012 |
| WO | 2012075429 | A1 | 6/2012 |
| WO | 2012082548 | A2 | 6/2012 |
| WO | 2012134808 | A1 | 10/2012 |
| WO | 2013003558 | A1 | 1/2013 |
| WO | 2013010094 | A1 | 1/2013 |
| WO | 2013012775 | A1 | 1/2013 |
| WO | 2018136783 | A1 | 7/2018 |
| WO | 2020257882 | A1 | 12/2020 |

OTHER PUBLICATIONS

Hu , et al., "Global analysis of seed transcriptomes reveals a novel PLATZ regulator for seed size and weight control in soybean", New Phytologist, 240:2436-2454 (2023).

Kausch , et al., "Maize tissue culture, transformation, and genome editing", In Vitro Cellular & Developmental Biology—Plant, 57:653-671 (2021).

Li , et al., "The Maize Imprinted Gene Floury3 Encodes a PLATZ Protein Required for tRNA and 5S rRNA Transcription through Interaction with RNA Polymerase III", The Plant Cell, 29:2661-2675 (2017).

Nagano , et al., "A novel class of plant-specific zinc-dependent DNA-binding protein that binds to A/T-rich DNA sequences", Nucleic Acids Research, 29(20):4097-4105 (2001).

Wang , et al., "Genome-wide analysis of the plant-specific PLATZ proteins in maize and identification of their general role in interaction with RNA polymerase III complex", BMC Plant Biology, 18(221):1-12 (2018).

Wang , et al., "The PLATZ Transcription Factor GL6 Affects Grain Length and Number in Rice", Plant Physiology, 180:2077-2090 (2019).

Zhang , et al., "A PLATZ transcription factor PhePLATZ8 from Moso bamboo (*Phyllostachys edulis*) plays a positive role in regulating growth and abiotic stress tolerance", Industrial Crops and Products, 221:119334 (2024).

* cited by examiner

METHODS AND COMPOSITIONS FOR IMPROVING YIELD CHARACTERISTICS IN PLANTS

STATEMENT REGARDING ELECTRONIC FILING OF A SEQUENCE LISTING

A Sequence Listing in XML format, entitled 1499-120_ST26.xml, 338,919 bytes in size, generated on Apr. 25, 2024, and filed herewith, is hereby incorporated by reference into the specification for its disclosures.

FIELD OF THE INVENTION

This invention relates to compositions and methods for modifying a Plant AT-rich sequence- and Zinc-binding protein 8 (PLATZ8) gene in plants to improve yield traits. The invention further relates to plants and plant parts produced using the methods and compositions of the invention.

BACKGROUND OF THE INVENTION

Intensive breeding across row crops has led to incremental increases in plant yield. However, genetic gain from breeding has started to plateau and assembling multiple small-effect genes in a breeding program has substantially increased research and development costs. Single gene solutions have been challenging for a complex trait such as yield, where background genetics and environment combine to reduce the impact of individual genes. Breeding has been successful by combining many individual genes with small contributing effects but is requiring greater resources to find unique combinations with improved effects. To increase the rate of yield gain, novel variation needs to be introduced in important genes and pathways that contribute to yield.

Transgenic approaches involving stable transformation to increase yield have largely been unsuccessful and there are no commercially relevant single gene approaches that have successfully created a step change in yield. Modifying hormone related pathways through GM approaches has not been fruitful because the simple over- or under-expression through transgene technology is not consistent with the fine-tuning effect required for improving plant yield.

The present invention addresses these shortcomings in the art by providing new compositions and methods for improving/enhancing yield traits in plants, including soybean, corn, and other plant species.

SUMMARY OF THE INVENTION

One aspect of the invention provides a plant or part thereof comprising at least one mutation in an endogenous Plant AT-rich sequence- and Zinc-binding protein 8 (PLATZ8) gene encoding a PLATZ8 transcription factor, optionally wherein the mutation may be a non-natural mutation.

A second aspect of the invention provides a plant cell comprising an editing system, the editing system comprising: (a) a CRISPR-Cas associated effector protein; and (b) a guide nucleic acid (gRNA, gDNA, crRNA, crDNA) having a spacer sequence with complementarity to an endogenous target gene encoding a Plant AT-rich sequence- and Zinc-binding protein 8 (PLATZ8) transcription factor.

A third aspect of the invention provides a plant cell comprising a mutation in a Plant AT-rich sequence- and Zinc-binding protein 8 (PLATZ8) transcription factor, wherein the mutation is a substitution, insertion and/or a deletion that is introduced into an endogenous PLATZ8 gene encoding the PLATZ8 transcription factor using an editing system that comprises a nucleic acid binding domain that binds to a target site within the endogenous PLATZ8 gene, wherein the endogenous PLATZ8 gene: (a) comprises a sequence having at least 80% sequence identity to the nucleotide sequence of SEQ ID NO:69 or SEQ ID NO:70; (b) comprises a region having at least 80% sequence identity to any one of the nucleotide sequences of SEQ ID NOs:72-75 or 76-80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 or 84-87, optionally wherein the mutation may be a non-natural mutation.

A fourth aspect of the invention provides a method of providing a plurality of plants having one or more improved yield traits, the method comprising planting two or more plants of the invention in a growing area, thereby providing a plurality of plants having one or more improved yield traits as compared to a plurality of control plants devoid of the at least one mutation.

In a fifth aspect, a method of producing/breeding a transgene-free genome-edited plant is provided, comprising: (a) crossing a plant of the invention with a transgene-free plant, thereby introducing the mutation into the plant that is transgene-free; and (b) selecting a progeny plant that comprises the mutation but is transgene-free, thereby producing a transgene-free genome-edited plant.

In a sixth aspect, a method of creating a mutation in an endogenous Plant AT-rich sequence- and Zinc-binding protein 8 (PLATZ8) gene in a plant is provided, comprising: (a) targeting a gene editing system to a portion of the PLATZ8 gene that comprises a sequence having at least 80% sequence identity to any one of SEQ ID NOs:72-75 or 76-80; and (b) selecting a plant that comprises a modification located in a region of the PLATZ8 gene having at least 80% sequence identity to any one of SEQ ID NOs:72-75 or 76-80, optionally wherein the mutation may be a non-natural mutation.

In a seventh aspect, a method of generating variation in a Plant AT-rich sequence- and Zinc-binding protein 8 (PLATZ8) transcription factor is provided, comprising: introducing an editing system into a plant cell, wherein the editing system is targeted to a region of an endogenous PLATZ8 gene that encodes the PLATZ8 transcription factor, and contacting the region of the endogenous PLATZ8 gene with the editing system, thereby introducing a mutation into the endogenous PLATZ8 gene and generating variation in the PLATZ8 transcription factor of the plant cell.

An eighth aspect provides a method of detecting a mutant Plant AT-rich sequence- and Zinc-binding protein 8 (PLATZ8) gene (a mutation in an endogenous PLATZ8 gene) in a plant comprising detecting in the genome of the plant a PLATZ8 gene having at least one mutation within a region having at least 80% sequence identity to a nucleotide sequence of any one of SEQ ID NOs:72-75 or 76-80.

A ninth aspect provides a method for editing a specific site in the genome of a plant cell, the method comprising cleaving, in a site-specific manner, a target site within an endogenous Plant AT-rich sequence- and Zinc-binding protein 8 (PLATZ8) gene in the plant cell, the endogenous PLATZ8 gene: (a) comprising a sequence having at least 80% sequence identity to any one of the nucleotide sequences of SEQ ID NO:69 or SEQ ID NO:70; (b) comprising a region having at least 80% sequence identity to any one of the nucleotide sequences of SEQ ID NOs:72-75 or 76-80; (c) encoding a polypeptide comprising a sequence having at least 80% sequence identity to the amino acid sequence of SEQ ID NO:71; and/or (d) encoding a region having at least 80% sequence identity to any one of the amino acid sequences of SEQ ID NOs:81-83 or 84-87, thereby generating an edit in the endogenous PLATZ8 gene of the plant cell.

In a tenth aspect, a method for making a plant is provided, the method comprising: (a) contacting a population of plant cells that comprise an endogenous gene encoding a Plant AT-rich sequence- and Zinc-binding protein 8 (PLATZ8) transcription factor with a nuclease targeted to the endogenous gene, wherein the nuclease is linked to a nucleic acid binding domain that binds to a target site within the endogenous gene, the endogenous gene (i) comprising a sequence having at least 80% sequence identity to any one of the nucleotide sequences of SEQ ID NO:69 or SEQ ID NO:70; (ii) comprising a region having at least 80% sequence identity to any one of the nucleotide sequences of SEQ ID NOs:72-75 or 76-80; (iii) encoding a polypeptide comprising a sequence having at least 80% sequence identity to the amino acid sequence of SEQ ID NO:71; and/or (iv) encoding a region having at least 80% sequence identity to any one of the amino acid sequences of SEQ ID NOs:81-83 or 84-87; (b) selecting a plant cell from the population comprising a mutation in the endogenous gene encoding a PLATZ8 transcription factor, wherein the mutation is a base insertion or base deletion in a region of the endogenous gene of (ii) or (iv), wherein the mutation modifies the PLATZ8 transcription factor, optionally the mutation modifies a region of the PLATZ8 transcription factor that comprises a zinc-binding domain (B-Box zinc-finger binding domain) or a region of the PLATZ8 transcription factor that comprises a PLATZ domain; and (c) growing the selected plant cell into a plant comprising the mutation in the endogenous gene encoding a PLATZ8 transcription factor.

In an eleventh aspect, a method for improving a yield characteristic in a plant is provided, the method comprising: (a) contacting a plant cell comprising an endogenous Plant AT-rich sequence- and Zinc-binding protein 8 (PLATZ8) gene encoding a PLATZ8 transcription factor with a nuclease targeted to the endogenous gene, wherein the nuclease is linked to a nucleic acid binding domain that binds to a target site within the endogenous PLATZ8 gene, the endogenous PLATZ8 gene: (i) comprising a sequence having at least 80% sequence identity to any one of the nucleotide sequences of SEQ ID NO:69 or SEQ ID NO:70; (ii) comprising a region having at least 80% sequence identity to any one of the nucleotide sequences of SEQ ID NOs:72-75 or 76-80; (iii) encoding a polypeptide comprising a sequence having at least 80% sequence identity to the amino acid sequences of SEQ ID NO:71; and/or (iv) encoding a region having at least 80% sequence identity to any one of the amino acid sequences of SEQ ID NOs:81-83 or 84-87, thereby producing a plant cell comprising a mutation in the endogenous PLATZ8 gene encoding a PLATZ8 transcription factor; and (b) growing the plant cell into a plant, thereby improving a yield characteristic in the plant.

In a twelfth aspect, a method for producing a plant or part thereof comprising at least one cell (e.g., one or more cells) having a mutation in an endogenous Plant AT-rich sequence- and Zinc-binding protein 8 (PLATZ8) gene, the method comprising contacting a target site within the endogenous PLATZ8 gene in the plant or part thereof with a nuclease comprising a cleavage domain and a nucleic acid binding domain, wherein the nucleic acid binding domain of the nuclease binds to a target site within the endogenous PLATZ8 gene, wherein the endogenous PLATZ8 gene: (a) comprises a sequence having at least 80% sequence identity to any one of the nucleotide sequences of SEQ ID NO:69 or SEQ ID NO:70; (b) comprises a region having at least 80% sequence identity to any one of the nucleotide sequences of SEQ ID NOs:72-75 or 76-80; (c) encodes a polypeptide comprising a sequence having at least 80% sequence identity to the amino acid sequences of SEQ ID NO:71; and/or (d) encodes a region having at least 80% sequence identity to any one of the amino acid sequences of SEQ ID NOs: 81-83 or 84-87, thereby producing a plant or part thereof comprising at least one cell having a mutation in the endogenous PLATZ8 gene.

In a thirteenth aspect, a method is provided for producing a plant or part thereof comprising a mutation in a zinc binding domain (B-Box zinc-finger binding domain) or a PLATZ domain of a Plant AT-rich sequence- and Zinc-binding protein 8 (PLATZ8) transcription factor, the method comprising contacting a target site within an endogenous Plant AT-rich sequence- and Zinc-binding protein 8 (PLATZ8) gene in the plant or part thereof with a nuclease comprising a cleavage domain and a nucleic acid binding domain, wherein the nucleic acid binding domain of the nuclease binds to the target site within the endogenous PLATZ8 gene, wherein the endogenous PLATZ8 gene: (a) comprises a sequence having at least 80% sequence identity to any one of the nucleotide sequences of SEQ ID NO:69 or SEQ ID NO:70; (b) comprises a region having at least 80% sequence identity to any one of the nucleotide sequences of SEQ ID NOs:72-75 or 76-80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 or 84-87, thereby producing a plant or part thereof having a mutated PLATZ8 transcription factor with a modified zinc-finger binding domain or a modified PLATZ domain.

In a fourteenth aspect, a method is provided for modifying an endogenous Plant AT-rich sequence- and Zinc-binding protein 8 (PLATZ8) gene in a corn plant or part thereof for improving a yield characteristic in the corn plant or part thereof, the method comprising modifying a target site within the endogenous PLATZ8 gene in the corn plant or a part thereof, wherein the endogenous PLATZ8 gene: (a) comprises a sequence having at least 80% sequence identity to the nucleotide sequence of SEQ ID NO:69 or SEQ ID NO:70; (b) comprises a region having at least 80% sequence identity to any one of the nucleotide sequences of SEQ ID NOs:72-75 or 76-80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 or 84-87, thereby modifying the endogenous PLATZ8 gene and improving a yield characteristic in the corn plant or part thereof. In some embodiments, the target site is a region of the PLATZ8 gene having at least 80% sequence identity to a nucleotide sequence of any one of SEQ ID NOs:72-75 or 76-80 or having at least 80% sequence identity to a nucleotide sequence encoding any one of the amino acid sequences of SEQ ID NOs:81-83 or 84-87.

In a fifteenth aspect, a guide nucleic acid is provided that binds to a target site within an endogenous gene encoding a Plant AT-rich sequence- and Zinc-binding protein 8 (PLATZ8) transcription factor, the endogenous gene comprising a sequence having at least 80% sequence identity to any one of the nucleotide sequences of SEQ ID NO:69 or SEQ ID NO:70; comprising a region having at least 80% sequence identity to any one of the nucleotide sequences of SEQ ID NOs:72-75 or 76-80; encoding a polypeptide comprising a sequence having at least 80% sequence identity to the amino acid sequence of SEQ ID NO:71; and/or encoding a region having at least 80% sequence identity to any one of the amino acid sequences of SEQ ID NOs:81-83 or 84-87.

A further aspect provides a system comprising a guide nucleic acid of the invention and a CRISPR-Cas effector protein that associates with the guide nucleic acid.

In another aspect gene editing system is provided that comprises a CRISPR-Cas effector protein in association with a guide nucleic acid, wherein the guide nucleic acid comprises a spacer sequence that binds to a Plant AT-rich sequence- and Zinc-binding protein 8 (PLATZ8) gene.

An additional aspect provides a complex comprising a CRISPR-Cas effector protein comprising a cleavage domain and a guide nucleic acid, wherein the guide nucleic acid binds to a target site within a Plant AT-rich sequence- and Zinc-binding protein 8 (PLATZ8) gene, the PLATZ8 gene: (a) comprising a sequence having at least 80% sequence identity to any one of the nucleotide sequences of SEQ ID NO:69 or SEQ ID NO:70; (b) comprising a region having at least 80% sequence identity to any one of the nucleotide sequences of SEQ ID NOs:72-75 or 76-80; (c) encoding a polypeptide comprising a sequence having at least 80% sequence identity to the amino acid sequence of SEQ ID NO:71; and/or (d) encoding a region having at least 80% sequence identity to any one of the amino acid sequences of SEQ ID NOs:81-83 or 84-87, wherein the cleavage domain cleaves a target strand in the PLATZ8 gene.

In a further aspect, an expression cassette is provided comprising (a) a polynucleotide encoding CRISPR-Cas effector protein comprising a cleavage domain and (b) a guide nucleic acid that binds to a target site within a Plant AT-rich sequence- and Zinc-binding protein 8 (PLATZ8) gene, wherein the guide nucleic acid comprises a spacer sequence that is complementary to and binds to the target site within the PLATZ8 gene, the PLATZ8 gene: (a) comprising a sequence having at least 80% sequence identity to any one of the nucleotide sequences of SEQ ID NO:69 or SEQ ID NO:70; (b) comprising a region having at least 80% sequence identity to any one of the nucleotide sequences of SEQ ID NOs:72-75 or 76-80; (c) encoding a polypeptide comprising a sequence having at least 80% sequence identity to the amino acid sequence of SEQ ID NO:71; and/or (d) encoding a region having at least 80% sequence identity to any one of the amino acid sequences of SEQ ID NOs:81-83 or 84-87.

An additional aspect provides a nucleic acid encoding a Plant AT-rich sequence- and Zinc-binding protein 8 (PLATZ8) transcription factor comprising a mutated zinc-binding domain (B-Box zinc-finger binding domain) or a mutated PLATZ domain, wherein the mutation is an in-frame base deletion or insertion or an out-of-frame base deletion or insertion, optionally wherein the mutation is located in the encoded zinc-binding domain or PLATZ domain of the PLATZ8 transcription factor.

In an additional aspect, a modified Plant AT-rich sequence- and Zinc-binding protein 8 (PLATZ8) transcription factor is provided, wherein the modified PLATZ8 transcription factor comprises a sequence having at least 90% sequence identity to any one of the amino acid sequences of SEQ ID NOs:93, 96, 101, 104, 107, 110, or 113.

A further aspect of the invention provides a corn plant or part thereof comprising at least one mutation in an endogenous PLATZ8 gene having the gene identification number (gene ID) (Maize Genetics and Genomics Database (Maize GDB)) of Zm00001d015394, optionally wherein the mutation is a non-natural mutation.

A still further aspect of the invention provides a guide nucleic acid that binds to a target nucleic acid in an endogenous PLATZ8 gene having the gene identification number (gene ID) (Maize Genetics and Genomics Database (Maize GDB)) of Zm00001d015394.

Further provided are plants, plant cells, and plant parts produced by the methods of the invention and comprising in their genomes one or more than one mutated Plant AT-rich sequence- and Zinc-binding protein 8 (PLATZ8) gene(s), as well as polypeptides, polynucleotides, nucleic acid constructs, expression cassettes and vectors for making a plant, plant cell, and/or plant part of this invention.

These and other aspects of the invention are set forth in more detail in the description of the invention below.

BRIEF DESCRIPTION OF THE SEQUENCES

SEQ ID NOs:1-17 are exemplary Cas12a amino acid sequences useful with this invention.

SEQ ID NOs:18-20 are exemplary Cas12a nucleotide sequences useful with this invention.

SEQ ID NO:21-22 are exemplary regulatory sequences encoding a promoter and intron.

SEQ ID NOs:23-29 are exemplary cytosine deaminase sequences useful with this invention.

SEQ ID NOs:30-40 are exemplary adenine deaminase amino acid sequences useful with this invention.

SEQ ID NO:41 is an exemplary uracil-DNA glycosylase inhibitor (UGI) sequences useful with this invention.

SEQ ID NOs:42-44 provide example peptide tags and affinity polypeptides useful with this invention.

SEQ ID NOs:45-55 provide example RNA recruiting motifs and corresponding affinity polypeptides useful with this invention.

SEQ ID NOs:56-57 are exemplary Cas9 polypeptide sequences useful with this invention.

SEQ ID NOs:58-68 are exemplary Cas9 polynucleotide sequences useful with this invention.

SEQ ID NO:69 is an example of a PLATZ8 genomic sequence.

SEQ ID NO:70 is an example of a PLATZ8 cDNA sequence, corresponding to genomic sequence SEQ ID NO:69.

SEQ ID NO:71 is an example PLATZ8 transcription factor sequence, encoded by genomic sequence SEQ ID NO:69 and cDNA sequence SEQ ID NO:70.

SEQ ID NOs:72-75, and 76-80 are example nucleic acid sequences (regions) from PLATZ8 polynucleotides.

SEQ ID NOs:81-83 and 84-87 are example regions from a PLATZ8 transcription factor.

SEQ ID NOs:88-90 are example spacer sequences for nucleic acid guides useful with this invention.

SEQ ID NOs:91, 94, 97, 99, 102, 105, 108, and 111 are examples of mutated PLATZ8 genomic sequences.

SEQ ID NOs:92, 95, 98, 100, 103, 106, 109, and 112 are examples of mutated PLATZ8 cDNA sequences, corresponding to genomic sequences 91, 94, 97, 99, 102, 105, 108, and 111, respectively.

SEQ ID NOs:93, 96, 101, 104, 107, 110, and 113 are examples of mutated PLATZ8 transcription factors encoded by one of SEQ ID NOs:91, 94, 97, 99, 102, 105, 108, and 111.

SEQ ID NOs:114, 115, 117, 118, and 119 are portions of consecutive nucleotides deleted from SEQ ID NO:69 resulting in the mutated PLATZ gene sequences of SEQ ID NOs:91, 94, 97, 102, and 108, respectively.

DETAILED DESCRIPTION

The present invention now will be described hereinafter with reference to the accompanying examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X.

A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 15%, 20%, 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In some embodiments, the reduction can result in no or essentially no (i.e., an insignificant amount, e.g., less than about 10% or even 5%) detectable activity or amount.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

As used herein, the term "heterologous" refers to a nucleotide/polypeptide that originates from a foreign species, or, if from the same species, is substantially modified from its native form in composition and/or genomic locus by deliberate human intervention. A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the reference organism. In some contexts, a "wild type nucleic acid" is a nucleic acid that is not edited as described herein and can differ from an "endogenous" gene that may be edited as described herein (e.g., a mutated endogenous gene). In some contexts, a "wild type nucleic acid" (e.g., an unedited wild type nucleic acid) may be heterologous to the organism in which the wild type nucleic acid is found (e.g., a transgenic organism). As an example, a "wild type endogenous PLATZ8 gene" is a PLATZ8 gene that is naturally occurring in or endogenous to the reference organism, e.g., a plant (e.g., a corn plant), and may be subject to modification as described herein, after which, such a modified endogenous gene is no longer wild type.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is non-functional.

A "knock-out mutation" is a mutation that results in a non-functional protein, but which may have a detectable transcript or protein.

A "recessive mutation" is a mutation in a gene that produces a phenotype when homozygous but the phenotype is not observable when the locus is heterozygous.

A "dominant mutation" is a mutation in a gene that produces a mutant phenotype in the presence of a non-mutated copy of the gene. A dominant mutation may be a loss or a gain of function mutation, a hypomorphic mutation, a hypermorphic mutation or a weak loss of function or a weak gain of function.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wild type gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "gain-of-function" allele or mutation is a mutation that confers a new function on the encoded gene product and/or confers a new gene expression pattern. In some embodiments, a gain-of-function mutation may be dominant or semi-dominant.

As used herein, a "non-natural mutation" refers to a mutation that is generated though human intervention and differs from mutations found in the same gene that have occurred in nature (e.g., occurred naturally).

A mutation that is "in or adjacent to" or "in or within the proximity of" a specified location in a gene, e.g., an exon or codon, means that the mutation is located at the specified location or about 1, 2, 3, 4, 5, 6, 7, 8, 9, 10, 11, 12 bases 5' (upstream) or 3' (downstream) of the specified location. By way of illustration, a mutation "in or adjacent to" an exon indicates that the mutation is within the boundaries of the exon or is between 1 and 12 base pairs 5' or 3' of a boundary of the exon. By comparison, a mutation that is "in and adjacent" a specified location in a gene, e.g., an exon or codon, means that the mutation encompasses all or a portion of the specified location and includes additional bases 5' and/or 3' of the specified location. For example, a mutation "in and adjacent to" an exon indicates that the mutation is within the boundaries of the exon and may include one or more base pairs 5' and/or 3' of the exon.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with increased yield under non-water stress conditions in a plant relative to a control plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

A plant in which at least one (e.g., one or more, e.g., 1, 2, 3, or 4, or more) endogenous PLATZ8 gene is modified as described herein (e.g., comprises a modification as described herein) may have improved yield traits as compared to a plant that does not comprise (is devoid of) the modification in the at least one endogenous PLATZ8 gene. As used herein, "improved yield traits" refers to any plant trait associated with growth, for example, biomass, yield, nitrogen use efficiency (NUE), inflorescence size/weight, fruit yield, fruit quality, fruit size, seed size (e.g., seed area, seed size), seed number, foliar tissue weight, nodulation number, nodulation mass, nodulation activity, number of seed heads, number of tillers, number of branches, number of flowers, number of tubers, tuber mass, bulb mass, number of seeds, total seed mass, rate of leaf emergence, rate of tiller/branch emergence, rate of seedling emergence, length of roots, number of roots, size and/or weight of root mass, or any combination thereof. In some aspects, "improved yield traits" may include, but are not limited to, increased inflorescence production, increased fruit production (e.g., increased number, weight and/or size of fruit; e.g., increased number, weight, and/or length of ears for, e.g., maize), increased fruit quality, increased number, size and/or weight of roots, increased meristem size, increased seed size (e.g., seed area and/or seed weight), increased biomass, increased leaf size, increased nitrogen use efficiency, increased height, increased internode number and/or increased internode length as compared to a control plant or part thereof (e.g., a plant that does not comprise a mutated endogenous PLATZ8 nucleic acid as described herein). In some aspects, improved yield traits can be expressed as quantity of grain/seed produced per area of land (e.g., bushels per acre of land). In some embodiments, a plant or part thereof comprising the at least one mutation may exhibit a phenotype of improved yield traits, optionally exhibiting an increased yield (bu/acre), increased biomass, increased number of seeds (kernels) per plant, increased number of seeds (kernels) per pod or ear, increased seed size, increased seed area, increased seed weight (e.g., increase in 100-seed weight), increased ear length, increased kernel row number (KRN) as compared to a plant that is devoid of the at least one mutation.

As used herein a "control plant" means a plant that does not contain an edited PLATZ8 gene as described herein. A control plant is used to identify and select a plant edited as described herein and that has an enhanced trait or altered phenotype as compared to the control plant. A suitable control plant can be a plant of the parental line used to generate a plant comprising a mutated PLATZ8 gene, for example, a wild type plant devoid of an edit in an endogenous PLATZ8 gene as described herein. A suitable control plant can also be a plant that contains recombinant nucleic acids that impart other traits, for example, a transgenic plant having enhanced herbicide tolerance. A suitable control plant can in some cases be a progeny of a heterozygous or hemizygous transgenic plant line that is devoid of the mutated PLATZ8 gene as described herein, known as a negative segregant, or a negative isogenic line.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. However, any technique can be used to measure the amount of, the comparative level of, or the difference in any selected chemical compound or macromolecule in the transgenic plants.

As used herein an "enhanced trait" means a characteristic of a plant resulting from mutations in a PLATZ8 gene as described herein. Such traits include, but are not limited to, an enhanced agronomic trait characterized by enhanced plant morphology, physiology, growth and development, yield, nutritional enhancement, disease or pest resistance, or environmental or chemical tolerance. In some embodiments, an enhanced trait/altered phenotype may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, and/or increased yield. In some embodiments, a trait is increased yield under nonstress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a mutation in an endogenous PLATZ8 gene as described herein relative to a plant not comprising the mutation, such as a wild-type plant, or a negative segregant. In some cases, the trait modification can be evaluated quantitatively. For example, the trait modification can entail an increase or decrease in an observed trait characteristic or phenotype as compared to a control plant. It is known that there can be natural variations in a modified trait. Therefore, the trait modification observed can entail a change of the normal distribution and magnitude of the trait characteristics or phenotype in the plants as compared to a control plant.

The present disclosure relates to a plant with improved economically relevant characteristics, more specifically one or more improved yield traits. More specifically the present disclosure relates to a plant comprising a mutation(s) in a PLATZ8 gene as described herein, wherein the plant exhibits an improved yield trait as compared to a control plant devoid of said mutation(s). In some embodiments, a plant of the present disclosure further exhibits an improved trait that is related to yield, including but not limited to increased nitrogen use efficiency, increased nitrogen stress tolerance, increased water use efficiency and/or increased drought tolerance, as defined and discussed infra.

Yield can be defined as the measurable produce of economic value from a crop. Yield can be defined in the scope of quantity and/or quality. Yield can be directly dependent on several factors, for example, the number and size of organs (e.g., number of flowers), plant architecture (such as the number of branches, plant biomass, e.g., increased root biomass, steeper root angle and/or longer roots, and the like), flowering time and duration, grain fill period. Root architecture and development, photosynthetic efficiency, nutrient uptake, stress tolerance, early vigor, delayed senescence and functional stay green phenotypes may be factors in determining yield. Optimizing the above-mentioned factors can therefore contribute to increasing crop yield.

Reference herein to an increase/improvement in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination.

"Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor, for example, can be a combination of the ability of seeds to germinate and emerge after planting and the ability of the young plants to grow and develop after emergence. Plants having early vigor also show increased seedling survival and better establishment of the crop, which often results in highly uniform fields with the majority of the plants reaching the various stages of development at substantially the same time, which often results in increased yield. Therefore, early vigor can be determined by measuring various factors, such as kernel weight, percentage germination, percentage emergence, seedling growth, seedling height, root length, root and shoot biomass, canopy size and color and others.

Further, increased yield can also manifest as increased total seed yield, which may result from one or more of an increase in seed biomass (seed weight) due to an increase in the seed weight on a per plant and/or on an individual seed basis an increased number of, for example, flowers/panicles per plant; an increased number of pods; an increased number of nodes; an increased number of flowers ("florets") per panicle/plant; increased seed fill rate; an increased number of filled seeds; increased seed size (length, width, area, perimeter, and/or weight), which can also influence the composition of seeds; and/or increased seed volume, which can also influence the composition of seeds. In one embodiment, increased yield can be increased seed yield, for example, increased seed weight; increased number of filled seeds; and/or increased harvest index.

Increased yield can also result in modified architecture, or can occur because of modified plant architecture.

Increased yield can also manifest as increased harvest index, which is expressed as a ratio of the yield of harvestable parts, such as seeds, over the total biomass The disclosure also extends to harvestable parts of a plant such as, but not limited to, seeds, leaves, fruits, flowers, bolls, pods, siliques, nuts, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Typically, plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the World Intellectual Property Organization (WIPO) Standard ST.26. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, 900, 950 or 1000 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a portion of a wild type CRISPR-Cas repeat sequence (e.g., a wild Type CRISR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a nucleic acid fragment or portion may comprise, consist essentially of or consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 101, 102, 103, 104, 105, 110, 111, 112, 113, 114, 115, 120, 121, 122, 123, 124, 125, 126, 127, 128, 129, 130, 135, 140, 141, 142, 143, 144, 145, 150, 151, 152, 153, 154, 155, 160, 165, 170, 175, 176, 177, 178, 179, 180, 185, 190, 191, 192, 193, 194, 195, 200, 205, 210, 215, 216, 217, 218, 219, 220, 221, 222, 223, 224, 225, 230, 235, 240, 245, 250, 255, 256, 257, 258, 259, 260, 265, 270, 271, 272, 273, 274, 275, 280, 285, 290, 295, 300, 305, 310, 320, 330, 335, 336, 337, 338, 339, 340, 350, 360, 370, 380, 390, 395, 400, 410, 415, 420, 425, 430, 435, 440, 445, 450, 500, 550, 600, 660, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 22, 2250, 2300, 2350, 2400, 2450, 2460, 2470, 2480, 2490, 2500, 2550, or 2600, or more consecutive nucleotides or any range or value therein, of a PLATZ8 polynucleotide (e.g., genomic DNA or cDNA), optionally a fragment of a PLATZ8 polynucleotide may be about 20 nucleotides to about 120 nucleotides, about 20 nucleotides to about 250 nucleotides, about 20 nucleotides to about 350 nucleotides, about 100 nucleotides to about 250 nucleotides, about 100 nucleotides to about 350 nucleotides, about 150 nucleotides to about 400 nucleotides e.g., about 60, 80, 100, 120, 140, 160, 180 or 200 nucleotides to about 210, 220, 240, 260, 280, 300, or 350 or more consecutive nucleotides (e.g., consecutive nucleotides of any one of SEQ ID NO:69 or SEQ ID NO:70, e.g., SEQ ID NOs:72-75 or 76-80, optionally to any one of SEQ ID NOs:72, 73, 74, 75, 76, 77, 78, 79 or 80.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 5, 6, 7, 8, 9, 10, 11, 12, 13, 14, 15, 20, 21, 22, 23, 24, 25, 26, 27, 28, 29, 30, 35, 40, 45, 46, 47, 48, 49, 50, 55, 60, 65, 70, 75, 80, 85, 90, 95, 100, 125, 150, 175, 200, 225, 250, 300, 350, 400 or more consecutive amino acids of a reference polypeptide. In some embodiments, a fragment of a PLATZ8 transcription factor comprises, consists essentially of or consists of at least about 5, 6, 7, 8, 9, 10, 11, 12, 13, 14, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, or 75 or more consecutive amino acids (e.g., a fragment or portion of SEQ ID NO:71, e.g., SEQ ID NOs:81-83 or 84-87).

In some embodiments, a "portion" may be related to the number of amino acids that are deleted from a polypeptide. Thus, for example, a deleted "portion" of a PLATZ8 transcription factor may comprise at least one amino acid residue (e.g., at least 1, or at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more consecutive amino acid residues) deleted from the amino acid sequence of SEQ ID NO:71, (or from a sequence having at least 80% sequence identity (e.g., at least 80, 81, 82, 83, 84, 85, 86, 87, 88, 89, 90, 91, 92, 93, 94, 95, 96, 97, 98, 99 or 100% identity) to the amino acid sequence of SEQ ID NO:71)(e.g., a deletion of about 1, 2, 3, 4, 5, 6, 7, 8, 9, or 10 to about 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 201, 202, 203, 204, 205, 206, 207, 208, 209, or 210 residues or any range or value therein). In some embodiments, the percent identity may be at least 85%. In some embodiments, the percent identity may be at least 90%. In some embodiments, the percent identity may be at least 95%. In some embodiments, the percent identity may be 100%. A "region" of a polynucleotide or a polypeptide refers to a portion of consecutive nucleotides or consecutive amino acid residues of that polynucleotide or a polypeptide, respectively. For example, a region of a PLATZ8 polynucleotide sequence may include, but is not limited to, to any one of the nucleic acid sequences of SEQ ID NOs:72-75 or 76-80. In some embodiments, a region of a PLATZ8 transcription factor sequence may include, but is not limited to, to the amino acid sequence of any one of SEQ ID NOs:81-83 or 84-87. In some embodiments, a region may be a target region or target site for modification in the PLATZ8 polynucleotide or PLATZ8 transcription factor.

In some embodiments, a "sequence-specific nucleic acid binding domain" (e.g., sequence-specific DNA binding domain) may bind to a PLATZ8 gene (e.g., SEQ ID NO:69 or SEQ ID NO:70) and/or to one or more fragments, portions, or regions of a PLATZ8 nucleic acid (e.g., SEQ ID NOs:72-75 or 76-80).

As used herein with respect to nucleic acids, the term "functional fragment" refers to nucleic acid that encodes a functional fragment of a polypeptide. A "functional fragment" with respect to a polypeptide is a fragment of a polypeptide that retains one or more of the activities of the native reference polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and noncoding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. A frameshift mutation can occur when deletions or insertions of one or more base pairs are introduced into a gene, optionally resulting in an out-of-frame mutation or an in-frame mutation. Frameshift mutations in a gene can result in the production of a polypeptide that is longer, shorter or the same length as the wild type polypeptide depending on when the first stop codon occurs following the mutated region of the gene. As an example, an out-of-frame mutation that produces a premature stop codon can produce a polypeptide that is shorter that the wild type polypeptide, or, in some embodiments, the polypeptide may be absent/undetectable. A DNA inversion is the result of a rotation of a genetic fragment within a region of a chromosome.

The terms "complementary" or "complementarity," as used herein, refer to the natural binding of polynucleotides under permissive salt and temperature conditions by basepairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity; e.g., substantial complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide. In regard to a PLATZ8 gene, a sequence may have 80% sequence identity to the nucleotide sequence of SEQ ID NO:69 or SEQ ID NO:70. In some embodiments, a PLATZ8 gene may have 85% sequence identity to the nucleotide sequence of SEQ ID NO:69 or SEQ ID NO:70. In some embodiments, a PLATZ8 gene may have 90% sequence identity to the nucleotide sequence of SEQ ID NO:69 or SEQ ID NO:70. In some embodiments, a PLATZ8 gene may have 95% sequence identity to the nucleotide sequence of SEQ ID NO:69 or SEQ ID NO:70, optionally wherein the PLATZ8 gene may have 100% sequence identity to the nucleotide sequence of SEQ ID NO:69 or SEQ ID NO:70. A PLATZ8 transcription factor polypeptide as described herein may have 80% sequence identity to the amino acid sequence of SEQ ID NO:71. In some embodiments, a PLATZ8 transcription factor polypeptide may have 85% sequence identity to the amino acid sequence of SEQ ID NO:71. In some embodiments, a PLATZ8 transcription factor polypeptide may have 90% sequence identity to the amino acid sequence of SEQ ID NO:71. In some embodiments, a PLATZ8 transcription factor polypeptide may have 95% sequence identity to the amino acid sequence of SEQ ID NO:71, optionally wherein the PLATZ8 transcription factor polypeptide may have 100% sequence identity to the amino acid sequence of SEQ ID NO:71. With regard to regions or portions of a PLATZ8 gene, the region or portion may have 80% sequence identity to the nucleotide sequence of any one of SEQ ID NOs:72-75 and/or 76-80, optionally at least about 80% sequence identity to any one of SEQ ID NOs:72, 73, 74, 75, 76, 77, 78, 79, and/or 80. In some embodiments, a region or portion of a PLATZ8 gene may have 85% sequence identity to the nucleotide sequence any one of SEQ ID NOs:72-75 and/or 76-80, optionally at least about 85% sequence identity to any one of SEQ ID NOs:72, 73, 74, 75, 76, 77, 78, 79, and/or 80. In some embodiments, a region or portion of a PLATZ8 gene may have 90% sequence identity to the nucleotide sequence any one of SEQ ID NOs:72-75 and/or 76-80, optionally at least about 90% sequence identity to any one of SEQ ID NOs:72, 73, 74, 75, 76, 77, 78, 79, and/or 80. In some embodiments, a region or portion of a PLATZ8 gene may have 95% sequence identity to the nucleotide sequence any one of SEQ ID NOs:72-75 and/or 76-80, optionally at least about 95% sequence identity to any one of SEQ ID NOs:72, 73, 74, 75, 76, 77, 78, 79, and/or 80. In some embodiments, a region or portion of the PLATZ8 gene may have at least about 95% sequence identity to the nucleotide sequence any one of SEQ ID NOs:72-75 and/or 76-80. In some embodiments, a region or portion of the PLATZ8 gene may have 100% sequence identity to any one of SEQ ID NOs:72, 73, 74, 75, 76, 77, 78, 79, and/or 80. With regard to regions or portions of a PLATZ8 transcription factor polypeptide, the region or portion may have 80% sequence identity to any one of the amino acid sequences of SEQ ID NOs:81-83 and/or 84-87, optionally at least 80% sequence identity to any one of SEQ ID NOs:81, 82, 83, 84, 85, 86 and/or 87. In some embodiments, a region or portion of a PLATZ8 transcription factor polypeptide may have 85% sequence identity to any one of the amino acid sequences of SEQ ID NOs:81-83 and/or 84-87, optionally at least 85% sequence identity to any one of SEQ ID NOs:81, 82, 83, 84, 85, 86 and/or 87. In some embodiments, a region or portion of a PLATZ8 transcription factor polypeptide may have 90% sequence identity to any one of the amino acid sequences of SEQ ID NOs:81-83 and/or 84-87, optionally at least 90% sequence identity to any one of SEQ ID NOs:81, 82, 83, 84, 85, 86 and/or 87. In some embodiments, a region or portion of a PLATZ8 transcription factor polypeptide may have 95% sequence identity to any one of the amino acid sequences of SEQ ID NOs:81-83 and/or 84-87, optionally at least 95% sequence identity to any one of SEQ ID NOs:81, 82, 83, 84, 85, 86 and/or 87. In some embodiments, a region or portion of the PLATZ8 transcription factor polypeptide may have 100% sequence identity to any one of the amino acid sequences of SEQ ID NOs:81-83 and/or 84-87, optionally at least 100% sequence identity to any one of SEQ ID NOs:81, 82, 83, 84, 85, 86 and/or 87. In some embodiments, a mutated PLATZ8 gene may have 80% sequence identity to any one of the nucleotide sequences of SEQ ID NOs:91, 92, 94, 95, 97, 98, 99, 100, 102, 103, 105, 106, 108, 109, 111, and/or 112. In some embodiments, a mutated PLATZ8 gene may have 85% sequence identity to any one of the nucleotide sequences of SEQ ID NOs:91, 92, 94, 95, 97, 98, 99, 100, 102, 103, 105, 106, 108, 109, 111, and/or 112. In some embodiments, a mutated PLATZ8 gene may have 90% sequence identity to any one of the nucleotide sequences of SEQ ID NOs:91, 92, 94, 95, 97, 98, 99, 100, 102, 103, 105, 106, 108, 109, 111, and/or 112. In some embodiments, a mutated PLATZ8 gene may have 95% sequence identity to any one of the nucleotide sequences of SEQ ID NOs:91, 92, 94, 95, 97, 98, 99, 100, 102, 103, 105, 106, 108, 109, 111, and/or 112, optionally wherein the mutated PLATZ8 gene may have 100% sequence identity to the nucleotide sequence of any one of the nucleotide sequences of SEQ ID NOs:91, 92, 94, 95, 97, 98, 99, 100, 102, 103, 105, 106, 108, 109, 111, and/or 112. In some embodiments, a mutated PLATZ8 transcription factor may have 80% sequence identity to any one of the amino acid sequences of SEQ ID NOs:93, 96, 101, 104, 107, 110, and/or 113. In some embodiments, a mutated PLATZ8 transcription factor may have 85% sequence identity to any one of the amino acid sequences of SEQ ID NOs:93, 96, 101, 104, 107, 110, and/or 113. In some embodiments, a mutated PLATZ8 transcription factor may have 90% sequence identity to any one of the amino acid sequences of SEQ ID NOs:93, 96, 101, 104, 107, 110, and/or 113. In some embodiments, a mutated PLATZ8 transcription factor may have 95% sequence identity to any one of the amino acid sequences of SEQ ID NOs:93, 96, 101, 104, 107, 110, and/or 113, optionally wherein the mutated PLATZ8 transcription factor may have 100% sequence identity to any one of the amino acid sequences of SEQ ID NOs:93, 96, 101, 104, 107, 110, and/or 113.

As used herein, the phrase "substantially identical," or "substantial identity" in the context of two nucleic acid molecules, nucleotide sequences or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more nucleotides in length, and any range therein, up to the full length of the sequence. In some embodiments, nucleotide sequences can be substantially identical over at least about 20 consecutive nucleotides (e.g., about 20, 21, 22, 23, 24, 25, 26, 27, 28, 29, 30, 31, 32, 33, 34, 35, 36, 37, 38, 39, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300 or more nucleotides). In some embodiments, two or more PLATZ8 genes may be substantially identical to one another over at least about 30 or more consecutive nucleotides (e.g., 30, 31, 32, 33, 34, 35, 36, 37, 38, 39, 40, 41, 42, 43, 44, 45, 46, 47, 48, 49, 50, 51, 52, 53, 54, 54, 56, 57, 58, 59, 60, 65, 70, 75, 80, 85, 90, 95, 100, 110, 120, 130, 140, 150, 160, 170, 180, 200, 220, 240, 260, 280, 300, 320, 340, 360, 380, 400, 420, 440, 460, 480, 500, 520, 540, 560, 580, 600, or more consecutive nucleotides) of any one of SEQ ID NO:69 or SEQ ID NO:70 (see, e.g., SEQ ID NOs:72-75 or 76-80).

In some embodiments of the invention, the substantial identity exists over a region of consecutive amino acid residues of a polypeptide of the invention that is about 3 amino acid residues to about 20 amino acid residues, about 5 amino acid residues to about 10 amino acid residues, about 5 amino acid residues to about 55 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8, 9, 10, 11, 12, 13, 14, or more consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 275, 300, 325, 350, 400, 450, 500, or more amino acids in length or more consecutive amino acid residues of SEQ ID NO:71). In some embodiments, two or more PLATZ8 transcription factors may be substantially identical to one another over at least about 10 to about 150 (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145 or 150 residues or more) consecutive amino acid residues of SEQ ID NO:71, or any range or value therein, see e.g., SEQ ID NOs:81-83 or 84-87). In some embodiments, a substantially identical nucleotide or protein sequence may perform substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific nucleic acid binding domain (e.g., a sequence-specific nucleic acid binding domain from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

A polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron) (see, e.g., SEQ ID NO:21 and SEQ ID NO:22).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a DNA binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. (2005) *Plant Cell Rep.* 23:727-735; Li et al. (2007) *Gene* 403:132-142; Li et al. (2010) *Mol Biol. Rep.* 37:1143-1154). PrbcS1 and Pactin are constitutive promoters and Pnr and Pdca1 are inducible promoters. Pnr is induced by nitrate and repressed by ammonium (Li et al. (2007) *Gene* 403:132-142) and Pdca1 is induced by salt (Li et al. (2010) *Mol Biol. Rep.* 37:1143-1154). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad.*

*Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al. (1991) *Plant Science* 79: 87-94), maize (Christensen et al. (1989) *Plant Molec. Biol.* 12: 619-632), and *Arabidopsis* (Norris et al. (1993) *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. ((1991) *Mol. Gen. Genet.* 231: 150-160) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula (1989) *Plant Molec. Biol.* 12:579-589). Non-limiting examples of tissue-specific promoters include those associated with genes encoding the seed storage proteins (such as 0-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf, or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond ((1991) *FEBS* 290:103-106; EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. (2015) *Plant Biotechnol. Reports* 9(5):297-306), ZmSTK2_USP from maize (Wang et al. (2017) *Genome* 60(6):485-495), LAT52 and LAT59 from tomato (Twell et al. (1990) *Development* 109(3):705-713), Zm13 (U.S. Pat. No. 10,421,972), PLA$_2$-δ promoter from *Arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. (2006) *The Plant Cell* 18:2958-2970), the root-specific promoters RCc3 (Jeong et al. (2010) *Plant Physiol.* 153:185-197) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989) supra), petunia chalcone isomerase promoter (van Tunen et al. (1988) *EMBO J.* 7:1257-1263), bean *Glycine* rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain (e.g., sequence-specific DNA binding domain), a polynucleotide encoding a nuclease polypeptide/domain, a polynucleotide encoding a deaminase protein/domain, a polynucleotide encoding a reverse transcriptase protein/ domain, a polynucleotide encoding a 5'-3' exonuclease poly- peptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same pro- moter, or they may be different promoters. Thus, a poly- nucleotide encoding a sequence specific nucleic acid binding domain, a polynucleotide encoding a nuclease protein/do- main, a polynucleotide encoding a CRISPR-Cas effector protein/domain, a polynucleotide encoding an deaminase protein/domain, a polynucleotide encoding a reverse tran- scriptase polypeptide/domain (e.g., RNA-dependent DNA polymerase), and/or a polynucleotide encoding a 5'-3' exo- nuclease polypeptide/domain, a guide nucleic acid, an extended guide nucleic acid and/or RT template when com- prised in a single expression cassette may each be operably linked to a single promoter, or separate promoters in any combination.

An expression cassette comprising a nucleic acid con- struct of the invention may be chimeric, meaning that at least one of its components is heterologous with respect to at least one of its other components (e.g., a promoter from the host organism operably linked to a polynucleotide of interest to be expressed in the host organism, wherein the polynucle- otide of interest is from a different organism than the host or is not normally found in association with that promoter). An expression cassette may also be one that is naturally occur- ring but has been obtained in a recombinant form useful for heterologous expression.

An expression cassette can optionally include a transcrip- tional and/or translational termination region (i.e., termina- tion region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initia- tion region, may be native to, for example, a gene encoding a sequence-specific DNA binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific DNA binding protein, a gene encoding a nuclease, a gene encoding a reverse tran- scriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid mol- ecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g., expression cassette(s)) comprising the nucleotide sequence(s) to be transferred, delivered, or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobi- lizable. In some embodiments, a viral vector can include, but is not limited, to a retroviral, lentiviral, adenoviral, adeno- associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g., higher plant, mammalian, yeast, or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific DNA binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific DNA binding protein, the reverse transcriptase and the deaminase are expressed and the sequence-specific DNA binding protein binds to the target nucleic acid, and the reverse transcriptase and/or deaminase may be fused to either the sequence-specific DNA binding protein or recruited to the sequence-specific DNA binding protein (via, for example, a peptide tag fused to the sequence-specific DNA binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

The term "regulating" as used in the context of a transcription factor "regulating" a phenotype, for example, a response to illumination (e.g., a light response, e.g., a shade avoidance response), means the ability of the transcription factor to affect the expression of a gene or genes such that a phenotype, for instance, a response to illumination, is modified.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. (2013) *Nat. Biotechnol.* 31:233-239; Ran et al. (2013) *Nature Protocols* 8:2281-2308). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska ((2002) *Cell. Mol. Biol. Lett.* 7:849-858).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

The PLATZ family of proteins is a class of plant-specific transcription factors with widespread distribution in dicots, monocots, mosses, and algae. PLATZ transcription factors bind to AT rich nucleotide sequences and function in transcriptional repression. The PLATZ protein encoded by the gene Os06g0666100 identified in QTL GL6 functions in the regulation of rice grain length, weight and spikelet number (Wang et al. (2019) *Plant Physiol.* 180:2077-2090). GL6 positively controls grain length by promoting cell proliferation in young panicles and grains. All PLATZ family members share a conserved PLATZ domain that is about 82 amino acids in length and consists of two noncanonical zinc finger domains (zinc-dependent DNA-binding proteins). PLATZ polypeptides bind to AT rich sequences and functions in transcriptional repression.

Seventeen PLATZ genes in the *Zea mays* genome have been described (Wang et al. (2018) *BMC Plant Biol.* 18:221). Of the PLATZ genes in maize, PLATZ8 has been shown to be highly expressed in immature ear and is the only member of the maize PLATZ transcription factors expressed in reproductive tissue at early stages. In addition to the conserved PLATZ domain (Pfam-family PLATZ: PF04640), the PLATZ8 transcription factor also includes a zinc-binding domain (B-Box zinc-finger binding domain; SMART accession number: SM00336), which is located at and overlaps with tie C-terminal portion of the PLATZ domain (Wang et al. (2018) supra).

The present invention is directed to modification of a Plant AT-rich sequence- and Zinc-binding protein 8 (PLATZ8) gene plants through editing technology to provide plants that exhibit one or more improved yield traits. Mutations that may be useful for producing plants with one or more improved yield traits include, for example, substitutions, deletions, and/or insertions. In some aspects, a mutation in the PLATZ8 gene results in a mutated PLATZ8 transcription factor having decreased activity. In some aspects, a mutation generated by the editing technology can be a point mutation. In some embodiments, a mutation may be a non-natural mutation. In some aspects, a mutation in the PLATZ8 gene may result in a mutated PLATZ8 transcription factor having decreased activity, specifically a decreased ability to repress gene expression. In some embodiments, a PLATZ8 transcription factor useful with the invention may comprise a PLATZ domain or zinc-finger binding domain (B-Box zinc-finger binding domain) within which a mutation may be generated. In some embodiments, mutations useful for improving one or more yield traits may be generated by truncating the PLATZ8 transcription factor. Without wishing to be limited by any particular theory, the mutation in the PLATZ8 gene may result in an encoded PLATZ8 transcription factor that is mutated in such a manner that the mutated PLATZ8 transcription factor may be non-functional in its ability to repress gene expression, but retains the ability to interact, bind, and/or form a complex with one or more proteins of the RNA polymerase III transcription machinery. Thus, in some aspects, the mutation in the PLATZ8 gene may result in a dominant allele, a dominant negative allele, a knock-out allele (null allele), a hypomorphic allele, or a loss of function allele.

As used herein, "a reduced ability to repress gene expression" or "reduced transcription repression activity" refers to a reduction in the ability of a PLATZ8 polypeptide encoded by a PLATZ gene mutated as described herein to repress the expression or transcription of the genes to which it binds. In some embodiments, the transcription repression activity of a PLATZ polypeptide mutated as described herein may be reduced by about 10% to about 100% (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%).

Accordingly, the present invention provides a plant or part thereof comprising at least one mutation (e.g., one or more mutations) in an endogenous Plant AT-rich sequence- and Zinc-binding protein 8 (PLATZ8) gene encoding a PLATZ8 transcription factor, wherein the mutation disrupts the ability of the encoded PLATZ8 transcription factor to ability to repress gene expression. In some embodiments, the PLATZ8 transcription factor comprises a zinc-finger binding domain (B-Box zinc-finger binding domain) and a PLATZ domain. In some embodiments, the at least one mutation is in and/or adjacent to the second exon and/or in and/or adjacent to the third exon of the endogenous PLATZ8 gene, optionally wherein the mutation disrupts the ability of the PLATZ8 transcription factor to repress gene expression. In some embodiments, the at least one mutation may be in a region of the endogenous PLATZ8 gene that encodes the zinc-binding domain of the PLATZ8 transcription factor, optionally in and/or adjacent to the second exon of the PLATZ8 gene, optionally wherein the mutation may disrupt the ability of the PLATZ8 transcription factor to repress gene expression. In some embodiments, the at least one mutation may be in a region of the endogenous PLATZ8 gene that encodes the PLATZ domain of the PLATZ8 transcription factor, optionally in and/or adjacent to the third exon of the PLATZ8 gene, optionally wherein the mutation may disrupt the ability of the PLATZ8 transcription factor to repress gene expression. In further embodiments, a mutation in an endogenous PLATZ8 gene encoding a PLATZ8 transcription factor may result in a dominant allele, a dominant negative allele, a knock-out allele (null allele), a hypomorphic allele, or a loss of function allele. The second exon of the endogenous PLATZ8 gene is located from nucleotide 7888 to nucleotide 7988 with reference to nucleotide position numbering of SEQ ID NO:69. The third exon of the endogenous PLATZ8 gene is located from nucleotide 8125 to nucleotide 8267 with reference to nucleotide position numbering of SEQ ID NO:69.

In some embodiments, an endogenous PLATZ8 gene useful with this invention: (a) comprises a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to the nucleotide sequence of any one of SEQ ID NO:69 or SEQ ID NO:70; (b) comprises a region having at least 80% sequence identity to any one of the nucleotide sequences of SEQ ID NOs:72-75 or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 or 84-87, optionally wherein the sequence identity of (a), (b), (c) and/or (d) may be at least 85%, or at least 90%, or it may be at least 95%, optionally the sequence identity may be 100%. In some embodiments, the at least one mutation may be in a region of the PLATZ8 transcription factor having at least 80% sequence identity to any one of the amino acid sequences of SEQ ID NOs:81-83 or 84-87, optionally to any one of SEQ ID NOs:81, 82, 83, 84, 85, 86 and/or 87. Thus, a plant or plant part of the invention may comprise at least one mutation (e.g., one or more mutations) in an endogenous PLATZ8 gene, optionally wherein the mutation decreases the ability of the encoded PLATZ8 transcription factor to repress the expression of genes that it binds to, wherein the endogenous gene encoding a PLATZ8 transcription factor (e.g., endogenous PLATZ8 gene) (a) comprises a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to the nucleotide sequence of any one of SEQ ID NO:69 or SEQ ID NO:70; (b) comprises a region having at least 80% sequence identity to any one of the nucleotide sequences of any one of SEQ ID NOs:72-75 or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%.

A mutation in an endogenous Plant AT-rich sequence- and Zinc-binding protein 8 (PLATZ8) gene in a plant may be any type of mutation including, but not limited to, a base substitution, a base deletion and/or a base insertion. In some embodiments, a mutation useful with the invention is a non-natural mutation.

In some embodiments, a mutation in an endogenous PLATZ8 gene may result in a PLATZ8 transcription factor having a mutation in the zinc-finger binding domain (B-Box zinc-finger binding domain) or in the PLATZ domain, optionally wherein the mutation reduces the ability of the PLATZ8 transcription factor to repress expression of the genes to which it binds, optionally wherein the mutated PLATZ8 transcription factor may retain the ability to interact, bind, and/or form a complex with one or more proteins of the RNA polymerase III transcription machinery. As an example, a mutation in a PLATZ8 gene may be a substitution, a deletion and/or an insertion of one or more bases. In some embodiments, the at least one mutation may result in a modification (e.g., substitution, insertion, deletion) of an amino acid residue in the PLATZ8 transcription factor. In some embodiments, the at least one mutation may be a base deletion or a base insertion, optionally an in-frame base deletion or an in-frame base insertion, optionally an out-of-frame deletion or an out-of-frame insertion, optionally, wherein the mutation reduces the ability of the PLATZ8 transcription factor to repress gene expression.

In some embodiments, the base deletion and/or base insertion may be an insertion or deletion of one to about 100 base pairs (e.g., about 1, 2, 3, 4, 5, 6, 7, 8, 9, 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs or more and any range or value therein). In some embodiments, an endogenous PLATZ8 gene comprises an out-of-frame deletion or out-of-frame insertion resulting in a premature stop codon and the encoded PLATZ8 transcription factor is truncated. In other embodiments, an endogenous PLATZ gene comprises an out-of-frame base deletion of one or more base pairs (e.g., 1 base pair to about 100 base pairs, optionally, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more base pairs), optionally wherein the encoded PLATZ8 transcription factor comprises a C-terminal truncation.

In some embodiments, the C-terminal truncation may comprise a truncation of one amino acid residue to about 250 amino acid residues (e.g., 1 or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 152, 154, 155, 154, 155, 156, 157, 158, 159, 160, 165, 166, 167, 168, 169, 170, 171, 172, 173, 174, 175, 176, 177, 178, 179, 180, 181, 182, 183, 184, 185, 186, 187, 188, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 or more amino acid residues. In some embodiments, an endogenous PLATZ gene comprises an in-frame base deletion of one or more base pairs, optionally an in-frame deletion of about 3, 6, 9, 12, 15, 18, 21, 24, 27, 30, 33, 36, 39, 42, 45, or 48, or more consecutive base pairs. In some embodiments, an in-frame deletion may result in a deletion of one amino acid residue to about 100 amino acid residues (e.g., 1 or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more amino acid residues.

In some embodiments, a mutation (e.g., one or more mutations) in an endogenous PLATZ8 gene may result in a dominant allele, a dominant negative allele, a knock-out allele (null allele), a hypomorphic allele, or a loss of function allele.

In some embodiments, a mutation in an endogenous Plant AT-rich sequence- and Zinc-binding protein 8 (PLATZ8) gene may result in a mutated PLATZ8 gene having at least 90% sequence identity (optionally the sequence identity may be at least 95%, optionally the sequence identity may be 100%) to any one of the nucleotide sequences of SEQ ID NOs:91, 92, 94, 95, 97, 98, 99, 100, 102, 103, 105, 106, 108, 109, 111, or 112 and/or a mutated PLATZ8 transcription factor having at least 90% sequence identity to any one of the amino acid sequences of SEQ ID NOs:93, 96, 101, 104, 107, 110, or 113.

In some embodiments, a plant or part thereof comprising a mutation in a PLATZ8 gene as described herein may exhibit a phenotype of improved yield traits, optionally exhibiting increased yield (bu/acre), increased biomass, increased number of seeds (kernels) per plant, increased number of seeds (kernels) per pod or ear, increased seed size, increased seed area, increased seed weight (e.g., increase in 100-seed weight), increased ear length, increased kernel row number (KRN) as compared to a plant that is devoid of the at least one mutation.

In some embodiments, a plant cell comprising an editing system is provided, the editing system comprising: (a) a CRISPR-Cas associated effector protein; and (c) a guide nucleic acid (gRNA, gDNA, crRNA, crDNA) having a spacer sequence with complementarity to an endogenous target gene encoding a Plant AT-rich sequence- and Zinc-binding protein 8 (PLATZ8) polypeptide. In some embodiments, an endogenous PLATZ8 gene encodes PLATZ8 transcription factor comprising a zinc-finger binding domain (B-Box zinc-finger binding domain) and a PLATZ domain. In some embodiments, a PLATZ8 gene to which a spacer sequence of the guide nucleic acid shares complementarity (a) comprises a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to the nucleotide sequence of any one of SEQ ID NO:69 or SEQ ID NO:70; (b) comprises a region having at least 80% sequence identity to any one of the nucleotide sequences of SEQ ID NOs:72-75 or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%. In some embodiments, a spacer sequence useful with this invention can include, but is not limited to, a nucleotide sequence of any one of SEQ ID NOs:88-90, or reverse complement thereof, or a combination thereof.

In some embodiments, a plant cell is provided that comprises a mutation in a Plant AT-rich sequence- and Zinc-binding protein 8 (PLATZ8) polypeptide, wherein the mutation is a substitution, insertion and/or a deletion that is introduced into an endogenous PLATZ8 gene encoding the PLATZ8 transcription factor using an editing system that comprises a nucleic acid binding domain that binds to a target site within the endogenous PLATZ8 gene, wherein the endogenous PLATZ8 gene: (a) comprises a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 or SEQ ID NO:70; (b) comprises a region having at least 80% sequence identity to any one of the nucleotide sequences of SEQ ID NOs:72-75 or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%. In some embodiments, the nucleic acid binding domain of the editing system may be from a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein.

In some embodiments, a deletion or insertion generated in an endogenous PLATZ8 gene may be a deletion or insertion of 1 base pair to about 100 base pairs (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs, or any value or range therein) or more. In some embodiments, the at least one mutation may be an in-frame deletion, an in-frame insertion, an out-of-frame deletion, or an out-of-frame insertion, optionally wherein the in-frame base deletion or in-frame base insertion is a deletion or insertion of three or more consecutive nucleotides, optionally 3, 6, 9, 12, 15, 18, 21, 24, 27, or 30 or more consecutive nucleotides. In some embodiments, the mutation may be in a region of the PLATZ8 gene that encodes a zinc-finger binding domain (B-Box zinc-finger binding domain) or a PLATZ domain. In some embodiments, an in-frame INDEL may be a deletion or insertion of any number of consecutive nucleotides, such that the deletion or insertion preserves the frame of translation and does not lead to an early stop codon.

In some embodiments, a mutation in a PLATZ8 gene may be located in a region of the PLATZ8 gene having at least 80% sequence identity (optionally the sequence identity may be 90% or it may be 95%, optionally the sequence identity may be 100%) to a nucleic acid sequence encoding the amino acid sequence of any one of SEQ ID NOs:81-83 or 84-87, optionally to any one of SEQ ID NOs:81, 82, 83, 84, 85, 86 and/or 87.

In some embodiments, at least one mutation (e.g., one or more mutations) in an endogenous PLATZ8 gene may result in a dominant allele, a dominant negative allele, a knock-out allele (null allele), a hypomorphic allele, or a loss of function allele. In some embodiments, the mutation may be a non-natural mutation.

A plant or plant part useful with this invention may be a dicot or a monocot. Non-limiting examples of a plant or part thereof useful with this invention include, but are not limited to, corn, soy, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, blackberry, raspberry, black raspberry or a *Brassica* spp. In some embodiments, the plant part may be a cell from a plant that includes, but is not limited to, a monocot or a dicot, optionally corn, soy, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, blackberry, raspberry, black raspberry or a *Brassica* spp. In some embodiments, a plant may be regenerated from a cell or plant part of this invention. In some aspects, a plant cell can be non-propagating plant cell that does not regenerate into a plant. Plants of this invention comprising at least one mutation in a PLATZ8 gene may comprise an improved yield trait as compared to a control plant devoid of the at least one mutation. In some embodiments, a plant regenerated from a plant cell of the invention comprising at least one mutation in a PLATZ8 gene may exhibit an improved yield trait, optionally wherein an improved yield trait can include, but is not limited to, increased yield (bu/acre), increased biomass, increased number of seeds (kernels) per plant, increased number of seeds (kernels) per pod or ear, increased seed size, increased seed area, increased seed weight (e.g., increase in 100-seed weight), increased ear length, increased kernel row number (KRN) as compared to a plant that is devoid of the at least one mutation.

As used herein, an "increase in yield" refers to an increase in grain or seed yield on a per acre, or per hectare basis of at least 10% to about 200% (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, 145, 150, 155, 160, 165, 170, 175, 180, 185, 190, 195, Or 200%) as compared to a control plant (e.g., a plant that is devoid of the mutation or edit).

As used herein, an "increased biomass" refers to an increase in biomass of at least about 20% to about 75%) (e.g., about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75%, or any value or range therein) as compared to a control plant (e.g., a plant that is devoid of the mutation or edit).

As used herein, an "increased number of seeds per plant" refers to an increase in the number of seeds per plant of at least about 10% to about 150%) (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, 145, or 150% or any value or range therein).

As used herein, an "increased number of seeds per pod" refers to an increase in the number of seeds per pod of about 1 to about 5 seeds (e.g., an increase of about 1, 2, 3, 4, or 5 seeds per pod).

As used herein, an "increased number of seeds per ear" refers to an increase in the number of seeds per ear of about 10 to about 80 seeds (e.g., an increase of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 seeds per ear).

As used herein, an "increased seed size" can mean a seed that is increased in area and/or an increase in seed weight (e.g., 100-seed weight). In some embodiments, a seed may be increased in area by up to about 70% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, 50, 51, 52, 53, 54, 55, 56, 57, 58, 59, 60, 61, 62, 63, 64, 65, 66, 67, 68, 69, 70%) as compared to a seed from a control plant (e.g., a plant not comprising the mutation in an endogenous PLATZ8 gene as described herein). As used herein, an "increased seed weight" (e.g., increase in 100-seed weight) refers to an increased in weight of at least about 2% to about 20% (e.g., about 2, 3, 4, 5, 6, 7, 8, 9, 10, 11, 12, 13, 14, 15, 16, 17, 18, 19, or 20%, or any value or range therein) as compared to a seed from a control plant (e.g., a plant not comprising the mutation in an endogenous PLATZ8 gene as described herein). In some embodiments, an increase in seed size can include an increase in both seed area and seed size. An increased seed size may be measured, for example, by 100-seed weight.

As used herein, an "increase in ear length" means an increase in the length of the ear of at least 1% (about 1% to about 30%, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% increase in ear length, or any range or value therein) as compared to a control plant that is devoid of the mutation as described herein.

As used herein, an "increase in kernel row number (KRN)" means an increase in the number of rows in an ear of at least about one to about five (e.g., about 1, 2, 3, 4, or 5) as compared to a control plant that is devoid of the mutation as described herein, optionally wherein ear length is not substantially reduced. As used herein, the phrase "ear length is not substantially reduced" can mean that the ear is not decreased in length by more than about 5, 6, 7, 8, 9, 10, 11, 12, 13, 14, 15, 16, 17, 18, 19, 20, 21, 22, 23, 24, 25, 26, 27, 28, 29, or 30% as compared to an ear of a plant devoid of the same mutation(s).

Also provided herein is a method of providing a plurality of plants having an increased yield trait (e.g., increased yield (bu/acre), increased biomass, increased number of seeds (kernels) per plant, increased number of seeds (kernels) per pod or ear, increased seed size, increased seed area, increased seed weight (e.g., increase in 100-seed weight), increased ear length, and/or increased kernel row number (KRN)), the method comprising planting two or more plants of the invention (e.g., 2, 3, 4, 5, 6, 7, 8, 9, 10, 20, 30, 40, 50, 100, 200, 300, 400, 500, 1000, 2000, 3000, 400, 5000, or 10,000 or more plants of the invention) (e.g., comprising a mutation in a PLATZ8 gene and having an improved yield trait) in a growing area, thereby providing a plurality of plants having an improved yield trait as compared to a plurality of control plants not comprising the mutation (e.g., as compared to an isogenic wild type plant not comprising the mutation). A growing area can be any area in which a plurality of plants can be planted together, including, but not limited to, a field (e.g., a cultivated field, an agricultural field), a growth chamber, a greenhouse, a recreational area, a lawn, and/or a roadside, and the like.

In some embodiments, a method of producing/breeding a transgene-free edited plant is provided, the method comprising: crossing a plant of the present invention (e.g., a plant comprising a mutation in an endogenous PLATZ8 gene as described herein (and having an improved yield trait) with a transgene-free plant, thereby introducing the at least one mutation (e.g., one or more mutations) into the plant that is transgene-free (e.g., into progeny plants); and selecting a progeny plant that comprises the at least one mutation and is transgene-free, thereby producing a transgene-free edited (e.g., base edited) plant.

In some embodiments, the present invention provides a method of creating a mutation in an endogenous Plant AT-rich sequence- and Zinc-binding protein 8 (PLATZ8) gene in a plant, comprising: (a) targeting a gene editing system to a portion of the PLATZ8 gene that comprises a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of SEQ ID NOs:72-75 and/or 76-80, optionally to any one of SEQ ID NOs:72, 73, 74, 75, 76, 77, 78, 79 and/or 80; and (b) selecting a plant that comprises a modification located in a region of the PLATZ8 gene having at least 80% sequence identity to any one of SEQ ID NOs:72-75 or 76-80. In some embodiments, the mutation that is created results in a nucleic acid having at least 90% sequence identity to SEQ ID NOs:91, 92, 94, 95, 97, 98, 99, 100, 102, 103, 105, 106, 108, 109, 111, and/or 112 and/or results in a polypeptide having at least 90% sequence identity to SEQ ID NOs:93, 96, 101, 104, 107, 110, and/or 113.

In some embodiments, a method of generating variation in an Plant AT-rich sequence- and Zinc-binding protein 8 (PLATZ8) polypeptide is provided, the method comprising: introducing an editing system into a plant cell, wherein the editing system is targeted to a region of an endogenous Plant AT-rich sequence- and Zinc-binding protein 8 (PLATZ8) gene that encodes the PLATZ8 transcription factor, and contacting the region of the endogenous PLATZ8 gene with the editing system, thereby introducing a mutation into the endogenous PLATZ8 gene and generating variation in the PLATZ8 transcription factor of the plant cell. In some embodiments, a PLATZ8 gene into which variation is generated comprises a nucleotide sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of SEQ ID NO:69 and/or SEQ ID NO:70 and/or encodes an amino acid sequence having at least 80% sequence identity to SEQ ID NO:71. In some embodiments, a region of the PLATZ8 gene that may be targeted comprises at least 80% sequence identity to a nucleotide sequence of any one of SEQ ID NOs:72-75 or 76-80, optionally to any one of SEQ ID NOs:72, 73, 74, 75, 76, 77, 78, 79 and/or 80, optionally where the region of the PLATZ8 gene that may be targeted encodes an amino acid sequence having at least 80% sequence identity to any one of SEQ ID NOs:81-83 or 84-87, optionally to any one of SEQ ID NOs:81, 82, 83, 84, 85, 86 and/or 87. In some embodiments, contacting a region of an endogenous PLATZ8 gene in a plant cell with an editing system produces a plant cell comprising in its genome an edited endogenous PLATZ8 gene. In some embodiments, the method may further comprise (a) regenerating a plant from the plant cell; (b) selfing the plant to produce progeny plants (E1); (c) assaying the progeny plants of (b) for an improved yield trait; and (d) selecting the progeny plants exhibiting an improved yield trait as compared to a control plant devoid of the mutation. In some embodiments, the method may further comprise (e) selfing the selected progeny plants of (d) to produce progeny plants (E2); (f) assaying the progeny plants of (e) for an improved yield trait; and (g) selecting the progeny plants exhibiting an improved yield trait as compared to a control plant, optionally repeating (e) through (g) one or more additional times.

In some embodiments, a mutated PLATZ8 gene produced by a method of the invention may comprise a sequence having at least 90% sequence identity to any one of SEQ ID NOs:91, 92, 94, 95, 97, 98, 99, 100, 102, 103, 105, 106, 108, 109, 111, and/or 112 and/or encode a modified PLATZ8 polypeptide, the modified PLATZ8 polypeptide comprising an amino acid sequence having at least 90% sequence identity to any one of SEQ ID NOs:93, 96, 101, 104, 107, 110, and/or 113. In some embodiments, a method of detecting a mutant PLATZ8 gene (a mutation in an endogenous PLATZ8 gene) in a plant or plant part (e.g., plant cell) is provided, the method comprising detecting in the genome of the plant a PLATZ8 gene having at least one mutation within a region having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to a nucleotide sequence of any one of SEQ ID NOs: 72-75 or 76-80, optionally wherein the mutation is a deletion or an insertion of at least one nucleotide (e.g., 1, 2, 3, 4, 5, 6, 7, 8, 9, or more) or at least 3 nucleotides (e.g., an in-frame deletion, in-frame insertion, out-of-frame deletion, or out-of-frame insertion). In some embodiments, a mutant PLATZ8 gene that is detected comprises a nucleic acid sequence having at least 90% sequence identity to any one of SEQ ID NOs:91, 92, 94, 95, 97, 98, 99, 100, 102, 103, 105, 106, 108, 109, 111, and/or 112, and/or a mutated PLATZ8 transcription factor having at least 90% sequence identity to any one of the amino acid sequences of SEQ ID NOs:93, 96, 101, 104, 107, 110, and/or 113.

In some embodiments, a method of detecting a mutant PLATZ8 gene (a mutation in an endogenous PLATZ8 gene) is provided, the method comprising detecting in the genome of a plant comprising a PLATZ8 gene having at least one mutation in a region having at least 80% sequence identity to any one of the nucleotide sequences of SEQ ID NOs:72, 73, 74, 75, 76, 77, 78, 79 and/or 80. In some embodiments, a method for editing a specific site in the genome of a plant cell is provided, the method comprising cleaving, in a site-specific manner, a target site within an endogenous Plant AT-rich sequence- and Zinc-binding protein 8 (PLATZ8) gene in the plant cell, the endogenous PLATZ8 gene: (a) comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to the nucleotide sequence of any one of SEQ ID NO:69 or SEQ ID NO:70; (b) comprising a region having at least 80% sequence identity to any one of the nucleotide sequences of SEQ ID NOs:72-75 or 76-80, optionally to any one of SEQ ID NOs:72, 73, 74, 75, 76, 77, 78, 79 and/or 80; (c) encoding a polypeptide comprising a sequence having at least 80% sequence identity to the amino acid sequence of SEQ ID NO:71; and/or (d) encoding a region having at least 80% sequence identity to any one of the amino acid sequences of SEQ ID NOs:81-83 or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%, thereby generating an edit in the endogenous PLATZ8 gene of the plant cell. In some embodiments, the PLATZ8 gene encodes a PLATZ8 transcription factor that comprises a zinc-finger binding domain (B-Box zinc-finger binding domain) and a PLATZ domain and the edit results in a mutation in the zinc-finger binding domain (B-Box zinc-finger binding domain) or PLATZ domain encoded by the endogenous PLATZ8 gene. In some embodiments, the edit results in a mutation, optionally a non-natural mutation, in the endogenous PLATZ8 gene, wherein the mutated PLATZ8 gene produces a PLATZ8 transcription factor optionally having reduced transcription repression activity, optionally wherein the mutated PLATZ8 gene produces a PLATZ8 transcription factor that retains the ability to interact, bind, and/or form a complex with one or more proteins of the RNA polymerase III transcription machinery. In some embodiments, the edit results in a mutation in a region of the endogenous PLATZ8 gene that encodes the zinc-binding domain (B-Box zinc-finger binding domain) of the PLATZ8 transcription factor, optionally in and/or adjacent to the second exon of the PLATZ8 gene. In other embodiments, the edit results in a mutation in a region of the endogenous PLATZ8 gene that encodes the PLATZ domain of the PLATZ8 transcription factor, optionally in and/or adjacent to the third exon of the PLATZ8 gene. The second exon of the endogenous PLATZ8 gene is located from nucleotide 7888 to nucleotide 7988 with reference to nucleotide position numbering of SEQ ID NO:69. The third exon of the endogenous PLATZ8 gene is located from nucleotide 8125 to nucleotide 8267 with reference to nucleotide position numbering of SEQ ID NO:69. In some embodiments, the edit may be located in a region of the PLATZ8 transcription factor having at least 80% sequence identity (e.g., at least about 80, 81, 82, 83, 84, 85, 86, 87, 88, 89, 90, 91, 92, 93, 94, 95, 96, 97, 99 or 100% sequence identity, optionally at least 90% or 95%, optionally 100%) to SEQ ID NOs:81-83 or 84-87. In some embodiments, an edit in an endogenous PLATZ8 gene may result in a mutated PLATZ8 gene having at least 90% sequence identity (e.g., 90, 91, 92, 93, 94, 95, 96, 97, 98, 99 or 100%, optionally the sequence identity may be 95%, optionally the sequence identity may be 100%) to any one of the nucleotide sequences of SEQ ID NOs:91, 92, 94, 95, 97, 98, 99, 100, 102, 103, 105, 106, 108, 109, 111, or 112 and/or a mutated PLATZ8 transcription factor having at least 90% sequence identity to any one of the amino acid sequences of SEQ ID NOs:93, 96, 101, 104, 107, 110, or 113.

In some embodiments, a plant may be regenerated from the plant cell comprising the edit in the endogenous PLATZ8 gene to produce a plant comprising the edit in its endogenous PLATZ8 gene. In some embodiments, a plant is not regenerated from a plant cell. In some embodiments, a plant comprising an edit in its endogenous PLATZ8 gene exhibits an improved yield trait compared to a control plant that does not comprise the edit, optionally wherein the improved yield trait may include but is not limited to, increased yield (bu/acre), increased biomass, increased number of seeds (kernels) per plant, increased number of seeds (kernels) per pod or ear, increased seed size, increased seed area, increased seed weight (e.g., increase in 100-seed weight), increased ear length, increased kernel row number (KRN) as compared to a plant that is devoid of the at least one mutation.

In some embodiments, a method for making a plant is provided, the method comprising: (a) contacting a population of plant cells that comprise an endogenous gene encoding a Plant AT-rich sequence- and Zinc-binding protein 8 (PLATZ8) polypeptide with a nuclease targeted to the endogenous gene, wherein the nuclease is linked to a nucleic acid binding domain that binds to a target site within the endogenous gene, the endogenous gene (i) comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 or SEQ ID NO:70; (ii) comprising a region having at least 80% sequence identity to any one of the nucleotide sequences of SEQ ID NOs:72-75 or 76-80, optionally to any one of SEQ ID NOs:72, 73, 74, 75, 76, 77, 78, 79 and/or 80; (iii) encoding a polypeptide comprising a sequence having at least 80% sequence identity to the amino acid sequence of SEQ ID NO:71; and/or (iv) encoding a region having at least 80% sequence identity to any one of the amino acid sequences of SEQ ID NOs:81-83 or 84-87, optionally to any one of SEQ ID NOs:81, 82, 83, 84, 85, 86 and/or 87, optionally wherein the sequence identity of (i), (ii), (iii) and/or (iv) may be at least 85%, or at least 90%, or it may be at least 95%, optionally the sequence identity may be 100%; (b) selecting a plant cell from the population comprising a mutation in the endogenous gene encoding a PLATZ8 transcription factor, wherein the mutation is a base insertion or base deletion in a region of the endogenous gene of (ii) or (iv), wherein the mutation modifies the PLATZ8 transcription factor, optionally the mutation modifies a region of the PLATZ8 transcription factor that comprises a zinc-binding domain (B-Box zinc-finger binding domain) or a region of the PLATZ8 transcription factor that comprises a PLATZ domain; and (c) growing the selected plant cell into a plant comprising the mutation in the endogenous gene encoding a PLATZ8 transcription factor, optionally wherein the mutation may reduce or eliminate the ability of the PLATZ8 transcription factor to repress gene expression. In some embodiments, the mutation in an endogenous PLATZ8 gene may result in a mutated PLATZ8 gene having at least 90% sequence identity (e.g., at least 90, 91, 92, 93, 94, 95, 96, 97, 98, 99 or 100% sequence identity, optionally the sequence identity may be at least 95%, optionally the sequence identity may be 100%) to any one of the nucleic acids of SEQ ID NOs:91, 92, 94, 95, 97, 98, 99, 100, 102, 103, 105, 106, 108, 109, 111, and/or 112, and/or may encode an amino acid sequence having at least 90% sequence identity to any one of SEQ ID NOs:93, 96, 101, 104, 107, 110, and/or 113.

In some embodiments, a method for improving a yield characteristic in a plant is provided, the method comprising (a) contacting a plant cell comprising an endogenous Plant AT-rich sequence- and Zinc-binding protein 8 (PLATZ8) gene encoding a PLATZ8 transcription factor with a nuclease targeted to the endogenous gene, wherein the nuclease is linked to a nucleic acid binding domain that binds to a target site within the endogenous PLATZ8 gene, the endogenous PLATZ8 gene: (i) comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 or SEQ ID NO:70; (ii) comprising a region having at least 80% sequence identity to any one of the nucleotide sequences of SEQ ID NOs:72-75 or 76-80, optionally to any one of SEQ ID NOs:72, 73, 74, 75, 76, 77, 78, 79 and/or 80; (iii) encoding a polypeptide comprising a sequence having at least 80% sequence identity to the amino acid sequence of SEQ ID NO:71; and/or (iv) encoding a region having at least 80% sequence identity to any one of the amino acid sequences of SEQ ID NOs:81-83 or 84-87, optionally to any one of SEQ ID NOs:81, 82, 83, 84, 85, 86 and/or 87, optionally wherein the sequence identity of (i), (ii), (iii) and/or (iv) may be at least 85%, or at least 90%, or it may be at least 95%, optionally the sequence identity may be 100%, thereby producing a plant cell comprising a mutation in the endogenous PLATZ8 gene encoding a PLATZ8 transcription factor; and (b) growing the plant cell into a plant, thereby improving a yield characteristic in the plant. In some embodiments, regenerated plant comprises a mutated PLATZ8 gene having at least 90% sequence identity (e.g., at least 90, 91, 92, 93, 94, 95, 96, 97, 98, 99 or 100% sequence identity, optionally the sequence identity may be at least 95%, optionally the sequence identity may be 100%) to any one of the nucleic acids of SEQ ID NOs:91, 92, 94, 95, 97, 98, 99, 100, 102, 103, 105, 106, 108, 109, 111, and/or 112, and/or may encode an amino acid sequence having at least 90% sequence identity to any one of SEQ ID NOs:93, 96, 101, 104, 107, 110, and/or 113.

In some embodiments, a method is provided for producing a plant or part thereof comprising at least one cell (e.g., one or more cells) having a mutation in an endogenous Plant AT-rich sequence- and Zinc-binding protein 8 (PLATZ8) gene, the method comprising contacting a target site within the endogenous PLATZ8 gene in the plant or part thereof with a nuclease comprising a cleavage domain and a nucleic acid binding domain, wherein the nucleic acid binding domain of the nuclease binds to a target site within the endogenous PLATZ8 gene, wherein the endogenous PLATZ8 gene: (a) comprises a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 or SEQ ID NO:70; (b) comprises a region having at least 80% sequence identity to any one of the nucleotide sequences of SEQ ID NOs:72-75 or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequences of SEQ ID NO:71; and/or (d) encodes a region having at least 80% sequence identity to any one of the amino acid sequences of SEQ ID NOs:81-83 or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%, thereby producing a plant or part thereof comprising at least one cell having a mutation in the endogenous PLATZ8 gene. In some embodiments, the at least one cell in the plant or part thereof having a mutated endogenous PLATZ8 gene, wherein the mutation optionally modifies a region of the PLATZ8 transcription factor that comprises a zinc-binding domain (B-Box zinc-finger binding domain) or a region of the PLATZ8 transcription factor that comprises a PLATZ domain. In some embodiments, the plant that is produced comprises a mutated PLATZ8 gene having at least 90% sequence identity (e.g., at least 90, 91, 92, 93, 94, 95, 96, 97, 98, 99 or 100% sequence identity, optionally the sequence identity may be at least 95%, optionally the sequence identity may be 100%) to any one of the nucleic acids of SEQ ID NOs:91, 92, 94, 95, 97, 98, 99, 100, 102, 103, 105, 106, 108, 109, 111, and/or 112, and/or may encode an amino acid sequence having at least 90% sequence identity to any one of SEQ ID NOs:93, 96, 101, 104, 107, 110, and/or 113.

In some embodiments, a method is provided for producing a plant or part thereof comprising a mutation in a zinc binding domain (B-Box zinc-finger binding domain) or a PLATZ domain of a Plant AT-rich sequence- and Zinc-binding protein 8 (PLATZ8) polypeptide, the method comprising contacting a target site within an endogenous Plant AT-rich sequence- and Zinc-binding protein 8 (PLATZ8) gene in the plant or part thereof with a nuclease comprising a cleavage domain and a nucleic acid binding domain, wherein the nucleic acid binding domain of the nuclease binds to the target site within the endogenous PLATZ8 gene, wherein the endogenous PLATZ8 gene: (a) comprises a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 or SEQ ID NO:70; (b) comprises a region having at least 80% sequence identity to any one of the nucleotide sequences of SEQ ID NOs:72-75 or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%, thereby producing a plant or part thereof having a mutated PLATZ transcription factor with a modified zinc-finger binding domain or a modified PLATZ domain. In some embodiments, the method may produce a plant or part thereof comprising a mutated PLATZ8 gene having at least 90% sequence identity (e.g., at least 90, 91, 92, 93, 94, 95, 96, 97, 98, 99 or 100% sequence identity, optionally the sequence identity may be at least 95%, optionally the sequence identity may be 100%) to any one of the nucleic acids of SEQ ID NOs:91, 92, 94, 95, 97, 98, 99, 100, 102, 103, 105, 106, 108, 109, 111, and/or 112, and/or may encode an amino acid sequence having at least 90% sequence identity to any one of SEQ ID NOs:93, 96, 101, 104, 107, 110, and/or 113.

In some embodiments, a target site may be a region or within a region of the PLATZ8 gene having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to a nucleotide sequence of any one of SEQ ID NOs:72-75 or 76-80, optionally to any one of SEQ ID NOs:72, 73, 74, 75, 76, 77, 78, 79 and/or 80 or having at least 80% sequence identity to a nucleotide sequence encoding any one of the amino acid sequences of SEQ ID NOs:81-83 or 84-87, optionally to any one of SEQ ID NOs:81, 82, 83, 84, 85, 86 and/or 87 (e.g., at least about 80, 81, 82, 83, 84, 85, 86, 87, 88, 89, 90, 91, 92, 93, 94, 95, 96, 97, 99 or 100% sequence identity, optionally the sequence identity may be at least 85%, or may be at least 90% or it may be at least 95%, optionally the sequence identity may be 100%).

In some embodiments, a mutation may be a base substitution, a base deletion and/or a base insertion, optionally a non-natural mutation. In some embodiments, a mutation is a base substitution to an A, a T, a G, or a C. In some embodiments, the mutation in the PLATZ8 gene is a deletion or an insertion, optionally an in-frame deletion, in-frame insertion, an out-of-frame deletion, or an out-of-frame insertion. In some embodiments, the mutation in the PLATZ8 gene is a deletion or an insertion, optionally wherein the deletion or an insertion is an out-of-frame deletion or out-of-frame insertion resulting in a premature stop codon and the encoded PLATZ8 transcription factor is truncated. In some embodiments, a mutation in an endogenous PLATZ8 gene may result in a PLATZ8 transcription factor having reduced transcription repression activity. In some embodiments, a mutation in an endogenous PLATZ8 gene may be a dominant allele, a dominant negative allele, a knock-out allele (null allele), a hypomorphic allele, or a loss of function allele.

In some embodiments, a plant or part thereof that is produced by the methods of this invention comprises a mutated endogenous PLATZ8 gene and mutated PLATZ8 transcription factor as described herein and exhibits an improved yield trait (e.g., one or more improved yield traits such as increased yield (bu/acre), increased biomass, increased number of seeds (kernels) per plant, increased number of seeds (kernels) per pod or ear, increased seed size, increased seed area, increased seed weight (e.g., increase in 100-seed weight), increased ear length, increased kernel row number (KRN)) as compared to a control plant that is devoid of the mutation in the endogenous PLATZ8 gene, e.g., the plant or plant part has not had a target site within its endogenous PLATZ8 gene contacted with an editing system or a nuclease comprising a cleavage domain and a nucleic acid binding domain (e.g., a DNA binding domain).

In some embodiments, the methods of the invention produce plants or parts thereof having a mutated PLATZ8 gene having at least 90% sequence identity (e.g., at least about 90, 91, 92, 93, 94, 95, 96, 97, 99 or 100% sequence identity, optionally the sequence identity may be 95%, optionally the sequence identity may be 100%) to any one of the nucleotide sequences of SEQ ID NOs:91, 92, 94, 95, 97, 98, 99, 100, 102, 103, 105, 106, 108, 109, 111, or 112 and/or a mutated PLATZ8 transcription factor having at least 90% sequence identity (e.g., at least about 90, 91, 92, 93, 94, 95, 96, 97, 99 or 100% sequence identity, optionally the sequence identity may be 95%, optionally the sequence identity may be 100%) to any one of the amino acid sequences of SEQ ID NOs:93, 96, 101, 104, 107, 110, or 113.

In some embodiments, a nuclease contacting a plant cell, a population of plant cells and/or a target site cleaves an endogenous PLATZ8 gene, thereby introducing a mutation into the endogenous PLATZ8 gene, optionally in and/or adjacent to the second exon and/or in and/or adjacent to the third exon of the endogenous PLATZ8 gene. A nuclease useful with the invention may be any nuclease that can be utilized to edit/modify a target nucleic acid. Such nucleases include, but are not limited to, a zinc finger nuclease, transcription activator-like effector nucleases (TALEN), endonuclease (e.g., Fok1) and/or a CRISPR-Cas effector protein. Likewise, any nucleic acid binding domain (e.g., DNA binding domain) useful with the nuclease of the invention may be any nucleic acid binding domain that can be utilized to edit/modify a target nucleic acid. Such a nucleic acid binding domain includes, but is not limited to, a zinc finger, transcription activator-like DNA binding domain (TAL), an argonaute and/or a CRISPR-Cas effector DNA binding domain. The second exon of the endogenous PLATZ8 gene is located from nucleotide 7888 to nucleotide 7988 with reference to nucleotide position numbering of SEQ ID NO:69. The third exon of the endogenous PLATZ8 gene is located from nucleotide 8125 to nucleotide 8267 with reference to nucleotide position numbering of SEQ ID NO:69.

In some embodiments a method is provided for modifying an endogenous Plant AT-rich sequence- and Zinc-binding protein 8 (PLATZ8) gene in a corn plant or part thereof for improving a yield characteristic in the corn plant or part thereof, the method comprising modifying a target site within the endogenous PLATZ8 gene in the corn plant or a part thereof, wherein the endogenous PLATZ8 gene: (a) comprises a sequence having at least 80% sequence identity to the nucleotide sequence of SEQ ID NO:69 or SEQ ID NO:70; (b) comprises a region having at least 80% sequence identity to any one of the nucleotide sequences of SEQ ID NOs:72-75 or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%, thereby modifying the endogenous PLATZ8 gene and improving a yield characteristic in the corn plant or part thereof. In some embodiments, the target site is a region of the PLATZ8 gene having at least 80% sequence identity to a nucleotide sequence of any one of SEQ ID NOs:72-75 or 76-80 or having at least 80% sequence identity to a nucleotide sequence encoding any one of the amino acid sequences of SEQ ID NOs:81-83 or 84-87. In some embodiments, the mutation to the endogenous PLATZ8 gene produces a mutated PLATZ8 transcription factor. In some embodiments, the improved yield characteristic can include, but is not limited to, increased yield (bu/acre), increased biomass, increased number of seeds (kernels) per plant, increased number of seeds (kernels) per ear, increased seed size, increased seed area, increased seed weight (e.g., increase in 100-seed weight), increased ear length, increased kernel row number (KRN) as compared to a control corn plant.

In some embodiments, a method of editing an endogenous PLATZ8 gene in a plant or plant part is provided, the method comprising contacting a target site within the PLATZ8 gene in the plant or plant part with a cytosine base editing system comprising a cytosine deaminase and a nucleic acid binding domain that binds to a target site within the PLATZ8 gene, wherein the PLATZ8 gene (a) comprises a sequence having at least 80% sequence identity to any one of the nucleotide sequences of SEQ ID NO:69 or SEQ ID NO:70; (b) comprises a region having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NOs:72-75 or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%, thereby producing the plant or part thereof comprising an endogenous PLATZ8 gene having a mutation. In some embodiments, the mutation may reduce protein-nucleic acid interactions at the zinc-binding domain (B-Box zinc-finger binding domain) or the PLATZ domain of the PLATZ8 transcription factor compared to a PLATZ8 transcription factor that is devoid of the at least one mutation. In some embodiments, the mutation may result in a PLATZ8 transcription factor having reduced transcription repression activity. In some embodiments, a plant comprising the endogenous PLATZ8 gene that comprises a mutation as described herein exhibits an improved yield trait as compared to a plant devoid of the mutation.

In some embodiments, a method of editing an endogenous PLATZ8 gene in a plant or plant part is provided, the method comprising contacting a target site within the PLATZ8 gene in the plant or plant part with a cytosine base editing system comprising an adenosine deaminase and a nucleic acid binding domain that binds to a target site within the PLATZ8 gene, wherein the PLATZ8 gene ((a) comprises a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 or SEQ ID NO:70; (b) comprises a region having at least 80% sequence identity to any one of the nucleotide sequences of SEQ ID NOs:72-75 or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%, thereby producing the plant or part thereof comprising an endogenous PLATZ8 gene having a mutation. In some embodiments, the mutation may reduce protein-nucleic acid interactions at the zinc-binding domain (B-Box zinc-finger binding domain) or the PLATZ domain of the PLATZ8 transcription factor compared to a PLATZ8 transcription factor that is devoid of the at least one mutation. In some embodiments, the mutation may result in a PLATZ8 transcription factor having a reduced transcription repression activity. In some embodiments, a plant comprising the endogenous PLATZ8 gene that comprises a mutation as described herein exhibits an improved yield trait as compared to a plant devoid of the mutation.

In some embodiments, the present invention provides a method of producing a plant comprising a mutation in an endogenous PLATZ8 gene and at least one polynucleotide of interest, the method comprising crossing a plant of the invention comprising at least one mutation in an endogenous PLATZ8 gene (a first plant) with a second plant that comprises the at least one polynucleotide of interest to produce progeny plants; and selecting progeny plants comprising at least one mutation in the PLATZ8 gene and the at least one polynucleotide of interest, thereby producing the plant comprising a mutation in an endogenous PLATZ8 gene and at least one polynucleotide of interest.

Further provided is a method of producing a plant comprising a mutation in an endogenous PLATZ8 gene and at least one polynucleotide of interest, the method comprising introducing at least one polynucleotide of interest into a plant of the present invention comprising at least one mutation in a PLATZ8 gene, thereby producing a plant comprising at least one mutation in a PLATZ8 gene and at least one polynucleotide of interest.

Additionally provided is a method of producing a plant comprising a mutation in an endogenous PLATZ8 gene and exhibiting a phenotype of improved yield traits, improved plant architecture and/or improved defense traits, comprising crossing a first plant, which is the plant of the present invention (e.g., comprising at least one mutation in an endogenous PLATZ8 gene), with a second plant that exhibits a phenotype of improved yield traits, improved plant architecture and/or improved defense traits; and selecting progeny plants comprising the mutation in the PLATZ8 gene and a phenotype of improved yield traits, improved plant architecture and/or improved defense traits, thereby producing the plant comprising a mutation in an endogenous PLATZ8 gene and exhibiting a phenotype of improved yield traits, improved plant architecture and/or improved defense traits as compared to a control plant.

In some embodiments, the invention provides a method of producing a plant comprising a mutation in an endogenous PLATZ8 gene and at least one polynucleotide of interest, the method comprising crossing a first plant, which is the plant of the present invention (e.g., comprising at least one mutation in an endogenous PLATZ8 gene), with a second plant that comprises the at least one polynucleotide of interest to produce progeny plants; and selecting progeny plants comprising the mutation in the PLATZ8 gene and the at least one polynucleotide of interest, thereby producing the plant comprising a mutation in an endogenous PLATZ8 gene and at least one polynucleotide of interest.

Also provided is a method of producing a plant comprising a mutation in an endogenous PLATZ8 gene and at least one polynucleotide of interest, the method comprising introducing at least one polynucleotide of interest into a plant of the present invention (e.g., comprising at least one mutation in an endogenous PLATZ8 gene), thereby producing a plant comprising a mutation in a PLATZ8 gene and at least one polynucleotide of interest.

In some embodiments, a method of producing a plant comprising a mutation in an endogenous a PLATZ8 gene and exhibiting a phenotype of improved yield traits, improved plant architecture and/or improved defense traits is provided, the method comprising crossing a first plant, which is the plant of the present invention (e.g., comprising at least one mutation in an endogenous PLATZ8 gene), with a second plant that exhibits a phenotype of improved yield traits, improved plant architecture and/or improved defense traits; and selecting progeny plants comprising the mutation in the a PLATZ8 gene and a phenotype of improved yield traits, improved plant architecture and/or improved defense traits, thereby producing the plant comprising a mutation in an endogenous a PLATZ8 gene and exhibiting a phenotype of improved yield traits, improved plant architecture and/or improved defense traits as compared to a control plant.

Further provided is a method of controlling weeds in a container (e.g., pot, or seed tray and the like), a growth chamber, a greenhouse, a field, a recreational area, a lawn, or on a roadside, the method comprising applying an herbicide to one or more (a plurality) plants of the present invention (e.g., comprising at least one mutation in an endogenous PLATZ8 gene) growing in a container, a growth chamber, a greenhouse, a field, a recreational area, a lawn, or on a roadside, thereby controlling the weeds in the container, the growth chamber, the greenhouse, the field, the recreational area, the lawn, or on the roadside in which the one or more plants are growing.

In some embodiments, a method of reducing insect predation on a plant is provided, the method comprising applying an insecticide to one or more plants of the invention (e.g., comprising at least one mutation in an endogenous PLATZ8 gene), thereby reducing insect predation on the one or more plants.

In some embodiments, a method of reducing fungal disease on a plant is provided, the method comprising applying a fungicide to one or more plants of the invention (e.g., comprising at least one mutation in an endogenous PLATZ8 gene), thereby reducing fungal disease on the one or more plants, optionally wherein the one or more plants are growing in a container, a growth chamber, a greenhouse, a field, a recreational area, a lawn, or on a roadside.

In some embodiments, a method of reducing bacterial disease on a plant is provided, the method comprising applying a bactericide to one or more plants of the invention (e.g., comprising at least one mutation in an endogenous PLATZ8 gene), thereby reducing bacterial disease on the one or more plants, optionally wherein the one or more plants are growing in a container, a growth chamber, a greenhouse, a field, a recreational area, a lawn, or on a roadside.

A polynucleotide of interest may be any polynucleotide that can confer a desirable phenotype or otherwise modify the phenotype or genotype of a plant. In some embodiments, a polynucleotide of interest may include, but is not limited to, a polynucleotide that confers herbicide tolerance, insect resistance, nematode resistance, disease resistance, increased yield, increased nutrient use efficiency and/or abiotic stress resistance.

Thus, plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further and particularly emphasized examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the Cry1A, Cry1Ab, Cry1Ac, Cry1IA, Cry1IIA, Cry1IIB2, Cry9c Cry2Ab, Cry3Bb and Cry1F proteins or toxic fragments thereof and also hybrids or combinations thereof, especially the Cry1F protein or hybrids derived from a Cry1F protein (e.g. hybrid Cry1A-Cry1F proteins or toxic fragments thereof), the Cry1A-type proteins or toxic fragments thereof, preferably the Cry1Ac protein or hybrids derived from the Cry1Ac protein (e.g. hybrid Cry1Ab-Cry1Ac proteins) or the Cry1Ab or Bt2 protein or toxic fragments thereof, the Cry2Ae, Cry2Af or Cry2Ag proteins or toxic fragments thereof, the Cry1A.105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci US A. 28; 93(11):5389-94, the Cry proteins as described in WO2001/47952, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g. WO2007/024782), a mutated *Arabidopsis* ALS/AHAS gene (e.g. U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US-A 2005-216969); Event 3006-210-23 (cotton, insect control—herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480);); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control—herbicide tolerance, deposited as ATCC PTA 11384, described in US-A 2006-070139); Event DAS-59132

(corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652);

Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control—herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS1 1 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/ SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control—herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VIP1034 (corn, insect control—herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/ FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8

(corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYHT0H2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDT09Y (corn, ATCC Accession No PTA-13025, WO2013/012775A1).

The genes/events (e.g., polynucleotides of interest), which impart the desired traits in question, may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEN$^{DTM}$, INTACTA RR2 PRO®, VISTIVE GOLD®, and/or XTENDFLEX™ trade names.

A PLATZ8 gene useful with this invention includes any endogenous PLATZ8 gene in which a mutation as described herein can confer improvement in one or more yield traits in a plant or part thereof comprising the mutation. In some embodiments, a PLATZ8 gene (a) comprises a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 and/or SEQ ID NO:70; (b) comprises a region having at least 80% sequence identity to any one of the nucleotide sequences of SEQ ID NOs:72-75 and/or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 and/or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%.

In some embodiments, an at least one mutation in an endogenous PLATZ8 gene may be any mutation that results in a mutated PLATZ8 transcription factor that can confer an improved yield trait on a plant comprising the mutated PLATZ8 gene. In some embodiments, the mutation in an endogenous PLATZ8 gene may be a non-natural mutation. In some embodiments, a mutation (e.g., one or more mutations) in an endogenous PLATZ8 gene may be a point mutation. In some embodiments, a mutation may be a base substitution, a base insertion and/or a base deletion. In some embodiments, the at least one mutation in an endogenous PLATZ8 gene may be a dominant mutation, a dominant negative mutation, a knock-out mutation (null mutation), a hypomorphic mutation, or a loss of function mutation. In some embodiments, the mutation in an endogenous PLATZ8 gene in a plant may be a base substitution, a base deletion and/or a base insertion that results in a plant having an improved yield trait. In some embodiments, the mutation in an endogenous PLATZ8 gene in a plant may be a substitution, a deletion and/or an insertion that results in a dominant mutation, a dominant negative mutation, a knock-out mutation (null mutation), a hypomorphic mutation, or a loss of function mutation. For example, the mutation may be a substitution, a deletion and/or an insertion of 1 nucleotide or of 2, 3, 4, or 5 consecutive nucleotides to about 150 consecutive nucleotides, optionally 3, 6, 9, 12, 18, 21, 24, 27, 30 or more consecutive nucleotides (e.g., an in-frame insertion or in-frame deletion). In some embodiments, the mutation may be a base substitution to an A, a T, a G, or a C. In some embodiments, the mutation in the PLATZ8 gene results in a deletion or insertion of one or more amino acid residues in the encoded PLATZ8 transcription factor, optionally wherein the deletion or insertion disrupts the zinc-finger binding domain or PLATZ domain of the PLATZ8 transcription factor.

In some embodiments, a guide nucleic acid (e.g., gRNA, gDNA, crRNA, crDNA) is provided that binds to a target site within an endogenous gene encoding a Plant AT-rich sequence- and Zinc-binding protein 8 (PLATZ8) polypeptide, the endogenous gene comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 and/or SEQ ID NO:70; comprising a region having at least 80% sequence identity to any one of the nucleotide sequences of SEQ ID NOs:72-75 or 76-80, optionally to any one of SEQ ID NOs:72, 73, 74, 75, 76, 77, 78, 79 and/or 80; encoding a polypeptide comprising a sequence having at least 80% sequence identity to the amino acid sequence of SEQ ID NO:71; and/or encoding a region having at least 80% sequence identity to any one of the amino acid sequences of SEQ ID NOs:81-83 and/or 84-87, optionally to any one of SEQ ID NOs:81, 82, 83, 84, 85, 86 and/or 87, and/or the target site comprising a nucleotide sequence (a) having at least 80% sequence identity to any one of the nucleotide sequences of SEQ ID NOs: 72-75 and/or 76-80 or (b) encoding an amino acid sequence having at least 80% sequence identity to any one of SEQ ID NOs:81-83 and/or 84-87.

In some embodiments, the guide nucleic acid binds to a target nucleic acid within an endogenous PLATZ8 gene having a gene identification number (gene ID) (Maize Genetics and Genomics Database (Maize GDB)) of Zm00001d015394 optionally wherein (a) a target region within Zm00001d015394 (SEQ ID NO:69) may comprise a portion of consecutive nucleotides of any one or more of the nucleotide sequences of SEQ ID NOs: 72-75 and/or 76-80 or may comprise a portion of consecutive nucleotides of a nucleic acid encoding any one of the amino acid sequences of SEQ ID NOs:81-83 and/or 84-87.

In some embodiments, the target site to which a guide nucleic acid of the invention may bind may comprise a nucleotide sequence, or portion thereof, having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences SEQ ID NOs:72-75 and/or 76-80, or optionally to any one of SEQ ID NOs:72, 73, 74, 75, 76, 77, 78, 79 and/or 80, and/or may encode a sequence having at least 80% sequence identity to the amino acid sequence of any one of SEQ ID NOs:81-83 and/or 84-87, or optionally to any one of SEQ ID NOs:81, 82, 83, 84, 85, 86 and/or 87.

Example spacer sequences useful with a guide of this invention may comprise complementarity to a fragment or portion of a nucleotide sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 and/or SEQ ID NO:70, optionally at least about 80, 81, 82, 83, 84, 85, 86, 87, 88, 89, 90, 91, 92, 93, 94, 95, 96, 97, 99 or 100% sequence identity (optionally at least 85% sequence identity or at least 90% sequence identity or at least 95% sequence identity, optionally wherein the sequence identity is 100%) to any one of the nucleotide sequences of SEQ ID NOs:72-75 and/or 76-80 (optionally to any one of SEQ ID NOs:72, 73, 74, 75, 76, 77, 78, 79 and/or 80); or a fragment or portion of a nucleotide sequence encoding a polypeptide comprising a sequence having at least 80% (e.g., at least about 80, 81, 82, 83, 84, 85, 86, 87, 88, 89, 90, 91, 92, 93, 94, 95, 96, 97, 99 or 100% sequence identity, optionally the sequence identity may be at least 85%, or at least 90%, or it may be at least 95%, optionally the sequence identity may be 100%) sequence identity to the amino acid sequence SEQ ID NO:71 and/or any one of SEQ ID NOs:81-83 and/or 84-87 (optionally to any one of SEQ ID NOs:81, 82, 83, 84, 85, 86 and/or 87).

In some embodiments, a target site within a target nucleic acid may comprise a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to a region, portion or fragment of any one of the nucleotide sequences of SEQ ID NO:69 and/or SEQ ID NO:70, see e.g., SEQ ID NOs:72-75 and/or 76-80, or may encode a region of an amino acid sequence having at least 80% sequence identity to the amino acid sequence of SEQ ID NO:71 (e.g., SEQ ID NOs:81-83 and/or 84-87.).

In some embodiments, a guide nucleic acid may comprise a spacer having the nucleotide sequence of any one of SEQ ID NOs:88-90, or the reverse complement thereof, or any combination thereof.

In some embodiments, a system is provided that comprises a guide nucleic acid of the present invention and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site within a gene.

In some embodiments, a gene editing system is provided, the gene editing system comprising a CRISPR-Cas effector protein in association with a guide nucleic acid, wherein the guide nucleic acid comprises a spacer sequence that binds to a Plant AT-rich sequence- and Zinc-binding protein 8 (PLATZ8) gene. In some embodiments, wherein the PLATZ8 gene: (a) comprises a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 and/or SEQ ID NO:70; (b) comprises a region having at least 80% sequence identity to any one of the nucleotide sequences of SEQ ID NOs:72-75 and/or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 and/or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%.

In some embodiments, the guide nucleic acid of a gene editing system can comprise a spacer sequence that has complementarity to a region, portion or fragment of a nucleotide sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences SEQ ID NO:69 and/or SEQ ID NO:70 (e.g., SEQ ID NOs:72-75 and/or 76-80), or may encode a region, portion or fragment of a sequence having at least 80% sequence identity to the amino acid sequence of SEQ ID NO:71 (e.g., SEQ ID NOs:81-83 and/or 84-87). In some embodiments, a gene editing system may further comprise a tracr nucleic acid that associates with the guide nucleic acid and a CRISPR-Cas effector protein, optionally wherein the tracr nucleic acid and the guide nucleic acid are covalently linked. In some embodiments, a guide nucleic acid is provided that that binds to a target nucleic acid in an endogenous PLATZ8 gene having a gene identification number (gene ID) (Maize Genetics and Genomics Database (Maize GDB)) of Zm00001d015394 (SEQ ID NO:69), optionally wherein (a) a target region within Zm00001d015394 (SEQ ID NO:69) may comprise a portion of consecutive nucleotides of any one or more of the nucleotide sequences of SEQ ID NOs:72-75 and/or 76-80 or may comprise a portion of consecutive nucleotides of a nucleic acid encoding any one of the amino acid sequences of SEQ ID NOs:81-83 and/or 84-87.

The present invention further provides a complex comprising a CRISPR-Cas effector protein comprising a cleavage domain and a guide nucleic acid, wherein the guide nucleic acid binds to a target site within a Plant AT-rich sequence- and Zinc-binding protein 8 (PLATZ8) gene, the PLATZ8 gene: (a) comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 and/or SEQ ID NO:70; (b) comprising a region having at least 80% sequence identity to any one of the nucleotide sequences of SEQ ID NOs:72-75 and/or 76-80, optionally to any one of SEQ ID NOs:72, 73, 74, 75, 76, 77, 78, 79 and/or 80; (c) encoding a polypeptide comprising a sequence having at least 80% sequence identity to the amino acid sequence of SEQ ID NO:71; and/or (d) encoding a region having at least 80% sequence identity to any one of the amino acid sequences of SEQ ID NOs:81-83 and/or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%, wherein the cleavage domain cleaves a target strand in the PLATZ8 gene.

Also provided herein are expression cassettes comprising a (a) polynucleotide encoding CRISPR-Cas effector protein comprising a cleavage domain and (b) a guide nucleic acid that binds to a target site within Plant AT-rich sequence- and Zinc-binding protein 8 (PLATZ8) gene, wherein the guide nucleic acid comprises a spacer sequence that is complementary to and binds to the target site within the PLATZ8 gene, the PLATZ8 gene: (a) comprising a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 and/or SEQ ID NO:70; (b) comprising a region having at least 80% sequence identity to any one of the nucleotide sequences of SEQ ID NOs:72-75 and/or 76-80, optionally to any one of SEQ ID NOs:72, 73, 74, 75, 76, 77, 78, 79 and/or 80; (c) encoding a polypeptide comprising a sequence having at least 80% sequence identity to the amino acid sequence of SEQ ID NO:71; and/or (d) encoding a region having at least 80% sequence identity to any one of the amino acid sequences of SEQ ID NOs:81-83 and/or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%.

In some embodiments, a nucleic acid is provided that encodes a Plant AT-rich sequence- and Zinc-binding protein 8 (PLATZ8) polypeptide comprising a mutated zinc-binding domain (B-Box zinc-finger binding domain) or a mutated PLATZ domain, wherein the mutation is an in-frame base deletion or insertion or an out-of-frame base deletion or insertion, optionally wherein the mutation is located in the encoded zinc-binding domain or PLATZ domain of the PLATZ8 transcription factor, optionally wherein the mutation reduces the transcription repression activity of the PLATZ8 transcription factor. In some embodiments, a nucleic acid is provided that comprises a mutated PLATZ8 gene having at least 90% sequence identity (e.g., at least about 90, 91, 92, 93, 94, 95, 96, 97, 99 or 100% sequence identity, optionally the sequence identity may be 95%, optionally the sequence identity may be 100%) to any one of the nucleotide sequences of SEQ ID NOs:91, 92, 94, 95, 97, 98, 99, 100, 102, 103, 105, 106, 108, 109, 111, and/or 112 and/or a mutated PLATZ8 transcription factor having at least 90% sequence identity (e.g., at least about 90, 91, 92, 93, 94, 95, 96, 97, 99 or 100% sequence identity, optionally the sequence identity may be 95%, optionally the sequence identity may be 100%) to any one of the amino acid sequences of SEQ ID NOs:93, 96, 101, 104, 107, 110, and/or 113.

In some embodiments, a modified PLATZ8 transcription factor is provided that comprises a sequence having at least 90% sequence identity (e.g., at least about 90, 91, 92, 93, 94, 95, 96, 97, 99 or 100% sequence identity, optionally the sequence identity may be 95%, optionally the sequence identity may be 100%) to any one of the mutated PLATZ8 transcription factors having at least 90% sequence identity to any one of the amino acid sequences of SEQ ID NOs:93, 96, 101, 104, 107, 110, and/or 113.

Further provided are plants or parts thereof comprising a mutated PLATZ8 nucleic acid and/or mutated PLATZ8 transcription factor as described herein. In some embodiments, the plant may be a corn (maize) plant. In some embodiments, a plant and/or a corn plant comprising a mutated PLATZ8 nucleic acid as described herein and having an improved yield trait optionally increased yield (bu/acre), increased biomass, increased number of seeds (kernels) per plant, increased number of seeds (kernels) per pod or ear, increased seed size, increased seed area, increased seed weight (e.g., increase in 100-seed weight), increased ear length, increased kernel row number (KRN) as compared to a plant that is devoid of the at least one mutation. In some embodiments, a corn plant or part thereof is provided that comprises a mutation in an endogenous Plant AT-rich sequence- and Zinc-binding protein 8 (PLATZ8) gene having the gene identification number (gene ID) (Maize Genetics and Genomics Database (Maize GDB)) of Zm00001d015394 (e.g., SEQ ID NO:69), optionally wherein the mutation is a non-natural mutation.

In some embodiments, a method of the present invention may further comprise regenerating a plant from a plant cell or plant part comprising a mutation (e.g., one or more mutations) in an endogenous PLATZ8 gene, optionally, wherein the mutation disrupts the PEST domain of the encoded PLATZ8 transcription factor. In some embodiments, a plant comprising a mutation in an endogenous PLATZ8 gene exhibits an improved yield trait, optionally increased yield (bu/acre), increased biomass, increased number of seeds (kernels) per plant, increased number of seeds (kernels) per pod or ear, increased seed size, increased seed area, increased seed weight (e.g., increase in 100-seed weight), increased ear length, increased kernel row number (KRN) as compared to a plant that is devoid of the at least one mutation. In some embodiments, the mutation may be a non-natural mutation. In some embodiments, the mutation is a base insertion or base deletion, optionally an in-frame base deletion, in-frame base insertion, out-of-frame deletion, or out-of-frame insertion. In some embodiments, the substitution results in a dominant allele, a dominant negative allele, a knock-out allele (null allele), a hypomorphic allele, or a loss of function allele.

An editing system useful with this invention can be any site-specific (sequence-specific) genome editing system now known or later developed, which system can introduce mutations in target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-gaided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing a PLATZ8 gene may comprise contacting a target nucleic acid (e.g., a nucleic acid encoding a PLATZ8 transcription factor) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific DNA binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing a PLATZ8 gene may comprise contacting a target nucleic acid (e.g., a nucleic acid encoding a PLATZ8 transcription factor) with a sequence-specific DNA binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific DNA binding fusion protein to the target nucleic acid and the sequence-specific DNA binding fusion protein is capable of recruiting the deaminase fusion protein to the target nucleic acid via the peptide tag-affinity polypeptide interaction, thereby editing a locus within the target nucleic acid. In some embodiments, the sequence-specific DNA binding fusion protein may be fused to the affinity polypeptide that binds the peptide tag and the deaminase may be fuse to the peptide tag, thereby recruiting the deaminase to the sequence-specific DNA binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific DNA binding fusion proteins, deaminase fusion proteins and guides may be provided as ribonucleoproteins (RNPs).

In some embodiments, methods such as prime editing may be used to generate a mutation in an endogenous PLATZ8 gene. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantageous of the various methods of recruiting proteins for use in the editing to the target site, such methods including both non-covalent and covalent interactions between the proteins and nucleic acids used in the selected process of genome editing.

In some embodiments, the mutation or modification of a PLATZ8 gene may be a base substitution, a base insertion, a base deletion and/or a point mutation that produces a mutated PLATZ8 transcription factor, optionally wherein the mutated PLATZ8 transcription factor exhibits reduced transcription repression activity, optionally wherein the mutated/modified PLATZ8 gene confers an improved yield trait on a plant or part thereof comprising the mutated/modified PLATZ8 gene. In some embodiments, a plant part may be a cell. In some embodiments, the plant or plant part thereof may be any plant or part thereof as described herein. In some embodiments, a plant useful with this invention may be corn, soy, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, blackberry, raspberry, black raspberry or a *Brassica* spp. In some embodiments, a plant comprising a mutated endogenous PLATZ8 transcription factor comprising a mutation in its zinc-finger binding domain (B-Box zinc-finger binding domain) or in its a PLATZ domain (e.g., comprising a mutated PLATZ8 gene comprising a mutation in the encoded zinc-finger binding domain or PLATZ domain) may comprise an improved yield trait, optionally, increased yield (bu/acre), increased biomass, increased number of seeds (kernels) per plant, increased number of seeds (kernels) per pod or ear, increased seed size, increased seed area, increased seed weight (e.g., increase in 100-seed weight), increased ear length, increased kernel row number (KRN) as compared to a plant that is devoid of the at least one mutation. In some embodiments, the plant may be a corn plant, the corn plant comprising a mutated endogenous PLATZ8 gene encoding a mutated zinc-finger binding domain (B-Box zinc-finger binding domain) or a mutated PLATZ domain (optionally, wherein the encoded mutated PLATZ8 transcription factor exhibits reduced or eliminated transcription repression activity) and, optionally, exhibiting increased yield (bu/acre), increased biomass, increased number of seeds (kernels) per plant, increased number of seeds (kernels) per pod or ear, increased seed size, increased seed area, increased seed weight (e.g., increase in 100-seed weight), increased ear length, increased kernel row number (KRN) as compared to a plant that is devoid of the at least one mutation.

In some embodiments, a mutation that is introduced into an endogenous PLATZ8 gene may be a non-natural mutation. In some embodiments, a mutation that is introduced into an endogenous PLATZ8 gene may be a substitution, an insertion and/or a deletion of at least one nucleotide, at least two consecutive nucleotides (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more) or at least three consecutive nucleotides (e.g., 3, 6, 9, 12, 15, 18, 21, 24, 27, or 30 or more; e.g., an in-frame mutation), wherein the mutation may be in and/or adjacent to the second exon and/or in and/or adjacent to the third exon of the encoded PLATZ8 transcription factor, optionally wherein the mutation results in a PLATZ8 transcription factor that exhibits reduced or eliminated transcription repression activity. The second exon of the endogenous PLATZ8 gene is located from nucleotide 7888 to nucleotide 7988 with reference to nucleotide position numbering of SEQ ID NO:69. The third exon of the endogenous PLATZ8 gene is located from nucleotide 8125 to nucleotide 8267 with reference to nucleotide position numbering of SEQ ID NO:69.

In some embodiments, a sequence-specific nucleic acid binding domain (sequence-specific DNA binding domains) of an editing system useful with this invention can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein.

In some embodiments, a sequence-specific nucleic acid binding domain may be a CRISPR-Cas effector protein, optionally wherein the CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain, e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g., Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, Streptococcus spp. (e.g., S. pyogenes, S. thermophilus), Lactobacillus spp., Bifidobacterium spp., Kandleria spp., Leuconostoc spp., Oenococcus spp., Pediococcus spp., Weissella spp., and/or Olsenella spp. Example Cas9 sequences include, but are not limited to, the amino acid sequences of SEQ ID NO:56 and SEQ ID NO:57 or the nucleotide sequences of SEQ ID NOs:58-68.

In some embodiments, the CRISPR-Cas effector protein may be a Cas9 polypeptide derived from Streptococcus pyogenes and recognizes the PAM sequence motif NGG, NAG, NGA (Mali et al. (2013) Science 339(6121):823-826). In some embodiments, the CRISPR-Cas effector protein may be a Cas9 polypeptide derived from Streptococcus thermophiles and recognizes the PAM sequence motif NGGNG and/or NNAGAAW (W=A or T) (See, e.g., Horvath et al (2010) Science 327(5962):167-170, and Deveau et al. (2008) J. Bacteriol. 190(4):1390-1400). In some embodiments, the CRISPR-Cas effector protein may be a Cas9 polypeptide derived from Streptococcus mutans and recognizes the PAM sequence motif NGG and/or NAAR (R=A or G) (See, e.g., Deveau et al. (2008) J. Bacteriol. 190(4):1390-1400). In some embodiments, the CRISPR-Cas effector protein may be a Cas9 polypeptide derived from Streptococcus aureus and recognizes the PAM sequence motif NNGRR (R=A or G). In some embodiments, the CRISPR-Cas effector protein may be a Cas9 protein derived from S. aureus, which recognizes the PAM sequence motif N GRRT (R=A or G). In some embodiments, the CRISPR-Cas effector protein may be a Cas9 polypeptide derived from S. aureus, which recognizes the PAM sequence motif N GRRV (R=A or G). In some embodiments, the CRISPR-Cas effector protein may be a Cas9 polypeptide that is derived from Neisseria meningitidis and recognizes the PAM sequence motif N GATT or N GCTT (R=A or G, V=A, G or C) (See, e.g., Hou et al (2013) Proc. Natl. Acad. Sci. USA 110 (39):15644-15649). In the aforementioned embodiments, N can be any nucleotide residue, e.g., any of A, G, C or T. In some embodiments, the CRISPR-Cas effector protein may be a Cas13a protein derived from Leptotrichia shahii, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease see, e.g., amino acid sequences of SEQ ID NOs:1-17, nucleic acid sequences of SEQ ID NOs:18-20. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. (2019) *Nat. Biotechnol.* 37:1070-1079, each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, an cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO:28 or SEQ ID NO:29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO:25 or SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of SEQ ID NO:23, SEQ ID NO:24, SEQ ID NO:25, SEQ ID NO:26, SEQ ID NO:27, SEQ ID NO:28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode an uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., Escherichia coli, Staphylococcus aureus, Haemophilus influenzae, Caulobacter crescentus, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from E. coli. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type E. coli TadA comprises the amino acid sequence of SEQ ID NO:30. In some embodiments, a mutated/evolved E. coli TadA* comprises the amino acid sequence of SEQ ID NOs:31-40 (e.g., SEQ ID NOs: 31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific DNA binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt transcription factor binding; and/or generation of point mutations in genomic DNA to disrupt splice junctions.

The nucleic acid constructs of the invention encoding a base editor comprising a sequence-specific DNA binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. (2007) Nucleic Acids Res. 35 (Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a portion of a target nucleic acid (e.g., target DNA) (e.g., protospacer). In some embodiments, the spacer sequences is complementary to a portion of consecutive nucleotides of a PLATZ8 gene, wherein the PLATZ8 gene (a) comprises a sequence having at least 80% sequence identity (e.g., at least about 80, 81, 82, 83, 84, 85, 86, 87, 88, 89, 90, 91, 92, 93, 94, 95, 96, 97, 99 or 100% sequence identity, optionally the sequence identity may be 90% or it may be 95%, optionally the sequence identity may be 100%) to any one of the nucleotide sequences of SEQ ID NO:69 and/or SEQ ID NO:70; (b) comprises a region having at least 80% sequence identity to any one of the nucleotide sequences of SEQ ID NOs:72-75 and/or 76-80, optionally to any one of SEQ ID NOs:72, 73, 74, 75, 76, 77, 78, 79 and/or 80; (c) encodes a polypeptide comprising a sequence having at least 80% sequence identity to the amino acid sequence of SEQ ID NO:71; and/or (d) encodes a region having at least 80% sequence identity to any one of the amino acid sequences of SEQ ID NOs:81-83 and/or 84-87, optionally to any one of SEQ ID NOs:81, 82, 83, 84, 85, 86 and/or 87, optionally wherein the sequence identity of (a), (b), (c) and/or (d) may be at least 85%, or at least 90%, or it may be at least 95%, optionally the sequence identity may be 100%. A spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%)) to a target nucleic acid. In some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length. In some embodiments, a spacer sequence may comprise any one of the sequences of SEQ ID NOs:88-90, or the reverse complement thereof, or any combination thereof.

In some embodiments, the 5' region of a spacer sequence of a guide nucleic acid may be identical to a target DNA, while the 3' region of the spacer may be substantially complementary to the target DNA (such as a spacer of a Type V CRISPR-Cas system), or the 3' region of a spacer sequence of a guide nucleic acid may be identical to a target DNA, while the 5' region of the spacer may be substantially complementary to the target DNA (such as a spacer of a Type II CRISPR-Cas system), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR- Cas systems, the PAM is located at the 5' end on the non-target strand and at the 3' end of the target strand (see below, as an example).

```
5'-NNNNNNNNNNNNNNNNNNNN-3'  RNA Spacer
   ||||||||||||||||||||
3'-AAANNNNNNNNNNNNNNNNNNNN-5'  Target strand
   ||||
5'-TTTNNNNNNNNNNNNNNNNNNNN-3'  Non-target strand
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems ((2015) *Nature Reviews Microbiology* 13:722-736). Guide structures and PAMs are described in by R. Barrangou ((2015) *Genome Biol.* 16:247).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. (2013) *Nat. Methods* 10:1116-1121; Jiang et al. (2013) *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. (2014) *Appl. Environ. Microbiol.* 80:994-1001; Mojica et al. (2009) Microbiology 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains, CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, an octapeptide sold under the tradename FLAG®, a strep tag or strep tag II, a V5 tag, and/or a VSV-G epitope. In some embodiments, a peptide tag may also include phosphorylated tyrosines in specific sequence contexts recognized by SH2 domains, characteristic consensus sequences containing phosphoserines recognized by 14-3-3 proteins, proline rich peptide motifs recognized by SH3 domains, PDZ protein interaction domains or the PDZ signal sequences, and an AGO hook motif from plants. Peptide tags are disclosed in WO 2018/136783 and US Patent Application Publication No. 2017/0219596, which are incorporated by reference for their disclosures of peptide tags. Any epitope that may be linked to a polypeptide and for which there is a corresponding affinity polypeptide that may be linked to another polypeptide may be used with this invention as a peptide tag. A peptide tag may comprise or be present in one copy or in 2 or more copies of the peptide tag (e.g., multimerized peptide tag or multimerized epitope) (e.g., about 2, 3, 4, 5, 6, 7, 8, 9, 10, 11, 12, 13, 14, 15, 16, 17, 18, 9, 20, 21, 22, 23, 24, or 25 or more peptide tags). When multimerized, the peptide tags may be fused directly to one another or they may be linked to one another via one or more amino acids (e.g., 1, 2, 3, 4, 5, 6, 7, 8, 9, 10, 11, 12, 13, 14, 15, 16, 17, 18, 19, 20 or more amino acids, optionally about 3 to about 10, about 4 to about 10, about 5 to about 10, about 5 to about 15, or about 5 to about 20 amino acids, and the like, and any value or range therein. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin, see, e.g., Sha et al. (2017) *Protein Sci.* 26(5):910-924; Gilbreth (2013) *Curr. Opin. Struc. Biol.* 22(4):413-420; and U.S. Pat. No. 9,982,053, each of which are incorporated by reference in their entireties for the teachings relevant to affibodies, anticalins, monobodies and/or DARPins. Example peptide tag sequences and their affinity polypeptides include, but are not limited to, the amino acid sequences of SEQ ID NOs:42-44.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases). Example RNA recruiting motifs and their affinity polypeptides include, but are not limited to, the sequences of SEQ ID NOs:45-55.

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide Pumilio/fem-3 mRNA binding factor (PUF).

In some embodiments, the components for recruiting polypeptides and nucleic acids may those that function through chemical interactions that may include, but are not limited to, rapamycin-inducible dimerization of FRB—FKBP; Biotin-streptavidin; SNAP tag; Halo tag; CLIP tag; DmrA-DmrC heterodimer induced by a compound; bifunctional ligand (e.g., fusion of two protein-binding chemicals together, e.g., dihydrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The nucleic acid constructs of the invention (e.g., a construct comprising a sequence specific nucleic acid binding domain, a CRISPR-Cas effector domain, a deaminase domain, reverse transcriptase (RT), RT template and/or a guide nucleic acid, etc) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, ribonucleoproteins (RNPs), nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, sclerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Any plant comprising an endogenous PLATZ8 gene, wherein when modified as described herein the modified PLATZ8 gene is capable of conferring an improved yield trait in the plant, is useful with this invention. In some embodiments, a plant may be a monocot. In some embodiments, a plant may be a dicot.

Non-limiting examples of plants that may be modified as described herein may include turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, *Papaya*, and lychee, a field crop plant such as clover, alfalfa, timothy, evening primrose, meadow foam, corn/maize (field, sweet, popcorn), hops, jojoba, buckwheat, safflower, *Quinoa*, wheat, rice, barley, rye, millet, sorghum, oats, triticale, sorghum, tobacco, kapok, a leguminous plant (beans (e.g., green and dried), lentils, peas (e.g., field peas, snow peas, snap peas), soybeans, garbanzo beans (chickpeas), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica*, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, or sunflower, and the like.

In some embodiments, a plant that may be modified as described herein may include, but is not limited to, corn, soy, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, blackberry, raspberry, black raspberry or a *Brassica* spp (e.g., *B. napus, B. oleraceae, B. rapa, B. juncea*, and/or *B. nigra*).

In some embodiments, a plant that may be modified as described herein is a soybean plant (*Glycine max*). In some embodiments, a plant that may be modified as described herein is a corn plant (i.e., maize, *Zea mays*). In some embodiments, a plant that may be modified as described herein is a wheat plant (e.g., *Triticum aestivum, T. durum*, and/or *T. compactum*).

The invention will now be described with reference to the following examples. It should be appreciated that these examples are not intended to limit the scope of the claims to the invention but rather are intended to be exemplary of certain embodiments. Any variations in the exemplified methods that occur to the skilled artisan are intended to fall within the scope of the invention.

EXAMPLES

Example 1. Editing Strategy

A strategy to generate edits in the zinc-finger binding domain (B-Box zinc-finger binding domain) or PLATZ domain of the maize Plant AT-rich sequence- and Zinc-binding protein 8 (PLATZ8) gene Zm00001d015394 (e.g., SEQ ID NO:69) was developed to generate corn plants with an improved yield trait, such as, for example, increased ear length. To generate a range of alleles, Cas12a guide nucleic acids comprising spacers (e.g., SEQ ID NOs:88-90) having complementarity to targets within zinc-finger binding domain (PWsp1234) or PLATZ domain (PWsp1196 and PWsp1197) of the PLATZ8 gene were designed and placed into vector constructs.

Regenerated lines carrying edits in the PLATZ8 genes were screened and those that showed edits in the targeted gene were transferred to the greenhouse to set E1 seed.

TABLE 1

| Spacers | | |
| --- | --- | --- |
| Spacer | Sequence | SEQ ID NO: |
| PWsp1234 | GCGCCAACTGCTATGTACGTGAT | 88 |
| PWsp1196 | GGAAGATCACCTTGGCACTGTTG | 89 |
| PWsp1197 | AGGAAGATCACCTTGGCACTGTT | 90 |

TABLE 2

Alleles, genomic, cDNA, protein and exemplary target regions for editing

| Endogenous gene/allele | Genomic Sequence | cDNA Sequence | Protein Sequence | Genomic Target Regions | cDNA Target Regions |
|---|---|---|---|---|---|
| Zm00001d015394-LOCUS324 | SEQ ID NO: 69 | SEQ ID NO: 70 | SEQ ID NO: 71 | Zn Finger domain | |
| | | | | SEQ ID NOs: 72-75 | SEQ ID NOs: 81-83 |
| | | | | PLATZ domain | |
| | | | | SEQ ID NOs: 76-80 | SEQ ID NOs: 84-87 |

Example 2. Edited Alleles of PLATZ8

TABLE 3

Editing of PLATZ8 Zn finger domain

| Allele | Description of edit | Description of protein |
|---|---|---|
| Allele A (SEQ ID NO: 91) | 11 bp deletion (TGTACGTGATC) (SEQ ID NO: 114) starting at position 7901 of SEQ ID NO: 69 for Zm00001d015394 genomic | Out of frame mutation leading to an early stop codon (SEQ ID NO: 93) |
| Allele B (SEQ ID NO: 94) | 24 bp deletion (TACGTGATCAGGTGCGGCGCTACG) (SEQ ID NO: 115) starting at position 7903 of SEQ ID NO: 69 for Zm00001d015394 genomic | In frame mutation that deletes the amino acids "RDQVRRYV" (SEQ ID NO: 116) at position 64-71 (inclusive) of SEQ ID NO: 71 Zm00001d015394 giving rise to the amino acid sequence of SEQ ID NO: 96 |
| Allele C (SEQ ID NO: 97) | 12 bp deletion (ATGTACGTGATC) (SEQ ID NO: 117) starting at position 7900 of SEQ ID NO: 69 for Zm00001d015394 genomic | Deletion that results in the creation of a stop codon at the mutation site (SEQ ID NO: 93) |
| Allele D (SEQ ID NO: 99) | 4 bp deletion (GTAC) starting at position 7902 of SEQ ID NO: 69 for Zm00001d015394 genomic | Out of frame mutation leading to an early stop codon (SEQ ID NO: 101) |
| Allele E (SEQ ID NO: 102) | 25 bp deletion (TTAGCGCCAACTGCTATGTACGTGA) (SEQ ID NO: 118) starting at position 7885 of SEQ ID NO: 69 for Zm00001d015394 genomic | Out of frame mutation leading to an early stop codon (SEQ ID NO: 104) |
| Allele F (SEQ ID NO: 105) | 6 bp deletion (TGTACG) starting at position 7901 of SEQ ID NO: 69 for Zm00001d015394 genomic | In frame deletion of the amino acids "VR" at position 63-64 of SEQ ID NO: 71 Zm00001d015394 giving rise to the amino acid sequence of SEQ ID NO: 107 |

TABLE 4

Edited alleles of PLATZ8 Platz domain

| Allele | Edit description | Protein description |
|---|---|---|
| Allele G (SEQ ID NO: 108) | 28 bp deletion (GCAGACCTACACAATCAACAGTGCCAAG) (SEQ ID NO: 119) starting at position 8121 of SEQ ID NO: 69 for Zm00001d015394 genomic | Deletion that affects a splice site and results in the deletion of the amino acids "TYTINSAKVIFLKPRPQSRPFKGSGNICLTCDRILQEPFHFCSLSCK" (SEQ ID NO: 120) position 92-138 (inclusive) of SEQ ID NO: 71 Zm00001d015394 giving rise to the amino acid sequence of SEQ ID NO: 110 |
| Allele H (SEQ ID NO: 111) | 6 bp deletion (CAGTGC) starting at position 8139 of SEQ ID NO: 69 for Zm00001d015394 genomic | In frame deletion of the amino acids "SA" at position 97-98 of SEQ ID NO: 71 Zm00001d015394 giving rise to the amino acid sequence SEQ ID NO: 113 |

Example 3. Phenotypic Assessment of Trait Activity

Seeds were-sown in flats and later transferred to pots after seedlings were established. All materials were cultivated under standard greenhouse conditions and grown to reproductive maturity. Following standard practices, emerging ears were covered with small paper bags prior to the emergence of silk, and tassels were covered during anthesis for the capture of pollen on a plant-by-plant basis. In some cases, anthesis and silking was not synchronized, and ears were not pollinated.

After ear harvest and dry-down, all ears were photo-documented with a Canon digital camera and EOS application. Images were subsequently imported into ImageJ and all ears were measured using the line trace function. Ear length and width was determined in centimeters by setting a scale in the image analysis program to output distance in centimeters after ears were traced with lines along the length and width of the ear where length was measured from the tip to the base of the ear. Un-edited germplasm, and lines transformed with a GUS plasmid were used as wild-type controls for phenotyping.

E1 generation seed was collected from self-pollinated E0 plants and evaluated as described above for ear length and ear width. The observations are summarized below in Tables 5-8 and indicate that ear length increased in the PLATZ8 edited lines without a significant increase in ear width thereby indicating that the edited alleles of PLATZ8 will increase plant yield.

TABLE 5

| | | | | | | | |
|---|---|---|---|---|---|---|---|
| | Ear length (cm) E1 generation | | | | | | |
| Genotype | Minimum | Median | Maximum | Mean | Standard Deviation | Number |
| Wild type control | 12.25 | 13.575 | 14.70 | 13.545 | 0.6317744 | 10 |
| Homozygous Allele B | 14.30 | 15.750 | 16.20 | 15.530 | 0.7726578 | 5 |
| Homozygous Allele A | 12.60 | 14.650 | 15.65 | 14.300 | 1.5548312 | 3 |
| Homozygous Allele C | 14.50 | 15.125 | 15.75 | 15.125 | 0.5204165 | 4 |

TABLE 6

| | | | | | | | |
|---|---|---|---|---|---|---|---|
| | Ear width (cm) phenotype E1 generation | | | | | | |
| Genotype | Minimum | Median | Maximum | Mean | Standard Deviation | Number |
| Wild type control | 3.45 | 3.80 | 4.00 | 3.715385 | 0.2024687 | 13 |
| Homozygous Allele B | 3.65 | 3.80 | 4.05 | 3.860000 | 0.1635543 | 5 |
| Homozygous Allele A | 3.80 | 3.90 | 4.05 | 3.916667 | 0.1258306 | 3 |
| Homozygous Allele C | 3.65 | 3.75 | 4.10 | 3.830000 | 0.2079663 | 5 |

TABLE 7

Ear length and width E1 generation

| Genotype | Ear length average (cm) | Ear width average (cm) | Number |
|---|---|---|---|
| Homozygous Allele D | 16.4 | 4 | 1 |
| Homozygous Allele E | 16.7 | 3.8 | 1 |
| Homozygous Allele F | 15.1 | 3.6 | 1 |
| Wild type control | 13.44 | 3.64 | 14 |

TABLE 8

Ear length and width E1 generation

| Genotype | Ear length average (cm) | Ear width average (cm) | Number |
|---|---|---|---|
| Heterozygous Allele G | 16.05 | 4.12 | 7 |
| Homozygous Allele G | 14.32 | 3.27 | 4 |
| Heterozygous Allele H | 16.22 | 4.21 | 6 |
| Homozygous Allele H | 13.29 | 2.58 | 2 |
| Wild type control | 14.98 | 4.3 | 11 |

In some jurisdictions, products obtained exclusively by essentially biological processes are excluded from patent protection. Accordingly, the claimed plants, plant parts and cells and their progeny can be defined as directed only to those plants, plant parts and cells and their progeny which are obtained by technical intervention (regardless of any further propagation through crossing and selection). An embodiment of the invention is directed at plants, or plant parts or progeny produced or obtainable using gene editing technology by introducing through stable or transient transformation an RNA-specific CRISPR/Cas system directed against or targeting a nucleotide sequence encoding the PLATZ8 protein, or one or more polynucleotide sequence(s) encoding said RNA-specific CRISPR/Cas system into the plant or the plant part. Alternatively, the subject matter excluded from patentability may be disclaimed. An embodiment of the invention is directed at plants, part of plants or progeny thereof comprising the alterations of the PLATZ8 gene as elsewhere herein described, provided that the plants, parts or plants or progeny are not obtained exclusively through essentially biological processes, wherein essentially biological processes are processes for the production of plants or animals if they consist entirely of natural phenomena such as crossing or selection, or wherein essentially biological processes are processes involving the sexual crossing of whole genomes.

The foregoing is illustrative of the present invention and is not to be construed as limiting thereof. The invention is defined by the following claims, with equivalents of the claims to be included therein.

What is claimed is:

1. A corn plant or part thereof comprising at least one mutation in an endogenous Plant AT-rich sequence- and Zinc-binding protein 8 (PLATZ8) gene encoding a PLATZ8 transcription factor, wherein the endogenous PLATZ8 gene:
   encodes a polypeptide comprising a sequence having at least 90% sequence identity to the amino acid sequence of SEQ ID NO:71; and
   encodes a region having at least 80% sequence identity to one or more of the amino acid sequences of SEQ ID NOs: 81-83 and to one or more of the amino acid sequences of SEQ ID NOS: 84-87,
   wherein the at least one mutation is in a region of the endogenous PLATZ8 gene that encodes a zinc-binding domain (B-Box zinc-finger binding domain) of the PLATZ8 transcription factor or in a region of the endogenous PLATZ8 gene that encodes a PLATZ8 domain of the PLATZ8 transcription factor, and
   wherein the at least one mutation results in decreased PLATZ8 transcription factor activity.

2. The corn plant or part thereof of claim 1, wherein the at least one mutation is in and/or adjacent to the second exon of the PLATZ8 gene.

3. The corn plant or part thereof of claim 1, wherein the at least one mutation is in and/or adjacent to the third exon of the PLATZ8 gene.

4. The corn plant or part thereof of claim 1, wherein the at least one mutation in the endogenous PLATZ8 gene results in a dominant negative allele, a knock-out allele, a hypomorphic allele, or a loss of function allele.

5. The corn plant or part thereof of claim 1, wherein the at least one mutation is a base substitution, a base deletion and/or a base insertion.

6. The corn plant or part thereof of claim 5, wherein the base deletion or a base insertion is an out-of-frame deletion, an out-of-frame insertion, an in-frame deletion or an in-frame insertion.

7. The corn plant or part thereof of claim 6, wherein the out-of-frame deletion or out-of-frame insertion results in a premature stop codon and the encoded PLATZ8 transcription factor is truncated.

8. The corn plant or part of claim 1, wherein the corn plant or part thereof comprising the at least one mutation exhibits an improved yield trait.

9. The corn plant or part thereof of claim 1, wherein the at least one mutation results in a mutated PLATZ8 gene that has at least 90% sequence identity to any one of the nucleotide sequences of SEQ ID NOs: 91, 92, 94, 95, 97, 98, 99, 100, 102, 103, 105, 106, 108, 109, 111, or 112 and/or that encodes a mutated PLATZ8 transcription factor having at least 90% sequence identity to any one of the amino acid sequences of SEQ ID NOs: 93, 96, 101, 104, 107, 110, or 113.

10. A method for producing a corn plant or part thereof comprising at least one cell having a mutation in an endogenous Plant AT-rich sequence- and Zinc-binding protein 8 (PLATZ8) gene, the method comprising contacting a target site within the endogenous PLATZ8 gene in the corn plant or part thereof with a nuclease comprising a cleavage domain and a nucleic acid binding domain, wherein the nucleic acid binding domain of the nuclease binds to a target site within the endogenous PLATZ8 gene, wherein the endogenous PLATZ8 gene:
    encodes a polypeptide comprising a sequence having at least 90% sequence identity to the amino acid sequence of SEQ ID NO:71; and
    encodes a region having at least 80% sequence identity to one or more of the amino acid sequences of SEQ ID NOs: 81-83 and to one or more of the amino acid sequences of SEQ ID NOs: 84-87, thereby producing the corn plant or part thereof comprising the at least one cell having the mutation in the endogenous PLATZ8 gene,
    wherein the mutation is in a region of the endogenous PLATZ8 gene that encodes a zinc-binding domain (B-Box zinc-finger binding domain) of the PLATZ8 transcription factor or in a region of the endogenous PLATZ8 gene that encodes a PLATZ8 domain of the PLATZ8 transcription factor, and
    wherein the mutation results in decreased PLATZ8 transcription factor activity.

11. The method of claim 10, wherein the nuclease cleaves the endogenous PLATZ8 gene and the mutation is introduced into the zinc-finger binding domain the PLATZ8 transcription factor.

12. The method of claim 10, wherein the mutation is a base deletion or base insertion.

13. The method of claim 12, wherein the mutation is an out-of-frame deletion or out-of-frame insertion that results in a premature stop codon and the encoded PLATZ8 transcription factor is truncated.

14. The method of claim 10, wherein the corn plant that is produced exhibits an improved yield trait as compared to a control corn plant.

15. The method of claim 10, wherein the mutation results in a mutated PLATZ8 gene having at least 90% sequence identity to any one of the nucleotide sequences of SEQ ID NOs: 91, 92, 94, 95, 97, 98, 99, 100, 102, 103, 105, 106, 108, 109, 111, or 112 and/or a mutated PLATZ8 transcription factor having at least 90% sequence identity to any one of the amino acid sequences of SEQ ID NOs: 93, 96, 101, 104, 107, 110, or 113.

* * * * *

SEQUENCE LISTING

```
Sequence total quantity: 120
SEQ ID NO: 1            moltype = AA  length = 1228
FEATURE                 Location/Qualifiers
source                  1..1228
                        mol_type = protein
                        note = Lachnospiraceae sp.
                        organism = unidentified
SEQUENCE: 1
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                     1228

SEQ ID NO: 2            moltype = AA  length = 1307
FEATURE                 Location/Qualifiers
source                  1..1307
                        mol_type = protein
                        organism = Acidaminococcus sp.
SEQUENCE: 2
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
```

-continued

```
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLN 1020
DKLNCLVLKD YPAEKVGGVL NPYQLTDQFT SFAKMGTQSG FLFYVPAPYT SKIDPLTGFV 1080
DPFVWKTIKN HESRKHFLEG FDFLHYDVKT GDFILHFKMN RNLSFQRGLP GFMPAWDIVF 1140
EKNETQFDAK GTPFIAGKRI VPVIENHRFT GRYRDLYPAN ELIALLEEKG IVFRDGSNIL 1200
PKLLENDDSH AIDTMVALIR SVLQMRNSNA ATGEDYINSP VRDLNGVCFD SRFQNPEWPM 1260
DADANGAYHI ALKGQLLLNH LKESKDLKLQ NGISNQDWLA YIQELRN               1307
```

```
SEQ ID NO: 3              moltype = AA   length = 1241
FEATURE                  Location/Qualifiers
source                   1..1241
                         mol_type = protein
                         organism = Butyrivibrio proteoclasticus
SEQUENCE: 3
MLLYENYTKR NQITKSLRLE LRPQGKTLRN IKELNLLEQD KAIYALLERL KPVIDEGIKD   60
IARDTLKNCE LSFEKLYEHF LSGDKKAYAK ESERLKKEIV KTLIKNLPEG IGKISEINSA  120
KYLNGVLYDF IDKTHKDSEE KQNILSDILE TKGYLALFSK FLTSRITTLE QSMPKRVIEN  180
FEIYAANIPK MQDALERGAV SFAIEYESIC SVDYYNQILS QEDIDSYNRL ISGIMDEDGA  240
KEKGINQTIS EKNIKIKSEH LEEKPFRILK QLHKQILEER EKAFTIDHID SDEEVVQVTK  300
EAFEQTKEQW ENIKKINGFY AKDPGDITLF IVVGPNQTHV LSQLIYGEHD RIRLLLEEYE  360
KNTLEVLPRR TKSEDARYDK FVNAVPKKVA KESHTFDGLQ KMTGDDRLFI LYRDELARNY  420
MRIKEAYGTF ERDILKSRRG IKGNRDVQES LVSFYDELTK FRSALRIINS GNDEKADPIF  480
YNTFDGIFEK ANRTYKAENL CRNYVTKSPA DDARIMASCL GTPARLRTHW WNGEENFAIN  540
DVAMIRRGDE YYYFVLTPDV KPVDLKTKDE TDAQIFVQRK GAKSFLGLPK ALFKCILEPY  600
FESPEHKNDK NCVIEEYVSK PLTIDRRAYD IFKNGTFKKT NIGIDGLTEE KPKDDCRYLI  660
DVYKEFIAVY TRYSCFNMSG LKRADEYNDI GEFFSDVDTR LCTMEWIPVS FERINDMVDK  720
KEGLLFLVRS MFLYNRPRKP YERTFIQLFS DSNMEHTSML LNSRAMIQYR AASLPRRVTH  780
KKGSILVALR DSNGEHIPMH IREAIYKMKN NFDISSEDFI MAKAYLAEHD VAIKKANEDI  840
IRNRRYTEDK FFLSLSYTKN ADISARTLDY INDKVEEDTQ DSRMAVIVTR NLKDLTYVAV  900
VDEKNNVLEE KSLNEIDGVN YRELLKERTK IKYHDKTRLW QYDVSSKGLK EAYVELAVTQ  960
ISKLATKYNA VVVVESMSST FKDKFSFLDE QIFKAFEARL CARMSDLSFN TIKEGEAGSI 1020
SNPIQVSNNN GNSYQDGVIY FLNNAYTRTL CPDTGFVDVF DKTRLITMQS KRQFFAKMKD 1080
IRIDDGEMLF TFNLEEYPTK RLLDRKEWTV KIAGDGSYFD KDKGEYVYVN DIVREQIIPA 1140
LLEDKAVFDG NMAEKFLDKT AISGKSVELI YKWFANALYG IITKKDGEKI YRSPITGTEI 1200
DVSKNTTYNF GKKFMFKQEY RGDGDFLDAF LNYMQAQDIA V                    1241
```

```
SEQ ID NO: 4              moltype = AA   length = 1238
FEATURE                  Location/Qualifiers
source                   1..1238
                         mol_type = protein
                         organism = Methanoplasma termitum
SEQUENCE: 4
MNNYDEFTKL YPIQKTIRFE LKPQGRTMEH LETFNFFEED RDRAEKYKIL KEAIDEYHKK   60
FIDEHLTNMS LDWNSLKQIS EKYYKSREEK DKKVFLSEQK RMRQEIVSEF KKDDRFKDLF  120
SKKLFSELLK EEIYKKGNHQ EIDALKSFDK FSGYFIGLHE NRKNMYSDGD EITAISNRIV  180
NENFPKFLDN LQKYQEARKK YPEWIIKAES ALVAHNIKMD IVFSLEYFNK VLNQEGIQRY  240
NLALGGYVTK SGEKMMGLND ALNLAHQSEK SSKGRIHMTP LFKQILSEKE SFSYIPDVFT  300
EDSQLLPSIG GFFAQIENDK DGNIFDRALE LISSYAEYDT ERIYIRQADI NRVSNVIFGE  360
WGTLGGLMRE YKADSINDIN LERTCKKVDK WLDSKEFALS DVLEAIDRTG NNDAFNEYIS  420
KMRTAREKID AARKEMKFIS EKISGDEESI HIIKTLLDSV QQFLHFFNLF KARQDIPLDG  480
AFYAEFDEVH SKLFAIVPLY NKVRNYLTKN NLNTKKIKLN FKNPTLANGW DQNKVYDYAS  540
LIFLRDGNYY LGIINPKRKK NIKFEQGSGN GPFYRKMVYK QIPGPNKNLR PVFLTSTKGK  600
KEYKPSKEII EGYEADKHIR GDKFDLDFCH KLIDFFKESI EKHKDWSKFN FYFSPTESYG  660
DISEFYLDVE KQGYRMHFEN ISAETIDEYV EKGDLFLFQI YNKDFVKAAT GKKDMHTIYW  720
NAAFSPENLQ DVVVKLNGEA ELFYRDKSDI KEIVHREGEI LVNRTYNGRT PVPDKIHKKL  780
TDYHNGRTKD LGEAKEYLDK VRYFKAHYDI TKDRRYLNDK IYFHVPLTLN FKANGKKNLN  840
KMVIEKFLSD EKAHIIGIDR GERNLLYYSI IDRSGKIIDQ QSLNVIDGFD YREKLNQREI  900
EMKDARQSWN AIGKIKDLKE GYLSKAVHEI TKMAIQYNAI VVMEELNYGF KRGRFKVEKQ  960
IYQKFENMLI DKMNYLVFKD APDESPGGVL NAYQLTNPLE SFAKLGKQTG ILFYVPAAYT 1020
SKIDPTTGFV NLFNTSSKTN AQERKEFLQK FESISYSAKD GGIFAFAFDY RKFGTSKTDH 1080
KNVWTAYTNG ERMRYIKEKK RNELFDPSKE IKEALTSSGI KYDGGQNILP DILRSNNNGL 1140
IYTMYSSFIA AIQMRVYDGK EDYIISPIKN SKGEFFRTDP KRRELPIDAD ANGAYNIALR 1200
GELTMRAIAE KFDPDSEKMA KLELKHKDWF EFMQTRGD                        1238
```

```
SEQ ID NO: 5              moltype = AA   length = 1281
FEATURE                  Location/Qualifiers
source                   1..1281
                         mol_type = protein
                         organism = Eubacterium eligens
SEQUENCE: 5
MNGNRSIVYR EFVGVIPVAK TLRNELRPVG HTQEHIIQNG LIQEDELRQE KSTELKNIMD   60
DYYREYIDKS LSGVTDLDFT LLFELMNLVQ SSPSKDNKKA LEKEQSKMRE QICTHLQSDS  120
```

```
NYKNIFNAKL LKEILPDFIK NYNQYDVKDK AGKLETLALF NGFSTYFTDF FEKRKNVFTK  180
EAVSTSIAYR IVHENSLIFL ANMTSYKKIS EKALDEIEVI EKNNQDKMGD WELNQIFNPD  240
FYNMVLIQSG IDFYNEICGV VNAHMNLYCQ QTKNNYNLFK MRKLHKQILA YTSTSFEVPK  300
MFEDDMSVYN AVNAFIDETE KGNIIGKLKD IVNKYDELDE KRIYISKDFY ETLSCFMSGN  360
WNLITGCVEN FYDENIHAKG KSKEEKVKKA VKEDKYKSIN DVNDLVEKYI DEKERNEFKN  420
SNAKQYIREI SNIITDTETA HLEYDDHISL IESEEKADEM KKRLDMYMNM YHWAKAFIVD  480
EVLDRDEMFY SDIDDIYNIL ENIVPLYNRV RNYVTQKPYN SKKIKLNFQS PTLANGWSQS  540
KEFDNNAIIL IRDNKYYLAI FNAKNKPDKK IIQGNSDKKN DNDYKKMVYN LLPGANKMLP  600
KVFLSKKGIE TFKPSDYIIS GYNAHKHIKT SENFDISFCR DLIDYFKNSI EKHAEWRKYE  660
FKFSATDSYS DISEFYREVE MQGYRIDWTY ISEADINKLD EEGKIYLFQI YNKDFAENST  720
GKENLHTMYF KNIFSEENLD KIIKLNGQAE LFYRRASVKN PVKHKKDSVL VNKTYKNQLD  780
NGDVVRIPIP DDIYNEIYKM YNGYIKESDL SEAAKEYLDK VEVRTAQKDI VKDYRYTVDK  840
YFIHTPITIN YKVTARNNVN DMVVKYIAQN DDIHVIGIDR GERNLIYISV IDSHGNIVKQ  900
KSYNILNNYD YKKKLVEKEK TREYARKNWK SIGNIKELKE GYISGVVHEI AMLIVEYNAI  960
IAMEDLNYGF KRGRFKVERQ VYQKFESMLI NKLNYFASKE KSVDEPGGLL KGYQLTYVPD 1020
NIKNLGKQCG VIFYVPAAFT SKIDPSTGFI SAFNFKSIST NASRKQFFMQ FDEIRYCAEK 1080
DMFSFGFDYN NFDTYNITMG KTQWTVYTNG ERLQSEFNNA RRTGKTKSIN LTETIKLLLE 1140
DNEINYADGH DIRIDMEKMD EDKKSEFFAQ LLSLYKLTVQ MRNSYTEAEE QENGISYDKI 1200
ISPVINDEGE FFDSDNYKES DDKECKMPKD ADANGAYCIA LKGLYEVLKI KSEWTEDGFD 1260
RNCLKLPHAE WLDFIQNKRY E                                          1281

SEQ ID NO: 6            moltype = AA   length = 1300
FEATURE                 Location/Qualifiers
source                  1..1300
                        mol_type = protein
                        organism = Francisella tularensis
SEQUENCE: 6
MSIYQEFVNK YSLSKTLRFE LIPQGKTLEN IKARGLILDD EKRAKDYKKA KQIIDKYHQF   60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SPKGWTTYFK  180
GFHENRKVNY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
APKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE 1020
KQVYQKLEKM LIEKLNYLVF KDNEFDKTGG VLRAYQLTAP FETFKKMGKQ TGIIYYVPAG 1080
FTSKICPVTG FVNQLYPKYE SVSKSQEFFS KFDKICYNLD KGYFEFSFDY KNFGDKAAKG 1140
KWTIASFGSR LINFRNSDKN HNWDTREVYP TKELEKLLKD YSIEYGHGEC IKAAICGESD 1200
KKFFAKLTSV LNTILQMRNS KTGTELDYLI SPVADVNGNF FDSRQAPKNM PQDADANGAY 1260
HIGLKGLMLL GRIKNNQEGK KLNLVIKNEE YFEFVQNRNN                       1300

SEQ ID NO: 7            moltype = AA   length = 1206
FEATURE                 Location/Qualifiers
REGION                  1..1206
                        note = Lachnospiraceae sp.
source                  1..1206
                        mol_type = protein
                        organism = unidentified
SEQUENCE: 7
MYYESLTKQY PVSKTIRNEL IPIGKTLDNI RQNNILESDV KRKQNYEHVK GILDEYHKQL   60
INEALDNCTL PSLKIAAEIY LKNQKEVSDR EDFNKTQDLL RKEVVEKLKA HENFTKIGKK  120
DILDLLEKLP SISEDDYNAL ESFRNFYTYF TSYNKVRENL YSDKEKSSTV AYRLINENFP  180
KFLDNVKSYR FVKTAGILAD GLGEEEQDSL FIVETFNKTL TQDGIDTYNS QVGKINSSIN  240
LYNQKNQKAN GFRKIPKMKM LYKQILSDRE ESFIDEFQSD KVLIDNVESY GSVLIESLKS  300
SKVSAFFDAL RESKGKNVYV KNDLAKTAMS VIVFENWRTF DDLLNQEYDL ANENKKKDDK  360
YFEKRQKELK KNKSYSLEHL CNLSEDSCNL IENYIHQISD DIENIIINNE TFLRIVINEH  420
DRSRKLAKNR KAVKAIKDFL DSIKVLEREL KLINSSGQEL EKDLIVYSAH EELLVELKQV  480
DSLYNMTRNY LTKKPFSTEK VKLNFNRSTL LNGWDRNKET DNLGVLLLKD GKYYLGIMNT  540
SANKAFVNPP VAKTEKVFKK VDYKLLPVPN QMLPKVFFAK SNDFYNPSS EIYSNYKKGT  600
HKKGNMFSLE DCHNLIDFFK ESISKHEDWS KFGFKFDTQA SYNDISEFYR EVEKQGYKLT  660
YTDIDETYIN DLIERNELYL FQIYNKDFSM YSKGKLNLHT LYFMMLFDQR NIDDVVYKLN  720
GEAEVFYRPA SISEDELIIH KAGEEIKNKN PNRARTKETS TFSYDIVKDK RYSKDKFTLH  780
IPITMNFGVD EVKRFNDAVN SAIRIDENVN VIGIDRGERN LLYVVVIDSK GNILEQISLN  840
SIINKEYDIE TDYHALLDER EGGRDKARKD WNTVENIRDL KAGLYLQVVN VVAKLVLKYN  900
AIICLEDLNF GFKRGRQKVE KQVYQKFEKM LIDKLNYLVI DKSREQTSPK ELGGALNALQ  960
LTSKFKSFKE LGKQSGVIYY VPAYLTSKID PTTGFANLFY MKCENVEKSK RFFDGFDFIR 1020
FNALENVFEF GFDYRSFTQR ACGINSKWTV CTNGERIIKY RNPDKNNMFD EKVVVVTDEM 1080
KNLFEQYKIP YEDGRNVKDM IISNEEAEFY RRLYRLLQQT LQMRNSTSDG TRDYIISPVK 1140
NKREAYFNSE LSDGSVPKDA DANGAYNIAR KGLWVLEQIR QKSEGEKINL AMTNAEWLEY 1200
AQTHLL                                                           1206
```

-continued

```
SEQ ID NO: 8            moltype = AA  length = 1233
FEATURE                 Location/Qualifiers
source                  1..1233
                        mol_type = protein
                        note = Lachnospiraceae sp.
                        organism = unidentified
SEQUENCE: 8
MDYGNGQFER RAPLTKTITL RLKPIGETRE TIREQKLLEQ DAAFRKLVET VTPIVDDCIR   60
KIADNALCHF GTEYDFSCLG NAISKNDSKA IKKETEKVEK LLAKVLTENL PDGLRKVNDI  120
NSAAFIQDTL TSFVQDDADK RVLIQELKGK TVLMQRFLTT RITALTVWLP DRVFENFNIF  180
IENAEKMRIL LDSPLNEKIM KFDPDAEQYA SLEFYGQCLS QKDIDSYNLI ISGIYADDEV  240
KNPGINEIVK EYNQQIRGDK DESPLPKLKK LHKQILMPVE KAFFVRVLSN DSDARSILEK  300
ILKDTEMLPS KIIEAMKEAD AGDIAVYGSR LHELSHVIYG DHGKLSQIIY DKESKRISEL  360
METLSPKERK ESKKRLEGLE EHIRKSTYTF DELNRYAEKN VMAAYIAAVE ESCAEIMRKE  420
KDLRTLLSKE DVKIRGNRHN TLIVKNYFNA WTVFRNLIRI LRRKSEAEID SDFYDVLDDS  480
VEVLSLTYKG ENLCRSYITK KIGSDLKPEI ATYGSALRPN SRWWSPGEKF NVKFHTIVRR  540
DGRLYYFILP KGAKPVELED MDGDIECLQM RKIPNPTIFL PKLVFKDPEA FFRDNPEADE  600
FVFLSGMKAP VTITRETYEA YRYKLYTVGK LRDGEVSEEE YKRALLQVLT AYKEFLENRM  660
IYADLNFGFK DLEEYKDSSE FIKQVETHNT FMCWAKVSSS QLDDLVKSGN GLLFEIWSER  720
LESYYKYGNE KVLRGYEGVL LSILKDENLV SMRTLLNSRP MLVYRPKESS KPMVVHRDGS  780
RVVDRFDKDG KYIPPEVHDE LYRFFNNLLI KEKLGEKARK ILDNKKVKVK VLESERVKWS  840
KFYDEQFAVT FSVKKNADCL DTTKDLNAEV MEQYSESNRL ILIRNTTDIL YYLVLDKNGK  900
VLKQRSLNII NDGARDVDWK ERFRQVTKDR NEGYNEWDYS RTSNDLKEVY LNYALKEIAE  960
AVIEYNAILI IEKMSNAFKD KYSFLDDVTF KGFETKKLAK LSDLHFRGIK DGEPCSFTNP 1020
LQLCQNDSNK ILQDGVIFMV PNSMTRSLDP DTGFIFAIND HNIRTKKAKL NFLSKFDQLK 1080
VSSEGCLIMK YSGDSLPTHN TDNRVWNCCC NHPITNYDRE TKKVEFIEEP VEELSRVLEE 1140
NGIETDTELN KLNERENVPG KVVDAIYSLV LNYLRGTVSG VAGQRAVYYS PVTGKKYDIS 1200
FIQAMNLNRK CDYYRIGSKE RGEWTDFVAQ LIN                             1233

SEQ ID NO: 9            moltype = AA  length = 1227
FEATURE                 Location/Qualifiers
source                  1..1227
                        mol_type = protein
                        note = Lachnospiraceae sp.
                        organism = unidentified
SEQUENCE: 9
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI ANINKCPKNI FKINTEVRVL LKHDDNPYVI GIDRGERNLL  840
YIVVVDGKGN IVEQYSLNEI INNFNGIRIK TDYHSLLDKK EKERFEARQN WTSIENIKEL  900
KAGYISQVVH KICELVEKYD AVIALEDLNS GFKNSRVKVE KQVYQKFEKM LIDKLNYMVD  960
KKSNPCATGG ALKGYQITNK FESFKSMSTQ NGFIFYIPAW LTSKIDPSTG FVNLLKTKYT 1020
SIADKKFISS FDRIMYVPEE DLFEFALDYK NFSRTDADYI KKWKLYSYGN RIRIFRNPKK 1080
NNVFDWEEVC LTSAYKELFN KYGINYQQGD IRALLCEQSD KAFYSSFMAL MSLMLQMRNS 1140
ITGRTDVDFL ISPVKNSDGI FYDSRNYEAQ ENAILPKNAD ANGAYNIARK VLWAIGQFKK 1200
AEDEKLDKVK IASNKEWLEY AQTSVKH                                    1227

SEQ ID NO: 10           moltype = AA  length = 1264
FEATURE                 Location/Qualifiers
source                  1..1264
                        mol_type = protein
                        organism = Leptospira inadai
SEQUENCE: 10
MEDYSGFVNI YSIQKTLRFE LKPVGKTLEH IEKKGFLKKD KIRAEDYKAV KKIIDKYHRA   60
YIEEVFDSVL HQKKKKDKTR FSTQFIKEIK EFSELYYKTE KNIPDKERLE ALSEKLRKML  120
VGAFKGEFSE EVAEKYKNL FSKELIRNEI EKFCETDEER KQVSNFKSFT TYFTGPHSNR  180
QNIYSDEKKS TAIGYRIIHQ NLPKFLDNLK IIESIQRRFK DFPWSDLKKN LKKIDKNIKL  240
TEYFSIDGFV NVLNQKGIDA YNTILGGKSE ESGEKIQGLN EYINLYRQKN NIDRKNPLNV  300
KILFKQILGD RETKSFIPEA FPDDQSVLNS ITEFAKYLKL DKKKSIIAE LKKFLSSFNR  360
YELDGIYLAN DNSLASISTF LFDDWSFIKK SVSFKYDESV GDPKKKIKSP LKYEKEKEKW  420
LKQKYYTISF LNDAIESYSK SQDEKRVKIR LEAYFAEFKS KDDAKKQFDL LERIEEAYAI  480
VEPLLGAEYP RDRNLKADKK EVGKIKDFLD SIKSLQFFLK PLLSAEIFDE KDLGFYNQLE  540
GYYEEIDISG HLYNKVRNYL TGKIYSKEKF KLNFENSTLL KGWDENREVA NLCVIFREDQ  600
KYYLGVMDKE NNTILSDIPK VKPNELFYEK MVYKLIPTPH MQLPRIIFSS DNLSIYNPSK  660
SILKIREAKS FKEGKNFKLK DCHKFIDFYK ESISKNEDWS RFDFKFSKTS SYENISEFYR  720
EVERQGYNLD FKKVSKFYID SLVEDGKLYL FQIYNKDFSI FSKGKPNLHT IYFRSLFSKE  780
NLKDVCLKLN GEAEMFFRKK SINYDEKKKR EGHHPELFEK LKYPILKDKR YSEDKFQFHL  840
```

-continued

```
PISLNFKSKE RLNFNLKVNE FLKRNKDINI IGIDRGERNL LYLVMINQKG EILKQTLLDS  900
MQSGKGRPEI NYKEKLQEKE IERDKARKSW GTVENIKELK EGYLSIVIHQ ISKLMVENNA  960
IVVLEDLNIG FKRGRQKVER QVYQKFEKML IDKLNFLVFK ENKPTEPGGV LKAYQLTDEF 1020
QSFEKLSKQT GFLFYVPSWN TSKIDPRTGF IDFLHPAYEN IEKAKQWINK FDSIRFNSKM 1080
DWFEFTADTR KFSENLMLGK NRVWVICTTN VERYFTSKTA NSSIQYNSIQ ITEKLKELFV 1140
DIPFSNGQDL KPEILRKNDA VFFKSLLFYI KTTLSLRQNN GKKGEEEKDF ILSPVVDSKG 1200
RFFNSLEASD DEPKDADANG AYHIALKGLM NLLVLNETKE ENLSRPKWKI KNKDWLEFVW 1260
ERNR                                                              1264

SEQ ID NO: 11          moltype = AA  length = 1373
FEATURE                Location/Qualifiers
source                 1..1373
                       mol_type = protein
                       organism = Moraxella bovoculi
SEQUENCE: 11
MLFQDFTHLY PLSKTVRFEL FIDRTLEHIH AKNFLSQDET MADMHQKVKV ILDDYHRDFI   60
ADMMGEVKLT KLAEFYDVYL KFRKNPKDDE LQKAQLKDLQ AVLRKEIVKP IGNGGKYKAG  120
YDRLFGAKLF KDGKELGDLA KFVIAQEGES SPKLAHLAHF EKFSTYFTGF HDNRKNMYSD  180
EDKHTAIAYR LIHENLPRFI DNLQILTTIK QKHSALYDQI INELTASGLD VSLASHLDGY  240
HKLLTQEGIT AYNTLLGGIS GEAGSPKIQG INELINSHHN QHCHKSERIA KLRPLHKQIL  300
SDGMSVSFLP SKFADDSEMC QAVNEFYRHY ADVFAKVQSL FDGFDDHQKD GIYVEHKNLN  360
ELSKQAFGDF ALLGRVLDGY YVDVVNPEFN ERFAKAKTDN AKAKLTKEKD KFIKGVHSLA  420
SLEQAIEHYT ARHDDESVQA GKLGQYFKHG LAGVDNPIQK IHNNHSTIKG FLERERPAGE  480
RALPKIKSGK NPEMTQLRQL KELLDNALNV AHFAKLLTTK TTLDNQDGNF YGEFGVLYDE  540
LAKIPTLYNK VRDYLSQKPF STEKYKLNFG NPTLLNGWDL NKEKDNFGVI LQKDGCYYLA  600
LLDKAHKKVF DNAPNTGKSI YQKMIYKYLE VRKQFPKVFF SKEAIAINYH PSKELVEIKD  660
KGRQRSDDER LKLYRFILEC LKIHPKYDKK FEGAIGDIQL FKKDKKGREV PISEKDLFKD  720
INGIFSSKPK LEMEDFFIGE FKRYNPSQDL VDQYNIYKKI DSNDNRKKEN FYNNHPKFKK  780
DLVRYYYESM CKHEEWEESF EFSKKLQDIG CYVDVNELFT EIETRRLNYK ISFCNINADY  840
IDELVEQGQL YLFQIYNKDF SPKAHGKPNL HTLYFKALFS EDNLADPIYK LNGEAQIFYR  900
KASLDMNETT IHRAGEVLEN KNPDNPKKRQ FVYDIIKDKR YTQKDFMLHV PITMNFGVQG  960
MTIKEFNKKV NQSIQQYDEV NVIGIDRGER HLLYLTVINS KGEILEQCSL NDITTASANG 1020
TQMTTPYHKI LDKREIERLN ARVGWGEIET IKELKSGYLS HVVHQISQLM LKYNAIVVLE 1080
DLNFGFKRGR FKVEKQIYQN FENALIKKLN HLVLKDKADD EIGSYKNALQ LTNNFTDLKS 1140
IGKQTGFLFY VPAWNTSKID PETGFVDLLK PRYENIQASQ AFFGKFDKIC YNADKDYFEF 1200
HIDYAKFTDK AKNSRQIWTI CSHGDKRYVY DKTANQNKGA AKGINVNDIL KSLFARHHIN 1260
EKQPNLVMDI CQNNDKEFHK SLMYLLKTLL ALRYSNASSD EDFILSPVAN DEGVFFNSAL 1320
ADDTQPQNAD ANGAYHIALK GLWLLNELKN SDDLNKVKLA IDNQTWLNFA QNR         1373

SEQ ID NO: 12          moltype = AA  length = 1352
FEATURE                Location/Qualifiers
source                 1..1352
                       mol_type = protein
                       note = Parcubacteria bacterium
                       organism = unidentified
SEQUENCE: 12
MENIFDQFIG KYSLSKTLRF ELKPVGKTED FLKINKVFEK DQTIDDSYNQ AKFYFDSLHQ   60
KFIDAALASD KTSELSFQNF ADVLEKQNKI ILDKKREMGA LRKRDKNAVG IDRLQKEIND  120
AEDIIQKEKE KIYKDVRTLF DNEAESWKTY YQEREVDGKK ITESKADLKQ KGADFLTAAG  180
ILKVLKYEFP EEKEKEFQAK NQPSLFVEEK ENPGQKRYIF DSFDKFAGYL TKFQQTKKNL  240
YAADGTSTAV ATRIADNFII FHQNTKVFRD KYKNNHTDLG FDEENIFEIE RYKNCLLQRE  300
IEHIKNENSY NKIIGRINKK IKEYRDQKAK DTKLTKSDFP FFKNLDKQIL GEVEKEKQLI  360
EKTREKTEED VLIERFKEFI ENNEERFTAA KKLMNAFCNG EFESEYEGIY LKNKAINTIS  420
RRWFVSDRDF ELKLPQQKSK NKSEKNEPKV KKFISIAEIK NAVEELDGDI FKAVFYDKKI  480
IAQGGSKLEQ FLVIWKYEFE YLFRDIEREN GEKLLGYDKA DLKIAKQLGIF PQEKEAREKA  540
```

```
GFYENRKNIY STKPQSTAIA YRLIHENLPK FIDNILVFQK IKEPIAKELE HIRADFSAGG   240
YIKKDERLED IFSLNYYIHV LSQAGIEKYN ALIGKIVTEG DGEMKGLNEH INLYNQQRGR   300
EDRLPLFRPL YKQILSDREQ LSYLPESFEK DEELLRALKE FYDHIAEDIL GRTQQLMTSI   360
SEYDLSRIYV RNDSQLTDIS KKMLGDWNAI YMARERAYDH EQAPKRITAK YERDRIKALK   420
GEESISLANL NSCIAFLDNV RDCRVDTYLS TLGQKEGPHG LSNLVENVFA SYHEAEQLLS   480
FPYPEENNLI QDKDNVVLIK NLLDNISDLQ RFLKPLWGMG DEPDKDERFY GEYNYIRGAL   540
DQVIPLYNKV RNYLTRKPYS TRKVKLNFGN SQLLSGWDRN KEKDNSCVIL RKGQNFYLAI   600
MNNRHKRSFE NKMLPEYKEG EPYFEKMDYK FLPDPNKMLP KVFLSKKGIE IYKPSPKLLE   660
QYGHGTHKKG DTFSMDDLHE LIDFFKHSIE AHEDWKQFSG KFSDTATYEN VSSFYREVED   720
QGYKLSFRKV SESYVYSLID QGKLYLFQIY NKDFSPCSKG TPNLHTLYWR MLFDERNLAD   780
VIYKLDGKAE IFFREKSLKN DHPTHPAGKP IKKKSRQKKG EESLFEYDLV KDRRYTMDKF   840
QFHVPITMNF KCSAGSKVND MVNAHIREAK DMHVIGIDRG ERNLLYICVI DSRGTILDQI   900
SLNTINDIDY HDLLESRDKD RQQEHRNWQT IEGIKELKQG YLSQAVHRIA ELMVAYKAVV   960
ALEDLNMGFK RGRQKVESSV YQQFEKQLID KLNYLVDKKK RPEDIGGLLR AYQFTAPFKS  1020
FKEMGKQNGF LFYIPAWNTS NIDPTTGFVN LFHVQYENVD KAKSFFQKFD SISYNPKKDW  1080
FEFAFDYKNF TKKAEGSRSM WILCTHGSRI KNFRNSQKNG QWDSEEFALT EAFKSLFVRY  1140
EIDYTADLKT AIVDEKQKDF FVDLLKLFKL TVQMRNSWKE KDLDYLISPV AGADGRFFDT  1200
REGNKSLPKD ADANGAYNIA LKGLWALRQI RQTSEGGKLK LAISNKEWLQ FVQERSYEKD  1260
```

```
SEQ ID NO: 14          moltype = AA  length = 1324
FEATURE                Location/Qualifiers
source                 1..1324
                       mol_type = protein
                       organism = Prevotella disiens
SEQUENCE: 14
MENYQEFTNL FQLNKTLRFE LKPIGKTCEL LEEGKIFASG SFLEKDKVRA DNVSYVKKEI   60
DKKHKIFIEE TLSSFSISND LLKQYFDCYN ELKAFKKDCK SDEEEVKKTA LRNKCTSIQR  120
AMREAISQAF LKSPQKKLLA IKNLIENVFK ADENVQHFSE FTSYFSGFET NRENFYSDEE  180
KSTSIAYRLV HDNLPIFIKN IYIFEKLKEQ FDAKTLSEIF ENYKLYVAGS SLDEVFSLEY  240
FNNTLTQKGI DNYNAVIGKI VKEDKQEIQG LNEHINLYNQ KHKDRRLPFF ISLKKQILSD  300
REALSWLPDM FKNDSEVIDA LKGFYIEDGF ENNVLTPLAT LLSSLDKYNL NGIFIRNNEA  360
LSSSLSQNVYR NFSIDEAIDA QNAELQTFNN YELIANALRA KIKKETKQGR KSFEKYEEYI  420
DKKVKAIDSL SIQEINELVE NYVSEFNSNS GNMPRKVEDY FSLMRKGDFG SNDLIENIKT  480
KLSAAEKLLG TKYQETAKDI FKKDENSKLI KELLDATKQF GEEADRDLVF  540
YGDFLPLYEK FEELTLLYNK VRNRLTQKPY SKDKIRLCFN KPKLMTGWVD SKTEKSDNGT  600
QYGGYLFRKK NEIGEYDYFL GISSKAQLFR KNEAVIGDYE RLDYYQPKAN TIYGSAYEGE  660
NSYKEDKKRL NKVIIAYIEQ IKQTNIKKSI IESISKYPNI SDDDKVTPSS LLEKIKKVSI  720
DSYNGILSFK SFQSVNKEVI DNLLKTISPL KNKAEFLDLI NKDYQIFTEV QAVIDEICKQ  780
KTFIYFPISN VELEKEMGDK DKPLCLFQIS NKDLSFAKTF SANLRKKRGA ENLHTMLFKA  840
LMEGNQDNLD LGSGAIFYRA KSLDGNKPTH PANEAIKCRN VANKDKVSLF TYDIYKNRRY  900
MENKFLFHLS IVQNYKAAND SAQLNSSATE YIRKADDLHI IGIDRGERNL LYYSVIDMKG  960
NIVEQDSLNI IRNNDLETDY HDLLDKREKE RKANRQNWEA VEGIKDLKKG YLSQAVHQIA  1020
QLMLKYNAII ALEDLGQMFV TRGQKIEKAV YQQFEKSLVD KLSYLVDKKR PYNELGGILK  1080
AYQLASSITK NNSDKQNGFL FYVPAWNTSK IDPVTGFTDL LRPKAMTIKE AQDFFGAFDN  1140
ISYNDKGYFE FETNYDKFKI RMKSAQTRWT ICTFGNRIKR KKDKNYWNYE EVELTEEFKK  1200
LFKDSNIDYE NCNLKEEIQN KDNRKFFDDL IKLLQLTLQM RNSDDKGNDY IISPVANAEG  1260
QFFDSRNGDK KLPLDADANG AYNIARKGLW NIRQIKQTKN KDDLNLSISS TEWLDFVREK  1320
PYLK                                                               1324
```

```
SEQ ID NO: 15          moltype = AA  length = 1484
FEATURE                Location/Qualifiers
VARIANT                1073
                       note = Xaa can be any naturally occurring amino acid
source                 1..1484
                       mol_type = protein
                       note = Peregrinibacteria bacterium
                       organism = unidentified
SEQUENCE: 15
MSNFFKNFTN LYELSKTLRF ELKPVGDTLT NMKDHLEYDE KLQTFLKDQN IDDAYQALKP   60
QFDEIHEEFI TDSLESKKAK EIDFSEYLDL FQEKKELNDS EKKLRNKIGE TFNKAGEKWK  120
KEKYPQYEWK KGSKIANGAD ILSCQDMLQF IKYKNPEDEK IKNYIDDTLK GFFTYFGGFN  180
QNRANYYETK KEASTAVATR IVHENLPKFC DNVIQFKHII KRKKDGTVEK TERKTEYLNA  240
YQYLKNNNKI TQIKDAETEK MIESTPIAEK IFDVYNFSSC LSQKQIEEYN RIIGHYNLLI  300
NLYNQAKRSE GKHLSANEKK YKDLPKFKTL YKQIGCGKKK DLFYTIKCDT EEEANKSRNE  360
GKESHSVEEI INKAQEAINK YFKSNNDCEN INTVPDFINY ILTKENYEGV YWSKAAMNTI  420
SDKYFANYHD LQDRLKEAKV FQKADKKSED DIKIPEAIEL SGLFGVLDSL ADWQTTLFKS  480
SILSNEKLKI ITDSQTPSEA LLKMIFNDIE KNMESFLKET NDIITLKKYK GNKEGTEKIK  540
QWFDYTLAIN RMLKYFLVKE NKIKGNSLDT NISEALKTLI YSDDAEWFKW YDALRNYLTQ  600
KPQDEAKENK LKLNFDNPSL AGGWDVNKEC SNFCVILKDK NEKKYLAMIK KGENTLFQKE  660
WTEGRGKNLT KKSNPLFEIN NCEILSKMEY DFWADVSKMI PKCSTQLKAV VNHFKQSDNE  720
FIFPIGYKVT SGEKFREECK ISKQDFELNN KVFNKNELSV TAMRYDLSST QEKQYIKAFQ  780
KEYWELLFKQ EKRDTKLTNN EIFNEWINFC NKKYSELLSW ERKYKDALTN WINFCKYFLS  840
KYPKTTLFNY SFKESENYNS LDEFYRDVDI CSYKLNINTT INKSILDRLV EEGKLYLFEI  900
KNQDSNDGKS IGHKNNLHTI YWNAIFENFD NRPKLNGEAE IFYRKAISKD KLGIVKGKKT  960
KNGTWIIKNY RFSKEKFILH VPITLNFCSN NEYVNDIVNT KFYNFSNLHF LGIDRGEKHL  1020
AYYSLVNKNG EIVDQGTLNL PFTDKDGNQR SIKKEKYFYN KQEDKWEAKE VDXWNYNDLL  1080
DAMASNRDMA RKNWQRIGTI KEAKNGYVSL VIRKIADLAV NNERPAFIVL EDLNTGFKRS  1140
RQKIDKSVYQ KFELALAKKL NFLVDKNAKR DEIGSPTKAL QLTPPVNNYG DIENKKQAGI  1200
MLYTRANYTS QTDPATGWRK TIYLKAGPEE TTYKKDGKIK NKSVKDQIIE TFTDIGFDGK  1260
```

```
DYYFEYDKGE FVDEKTGEIK PKKWRLYSGE NGKSLDRFRG EREKDKYEWK IDKIDIVKIL    1320
DDLFVNFDKN ISLLKQLKEG VELTRNNEHG TGESLRFAIN LIQQIRNTGN NERDNDFILS    1380
PVRDENGKHF DSREYWDKET KGEKISMPSS GDANGAFNIA RKGIIMNAHI LANSDSKDLS    1440
LFVSDEEWDL HLNNKTEWKK QLNIFSSRKA MAKRKKKRPA ATKK                     1484

SEQ ID NO: 16          moltype = AA  length = 1245
FEATURE                Location/Qualifiers
source                 1..1245
                       mol_type = protein
                       organism = Porphyromonas macacae
SEQUENCE: 16
MKTQHFFEDF TSLYSLSKTI RFELKPIGKT LENIKKNGLI RRDEQRLDDY EKLKKVIDEY     60
HEDFIANILS SFSFSEEILQ SYIQNLSISE ARAKIEKTMR DTLAKAFSED ERYKSIFKKE    120
LVKKDIPVWC PAYKSLCKKF DNFTTSLVPF HENRKNLYTS NEITASIPYR IVHVNLPKFI    180
QNIEALCELQ KKMGADLYLE MMENLRNVWP SFVKTPDDLC NLKTYNHLMV QSSISEYNRF    240
VGGYSTEDGT KHQGINEWIN IYRQRNKEMR LPGLVFLHKQ ILAKVDSSSF ISDTLENDDQ    300
VFCVLRQFRK LFWNTVSSKE DDAASLKDLF CGLSGYDPEA IYVSDAHLAT ISKNIFDRWN    360
YISDAIRRKT EVLMPRKKES VERYAEKISK QIKKRQSYSL AELDDLLAHY SEESLPAGFS    420
LLSYFTSLGG QKYLVSDGEV ILYEEGSNIW DEVLIAFRDL QVILDKDFTE KKLGKDEEAV    480
SVIKKALDSA LRLRKFFDLL SGTGAEIRRD SSFYALYTDR MDKLKGLLKM YDKVRNYLTK    540
KPYSIEKFKL HFDNPSLLSG WDKNKELNNL SVIFRQNGYY YLGIMTPKGK NLFKTLPKLG    600
AEEMFYEKME YKQIAEPMLM LPKVFFPKKT KPAFAPDQSV VDIYNKKTFK TGQKGFNKKD    660
LYRLIDFYKE ALTVHEWKLF NFSFSPTEQY RNIGEFFDEV REQAYKVSMV NVPASYIDEA    720
VENGKLYLFQ IYNKDFSPYS KGIPNLHTLY WKALFSEQNQ SRVYKLCGGG ELFYRKASLH    780
MQDTTVHPKG ISIHKKNLNK KGETSLFNYD LVKDKRFTED KFFFHVPISI NYKNKKITNV    840
NQMVRDYIAQ NDDLQHGIDR GERNLLYISR IDTRGNLLEQ FSLNVIESDK GDLRTDYQKI    900
LGDREQERLR RRQEWKSIES IKDLKDGYMS QVVHKICNMV VEHKAIVVLE NLNLSFMKGR    960
KKVEKSVYEK FERMLVDKLN YLVVDKKNLS NEPGGLYAAY QLTNPLFSFE ELHRYPQSGI   1020
LFFVDPWNTS LTDPSTGFVN LLGRINYTNV GDARKFFDRF NAIRYDGKGN ILFDLDLSRF   1080
DVRVETQRKL WTLTTFGSRI AKSKKSGKWM VERIENLSLC FLELFEQFNI GYRVEKDLKK   1140
AILSQDRKEF YVRLIYLFNL MMQIRNSDGE EDYILSPALN EKNLQFDSRL IEAKDLPVDA   1200
DANGAYNVAR KGLMVVQRIK RGDHESIHRI GRAQWLRYVQ EGIVE                   1245

SEQ ID NO: 17          moltype = AA  length = 1250
FEATURE                Location/Qualifiers
source                 1..1250
                       mol_type = protein
                       organism = Smithella sp.
SEQUENCE: 17
MQTLFENFTN QYPVSKTLRF ELIPQGKTKD FIEQKGLLKK DEDRAEKYKK VKNIIDEYHK     60
DFIEKSLNGL KLDGLEKYKT LYLKQEKDDK DKKAFDKEKE NLRKQIANAF RNNEKFKTLF    120
AKELIKNDLM SFACEEDKKN VKEFEAFTTY FTGFHQNRAN MYVADEKRTA IASRLIHENL    180
PKFIDNIKIF EKMKKEAPEL LSPFNQTLKD MKDVIKGTTL EEIFSLDYFN KTLTQSGIDI    240
YNSVIGGRTP EEGKTIKGL NEYINTDFNQ KQTDKKKRQP KFKQLYKQIL SDRQSLSFIA    300
EAFKNDTEIL EAIEKFYVNE LLHFSNEGKS TNVLDAIKNA VSNLESFNLT KMYFRSGASL    360
TDVSRKVFGE WSIINRALDN YYATTYPIKP REKSEKYEER KEKWLKQDFN VSLIQTAIDE    420
YDNETVKGKN SGKVIADYFA KFCDDKETDL IQKVNEGYIA VKDLLNTPCP ENEKLGSNKD    480
QVKQIKAFMD SIMDIMHFVR PLSLKDTDKE KDETFYSLFT PLYDHLTQTI ALYNKVRNYL    540
TQKPYSTEKI KLNFENSTLL GGWDLNKETD NTAIILRKDN LYYLGIMDKR HNRIFRNVPK    600
ADKKDFCYEK MVYKLLPGAN KMLPKVFFSQ SRIQEFTPSA KLLENYANET HKKGDNFNLN    660
HCHKLIDFFK DSINKHEDWK NFDFRFSATS TYADLSGFYH EVEHQGYKIS FQSVADSFID    720
DLVNEGKLYL FQIYNKDFSP FSKGKPNLHT LYWKMLFDEN NLKDVVYKLN GEAEVFYRKK    780
SIAEKNTTIH KANESIINKN PDNPKATSTF NYDIVKDKRY TIDKFQFHIP ITMNFKAEGI    840
FNMNQRVNQF LKANPDINII GIDRGERHLL YYALINQKGK ILKQDTLNVI ANEKQKVDYH    900
NLLDKKEGDR ATARQEWGVI ETIKELKEGY LSQVIHKLTD LMIENNAIIV MEDLNFGFKN    960
GRQKVEKQVY QKFEKMLIDK LNYLVDKNKK ANELGGLLNA FQLANKFESF QKMGKQNGFI   1020
FYVPAWNTSK TDPATGFIDF LKPRYENLNQ AKDFFEKFDS IRLNSKADYF EPAFDFKNFT   1080
EKADGGRTKW TVCTTNEDRY QWNRALNNNR GSQEKYDITA ELKSLFDGKV DYKSGKDLKQ   1140
QIASQESADF FKALMKNLSI TLSLRHNNGE KGDNEQDYIL SPVADSKGRF FDSRKADDDM   1200
PKNADANGAY HIALKGLWCL EQISKTDDLK KVKLAISNKE WLEFVQTLKG             1250

SEQ ID NO: 18          moltype = DNA  length = 3987
FEATURE                Location/Qualifiers
source                 1..3987
                       mol_type = other DNA
                       organism = synthetic construct
SEQUENCE: 18
atggccggga gcaagaagcg ccggataaag caggacacgc agttcgaggg cttcaccaac     60
ctgtaccaag tctccaagac gctccggttc gagcttatcc cgcaagggga gaccctgaaa    120
cacatccagg aacaaggttt catcgaggag gacaaggccc gcaacgacca ctacaaggag    180
ctcaagccca taatcgatcg gatctacaag acgtacgccg accagtgcct ccaactggtg    240
cagtcgact gggagaacct gagcgccgcc attgacagct accgcaagga aaagacggag    300
gagacgcgca cgcccttat tgaggagcaa gccacctacc gcaacgccat ccacgactac    360
ttcatcgggc gcaccgacaa cctgacggac gcgatcaaca gcgccggcga gaaatctac    420
aagggcccttt tcaaggccga gctcttcaac gggaaggtcc taaaacagct cgggactgtc    480
acgacaaccg agcatgagaa cgccctcctt cgcagcttcg acaagttcac cacatacttc    540
tcgggcttct accggaaccg caagaacgtt ttcagcgccg aggacatctc caccgccatc    600
ccgcacagga tcgtccagga caacttcccc aagttcaagg agaactgcca catcttcacg    660
cgcctgatta cagccgtacc ttcacttcgt gagcacttcg agaacgtcaa aaaggccatc    720
```

-continued

```
gggatcttcg tctccacgtc catcgaggag gtattctctt tcccgttcta taaccagctc   780
ctgacccaga cgcagatcga cctctacaac cagctactgg gcggcatcag ccggggaggcc   840
gggaccgaga aaataaaggg cctcaacgaa gttctcaacc tggccatcca gaagaacgac   900
gagaccgcgc atatcatcgc atccctgccg catcgcttca ttcctttgtt caagcagata   960
ttgagcgacc ggaacaccct ctcgttcatc ctcgaagaat tcaagagcga cgaggaggtc  1020
attcagtctt tctgcaagta caagacgctc ctacggaatg agaatgtgct ggagaccgcg  1080
gaggcactct tcaatgagct gaactccatt gacctgaccc acatcttcat tagccacaag  1140
aaaactggaga cgatctccag cgccctgtgc gaccactggg acactctccg caacgccctc  1200
tacgaacggc ggatctccga acttaccggc aagataacta agtcggctaa ggagaaggtg  1260
caacgagagcc tcaagcacga ggacatcaac cttcaggaaa tcatctcagc cgcgggcaag  1320
gagctgagcg aggcgtttaa gcagaaaaca tcggagatac tgagccacgc gcacgcggcc  1380
ctggatcaac cgctgccgac gactctcaag aagcaagagg agaaggaaat ccttaagtcc  1440
cagctcgact cgctgctcgg cctctatcac ttgctcgact ggttcgcggt tgatgagtcc  1500
aacgaggtgg acccggagtt ctccgcgcgc ctcacgggta ttaagctgga gatggagcca  1560
agcttaagct tctacaacaa ggcccgcaac tacgcgacca aaaaaccgta ctcagtcgag  1620
aaattcaagc tgaatttcca gatgcctaca ttggcgaggg ggtgggacgt gaaccgcgag  1680
aagaacaatg gagccatcct gttcgtcaaa aatgggttgt actacctggg catcatgccc  1740
aagcagaagg gccgttacaa ggccctgtca ttcgagccta ccgagaagac ctcggagggc  1800
ttcgacaaga tgtactacga ctatttcccg gacgccgcca agatgatccc gaagtgctcc  1860
acgcagctca aagccgtcac ggcccacttc cagacgcata ccacgccgat acttctgagc  1920
aacaacttca ttgagccgct agagatcacg aaggagatat acgacctaaa caaccccgaa  1980
aaggagccca agaagttcca gacagcctac gctaagaaga caggtgatca gaagggatat  2040
agggaggcac tctgcaagtg gatcgacttc acgcgcgact tcctgtcgaa atatacaaag  2100
acgaccagca ttgacctaag ttctctccgc ccatcctccc agtacaagga tctgggcgag  2160
tattatgcgg agctgaaccc attgctgtac cacatcagct tccagaggat cgccgagaag  2220
gagattatgg acgcggtgga gacggggaaa ctatacctgt tccaaatata taacaaggac  2280
ttcgctaaag ggcaccacgg gaagcccaac ctgcacacac tctactggac gggcttgttt  2340
tcgccagaaa atttggccaa gacttcgatc aagctcaacg gccaggcgga gttgtttttac  2400
cgtcccaagt ctcgcatgaa gcgcatggcg catcgcctcg gagagaaaat gcttaacaag  2460
aagctcaagg atcagaagac gcccatacct gatacgttgt accaggaatt gtacgactac  2520
gtgaaccacc gcctatcgca cgacctctca gacgaggccc gcgccctcct cccaaacgtg  2580
attactaagg aggtttccca tgaaataatc aaggaccgac ggttcaccag cgacaaattt  2640
tttttccacg tgcctatcac gctcaattac caggcggcca actccccatc gaagttcaac  2700
cagcgcgtga acgcctacct taaggagcac ccggagaccc caatcatcgg gatcgaccgt  2760
ggcgagcgga acctgatcta tattacggtg atcgatagca ccgggaagat cctggagcag  2820
cgctccctga acacaatcca gcagtttgac taccagaaga aactcgacaa ccgggagaag  2880
gagcgcgtcg cagcccggca agcatggagt gtggtcggca ccataaagga cctgaaacag  2940
ggttacctaa gtcaagttat ccacgagatc gttgacctga tgatacacta tcaagccgta  3000
gtcgtgctgg agaacctcaa cttcgggttt aagtccaagc gcaccggcat cgcggagaag  3060
gcggtgtacc agcagttcga gaagatgctg atcgacaagc tgaactgcct ggtgctcaag  3120
gactaccctg cggagaaggt cggcggggtc ttgaacccgt accagctaac cgaccagttc  3180
acgagcttcg ccaaaatggg cacgcagtcc ggattcttgt tttatgtccc ggctccatat  3240
acaagtaaga tcgacccgct gacagggttt gttgacccat tcgtgtggaa gaccatcaag  3300
aaccacgaga gcaggaaaca cttcttagag ggcttcgact tcctgcatta cgacgttaag  3360
acaggcgact tcatcctgca cttcaagatg aaccgcaacc tgtcgttcca gaggggcctg  3420
cccggcttca tgcccgcctg ggatatcgtc tttgagaaga atgagacgca gttcgacgcg  3480
aaggggacgc cgttcatcgc tggaaagcgg atcgtgcctg tcatcgagaa ccaccgcttc  3540
acgggtcgct accgagattt ataccccgcc aacgaactaa ttgcgctgct ggaggagaag  3600
gggatcgtgt tccgagatgg cagcaacatt ctcccgaagc tgctggagaa cgacgactcg  3660
cacgctattg acacgatggt cgccctcata cggagcgtgc ttcagatgcg gaacagtaac  3720
gctgccacgg gcgaggacta cattaactcc cccgtccgcg acctcaacgg ggtctgcttc  3780
gatagccgct tccagaaccc gggagtggcct atggatgcgg acgcgaacgg ggcctaccac  3840
atcgccctca agggccaact cctgctcaac cacttgaagg aaagcaaaga cctcaaattg  3900
cagaatggca tcagtaacca ggactggctc gcgtacatcc aggaactgag aaacgggtcc  3960
aagaagcggc gtatcaagca agattga                                      3987
```

```
SEQ ID NO: 19            moltype = DNA   length = 3987
FEATURE                  Location/Qualifiers
source                   1..3987
                         mol_type = other DNA
                         organism = synthetic construct
SEQUENCE: 19
atggcgggaa gcaaaaagcg ccggattaag caagacacgc agttcgaggg cttcacgaac   60
ctctaccaag tcagcaagac cctccggttc gagctgatac cacagggaag gacgctcaag  120
cacatccagg aacagggctt catcgaggag gacaaggcgc gcaacgacca ctacaaggag  180
ttgaaaccga tcatcgaccg catctacaag acgtacgccg accagtgcct ccagctcgtg  240
cagctcgact gggagaacct ctccgccgcc attgactcgt accggaagga gaagactgag  300
gagacccgca acgccctgat cgaggagcaa gcaacctacc ggaacgccat ccacgactac  360
ttcatcggcc gcaccgacaa cctcaccgac gcgatcaaca agcgcacgc ggagatatac  420
aaagggctgt tcaaggcgga gctgttcaac ggcaaggtgc tcaagcagct agggacggtg  480
accacgaccg agcacgagaa cgcgctcctc cgcagcttcg acaagttcac cacctacttc  540
agcggcttct accggaaccg caagaatgtg ttcagcgcgg aggacatcag cacggccatc  600
ccgcaccgca tcgtccagga caacttcccg aagttcaagg agaactgcca catcttcacc  660
cgcctgataa ccgccgtccc ctccctgcgg gagcacttcg aaacgtcaa aaaggcaatt  720
gggatcttcg tctcgaccag cattgaggag gtgttcagct tcccccttcta caaccagctc  780
ctcacccaga cgcagatcga cctgtacaat cagttgctcg gcgggataag ccgcgaggcg  840
ggaaccgaaa aaatcaaggg gctgaacgaa gtgttgaacc tcgccatcca gaagaacgac  900
gagaccgcgc acatcatcgc ctccctgccc caccggttca tcccgctgtt caagcagatc  960
ctctctgacc ggaacaccct gtccttcatt cttgaggagt tcaagtcgga cgaggaggtc  1020
```

-continued

```
atccagagct tctgcaagta caagacgctg ctacggaacg agaacgtgct ggagacggcg   1080
gaggcactgt tcaacgagct aaacagcatc gacctcacgc acatcttcat cagtcacaag   1140
aaactggaga ccatctcctc cgcgctgtgc gaccactggg acacgctcag gaacgcgctc   1200
tacgagcgcc gaatcagtga gctgacgggc aagatcacga agtccgcgaa ggagaaggtg   1260
cagcggtccc tcaagcacga ggacatcaac ctccaggaga tcatctcagc ggctgggaaa   1320
gagctgtccg aggcgttcaa gcagaaaacg agcgaaatcc tgtcccacgc gcacgcggcc   1380
ctggatcagc ctctgccgac gaccctcaag aaacaagaag aaaaggaaat cctcaagtcg   1440
cagctcgact cgctgctggg cctgtaccat ctcctcgact ggttcgccgt ggacgagagc   1500
aacgaggtgg acccccgagtt ctccgcgcgg cttacgggga tcaagctgga gatggagccc   1560
agcctgtcct tctacaacaa ggcgcgcaac tacgccacca agaagcccta cagcgtggag   1620
aagttcaagc tcaacttcca gatgcccact ctcgcacgtg ggtgggacgt caaccgcgaa   1680
aaaaataatg gggcgatcct gttcgtcaag aacggcctgt actacttggg catcatgccg   1740
aaacagaagg gccgctacaa ggccctgagc ttcgaaccga ccgagaaaac gagcgagggg   1800
ttcgacaaga tgtactacga ctacttcccc gacgccggca agatgattcc aaagtgctcc   1860
acgcagctta aggccgtgac ggcccacttc cagacgcaca cgaccccgat cctcctcagc   1920
aacaacttca tcgagcccct ggagatcacg aaggagatat acgacctgaa caacccggag   1980
aaggagccca agaaattcca gaccgcctac gccaagaaga caggcgacca aaagggttac   2040
agggaggccc tctgcaagtg gatcgacttc actagggact tcctgtccaa gtacaccaag   2100
actacctcta tcgacctgtc cagcctccgc ccgtcgtccc agtacaaaga tttgggcgag   2160
tattacgcgg agctgaaccc actgctctac cacatcagct tccagcgcat cgcggagaag   2220
gagatcatgg acgcagtgga gacgggcaag ctataccctat ttcagatata caacaaagac   2280
ttcgctaagg gacaccacgg caagcctaac ctgcacacct tctactggac ggggctcttc   2340
agcccggaga acctcgccaa gacctcgatc aagctcaacg gccaggccga gctgttctac   2400
cggcccaagt cccgcatgaa gcggatggcc caccggctcg gggagaaaat gctcaacaag   2460
aaattgaagg accaaaaaac gccgatacccc gacaccctat accaggagct gtacgactat   2520
gtgaaccacc gcctgagcca cgacctcagc gacgaggcgg gggccctcct gccgaacgtc   2580
atcacaaagg aggtcagcca cgagatcatc aaggaccggc gcttcacctc cgacaagttt   2640
ttctttcacg tgcccatcac gctcaactac caggccgcca actcgccgtc caagttcaac   2700
cagcgcgtga acgcctacct caaggagcac cccgagaccc cgatcatcgg gattgaccga   2760
ggggagcgga acctcatcta catcaccgtc atcgacaagc ccggaaagt ccttgaacag   2820
cggtcgctca acaccatcca gcagttcgac taccagaaga aactcgacaa ccgggagaag   2880
gagagagtgg cggcccgcca ggcttggtcc gtcgtcggga cgattaagga cttgaaacaa   2940
ggttacctgt cgcaagtgat ccacgagatc gttgacctga tgatccacta ccaagccgtc   3000
gtggtcctgg agaacctcaa cttcggcttc aagagcaaac gaaccggcat cgcggagaag   3060
gccgtgtacc agcagttcga aaaaatgctg atcgacaagc tgaactgcct cgtgctcaag   3120
gactacccccg ctgagaaggt cggcggggtg ctgaaccgt accagctcac tgaccagttc   3180
accagcttcg caaagatggg cacccagtcc ggcttcctgt tctacgtgcc tgcgccatac   3240
acctcgaaga tcgacccgct caccgggttc gtggaccccct tcgtctggaa gaccatcaag   3300
aaccacgaga gccgcaagca cttcctggag ggcttcgact tcctccacta cgacgtcaag   3360
accggggact tcatcctgca cttcaagatg aaccgcaacc tcagtttcca gcgcggcctg   3420
ccgggggttca tgcccgcttg ggatatagtc ttcgagaaga atgagacgca gttcgacgcg   3480
aagggcaccc cgttcatcgc cgggaagcgc atcgtgccgg tcatcgagaa ccaccggttc   3540
accgggcgct accgcgacct atacccggcg aacgagttga tcgccctcct ggaggagaag   3600
ggcatcgtgt tccgcgacgg ctccaacatc ctcccgaagc tgctcgaaaa cgacgactcc   3660
cacgccatcg acacgatggt cgcgctgatc cggtcggtgc tccagatgcg gaactccaac   3720
gccgcgacgg gcgaggacta catcaacagt ccggtccgcg atctgaacgg cgtctgcttc   3780
gactcccggt tccagaaccc cgagtggccg atggacgcgg acgcgaacgg cgcataccac   3840
atcgccctaa aagggcaatt gctgctcaac cacctcaagg aatccaaaga cctaaagctc   3900
cagaacggca tctccaacca ggactggctg gcgtacatcc aggaactgcg gaacgggagc   3960
aaaaaacgtc ggatcaagca agattga                                       3987
```

```
SEQ ID NO: 20          moltype = DNA  length = 3987
FEATURE                Location/Qualifiers
source                 1..3987
                       mol_type = other DNA
                       organism = synthetic construct
SEQUENCE: 20
atggcgggct ccaagaaacg ccggattaag caagataccc agttcgaggg gttcacgaac   60
ctctaccaag tgagcaagac cctccgattc gaactgattc ctcagggga gaccctcaag   120
cacatccagg agcaagggt catcgaggag gacaaggcgc ggaacgacca ctacaaggaa   180
ctcaaacccca tcatcgaccg catctacaag acctacgccg atcagtgcct ccagctcgtg   240
cagttggact gggagaacct cagcgcggcc attgactcct accggaagga gaaaacggag   300
gagacgcgca acgcgctcat cgaggaacag gcaacctatc gcaacgccat ccacgactac   360
ttcatcggga ggactgacaa cctcactgac gcgattaaca agcgcacgc ggagatatac   420
aagggactct tcaaagcgga gctgtttaac ggcaaggttc tcaagcaact cggcactgtg   480
accacgaccg agcatgagaa cgccctgctc cgctccttcg acaagttcac cacctacttc   540
tccgggttct accgcaaccg caagaatgtc ttcagcgcgg aggacatcag cacggccatt   600
ccacatcgaa tcgtccaaga taacttcccg aagttcaagg agaactgcca catcttcacc   660
cgactcatta ctgctgtacc gtcgttacgc gaacacttcg agaacttcag gaggcaatt   720
ggaatcttcg tctctacgtc aatagaggag gtgttcagct tcccttttcta caaccagctc   780
cttacgcaga cccagataga cctgtacaat cagctcctcg gtgggatcag ccgggaggcg   840
gggactgaga agattaaagg gctcaacgag gtcttgaacc tggccatcca aaaaaacgat   900
gagacggcgc acatcatcgc ctcgctgccc caccggttca tcccgctgtt caagcagatc   960
ctcagtgaca ggaacacctt gagctttatc ctagaggagt tcaagacgca gaggaggtg   1020
atccagagct tctgcaagta caaaaccctg ctgaggaacg agaacgtcct ggagacggcg   1080
gaggcgctgt tcaacgagct gaactctatc gacttaactc acatattcat ctcgcacaag   1140
aagctggaga ctattagctc tgcactctgc gaccactggg acaccctccg caacgcgctc   1200
tacgagcgcc gcatctcgga gctgaccggg aagatcacca aatccgcgaa ggaaaaggtc   1260
cagcgttccc tcaaacacga ggatattaac ttacaggaga ttatctcagc ggctgggaag   1320
```

-continued

```
gagttgtcag aggcgttcaa gcagaaaact tccgagatcc tgagccacgc gcacgcagcg  1380
ctcgaccagc ctctgcccac caccctcaaa aagcaggaag aaaaagagat cctcaagagc  1440
cagttggact ccctgctggg gctctatcac cttctcgact ggttcgccgt cgatgagtcg  1500
aacgaggtg accccgagtt ctccgcccgg ctgaccggca tcaagctaga gatggagccg  1560
tccctcagct tctacaataa ggcccgcaac tacgcgacca aaaaacccta cagcgtggag  1620
aagttcaagc tgaacttcca gatgccgacc ttagcacgcg gttgggacgt aaacaggggag  1680
aagaacaatg gagccatcct gttcgtcaag aacgggcttt actacctcgg gataatgccc  1740
aagcagaagg gccgctacaa ggcccttttcc ttcgagccga cggagaaaac ctccgagggg  1800
ttcgacaaga tgtactacga ctacttcccc gacgccgaca agatgatccc gaagtgctca  1860
acgcagctaa aagccgtgac cgcccacttc cagaccccaca cgacgccgat cctgctgagc  1920
aacaacttca tcgagcccct tgagatcact aaggagatat acgacctgaa caaccccgag  1980
aaggagccca agaagtttca aaccgcctac gccaaaaaaa ctggcgacca aaagggctac  2040
agggaggcgc tgtgtaagtg gatcgacttc acacgcgact tcctttcgaa gtatacgaag  2100
acaacctcta ttgacctgag cagcctgcgt cctagctccc agtacaaaga tttgggcgag  2160
tactacgcgg agcttaatcc actactctac cacatctcat tccagcgcat cgctgagaag  2220
gaaatcatgg acgcggtgga gacaggcaaa ctgtacctct tccagatata caacaaagac  2280
ttcgctaagg ggcaccacgg gaagcccaac cttcatacgc tctactggac gggcctattc  2340
agcccgaaa atctggccaa gacctccatc aagctgaacg gccaagcgga gctgttctac  2400
agacccaaga gccggatgaa gcggatggcc cacaggctcg gcgagaaaat gcttaacaaa  2460
aagttgaagg accagaaaac ccctatcccc gacaccctct accaggaact gtacgactac  2520
gtgaaccaca ggctctcgca cgacctttcc gacgaggccc gtgccctact cccgaacgtc  2580
attaccaaag aggtttcgca cgagatcatc aaggaccggc ggttcacgag cgacaagttt  2640
ttctttcacg tccccatcac ccttaactac caggcggcca actccccatc caagttcaac  2700
cagcgtgtga atgcctacct caaggagcac ccagagaccc cgatcattgg gatcgaccgg  2760
ggcgagcgga acctgatcta catcaccgtc atcgactcga cgggcaagat tcttgagcag  2820
agatcgttga ataccataca gcagttcgac taccagaaga aactcgacaa ccgcgagaag  2880
gagcgcgtgg cggcccgcca ggcgtggtcc gtcgttggga cgattaagga cttgaaacaa  2940
ggttatctgt cccaagtcat ccacgagatc gttgatctga tgatccacta tcaggcagtg  3000
gtggtgctgg agaatctcaa cttcggcttc aagagtaagc ggacgggaat cgccgagaag  3060
gccgtgtacc agcagttcga gaagatgctg atcgacaagc tcaactgcct tgtgctgaaa  3120
gactacccgg ccgagaaggt cggcggcgtc ctcaacccgt accaacttac cgaccagttc  3180
acctccttcg ccaagatggg cactcagtcc gggttcttgt tctacgtccc cgcaccttac  3240
acctctaaga tcgaccctct gactggcttc gtagatccat tcgtgtggaa gaccattaag  3300
aaccacgaga gccgcaagca cttcctggag ggcttcgact tcctgcacta cgacgtgaag  3360
accgggggact tcatccttca cttcaagatg aaccggaacc tcagcttcca gcgggggcctg  3420
ccgggggttca tgcccgcctg ggacatcgtg ttcgagaaga acgagacccca gttcgacgcg  3480
aagggcacgc ccttcatcgc cgggaagcgt atcgtgccgg tgatcgagaa ccatcgtttc  3540
acgggtcgct accgtgacct ctaccgggcg aacgagctta tcgcactcct ggaggagaag  3600
ggcatcgtct tccgggaacgg ctccaacatc ctcccgaaac tgctggaaaa cgacgactct  3660
cacgccatcg acacgatggt ggccctcatc cggtccgtgc tccaaatgcg gaacagcaac  3720
gccgccaccg gtgaggacta catcaacagc ccggtccggg atctgaacgg ggtgtgcttc  3780
gattcgcggt tccagaatcc tgagtggccg atggacgcgg atgcaaacgg ggcgtaccac  3840
atcgcgctca agggccagtt acttctgaac caccttaagg agtctaaaga tttgaaactc  3900
cagaacggga tctcgaacca ggactggctg gcctacatcc aagagttgcg gaacggcagc  3960
aagaagcggc ggattaagca agattag                                      3987
```

```
SEQ ID NO: 21        moltype = DNA   length = 1592
FEATURE              Location/Qualifiers
source               1..1592
                     mol_type = other DNA
                     organism = Medicago truncatula
SEQUENCE: 21
actgttaata attttttaaac gtcagcgcac taaaaaaacg aaaagacgga cacgtgaaaa  60
taaaaaacac acactagttt atgacgcaat actattttac ttatgatttg ggtacattag  120
acaaaaccgt gaaagagatg tatcagctat gaaacctgta tacttcaata cagagactta  180
ctcatatcgg atacgtacgc acgaagtatc atattaatta ttttaatttt taataaaatat  240
tttatcggat acttatgtga tactctacat atacacaagg atatttctaa gatactttat  300
agatacgtat cctagaaaaa catgaagagt aaaaagtga gacaatgttg taaaaattca  360
ttataaatgt atatgattca attttagata tgcatcagta taattgattc tcgatgaaac  420
acttaaaatt atatttcttg tggaagaacg tagcgaagaa ggtgattcag ttagacaaca  480
ttaaataaaa ttaatgttaa gttctttttaa tgatgtttct ctcaatatca catcatatga  540
aaatgtaata tgatttataa gaaaatttttt aaaaaattta ttttaataat cacatgtact  600
atttttttaaa aattgtatct tttataataa tacaataata aagagtaatc agtgttaatt  660
tttcttcaaa tataagtttt attataaatc attgttaacg tatcataagt cattaccgta  720
tcgtatctta attttttttt aaaaaccgct aattcacgta cccgtattgt attgtacccg  780
cacctgtatc acaatcgatc ttagttagaa gaattgtctc gaggcggtgc aagacagcat  840
ataatagacg tggactctct tataccaaac gttgtcgtat cacaaagggt taggtaacaa  900
gtcacagttt gtcacgtgt cacgttttaa ttggaagagg tgccgttggc gtaatataac  960
agccaatcga tttttgctat aaaagcaaat caggtaaact aaacttcttc attctttttct  1020
tccccatcgc tacaaaaccg gttccttttgg aaaagagatt cattcaaacc tagcacccaa  1080
ttccgtttca aggtataatc tactttctat tcttcgatta ttttattatt attagctact  1140
atcgtttaat cgatctttttc ttttgatccg tcaaatttaa attcaattag ggttttgttc  1200
ttttctttca tctgattgaa atccttctga attgaaccgt ttacttgatt ttactgttta  1260
ttgtatgatt taatcctttg ttttcaaag acagtcttta gattgtgatt aggggttcat  1320
ataaatttt agatttggat ttttgtattg tatgattcaa aaaatacgtc cttttaattag  1380
attagtacat ggatatttt tacccgatt attgattgtc agggagaatt tgatgagcaa  1440
gtttttttga tgtctgttgt aaattgaatt gattataatt gctgatctgc tgcttccagt  1500
tttcataacc catattcttt taaccttgtt gtacacacaa tgaaaaattg gtgattgatt  1560
catttgtttt tctttgtttt ggattataca gg                                1592
```

```
SEQ ID NO: 22              moltype = DNA  length = 2000
FEATURE                    Location/Qualifiers
source                     1..2000
                           mol_type = other DNA
                           organism = Zea mays
SEQUENCE: 22
gtcgtgcccc tctctagaga taaagagcat tgcatgtcta aagtataaaa aattaccaca   60
tatttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttttg caaatagctt gacctatata  300
atacttcatc cattttatta gtacatccat ttaggattta gggttgatgg tttctataga  360
ctaattttta gtacatccat tttattcttt ttagtctcta aatttttttaa aactaaaact  420
ctattttagt ttttttattta ataatttaga tataaaatga aataaaataa attgactaca  480
aataaaacaa atacccttta agaaataaaa aaactaagca aacattttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctag  660
accctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acggggggatt cctttccccac cgctccttcg ctttcccttc ctcgcccgcc  840
gtaataaaata gacacccccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccccc cctctctcta ccttctctag atcggcgatc cggtccatgg 1020
ttaggccccg gtagttctac ttctgttcat gtttgtgtta gagcaaacat gttcatgttc 1080
atgtttgtga tgatgtggtc tggttgggcg gtcgttctag atcggagtag gatactgttt 1140
caagctacct ggtggattta ttaattttgt atctgtatgt gtgtgccata catcttcata 1200
gttacgagtt taagatgatg gatggaaata tcgatctagg ataggtatac atgttgatgc 1260
gggttttact gatgcatata cagagatgct ttttttctcg cttggttgtg atgatatggt 1320
ctggttgggc ggtcgttcta gatcggagta gaatactgtt tcaaactacc tggtggattt 1380
attaaaggat aaagggtcgt tctagatcgg agtagaatac tgtttcaaac tacctggtag 1440
atttattaaa ggatcgtgtat gtatgtgcct acatcttcat agttacgagt ttaagatgat 1500
ggatggaaat atcgatctag gataggtata catgttgatg cggggttttac tgatgcatat 1560
acagagatgc ttttttttcgc ttggttgtga tgatgtggtc tggttgggcg gtcgttctag 1620
atcggagtag aatactgttt caaactacct ggtggattta ttaattttgt atctttatgt 1680
gtgtgccata catcttcata gttacgagtt taagatgatg gatggaaata ttgatctagg 1740
ataggtatac atgttgatgt gggttttact gatgcatata catgatggca tatgcggcat 1800
ctattcatat gctctaacct tgagtaccta tctattataa taaacaagta tgtttttataa 1860
ttattttgat cttgatatac ttggatgatg gcatatgcag cagctatatg tggatttttt 1920
agccctgcct tcatacgcta tttatttgct tggtactgtt tctttttgtcc gatgctcacc 1980
ctgttgtttg gtgatacttc                                             2000

SEQ ID NO: 23              moltype = AA  length = 228
FEATURE                    Location/Qualifiers
source                     1..228
                           mol_type = protein
                           organism = Rattus norvegicus
SEQUENCE: 23
SSETGPVAVD PTLRRRIEPH EFEVFFDPRE LRKETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLK              228

SEQ ID NO: 24              moltype = AA  length = 199
FEATURE                    Location/Qualifiers
source                     1..199
                           mol_type = protein
                           organism = Homo sapiens
SEQUENCE: 24
MEASPASGPR HLMDPHIFTS NFNNGIGRHK TYLCYEVERL DNGTSVKMDQ HRGFLHNQAK   60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                              199

SEQ ID NO: 25              moltype = DNA  length = 621
FEATURE                    Location/Qualifiers
source                     1..621
                           mol_type = other DNA
                           organism = Petromyzon marinus
SEQUENCE: 25
acagatgcag agtatgtgag aattcacgaa aagctggaca tctatacctt caagaagcag   60
ttctttaaca ataagaagtc tgtgagccat aggtgctacg tgctgttcga gctgaagaga  120
agggggtgaaa gaagggcatg ttttttgggggg tatgctgtga acaagcccca gtctggaact  180
gagagaggca ttcacgccga aattttcagc atcagaaagg tggaggaata cctgaaggat  240
aaccctggac agtttacaat taattggtat tctagctggt ctccatgcgc tgactgtgcc  300
gagaagatcc tggaatggta caaccaggag ctgagaggaa atggccatac cctgaagatt  360
tgggcctgca agctgtacta tgaaaagaac gcaagaaatc agatcggact gtggaacctg  420
agggataatg gtgtggggct gaacgtgatg gtgtccgagc actatcagtg ctgtagaaag  480
attttcattc agtcctcaca taatcagctg aacgagaata gatggctgga aaagactctg  540
```

```
aagagggctg agaagagaag gtccgaactg tcaattatga tccaggtgaa gatcctgcac   600
accactaagt cacctgccgt g                                              621

SEQ ID NO: 26                moltype = AA  length = 160
FEATURE                      Location/Qualifiers
source                       1..160
                             mol_type = protein
                             organism = synthetic construct
SEQUENCE: 26
FERNYDPREL RKETYLLYEI KWGKSGKLWR HWCQNNRTQH AEVYFLENIF NARRFNPSTH   60
CSITWYLSWS PCAECSQKIV DFLKEHPNVL EIYVARLYYH EDERNRQGLR DLVNSGVTIR   120
IMDLPDYNYC WKTFVSDQGG DEDYWPGHFA PWIKQYSLKL                         160

SEQ ID NO: 27                moltype = AA  length = 207
FEATURE                      Location/Qualifiers
source                       1..207
                             mol_type = protein
                             organism = synthetic construct
SEQUENCE: 27
TDAEYVRIHE KLDIYTFKKQ FSNNKKSVSH RCYVLFELKR RGERRACFWG YAVNKPQSGT   60
ERGIHAEIFS IRKVEEYLRD NPGQFTINWY SSWSPCADCA EKILEWYNQE LRGNGHTLKI   120
WVCKLYYEKN ARNQIGLWNL RDNGVGLNVM VSEHYQCCRK IFIQSSHNQL NENRWLEKTL   180
KRAEKRRSEL SIMFQVKILH TTKSPAV                                       207

SEQ ID NO: 28                moltype = AA  length = 228
FEATURE                      Location/Qualifiers
source                       1..228
                             mol_type = protein
                             organism = synthetic construct
SEQUENCE: 28
SSKTGPVAVD PTLRRRIEPH EFEVFFDPRE LRKETCLLYE INWGGRHSIW RHTSQNTNKH   60
VEVNFIEKFT TERYFCPNTR CSITWFLSWS PCGECSRAIT EFLSRYPNVT LPIYIARLYH   120
LANPRNRQGL RDLISSGVTI QIMTEQESGY CWHNFVNYSP SNESHWPRYP HLWVRLYVLE   180
LYCIILGLPP CLNILRRKQS QLTSFTIALQ SCHYQRLPPH ILWATGLK               228

SEQ ID NO: 29                moltype = AA  length = 162
FEATURE                      Location/Qualifiers
source                       1..162
                             mol_type = protein
                             organism = synthetic construct
SEQUENCE: 29
SFERNYDPRE LRKETYLLYE IKWGKSGKLW RHWCQNNRTQ HAEVYFLENI FNARRFNPST   60
HCSITWYLSW SPCAECSQKI VDFLKEHPNV NLEIYVARLY YPENERNRQG LRDLVNSGVT   120
IRIMDLPDYN YCWKTFVSDQ GGDEDYWPGH FAPWIKQYSL KL                     162

SEQ ID NO: 30                moltype = AA  length = 166
FEATURE                      Location/Qualifiers
source                       1..166
                             mol_type = protein
                             organism = Escherichia coli
SEQUENCE: 30
SEVEFSHEYW MRHALTLAKR AWDEREVPVG AVLVHNNRVI GEGWNRPIGR HDPTAHAEIM   60
ALRQGGLVMQ NYRLIDATLY VTLEPCVMCA GAMIHSRIGR VVFGARDAKT GAAGSLMDVL   120
HHPGMNHRVE ITEGILADEC AALLSDFFRM RRQEIKAQKK AQSSTD                 166

SEQ ID NO: 31                moltype = AA  length = 166
FEATURE                      Location/Qualifiers
source                       1..166
                             mol_type = protein
                             organism = synthetic construct
SEQUENCE: 31
SEVEFSHEYW MRHALTLAKR ARDEREVPVG AVLVLNNRVI GEGWNRAIGL HDPTAHAEIM   60
ALRQGGLVMQ NYRLIDATLY VTFEPCVMCA GAMIHSRIGR VVFGVRNAKT GAAGSLMDVL   120
HYPGMNHRVE ITEGILADEC AALLCYFFRM PRQVFNAQKK AQSSTD                 166

SEQ ID NO: 32                moltype = AA  length = 166
FEATURE                      Location/Qualifiers
source                       1..166
                             mol_type = protein
                             organism = synthetic construct
SEQUENCE: 32
SEVEFSHEYW MRHALTLAKR AWDEREVPVG AVLVLNNRVI GEGWNRSIGL HDPTAHAEIM   60
ALRQGGLVMQ NYRLIDATLY VTFEPCVMCA GAMIHSRIGR VVFGVRNAKT GAAGSLMDVL   120
HYPGMNHRVE ITEGILADEC AALLCYFFRM RRQVFNAQKK AQSSTD                 166

SEQ ID NO: 33                moltype = AA  length = 166
FEATURE                      Location/Qualifiers
source                       1..166
                             mol_type = protein
```

-continued

```
                            organism = synthetic construct
SEQUENCE: 33
SEVEFSHEYW MRHALTLAKR ALDEREVPVG AVLVLNNRVI GEGWNRAIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC NALLCYFFRM RRQVFNAQKK AQSSTD                  166

SEQ ID NO: 34            moltype = AA   length = 166
FEATURE                  Location/Qualifiers
source                   1..166
                         mol_type = protein
                         organism = synthetic construct
SEQUENCE: 34
SEVEFSHEYW MRHALTLAKR ALDEREVPVG AVLVLNNRVI GEGWNRAIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC NALLCYFFRM PRQVFNAQKK AQSSTD                  166

SEQ ID NO: 35            moltype = AA   length = 1763
FEATURE                  Location/Qualifiers
source                   1..1763
                         mol_type = protein
                         organism = synthetic construct
SEQUENCE: 35
SEVEFSHEYW MRHALTLAKR AWDEREVPVG AVLVHNNRVI GEGWNRPIGR HDPTAHAEIM    60
ALRQGGLVMQ NYRLIDATLY VTLEPCVMCA GAMIHSRIGR VVFGARDAKT GAAGSLMDVL   120
HHPGMNHRVE ITEGILADEC AALLSDFFRM RRQEIKAQKK AQSSTDSGGS SGGSSGSETP   180
GTSESATPES SGGSSGGSSE VEFSHEYWMR HALTLAKRAR DEREVPVGAV LVLNNRVIGE   240
GWNRAIGLHD PTAHAEIMAL RQGGLVMQNY RLIDATLYVT FEPCVMCAGA MIHSRIGRVV   300
FGVRNAKTGA AGSLMDVLHY PGMNHRVEIT EGILADECAA LLCYFFRMPR QVFNAQKKAQ   360
SSTDSGGSSG GSSGSETPGT SESATPESSG GSSGGSDKKY SIGLAIGTNS VGWAVITDEY   420
KVPSKKFKVL GNTDRHSIKK NLIGALLFDS GETAEATRLK RTARRRYTRR KNRICYLQEI   480
FSNEMAKVDD SFFHRLEESF LVEEDKKHER HPIFGNIVDE VAYHEKYPTI YHLRKKLVDS   540
TDKADLRLIY LALAHMIKFR GHFLIEGDLN PDNSDVDKLF IQLVQTYNQL FEENPINASG   600
VDAKAILSAR LSKSRRLENL IAQLPGEKKN GLFGNLIALS LGLTPNFKSN FDLAEDAKLQ   660
LSKDTYDDDL DNLLAQIGDQ YADLFLAAKN LSDAILLSDI LRVNTEITKA PLSASMIKRY   720
DEHHQDLTLL KALVRQQLPE KYKEIFFDQS KNGYAGYIDG GASQEEFYKF IKPILEKMDG   780
TEELLVKLNR EDLLRKQRTF DNGSIPHQIH LGELHAILRR QEDFYPFLKD NREKIEKILT   840
FRIPYYVGPL ARGNSRFAWM TRKSEETITP WNFEEVVDKG ASAQSFIERM TNFDKNLPNE   900
KVLPKHSLLY EYFTVYNELT KVKYVTEGMR KPAFLSGEQK KAIVDLLFKT NRKVTVKQLK   960
EDYFKKIECF DSVEISGVED RFNASLGTYH DLLKIIKDKD FLDNEENEDI LEDIVLTLTL  1020
FEDREMIEER LKTYAHLFDD KVMKQLKRRR YTGWGRLSRK LINGIRDKQS GKTILDFLKS  1080
DGFANRNFMQ LIHDDSLTFK EDIQKAQVSG QGDSLHEHIA NLAGSPAIKK GILQTVKVVD  1140
ELVKVMGRHK PENIVIEMAR ENQTTQKGQK NSRERMKRIE EGIKELGSQI LKEHPVENTQ  1200
LQNEKLYLYY LQNGRDMYVD QELDINRLSD YDVDHIVPQS FLKDDSIDNK VLTRSDKNRG  1260
KSDNVPSEEV VKKMKNYWRQ LLNAKLITQR KFDNLTKAER GGLSELDKAG FIKRQLVETR  1320
QITKHVAQIL DSRMNTKYDE NDKLIREVKV ITLKSKLVSD FRKDFQFYKV REINNYHHAH  1380
DAYLNAVVGT ALIKKYPKLE SEFVYGDYKV YDVRKMIAKS EQEIGKATAK YFFYSNIMNF  1440
FKTEITLANG EIRKRPLIET NGETGEIVWD KGRDFATVRK VLSMPQVNIV KKTEVQTGGF  1500
SKESILPKRN SDKLIARKKD WDPKKYGGFD SPTVAYSVLV VAKVEKGKSK KLKSVKELLG  1560
ITIMERSSFE KNPIDFLEAK GYKEVKKDLI IKLPKYSLFE LENGRKRMLA SAGELQKGNE  1620
LALPSKYVNF LYLASHYEKL KGSPEDNEQK QLFVEQHKHY LDEIIEQISE FSKRVILADA  1680
NLDKVLSAYN KHRDKPIREQ AENIIHLFTL TNLGAPAAFK YFDTTIDRKR YTSTKEVLDA  1740
TLIHQSITGL YETRIDLSQL GGD                                         1763

SEQ ID NO: 36            moltype = AA   length = 1565
FEATURE                  Location/Qualifiers
source                   1..1565
                         mol_type = protein
                         organism = synthetic construct
SEQUENCE: 36
SEVEFSHEYW MRHALTLAKR ARDEREVPVG AVLVLNNRVI GEGWNRAIGL HDPTAHAEIM    60
ALRQGGLVMQ NYRLIDATLY VTFEPCVMCA GAMIHSRIGR VVFGVRNSKR GAAGSLMNVL   120
NYPGMNHRVE ITEGILADEC AALLCDFYRM PRQVFNAQKK AQSSINSGGS SGGSSGSETP   180
GTSESATPES SGGSSGGSDK KYSIGLAIGT NSVGWAVITD EYKVPSKKFK VLGNTDRHSI   240
KKNLIGALLF DSGETAEATR LKRTARRRYT RRKNRICYLQ EIFSNEMAKV DDSFFHRLEE   300
SFLVEEDKKH ERHPIFGNIV DEVAYHEKYP TIYHLRKKLV DSTDKADLRL IYLALAHMIK   360
FRGHFLIEGD LNPDNSDVDK LFIQLVQTYN QLFEENPINA SGVDAKAILS ARLSKSRRLE   420
NLIAQLPGEK KNGLFGNLIA LSLGLTPNFK SNFDLAEDAK LQLSKDTYDD DLDNLLAQIG   480
DQYADLFLAA KNLSDAILLS DILRVNTEIT KAPLSASMIK RYDEHHQDLT LLKALVRQQL   540
PEKYKEIFFD QSKNGYAGYI DGGASQEEFY KFIKPILEKM DGTEELLVKL NREDLLRKQR   600
TFDNGSIPHQ IHLGELHAIL RRQEDFYPFL KDNREKIEKI LTFRIPYYVG PLARGNSRFA   660
WMTRKSEETI TPWNFEEVVD KGASAQSFIE RMTNFDKNLP NEKVLPKHSL YEYFTVYNE   720
LTKVKYVTEG MRKPAFLSGE QKKAIVDLLF KTNRKVTVKQ LKEDYFKKIE CFDSVEISGV   780
EDRFNASLGT YHDLLKIIKD KDFLDNEENE DILEDIVLTL TLFEDREMIE ERLKTYAHLF   840
DDKVMKQLKR RRYTGWGRLS RKLINGIRDK QSGKTILDFL KSDGFANRNF MQLIHDDSLT   900
FKEDIQKAQV SGQGDSLHEH IANLAGSPAI KKGILQTVKV VDELVKVMGR HKPENIVIEM   960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
```

```
LESEFVYGDY KVYDVRKMIA KSEQEIGKAT AKYFFYSNIM NFFKTEITLA NGEIRKRPLI   1260
ETNGETGEIV WDKGRDFATV RKVLSMPQVN IVKKTEVQTG GFSKESILPK RNSDKLIARK   1320
KDWDPKKYGG FDSPTVAYSV LVVAKVEKGK SKKLKSVKEL LGITIMERSS FEKNPIDFLE   1380
AKGYKEVKKD LIIKLPKYSL FELENGRKRM LASAGELQKG NELALPSKYV NFLYLASHYE   1440
KLKGSPEDNE QKQLFVEQHK HYLDEIIEQI SEFSKRVILA DANLDKVLSA YNKHRDKPIR   1500
EQAENIIHLF TLTNLGAPAA FKYFDTTIDR KRYTSTKEVL DATLIHQSIT GLYETRIDLS   1560
QLGGD                                                               1565

SEQ ID NO: 37            moltype = AA   length = 1565
FEATURE                  Location/Qualifiers
source                   1..1565
                         mol_type = protein
                         organism = synthetic construct
SEQUENCE: 37
SEVEFSHEYW MRHALTLAKR ARDEREVPVG AVLVLNNRVI GEGWNRAIGL HDPTAHAEIM   60
ALRQGGLVMQ NYRLYDATLY STFEPCVMCA GAMIHSRIGR VVFGVRNAKT GAAGSLMDVL   120
HHPGMNHRVE ITEGILADEC AALLCRFFRM PRRVFNAQKK AQSSTDSGGS SGGSSGSETP   180
GTSESATPES SGGSSGGSDK KYSIGLAIGT NSVGWAVITD EYKVPSKKFK VLGNTDRHSI   240
KKNLIGALLF DSGETAEATR LKRTARRRYT RRKNRICYLQ EIFSNEMAKV DDSFFHRLEE   300
SFLVEEDKKH ERHPIFGNIV DEVAYHEKYP TIYHLRKKLV DSTDKADLRL IYLALAHMIK   360
FRGHFLIEGD LNPDNSDVDK LFIQLVQTYN QLFEENPINA SGVDAKAILS ARLSKSRRLE   420
NLIAQLPGEK KNGLFGNLIA LSLGLTPNFK SNFDLAEDAK LQLSKDTYDD DLDNLLAQIG   480
DQYADLFLAA KNLSDAILLS DILRVNTEIT KAPLSASMIK RYDEHHQDLT LLKALVRQQL   540
PEKYKEIFFD QSKNGYAGYI DGGASQEEFY KFIKPILEKM DGTEELLVKL NREDLLRKQR   600
TFDNGSIPHQ IHLGELHAIL RRQEDFYPFL KDNREKIEKI LTFRIPYYVG PLARGNSRFA   660
WMTRKSEETI TPWNFEEVVD KGASAQSFIE RMTNFDKNLP NEKVLPKHSL LYEYFTVYNE   720
LTKVKYVTEG MRKPAFLSGE QKKAIVDLLF KTNRKVTVKQ LKEDYFKKIE CFDSVEISGV   780
EDRFNASLGT YHDLLKIIKD KDFLDNEENE DILEDIVLTL TLFEDREMIE ERLKTYAHLF   840
DDKVMKQLKR RRYTGWGRLS RKLINGIRDK QSGKTILDFL KSDGFANRNF MQLIHDDSLT   900
FKEDIQKAQV SGQGDSLHEH IANLAGSPAI KKGILQTVKV VDELVKVMGR HKPENIVIEM   960
ARENQTTQKG QKNSRERMKR IEEGIKELGS QILKEHPVEN TQLQNEKLYL YYLQNGRDMY   1020
VDQELDINRL SDYDVDHIVP QSFLKDDSID NKVLTRSDKN RGKSDNVPSE EVVKKMKNYW   1080
RQLLNAKLIT QRKFDNLTKA ERGGLSELDK AGFIKRQLVE TRQITKHVAQ ILDSRMNTKY   1140
DENDKLIREV KVITLKSKLV SDFRKDFQFY KVREINNYHH AHDAYLNAVV GTALIKKYPK   1200
LESEFVYGDY KVYDVRKMIA KSEQEIGKAT AKYFFYSNIM NFFKTEITLA NGEIRKRPLI   1260
ETNGETGEIV WDKGRDFATV RKVLSMPQVN IVKKTEVQTG GFSKESILPK RNSDKLIARK   1320
KDWDPKKYGG FDSPTVAYSV LVVAKVEKGK SKKLKSVKEL LGITIMERSS FEKNPIDFLE   1380
AKGYKEVKKD LIIKLPKYSL FELENGRKRM LASAGELQKG NELALPSKYV NFLYLASHYE   1440
KLKGSPEDNE QKQLFVEQHK HYLDEIIEQI SEFSKRVILA DANLDKVLSA YNKHRDKPIR   1500
EQAENIIHLF TLTNLGAPAA FKYFDTTIDR KRYTSTKEVL DATLIHQSIT GLYETRIDLS   1560
QLGGD                                                               1565

SEQ ID NO: 38            moltype = AA   length = 364
FEATURE                  Location/Qualifiers
source                   1..364
                         mol_type = protein
                         organism = synthetic construct
SEQUENCE: 38
SEVEFSHEYW MRHALTLAKR AWDEREVPVG AVLVHNNRVI GEGWNRPIGR HDPTAHAEIM   60
ALRQGGLVMQ NYRLIDATLY VTLEPCVMCA GAMIHSRIGR VVFGARDAKT GAAGSLMDVL   120
HHPGMNHRVE ITEGILADEC AALLSDFFMR RRQEIKAQKK AQSSTDSGGS SGGSSGSETP   180
GTSESATPES SGGSSGGSSE VEFSHEYWMR HALTLAKRAR DEREVPVGAV LVLNNRVIGE   240
GWNRAIGLHD PTAHAEIMAL RQGGLVMQNY RLIDATLYVT FEPCVMCAGA MIHSRIGRVV   300
FGVRNAKTGA AGSLMDVLHY PGMNHRVEIT EGILADECAA LLCYFFRMPR QVFNAQKKAQ   360
SSTD                                                                364

SEQ ID NO: 39            moltype = AA   length = 167
FEATURE                  Location/Qualifiers
source                   1..167
                         mol_type = protein
                         organism = synthetic construct
SEQUENCE: 39
MSEVEFSHEY WMRHALTLAK RARDEREVPV GAVLVLNNRV IGEGWNRAIG LHDPTAHAEI   60
MALRQGGLVM QNYRLYDATL YSTFEPCVMC AGAMIHSRIG RVVFGVRNAK TGAAGSLMDV   120
LHHPGMNHRV EITEGILADE CAALLCRFFR MPRRVFNAQK KAQSSTD                 167

SEQ ID NO: 40            moltype = AA   length = 167
FEATURE                  Location/Qualifiers
source                   1..167
                         mol_type = protein
                         organism = synthetic construct
SEQUENCE: 40
MSEVEFSHEY WMRHALTLAK RARDEREVPV GAVLVLNNRV IGEGWNRAIG LHDPTAHAEI   60
MALRQGGLVM QNYRLIDATL YVTFEPCVMC AGAMIHSRIG RVVFGVRNSK RGAAGSLMNV   120
LNYPGMNHRV EITEGILADE CAALLCDFYR MPRQVFNAQK KAQSSIN                 167

SEQ ID NO: 41            moltype = AA   length = 83
FEATURE                  Location/Qualifiers
source                   1..83
```

```
                         mol_type = protein
                         note = Bacillus phage AR9
                         organism = unidentified
SEQUENCE: 41
TNLSDIIEKE TGKQLVIQES ILMLPEEVEE VIGNKPESDI LVHTAYDEST DENVMLLTSD    60
APEYKPWALV IQDSNGENKI KML                                            83

SEQ ID NO: 42           moltype = AA  length = 24
FEATURE                 Location/Qualifiers
source                  1..24
                         mol_type = protein
                         organism = synthetic construct
SEQUENCE: 42
EELLSKNYHL ENEVARLKKG SGSG                                           24

SEQ ID NO: 43           moltype = AA  length = 241
FEATURE                 Location/Qualifiers
source                  1..241
                         mol_type = protein
                         organism = synthetic construct
SEQUENCE: 43
EEELLSKNYH LENEVARLKK GSGSGEELLS KNYHLENEVA RLKKGSGSGE ELLSKNYHLE    60
NEVARLKKGS GSGEELLSKN YHLENEVARL KKGSGSGEEL LSKNYHLENE VARLKKGSGS   120
GEELLSKNYH LENEVARLKK GSGSGEELLS KNYHLENEVA RLKKGSGSGE ELLSKNYHLE   180
NEVARLKKGS GSGEELLSKN YHLENEVARL KKGSGSGEEL LSKNYHLENE VARLKKGSGS   240
G                                                                  241

SEQ ID NO: 44           moltype = AA  length = 277
FEATURE                 Location/Qualifiers
source                  1..277
                         mol_type = protein
                         organism = synthetic construct
SEQUENCE: 44
MGPDIVMTQS PSSLSASVGD RVTITCRSST GAVTTSNYAS WVQEKPGKLF KGLIGGTNNR    60
APGVPSRFSG SLIGDKATLT ISSLQPEDFA TYFCALWYSN HWVFGQGTKV ELKRGGGGSG   120
GGGSGGGGSS GGGSEVKLLE SGGGLVQPGG SLKLSCAVSG FSLTDYGVNW VRQAPGRGLE   180
WIGVIWGDGI TDYNSALKDR FIISKDNGKN TVYLQMSKVR SDDTALYYCV TGLFDYWGQG   240
TLVTVSSYPY DVPDYAGGGG GSGGGGSGGG GSGGGGS                           277

SEQ ID NO: 45           moltype = DNA  length = 66
FEATURE                 Location/Qualifiers
source                  1..66
                         mol_type = other DNA
                         organism = Saccharomyces bayanus
SEQUENCE: 45
ttcttgtcgt acttatagat cgctacgtta tttcaatttt gaaaatctga gtcctgggag    60
tgcgga                                                               66

SEQ ID NO: 46           moltype = AA  length = 605
FEATURE                 Location/Qualifiers
source                  1..605
                         mol_type = protein
                         organism = Homo sapiens
SEQUENCE: 46
MSGWESYYKT EGDEEAEEEQ EENLEASGDY KYSGRDSLIF LVDASKAMFE SQSEDELTPF    60
DMSIQCIQSV YISKIISSDR DLLAWFYGTE KDKNSVNFKI YVLQELDNPG AKRILELDQF   120
KGQQGQKRFQ DMMGHGSDYS LSEVLWVCAN LFSDVQFKMS HKRIMLFTNE DNPHGNDSAK   180
ASRARTKAGD LRDTGIFLDL HLKKPGGFDI SLFYRDIISI AEDEDLRVHF EESSKLEDLL   240
RKVRAKETRK RALSRLKLKL NKDIVISVGI YNLVQKALKP PPIKLYRETN EPVKTKTRTF   300
NTSTGGLLLP SDTKRSQIYG SRQIILEKEE TEELKRFDDP GLMLMGFKPL VLLKKHHYLR   360
PSLFVYPEES LVIGSSTLFS ALLIKCLEKE VAALCRYTPR RNIPPYFVAL VPQEEELDDQ   420
KIQVTPPGFQ LVFLPFADDK RKMPFTEKIM ATPEQVGKMK AIVEKLRFTY RSDSFENPVL   480
QQHFRNLEAL ALDLMEPEQA VDLTLPKVEA MNKRLGSLVD EFKELVYPPD YNPEGKVTKR   540
KHDNEGSGSK RPKVEYSEEE LKTHISKGTL GKFTVPLKEA CRAYGLKSGL KKQELLEALT   600
KHFQD                                                              605

SEQ ID NO: 47           moltype = AA  length = 482
FEATURE                 Location/Qualifiers
source                  1..482
                         mol_type = protein
                         organism = synthetic construct
SEQUENCE: 47
MVRSGNKAAW LCMDVGFTMS NSIPGIESPF EQAKKVITMF VQRQVFAENK DEIALVLFGT    60
DGTDNPLSGG DQYQNITVHR HLMLPDFDLL EDIESKIQPG SQQADFLDAL IVSMDVIQHE   120
TIGKKFEKRH IEIFTDLSSR FSKSQLDIII HSLKKCDISE RHSIHWPCRL TIGSNLSIRI   180
AAYKSILQER VKKTTWDAKT LKKEDIQKET VYCLNDDDET EVLKEDIIQG FRYGSDIVPF   240
SKVDEEQMKY KSEGKCFSVL GFCKSSQVQR RFFMGNQVLK VFAARDDEAA AVALSSLIHA   300
LDDLDIWAIV RYAYDKRANP QVGVAFPHIK HNYECLVYVQ LPFMEDLRQY MFSSLKNSKK   360
YAPTEAQLNA VDALIDSMSL AKKDEKTDTL EDLFPTTKIP NPRFQRLFQC LLHRALHPRE   420
```

```
PLPPIQQHIW NMLNPPAEVT TKSQIPLSKI KTLFPLIEAK KKDQVTAQEI FQDNHEDGPT  480
AK                                                                         482

SEQ ID NO: 48           moltype = DNA   length = 10
FEATURE                 Location/Qualifiers
source                  1..10
                        mol_type = other DNA
                        organism = Methanobacterium thermoautotrophicum
SEQUENCE: 48
aatttttgga                                                                  10

SEQ ID NO: 49           moltype = AA   length = 83
FEATURE                 Location/Qualifiers
source                  1..83
                        mol_type = protein
                        organism = Methanobacterium thermoautotrophicum
SEQUENCE: 49
GSVIDVSSQR VNVQRPLDAL GNSLNSPVII KLKGDREFRG VLKSFDLHMN LVLNDAEELE  60
DGEVTRRLGT VLIRGDNIVY ISP                                            83

SEQ ID NO: 50           moltype = DNA   length = 25
FEATURE                 Location/Qualifiers
source                  1..25
                        isolate = Escherichia phage MS2
                        mol_type = other DNA
                        organism = Emesvirus zinderi
SEQUENCE: 50
gcgcacatga ggatcaccca tgtgc                                                 25

SEQ ID NO: 51           moltype = AA   length = 116
FEATURE                 Location/Qualifiers
source                  1..116
                        mol_type = protein
                        note = Escherichia phage MS2
                        organism = Emesvirus zinderi
SEQUENCE: 51
MASNFTQFVL VDNGGTGDVT VAPSNFANGI AEISSNSRSQ AYKVTCSVRQ SSAQNRKYTI  60
KVEVPKGAWR SYLNMELTIP IFATNSDCEL IVKAMQGLLK DGNPIPSAIA ANSGIY        116

SEQ ID NO: 52           moltype = DNA   length = 26
FEATURE                 Location/Qualifiers
source                  1..26
                        isolate = Bacteriophage PP7
                        mol_type = other DNA
                        organism = Pepevirus rubrum
SEQUENCE: 52
ataaggagtt tatatggaaa ccctta                                                26

SEQ ID NO: 53           moltype = AA   length = 127
FEATURE                 Location/Qualifiers
source                  1..127
                        mol_type = protein
                        note = Bacteriophage PP7
                        organism = Pepevirus rubrum
SEQUENCE: 53
MSKTIVLSVG EATRTLTEIQ STADRQIFEE KVGPLVGRLR LTASLRQNGA KTAYRVNLKL  60
DQADWDCSTS VCGELPKVRY TQVWSHDVTI VANSTEASRK SLYDLTKSLV ATSQVEDLVV  120
NLVPLGR                                                             127

SEQ ID NO: 54           moltype = DNA   length = 19
FEATURE                 Location/Qualifiers
misc_feature            1..19
                        note = Shigella phage
source                  1..19
                        mol_type = other DNA
                        organism = unidentified
SEQUENCE: 54
ctgaatgcct gcgagcatc                                                        19

SEQ ID NO: 55           moltype = AA   length = 62
FEATURE                 Location/Qualifiers
REGION                  1..62
                        note = Shigella phage
source                  1..62
                        mol_type = protein
                        organism = unidentified
SEQUENCE: 55
MKSIRCKNCN KLLFKADSFD HIEIRCPRCK RHIIMLNACE HPTEKHCGKR EKITHSDETV  60
RY                                                                  62
```

SEQ ID NO: 56          moltype = AA   length = 1367
FEATURE                Location/Qualifiers
source                 1..1367
                       mol_type = protein
                       organism = synthetic construct
SEQUENCE: 56
DKKYSIGLAI GTNSVGWAVI TDEYKVPSKK FKVLGNTDRH SIKKNLIGAL LFDSGETAEA   60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM 1020
IAKSEQEIGK ATAKYFFYSN IMNFFKTEIT LANGEIRKRP LIETNGETGE IVWDKGRDFA 1080
TVRKVLSMPQ VNIVKKTEVQ TGGFSKESIL PKRNSDKLIA RKKDWDPKKY GGFDSPTVAY 1140
SVLVVAKVEK GKSKKLKSVK ELLGITIMER SSFEKNPIDF LEAKGYKEVK KDLIIKLPKY 1200
SLFELENGRK RMLASAGELQ KGNELALPSK YVNFLYLASH YEKLKGSPED NEQKQLFVEQ 1260
HKHYLDEIIE QISEFSKRVI LADANLDKVL SAYNKHRDKP IREQAENIIH LFTLTNLGAP 1320
AAFKYFDTTI DRKRYTSTKE VLDATLIHQS ITGLYETRID LSQLGGD           1367

SEQ ID NO: 57          moltype = AA   length = 1367
FEATURE                Location/Qualifiers
source                 1..1367
                       mol_type = protein
                       organism = synthetic construct
SEQUENCE: 57
DKKYSIGLAI GTNSVGWAVI TDEYKVPSKK FKVLGNTDRH SIKKNLIGAL LFDSGETAEA   60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLADDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PALESEFVYG DYKVYDVRKM 1020
IAKSEQEIGK ATAKYFFYSN IMNFFKTEIT LANGEIRKRP LIETNGETGE IVWDKGRDFA 1080
TVRKVLSMPQ VNIVKKTEVQ TGGFSKESIL PKRNSDKLIA RKKDWDPKKY GGFDSPTVAY 1140
SVLVVAKVEK GKSKKLKSVK ELLGITIMER SSFEKNPIDF LEAKGYKEVK KDLIIKLPKY 1200
SLFELENGRK RMLASAGELQ KGNELALPSK YVNFLYLASH YEKLKGSPED NEQKQLFVEQ 1260
HKHYLDEIIE QISEFSKRVI LADANLDKVL SAYNKHRDKP IREQAENIIH LFTLTNLGAP 1320
AAFKYFDTTI DRKRYTSTKE VLDATLIHQS ITGLYETRID LSQLGGD           1367

SEQ ID NO: 58          moltype = DNA   length = 4101
FEATURE                Location/Qualifiers
source                 1..4101
                       mol_type = other DNA
                       organism = synthetic construct
SEQUENCE: 58
gacaagaagt acagcatcgg gctggcgatc gggaccaact ccgtcggctg ggctgtgatt   60
accgacgagt acaaggtgcc atccaagaag ttcaaggtcc tcggcaacac tgaccggcac  120
agcattaaga agaacctgat tgggggcgctg ctgttcgatt cgggggagac tgcggaggcg  180
accaggctga gcggactgc gcgccggagg tacaccagga ggaagaatcg gatctgctac  240
ctccaggaga ttttctcgaa tgagatggcc aaggtggacg attccttctt ccatcgcctg  300
gaggagtcgt tcctcgttga ggaggacaag aagcatgaga ggcatccat tttcgggaat  360
atcgttgacg aggtggctta ccatgagaag taccgcacct tctaccatct gcggaagaag  420
ctcgtcgatt cgaccgataa ggccgacctg cggctgatct acctggccct cgcgcacatg  480
attaagttcc ggggccattt cctcatcgag ggcgacctca acccgacaa ctcggacgtg  540
gataagctct tcattcagct cgtgcagaca tacaaccagc tcttcgagga gaatcccatt  600
aacgcctcgg gggtcgacgc taaggctatt ctctcggctc ggctgtcgaa gtcgcgccgg  660
ctggagaatc tcattgccca gctcccaggc gagaagaaga acggcctctt cggcaacctg  720

```
attgccctgt cgctggggct cacaccgaat ttcaagtcga acttcgacct cgccgaggac  780
gctaagctcc agctcagcaa ggatacttac gatgatgacc tcgataacct gctcgcccag  840
attggggatc agtacgcgga tctgttcctc gcggccaaga atctcagcga tgctattctc  900
ctgtcggaca ttctccgcgt caacacagag attactaagg ccccactgtc ggcgagcatg  960
attaagaggt acgatgagca tcatcaggac ctgacactgc tcaaggcgct ggtccggcag 1020
cagctccccg agaagtacaa ggagattttc ttcgatcagt caaagaatgg gtacgcgggc 1080
tacattgatg gcggcgcgtc ccaggaggag ttctacaagt tcattaagcc catcctggag 1140
aagatggacg ggaccgagga gctgctggtg aagctcaatc gggaggacct gctccggaag 1200
cagcgcacat tcgacaatgg ctcgattcct caccagattc acctgggcga gctgcacgcc 1260
attctccgca ggcaggagga cttctacccg ttcctcaagg acaaccgcga gaagatcgag 1320
aagatcctga ccttccggat tccatactac gtggggccgc tcgcgcgggg gaactcccgg 1380
ttcgcgtgga tgactcgcaa gtccgaagaa acgattacac cgtggaattt cgaggaggtc 1440
gtcgacaagg gcgctagtgc gcagtcattc attgagagga tgaccaattt cgataagaac 1500
ctgcctaacg agaaggtgct gccgaagcat tcgctgctct acgagtactt caccgtttac 1560
aatgagctga ccaaggtgaa gtatgtgact gagggcatga ggaagccagc gttcctgagc 1620
ggcgagcaga agaaggctat cgtggacctg ctcttcaaga ctaaccggaa ggtgactgtg 1680
aagcagctca aggaggacta cttcaagaag attgagtgct tcgattccgt tgagattagc 1740
ggggtgaggg atcggttcaa tgcttcgctc gggacataccc acgatctcct gaagatcatt 1800
aaggataagg acttcctcga caacgaggag aacgaggaca ttctcgaaga tattgtcctg 1860
accctcaccc tcttcgagga tcgggagatg atcgaggaga ggctcaagac atacgctcat 1920
ctgttcgatg ataaggtcat gaagcagctg aagcgcaggc ggtacacagg gtgggggcgg 1980
ctgagccgga agctgatcaa cgggattcgg gataagcagt ccgggaagac aattctcgac 2040
ttcctcaagt ccgacgggtt cgctaaccgg aacttcatgc agctcattca tgatgactcg 2100
ctgacattca aggaggatat tcagaaggcg caggtttcgg ggcagggcga ctcgctccac 2160
gagcatattg cgaatctggc gggctccccc gcgattaaga agggcattct gcaaaccgtc 2220
aaggtggttg atgagctggt caaggtcatg gggcggcata agccagagaa tattgtcatc 2280
gagatggcgc gggagaatca gaccacacag aaggggcaga agaactcacg ggagcggatg 2340
aagcgcatcg aggagggcat caaggagctg gggtcgcaga tcctgaagga gcatcccgtg 2400
gagaacactc agctgcaaaa tgagaagctg tacctctact acctccagaa cgggagggac 2460
atgtatgtgg atcaggagct ggatattaat aggctgagcg attacgatgt cgaccacatt 2520
gtcccacagt cgttcctgaa ggacgacagc attgacaaca aggtgctgac ccgctcggat 2580
aagaacaggg gcaagagcga taatgttcca agcgaggagg ttgtgaagaa gatgaagaac 2640
tactggcggc agctcctgaa cgcgaagctc atcacacagc ggaagttcga caacctcacc 2700
aaggctgagc gcgggggcct gagcgagctg gacaaggcgg ggttcattaa gaggcagctg 2760
gtcgacacac ggcagattac aaagcatgtt gcgcagattc tcgattcccg gatgaacacc 2820
aagtacgatg agaacgataa gctgattcgg gaggtcaagg taattaccct gaagtccaag 2880
ctggtgtccg acttcaggaa ggacttccag ttctacaagg ttcgggagat caacaactac 2940
caccacgcgc atgatgccta cctcaacgcg gtcgtgggga ccgctctcat caagaagtac 3000
ccaaagctgg agtcagagtt cgtctacggg gattacaagg tttacgacgt gcggaagatg 3060
atcgctaaga gcgagcagga gattggcaag gctaccgcta agtacttctt ctactccaac 3120
atcatgaact tcttcaagac agagattacc ctcgcgaatg gcgagatccg gaagaggccc 3180
ctcatcgaga caaatgggga gacaggggag attgtctggg ataaggggcg ggatttcgcg 3240
accgtccgga aggtcctgtc gatgccccag gttaatattg tcaagaagac tgaggtccag 3300
actggcggct tctcaaagga gtcgattctc ccaaagagga actccgataa gctcattgct 3360
cggaagaagg attgggaccc caagaagtac ggggggattcg actcccccac tgttgcttac 3420
tctgttctgg ttgttgctaa ggtggagaag gggaagtcga gaagctgaa gagcgtgaag 3480
gagctgctcg ggattacaat tatggagagg tcatccttcg agaagaatcc catcgacttc 3540
ctggaggcca agggctacaa ggaggtgaag aaggacctga ttattaagct gcccaagtac 3600
tcgctcttcg agctggagaa tgggcggaag cggatgctgg cgtccgcggg ggagctgcaa 3660
aagggcaacg agctggcgct cccctccaag tatgtgaact tcctctacct ggcgtcgcac 3720
tacgagaagc tgaaggggtc cccagaggat aatgagcaga agcagctctt cgtcgagcag 3780
cataagcact acctggacga gattatcgag cagattagcg agttctcgaa gcgggtcatc 3840
ctcgcggatg cgaacctgga taaggtgctc agcgcctaca taagcaccg ggacaagccg 3900
attcgggagc aggcggagaa tattattcac ctcttcacac tcaccaacct cggggcacca 3960
gctgcgttca agtacctcga cactactatc gaccggaagc ggtacacctc gacgaaggag 4020
gtgctcgacg ccaccctcat tcaccagtcg atcacaggcc tgtacgagac acggattgac 4080
ctgtcccagc tcgggggcga c                                             4101
```

```
SEQ ID NO: 59            moltype = DNA   length = 4101
FEATURE                  Location/Qualifiers
source                   1..4101
                         mol_type = other DNA
                         organism = synthetic construct
SEQUENCE: 59
gacaagaagt actccattgg cctggcgatt gggacaaact cggtggggtg ggccgtgatt   60
acggatgagt acaaggttcc aagcaagaag ttcaaggtcc tcgggaacac agatcggcat  120
tcgattaaga agaatctcat tggggcgctc ctcttcgact cggggagac agcggaggct  180
accaggctca agcggacagc caggcggcgg tacacaaggc ggaagaatcg catctgctac  240
ctccaggaga tttttctcga agatgatggcg aaggtgacg acagcttctt ccatcggctg  300
gaggagtcct tcctggtgga ggaggataag aagcacgaca ggcatccaat tttcgggaac  360
atcgtggacg aggttgcgta ccatgagaag taccctacaa tctaccatct gcggaagaag  420
ctggttgact ccacagacaa ggcggacctg aggctgatct acctcgctct ggcccacatg  480
attaagttcc gcgggcattt cctgatcgag ggggacctga tcccgacaa ttcggatgtg  540
gacaagctgt tcatccagct ggtgcagacc tacaaccgc tgttcgagga gaatcccatc  600
aatgcgtcgg gcgttgacgc taaggccatt ctgtccgcta ggctgtcgaa gagcaggagg  660
ctggagaacc tgatcgccca gctgccaggc gagaagaaga tgggctct cgggaatctg  720
attgcgctct ccctggggct gacaccgaac ttcaagagca attctgatct ggctgaggac  780
gcgaagctcc agctctcgaa ggacacttac gacgatgacc tcgataacct cctcgcgcag  840
atcggggacc agtacgctga tctcttcctc gccgctaaga acctctcgga tgctatcctg  900
```

```
ctctccgaca ttctccgggt taataccgag attacaaagg ccccactgtc ggcgtccatg    960
atcaagcggt acgatgagca tcatcaggat ctcaccctgc tcaaggccct cgtgcggcag   1020
cagctgcccg agaagtacaa ggagattttc ttcgaccaga gcaagaatgg gtacgctggc   1080
tacattgacg gcggggcctc acaggaggag ttctacaagt tcatcaagcc aatcctggag   1140
aagatggatg ggacagagga gctgctggtg aagctcaacc gggaggatct gctcaggaag   1200
cagcggacgt tcgacaacgg gtcgattccc catcagatcc acctggggga gctgcacgcg   1260
atcctgcgcc ggcaggagga tttctaccct ttcctgaagg ataatcggga gaagatcgag   1320
aagattctca ccttccggat tccctactac gtcgggccac tcgcgcgggg caatagcagg   1380
ttcgcctgga tgacacggaa gagcgaggag acaatcaccc cctggaactt cgaggaggtt   1440
gtcgacaagg gggcgtccgc ccagtcattc attgagcgga tgaccaattt cgacaagaat   1500
ctgccaaatg agaaggttct cccaaagcat agcctcctct acgagtactt cactgtttac   1560
aacgagctga ccaaggtgaa gtatgtgacc gagggcatgc ggaagcccgc gttcctgtcc   1620
ggcgagcaga agaaggccat tgtggacctc ctgttcaaga ccaatcgcaa ggtcacagtc   1680
aagcagctca aggaggatta cttcaagaag atcgagtgct tcgactcggt tgagattagc   1740
ggggtggagg atcggttcaa cgcgagcctc ggcacttacc acgacctcct gaagatcatc   1800
aaggataagg acttcctcga caacgaggag aacgaggata ttctggagga catcgtgctc   1860
accctgacgc tgttcgagga tcgggagatg atcgaggagc gcctgaagac ctacgctcat   1920
ctcttcgatg ataaggtcat gaagcagctg aagaggaggc ggtacaccgg gtggggccgc   1980
ctgagcagga agctcattaa cgggatcagg gacaagcaga gcggcaagac catcctggac   2040
ttcctcaaga gcgatggctt cgccaaccgg aatttcatgc agctcatcca cgacgactcc   2100
ctcaccttca aggaggacat tcagaaggct caggtcagcg gccagggcga ctcgctgcat   2160
gagcacatcg ctaacctggc gggcagccca gccatcaaga gaggcatcct ccagacagtg   2220
aaggtcgtgg atgagctggt gaaggtcatg ggccggcata gcccgagaa tattgtgatt   2280
gagatggcgc gggagaatca gaccactcag aagggccaga agaactcgcg ggagcgcatg   2340
aagaggatcg aggagggggat taaggagctg ggcagccaga ttctcaagga gcaccccgtg   2400
gagaataccc agctccagaa cgagaagctg tacctctact acctccagaa tgggcgggac   2460
atgtatgttg atcaggagct ggacatcaat cgcctctcgg attacgacgt ggaccacatc   2520
gtgccccaga gcttcctgaa ggatgatagc atcgacaata aggtcctgac ccgctccgac   2580
aagaatcgcg gcaagagcga caacgtgccg agcgaggagg tcgtgaagaa gatgaagaac   2640
tactggcggc agctgctgaa cgcgaagctc attacacagc ggaagttcga taacctgacg   2700
aaggcggaga ggggcgggcct ctccgagctg gacaaggcgg gcttcattaa gaggcagctc   2760
gtggagactc gccagatcac caagcacgtg gctcagatcc tcgatagccg gatgaatacg   2820
aagtacgatg agaatgacaa gctcatccgg gaggtgaagg taatcaccct gaagtcaaag   2880
ctcgttagcg atttccggaa ggacttccag ttctacaaag tgcggggagat taacaactac   2940
catcatgcgc acgatgcgta cctcaatgcg gtggtgggca cagccctgat taagaagtac   3000
cccaagctgg agagcgagtt cgtctacggg gactacaagg tgtacgatgt tcggaagatg   3060
atcgccaaga gcgagcagga gattgggaag gccaccgcta agtacttctt ctactcgaat   3120
attatgaatt tcttcaagac cgagatcaca ctcgctaatg gggagattcg gaagcggccc   3180
ctcatcgaga ctaacgggga gactggcgag attgtgtggg acaaggggcg cgacttcgct   3240
accgtgcgca aggtcctctc gatgcccag gttaatattg ttaagaagac agaggtgcag   3300
acgggcgggt tctccaagga gtctatcctg ccgaagcgga actcggacaa gctgatcgcc   3360
cgcaagaagg attgggaccc caagaagtac gggggattcg atagcccaac cgtggcttac   3420
agcgtcctgg tggtcgccaa ggttgagaag gggaagtcga agaagctcaa gagcgttaag   3480
gagctgctgg gcatcaccat catggagcgg tccagcttcg agaagaatcc tatcgacttc   3540
ctggaggcta aggggtacaa ggaggtcaag aaggacctga tcattaagct gcccaagtac   3600
tctctgttcg agctggagaa cgggaggaag cggatgctgg cgtctgctgg cgagctacag   3660
aagggcaatg agctggcgct cccctcgaag tatgtcaact tcctctacct ggcttcccat   3720
tacgagaagc tgaaggggctc gcccgaggat aatgagcaga agcagctctt cgtggagcag   3780
cacaagcact acctcgacga gatcattgag cagatttcgg agttctcgaa gcgggtcatt   3840
ctcgcggacg cgaacctcga caaggtcctc tcggcgtaca caagcaccg ggacaagccc   3900
atccggaagc aggccgagaa cattatccac ctcttcacac tgaccaacct cggcgctccc   3960
gccgcgttca gtacttcga caccaccatt gaccgcaaga gatacacatc caccaaggag   4020
gtgctggacg cgaccctcat ccaccagagc atcacaggcc tctacgagac acggatcgac   4080
ctctcgcagc tcggggggcga t                                            4101
```

```
SEQ ID NO: 60         moltype = DNA   length = 4092
FEATURE               Location/Qualifiers
source                1..4092
                      mol_type = other DNA
                      organism = synthetic construct
SEQUENCE: 60
gacaagaagt actcgatcgg cctggcgatt ggcacaaaca gcgtggggtg ggctgtgatc     60
actgatgagt acaaggtgcc atcgaagaag ttcaaggtgc tggggaatac agaccggcat    120
tcgatcaaga agaatctcat tggcgctctc ctcttcgatt ccggcagcga tgctgaggcg    180
acccgcctga agcgcaccgc ccggcggcgc tacactcggc ggaagaatag gatttgctac    240
ctccaggaga ttttctcgaa tgagatggcg aaggtggatg acagcttctt ccaccgcctg    300
gaggagtcgt tcctggtcga ggaggacaag aagcatgagc ggcacccat cttcgggaat    360
atcgttgatg aggtcgccta ccacgagaag taccccacta tctaccatct ccgcaagaag    420
ctcgtggaca gcacagataa ggccgacctc cgcctgatct acctcgccct cgcgcacatg    480
attaagttcc ggggggcactt cctcattgag ggggatctga atcccgataa ctccgacgtg    540
gacaagctgt catccagct ggtgcagaca tacaaccagc tgttcgagga gaatcccatc    600
aacgcgagcg cgtggacgc taaggccatt ctgtcggcta ggctctcgaa gtcgaggcgg    660
ctggagaacc tgattgcgca gctccccggc gagaagaaga cgggctgtt cgggaatctc    720
atcgccctc ccctcggcct cacaccaaac ttcaagagc atttcgacct ggctgaggac    780
gctaagctgc aactctcaaa ggatacatac gatgacgacc tggacaatct cctggctcag    840
atcggcgacc agtacgctga cctgttcctc gcggccaaga tctgtcggga cgcgattctc    900
ctcagcgaca tcctgcgcgt caataccgag attacgaagg ctccactgtc tgcgtcaatg    960
attaagcggt acgatgagca tcaccaggat ctgaccctcc tgaaggcgct cgtgcggcag   1020
cagctgcccg agaagtacaa ggagatttc ttcgatcaga gcaagaatgg ctacgccggc   1080
```

-continued

```
tacatcgacg ggggcgcgag ccaggaggag ttctacaagt tcatcaagcc catcctggag 1140
aagatggacg gcaccgagga gctactcgtg aagctcaatc gggaggatct cctccggaag 1200
cagcggacat tcgataacgg gtctatccca caccagatcc acctcggcga gctgcatgcg 1260
attctgcggc ggcaggagga tttctaccct ttcctgaagg acaaccggga gaagatcgag 1320
aagatcctca cattccggat tccatactac gtcggccccc tggcgagggg caatagccgg 1380
ttcgcgtgga tgacaaggaa gtccgaggag actattaccc cgtggaattt cgaggaggtg 1440
gttgacaagg gcgcttccgc gcagagcttc attgagcgga tgacaaactt cgacaagaat 1500
ctccccaacg agaaggtcct gccgaagcat agcctcctgt acgagtactt caccgtctac 1560
aatgagctaa ctaaggtcaa gtatgtgaca gagggcatga ggaagccagc cttcctctca 1620
ggcgagcaga agaaggccat tgtggacctc ctgttcaaga caaaccgcaa ggtgacagtg 1680
aagcagctga aggaggatta cttcaagaag attgagtgct tcgactcagt ggagatttca 1740
ggcgtggagg atcggttcaa cgcgagcctg gggacttacc acgacctgct gaagattatt 1800
aaggacaagg acttcctgga taacgaggag aatgaggaca tcctggagga tattgtgctc 1860
accctcaccc tgttcgagga cagggagatg attgaggaga ggctcaagac ctacgcgcac 1920
ctgttcgatg acaaggtcat gaagcagctg aagaggcggc gctacactgg gtggggccgc 1980
ctgtcgcgga agctgatcaa cggcattcgg gataagcagt ccgggaagac cattctggat 2040
ttcctgaagt cggacggctt cgccaacagg aatttcatgc agctgatcca cgacgactcc 2100
ctcaccttca aggaggacat tcagaaggcc caggttagcg gccaggggga ctcactccac 2160
gagcatattg ccaatctggc cggctctcca gctatcaaga agggcatcct gcaaacagtt 2220
aaggttgttg acgagctggt taaggtcatg gggcggcata agcccgagaa cattgtcatc 2280
gagatggctc gggagaacca gacaactcag aagggccaga agaactccag ggagcgcatg 2340
aagcggattg aggagggcat taaggagctg gggtcccaga tcctcaagga gcaccctgtc 2400
gagaacactc agctgcaaaa cgagaagctc tacctgtact acctccagaa cgggcgggat 2460
atgtatgtgg atcaggagct ggacatcaac aggctctccg actacgacgt ggatcacatt 2520
gtcccacagt ctttcctcaa ggatgattcc atcgacaaca aggtgctgac gcgcagcgac 2580
aagaataggg ggaagtcgga caacgttccg agcgaggagg tcgtgaagaa gatgaagaat 2640
tactggaggc agctcctgaa tgcgaagctg atcactcaga ggaagttcga caatctgaca 2700
aaggcggaga ggggcgggct ctcggagctg gataagcgg gcttcatcaa gcggcagctc 2760
gttgaaaccc ggcagatcac caagcatgtc gcccagatcc tcgatagccg catgaacacc 2820
aagtacgatg agaacgacaa gctcattcgg gaggttaagg tcattacgct gaagtccaag 2880
ctcgtcagcg acttcaggaa ggatttccag ttctacaagg ttcgggagat taacaactac 2940
caccacgcgc atgatgcgta cctgaacgct gttgtcggca ctgctctcat caagaagtac 3000
ccaaagctga gtccgagtt cgtctacggg gactacaag tctacgatgt ccggaagatg 3060
atcgccaagt cggagcagga gatcgggaag gctactgcga agtacttctt ctacagcaac 3120
attatgaatt tcttcaagac ggagattacg ctggcgaacg gggagattag gaagaggccc 3180
ctcattgaga ctaatgggga gacaggcgag attgtttggg acaagggccg cgacttcgcg 3240
actgtgcgga aggtcctgtc catgccacag gtgaatattg ttaagaagac agaggtgcag 3300
actgggggct tctcgaagga gagcattctc ccaaagcgga acagcgataa gctcatcgcg 3360
cgcaagaagg attgggaccc taagaagtac ggcgggtcg attctcccac tgtggcctac 3420
tccgttctcg tggttgccaa ggttgagaag gggaagtcga agaagctgaa gtcggtcaag 3480
gagctgctcg ggattacaat catggagcgg agcagcttcg agaagaaccc tattgatttc 3540
ctggaggcca agggctacaa ggaggttaag aaggatctca ttatcaagct ccctaagtac 3600
tctctgttcg agctggagaa tggccggaag aggatgctgg cctcggctgg cgagctacag 3660
aaggggaatg agctggccct cccgtcgaag tatgtgaatt tcctgtacct cgcgtcgcac 3720
tacgagaagc tcaagggcag cccggaggat aatgagcaga agcagctctt cgtggagcag 3780
cataagcact acctggacga gatcattgag cagatcagcg agttctcgaa gcgggttatt 3840
ctggctgatg ctaacctgga caaggttctg agcgcctaca ataagcatcg cgacaagccg 3900
attcgcgagc aggcggagaa tattatccac ctgttcaccc tcactaacct cggggctccc 3960
gcggccttca agtacttcga taccacaata gataggaagc ggtacacctc gacgaaggag 4020
gtcctcgacg ccacactcat ccatcagtcg attacaggcc tgtacgagac acggattgac 4080
ctctcgcagc tg                                                      4092
```

SEQ ID NO: 61          moltype = DNA   length = 4101
FEATURE                Location/Qualifiers
source                 1..4101
                       mol_type = other DNA
                       organism = synthetic construct
SEQUENCE: 61

```
gacaagaagt attccatagg cctggctatc ggcaccaaca gcgtgggctg ggccgtcatc 60
accgacgagt acaaagtgcc gagtaaaaag ttcaaagtgc tcggcaacac cgaccgccac 120
tccataaaga aaaacctgat cggggcgctc ctgttcgaca gcggcgagac ggcggaggcc 180
acccgcttga aacgcacggc ccgacggcgc tacacgcggc gcaagaaccg gatctgttac 240
ctacaggaga tttttctctaa cgagatggcg aaggtggacg actcgttctt tcaccgcctc 300
gaagatcct tcctcgtgga ggaggacaag aaacacgagc gccaccgat cttcggcaac 360
atcgtggacg aggtggccta ccacgagaag tacccgacca tctaccacct ccggaagaaa 420
ctcgtggaca gcacggacaa ggccgacctg aggctcatct acctgccct ggcgcacatg 480
attaagttcc ggggccactt cctgatcgag ggcgacctga acccggacaa cagcgacgtg 540
gacaagctgt tcatccagct agtccagacc tacaaccagc ttttcgagga aaaccccatc 600
aacgccagcg gggtggacgc gaaggcgatc ctgtccggcc ggctgagcaa gtcccggccg 660
ctggagaacc tcatcgcgca gttgcccggc gagaagaaga acgggctgtt cgggaacctg 720
atcgccctct ccctggggct caccccgaac ttcaagtcca acttcgacct cgccgaggac 780
gccaaactac agctgagcaa ggacacctac gacgacgacc tcgacaacct gctggcccag 840
atcggggacc agtacgcaga cctgttcctc gccgccaaga acctctccga cgccatcctg 900
ctgtcggaca tcctgcgggt gaacacggag atcacgaagg cccccgctctc ggcctcgatg 960
attaaacgct acgacgagca ccaccaggac ttgaccctcc tcaaggcgct ggtccggcag 1020
cagcttccg agaagtacaa ggaaatcttt ttcgatcaga gcaagaacgg gtacgccggg 1080
tacatcgacg gcgggcgtc ccaggaggag ttctacaagt tcatcaagcc catcctggag 1140
aaaatggacg ggaccgagga gctgctcgtg aagctcaacc gcgaagattt gctccgcaag 1200
cagcgcacgt tcgacaacgg gtcgatcccg caccagatcc acctgggcga gctgcacgcg 1260
```

```
atcctcaggc gtcaggaaga cttctacccc ttcctcaagg acaaccgcga gaagatagag   1320
aagattctga ccttcagaat tccttattac gtgggcccgc tggctcgggg caactcgcgc   1380
ttcgcctgga tgacgcgcaa gtccgaggag accatcaccc cgtggaactt cgaggaggtg   1440
gtggataagg gtgcctcggc ccagtccttc atcgagcgga tgaccaactt cgacaagaac   1500
ctgccgaacg agaaggtgct ccccaagcac agcctgctct acgaatattt cacggtgtac   1560
aacgagctga cgaaggtcaa gtacgtgacc gagggaatga ggaaacctgc attcctctcc   1620
ggggagcaga agaaagccat agtcgacctc ctgttcaaga ccaaccggaa ggtcaccgtc   1680
aagcagctca aggaggacta cttcaagaag atcgagtgct tcgattcagt ggagatcagc   1740
ggcgtcgagg accggttcaa cgccagcctg ggcacctacc acgacctgct caagatcatc   1800
aaggacaagg acttcctcga caacgaggag aacgaggaca tcctggagga catcgtgctg   1860
accctgacgc tcttcgagga ccgcgagatg atcgaggagc gcctcaagac ctacgcccac   1920
ctgttcgacg acaaggtgat gaagcagctc aagcggcgga gatatactgg gtggggccgc   1980
ctctcccgga agctcattaa cggtatcagg gataagcagt ccgggaagac gatcctcgac   2040
ttcctcaagt cggacggggt cgccaaccgc aacttcatgc agctcatcca cgacgactcc   2100
ctgacgttca aggaggacat ccagaaggcc caagtgtctg gtcaaggtga ctcgctccac   2160
gagcacatcg ccaacctcgc gggcagcccg gccatcaaga agggaatact ccagaccgtc   2220
aaggtggtgg acgagctggt gaaggtcatg ggccgccaca agccggagaa catcgtcatc   2280
gagatggcgc gggagaacca gaccacgcag aagggggcag aaaatagccg tgagcgcatg   2340
aagcgcatcg aggaggggat taaggagttg ggcagccaga tcctcaagga gcaccctgtg   2400
gagaacacgc agttgcaaaa cgagaagctc tacctgtact acctccagaa cgggagggat   2460
atgtacgtgg accaagaact ggacatcaac cgcctgtccg actacgacgt ggaccacatc   2520
gtgccgcaga gcttcctcaa ggacgacagc atcgacaaca aggtgctcac ccggtccgac   2580
aagaatcggg gcaagtccga caacgtgccc agcgaggagg tcgtcaaaaa gatgaaaaac   2640
tactggcgac aactactgaa cgccaagctc atcacccagc gcaagttcga caacctcaca   2700
aaagccgagc gcggcgggtt gagcgagctg gacaaggccg ggttcatcaa gcgccagctc   2760
gtcgagacgc gccagatcac gaagcacgtc gcgcagatac tcgacagccg gatgaacacc   2820
aagtacgacg agaacgacaa gctcatccgg gaggtgaagg tcatcaccct caagtcgaag   2880
ctcgtgagcg acttccgcaa ggacttccag ttctacaagg tccgggagat caacaactac   2940
caccacgccc acgatgctta tcttaacgcc gtggtgggga cggccctcat taagaaatac   3000
ccgaagctgg agtcggagtt cgtgtacggc gactacaagg tgtacgacgt caggaagatg   3060
atcgccaagt ccgaacagga gatcgggaag gccacggcga aatacttctt ctacagcaac   3120
atcatgaact tcttcaagac cgagatcacc ctcgccaacg gcgagatccg caagcgcccg   3180
ctcatcgaga cgaacgggga gaccggcgag atcgtctggg acaaggggcg cgacttcgcc   3240
actgtgcgga aggtgctgtc gatgccccag gtcaacatcg tcaagaagac ggaggtccag   3300
acgggcgggt tcagcaagga gagcatcctg ccgaagcgca acagcgacaa gctgatcgcc   3360
cgcaaaaagg actgggatcc aaaaaagtac ggcggcttcg acagccccac cgtcgcctac   3420
agcgtcctcg tcgtcgctaa agtcgagaag ggcaagtcca aaaagctcaa gagcgtcaag   3480
gagctgctcg ggatcaccat catggagcgg tccagcttcg agaagaaccc aattgatttc   3540
ctggagcgca agggctacaa ggaggtcaag aaagacctca tcataaagct gccgaagtac   3600
tcactcttcg agctggagaa cgggcgcaag cggatgctgg cgtcggccgg agagctccaa   3660
aagggcaacg agctggcgct gccgagcaag tacgtgaact tcctctacct ggcgtcccac   3720
tacgagaagc tcaagggcag tccagaggat aacgagcaga agcagctatt cgtggagcag   3780
cacaagcact acctggacga gatcatcgag cagatcagcg agttctccaa gcgcgtcatc   3840
ctggcggacg ccaacctgga caaggtgctg tccgcgtaca acaagcaccg cgacaagccg   3900
atccgcgagc aagccgagaa catcatccac ctgttcaccc tcacgaacct cggggcaccc   3960
gccgccttca aatatttcga cacgaccatc gaccgcaagc gctacaccag cacgaaggag   4020
gtgctcgacg ccaccctgat ccaccagagc atcaccgggc tgtacgagac ccgcatcgac   4080
ctctcgcagc tcggcggga c                                              4101
```

```
SEQ ID NO: 62          moltype = DNA  length = 4101
FEATURE                Location/Qualifiers
source                 1..4101
                       mol_type = other DNA
                       organism = synthetic construct
SEQUENCE: 62
gacaagaagt acagtattgg attggccatc gggacgaaca gcgtgggctg ggccgtcatc   60
accgacgagt acaaggtgcc atccaagaag tttaaggttc tggggaatac cgaccgccac   120
tcgatcaaga aaaatctcat cggggcgctg ctttttcgaca cgcggcgagac ggcggaagcg   180
acgcggctca agcggacggc tcgtcgccgt tacacccgga gtaagaaccg catctgttac   240
ctccaggaga tattcagcaa cgagatggcg aaggtgacg actcctttt ccaccgtctt   300
gaggagtcct tcctggtcga ggaggacaag aagcacgagc gccacccgat cttcgggaac   360
atcgtggacg aggtggccta ccacgagaag tacccacga tctaccacct ccgcaaaaaa   420
ctcgtggact caactgacaa ggccgatttg aggcttatct acctcgccct cgcccacatg   480
attaagttcc gtgggcactt cctaatcgag ggtgacctca acccgacaa ctctgacgtg   540
gacaagctgt tcatccagct tgtgcagacc tacaatcagc tctttgagga gaatccgatc   600
aacgcatctg gtgtggacgc aaaggccatc ctcagcgcgc ggctgagcaa gtctaggcgg   660
ttggagaacc tgatcgccca actgcccggc gagaagaaaa tggcctctt cggcaacctg   720
atcgccctgt cgctgggggct cacgccgaac ttcaagagta actttgacct ggcggaggac   780
gctaagctcc agctatctaa ggacacatac gacgacgacc tggacaacct gctggccag   840
atcggcgacc agtacgccga cctcttccta gccgccaaga acctgtccga cgccatcctc   900
ctcagcgaca tcctgcgcgt gaacacggag atcacgaagg ctccgctcag cgcctccatg   960
attaagcggt acgacgagca ccaccaagac ctaactttac tcaaagccct cgtgcggcag   1020
cagcttcccg agaagtacaa agagatattt tttgatcagt ccaagaacgg ttatgcgggc   1080
tacatcgacg gcggcgcgag ccaggaggaa ttctacaagt tcatcaagcc catcctggag   1140
aagatggacg gcacggagga gctgctcgtg aagctcaacc gtgaagacct cctgcgaaag   1200
cagcgaacct cgacaacgg ttcgatcccg caccagatcc acctcgggga gctgcacgcc   1260
atcctgaggc gacaggagga cttctaccct ttcctaaagg acaaccgcga gaagattgaa   1320
aaaatcctga cgtttcgcat acctactac gtcggccgc tggcgcgcgg caactcccgg   1380
ttcgcctgga tgacccgtaa gagcgaggag acgatcaccc cgtggaactt cgaggaggtc   1440
```

-continued

```
gtggacaagg gcgcgagcgc gcagagcttc atcgagcgca tgaccaactt cgacaagaac  1500
ctcccgaacg agaaggtgct cccaaagcac tccctcctgt acgagtattt caccgtgtac  1560
aacgagttga caaaggtgaa gtacgtgacg gaggggaatgc ggaagcctgc gttcctctcg  1620
ggcgagcaga agaaggcaat cgtggacctg ctcttcaaga ccaaccggaa ggtgacggtg  1680
aagcagctca aggaggacta cttcaaaaaa atcgagtgct tcgactccgt ggagataagc  1740
ggcgtggagg accgattcaa cgcctccctc ggcacctacc acgacctcct taagatcatc  1800
aaggacaagg acttcctgga caacgaggag aacgaggaca tcctggagga catcgtgctc  1860
accctgaccc tcttcgagga ccgggagatg atcgaggagc gcctcaagac gtacgcccac  1920
ttgttcgacg acaaggtgat gaagcagctc aagcggcggc gatacaccgg gtggggccgc  1980
ctatcccgca aacttatcaa cggcatccgc gacaagcagt ccggcaagac gatcctggat  2040
ttcctcaagt cggacgggtt cgccaaccgg aacttcatgc agctcatcca cgacgacagc  2100
ctcacgttca aggaggacat ccagaaggcc caagtgagcg gtcaagggga cagcctccac  2160
gagcacattg cgaaccttgc tgggagccct gcgatcaaga aggggatatt gcaaaccgtg  2220
aaggtcgtgg acgagttggt gaaggtcatg gggcgacaca agcccgagaa catcgtgatc  2280
gagatggcca gggaaaatca gaccacgcag aagggccaaa aaaacagccg cgagcggatg  2340
aagcggatcg aggagggcat caaggagctg gggtcgcaga tcctcaagga gcacccggtg  2400
gagaacacgc agctccagaa cgagaagctg tacctctatt acctacagaa cgggcgggat  2460
atgtacgtgg accaggagct agacatcaac cgcctgtccg actacgacgt ggaccatatc  2520
gtcccgcagt cgttcttgaa ggacgacagc atcgacaaca aggtgctcac aagatcggat  2580
aagaatcgag gcaagtccga caacgtgccc tcggaggagg tggtcaagaa aatgaaaaac  2640
tactggcggc agttgctgaa cgccaagctc attacgcagc ggaagttcga caacctgacg  2700
aaggctgaac gtggtgggct cagcgagcta gacaaggcgg ggttcatcaa gcggcagctc  2760
gtcgagaccc ggcagatcac caagcacgtg gcgcagatcc tggactcgcg catgaacacc  2820
aagtacgacg agaacgacaa gctcatccgt gaggtgaagg tcatcaccct taagtctaag  2880
ctggtcagtg acttccgcaa ggacttccag ttctacaagg tccgggagat caacaactac  2940
caccacgcgc acgacgccta cctcaacgcg gtggtgggga cggcgcttat taagaaaat  3000
cccaagctgg aaagcgagtt cgtttacggc gactacaagg tgtacgacgt ccgcaagatg  3060
atcgcaaagt cggaacagga aatcggaaag gcgacggcca aatatttctt ttactccaac  3120
atcatgaatt tttttaagac ggagatcacc ctggcgaacg gggagatccg caagcggccc  3180
ctcatcgaga ccaacgggga gacgggcgag atcgtctgga acaagggccg ggacttcgcc  3240
accgtgcgga aggtgctttc tatgcctcaa gtcaatatcg tcaaaaagac agaggtgcag  3300
accggcgggt tcagcaagga gtctatcctg ccgaagcgca actcggacaa gctcatcgcg  3360
cgcaagaaag actgggaccc caaaaaatat ggcgggttcg actcgccgac cgtcgcctac  3420
agcgtcctcg tggtggctaa ggtcgagaag ggcaagagca aaaagctaaa gtcggtgaag  3480
gagctgctgg gcatcaccat catggagcgc tcgtcttcg agaagaatcc aatcgacttc  3540
ctagaggcga aggggtacaa ggaggtcaaa aaggatctta tcatcaaact gccgaagtac  3600
agtctgttcg agctggagaa cgggcggaag cggatgctgg ctagtgcggg cgagttgcag  3660
aagggcaacg agttggcact gccctccaag tacgtgaact tcctgtacct ggcctccac  3720
tacgagaagc tcaaggggag ccccgaggac aacgagcaga agcagctatt cgtcgagcag  3780
cacaagcact acctggacga gatcatcgag cagatcagtg agttctccaa gcgggtcatc  3840
ctcgcggacg ccaacctgga caaggtgctg agcgcgtaca caaagcacag ggacaagcca  3900
atcagggaac aggccgagaa catcatccac ctgttcaccc tgaccaacct gggtgcaccg  3960
gctgccttca gtactttga cacgaccatc gaccggaagc gctacacctc cacgaaggag  4020
gtgctggacg ccacgctgat ccaccagagc atcaccgggc tctacgagac acggatcgac  4080
ctgagccagc ttggcggggga c                                          4101
```

SEQ ID NO: 63          moltype = DNA  length = 4092
FEATURE                Location/Qualifiers
source                 1..4092
                       mol_type = other DNA
                       organism = synthetic construct
SEQUENCE: 63

```
gacaaaaagt attccattgg actcgctatc ggcacgaaca gcgtcgggtg ggcggtcatc  60
actgacgagt acaaggtgcc gagcaagaag tttaaggtgc tgggaaacac cgacaggcac  120
tcgatcaaga aaatcttat cggggcccta ctcttcgact ccggagaaac cgccgaggcc  180
acccggttga agcgcacggc ccgggcgtcgc tacaccaggc gcaagaaccg gatctgctac  240
ctccaggaga tattcagcaa tgagatggcg aaggtggacg actcgtTTTT tcacaggcta  300
gaggagtctt tcctcgtgga ggaggacaag aaacacgagc gccaccccat cttcggcaac  360
atcgtggatg aggtggcata tcacgagaag tacccaacca tctaccacct ccgcaaaaag  420
ctcgtggact ctaccgacaa ggccgacctc cgtctgatct acctcgcgct ggcccacatg  480
attaagttcc gaggacactt tctgatcgag ggcgacctga acccagacaa cagcgacgtg  540
gacaagctgt tcatccaact tgtccagacc tacaatcagc tcttcgagga gaaccctatc  600
aacgcctcgg gcgtggacgc gaaggccatc ctgtccgccc gcctgagcaa gtcgcggcgg  660
ctggagaacc tgatcgccca gctccccggc gaaaaaagaa acggcctctt cggcaacctc  720
atcgcgttgt cgctggggct caccccgaac ttcaagtcca acttcgacct ggccgaggac  780
gctaaactcc agctctcgaa ggataacctac gacgacgacc tcgacaacct gctggcccag  840
atcggcgacc agtacgcgga cctttttcctg gcggccaaga acctgagcga cgcgatcctc  900
cttagcgaca tactccgtgt gaacaccgag atcacgaagg ccccgctctc cgcgtccatg  960
attaagcgct acgacgagca ccaccaagac cttaccctgc ttaaggcgct ggtcaggcag  1020
cagttaccgg agaagtacaa ggagatcttt tttgatcaat ctaagaacgg ttacgccggg  1080
tacatcgacg gcggcgcgtc ccaggaggag ttctacaagt catcaagcc gatcttggag  1140
aaaatggacg ggaccgagga gctgctcgtg aagctcaacc gcgaagacct cctccgcaag  1200
cagcgcacct tcgacaacgg gagcatcccg caccagatcc acctgggaga gctgcacgcg  1260
atcctgcgga gacaagagga cttctacccc ttcctcaagg acaaccggga gaagattgaa  1320
aaaatactta ctttttcgtat cccgtactac gtcgggcccc ttgcgagggg caactccaga  1380
ttcgcgtgga tgacccgcaa gtccgaggag accatccccc cgtggaactt cgaggaggtg  1440
gtggacaagg gcgcgtcggc ccagtcgttc atcgagcgca tgaccaactt cgacaagaac  1500
cttccgaacg agaaggtgct cccgaagcac agcctgctct acgaatattt tactgtgtac  1560
aacgagctga cgaaggtcaa gtacgttacg gaggggatga ggaagcccgc cttcctctcc  1620
```

-continued

```
ggcgagcaga agaaagccat tgtggatctc ctgttcaaga ccaaccgcaa ggtgacggtg  1680
aaacagctca aagaggacta cttcaagaag atcgagtgct tcgactccgt agagatcagc  1740
ggggtcgagg accgcttcaa cgcctcgctg ggcacgtacc acgacctgct aaagattatc  1800
aaggacaaag acttcctaga caatgaggag aacgaggaca ttctggagga catcgtgctg  1860
actctgacgc tgttcgaaga ccgcgagatg atcgaggagc ggcttaagac gtacgcccac  1920
ctgttcgacg acaaggtgat gaagcagttg aaacggcggc gctacaccgg gtggggccgc  1980
ctctcccgca agctcatcaa cggcatccgc gacaagcagt cggggaagac gatcctggac  2040
ttcctcaaga gcgacggctt cgccaaccga aacttcatgc agctaatcca cgacgacagc  2100
ctgacgttca aggaggacat ccagaaggcc caagtgagcg gccagggaga ctcgctacac  2160
gagcatatcg ccaacctggc tggcagcccg gcgattaaga aaggaatcct ccaaaccgtc  2220
aaagtggtgg acgagctggt gaaggtgatg ggccgccaca agcccgagaa cattgtgatc  2280
gagatggcgc gggagaacca gacgacgcag aagggccaaa aaaatagcag ggaaaggatg  2340
aagcgaatag aggaggggat caaggagctg gggagccaga ttctcaaaga gcacccggtc  2400
gagaacacac agctccagaa cgagaagctg tacctctact acctccaaaa cggccgcgat  2460
atgtacgtgg accaggaact agacatcaac cggctgagcg actatgacgt ggaccacatc  2520
gtgccgcagt ccttcctcaa ggacgactcg attgacaaca aagtgctcac tagatccgac  2580
aagaacagag gcaagagcga taacgtcccg tcggaggagg tcgtcaagaa aatgaaaaac  2640
tactggcggc agctcctaaa cgccaagctc atcacgcagc gtaagttcga caacctgacg  2700
aaggcggagc ggggcgggct gagcgagctg gacaaagcgg ggttcatcaa gcggcagctc  2760
gttgagacgc ggcagatcac aaagcacgtc gcgcaaatcc tcgactcccg catgaacacc  2820
aagtacgacg agaacgacaa gctcatccgg gaggtgaagg tcattaccct taaatcgaag  2880
ctcgtcagcg actttcgtaa ggacttccag ttctacaagg tcagagagat caacaactac  2940
caccacgccc acgacgccta tctgaacgcc gtggtgggca ccgcgcttat taagaagtac  3000
cccaagctgg agtccgagtt cgtgtacggc gactacaagg tttatgacgt caggaagatg  3060
atcgccaagt cggaacagga gatcggaaaa gctaccgcca aatatttctt ctatagcaac  3120
atcatgaact tcttcaaaac cgagatcacc ctcgccaacg gcgagatccg gaagcgccac  3180
ctcatcgaga ccaacgggga gaccggggag atcgtctggg acaaggggcg ggacttcgct  3240
actgtccgaa aggtgctctc catgccacaa gtgaatatcg tcaagaaaac agaggtgcag  3300
accggagggt tcagtaagga gtccatcctg cccaagcgga actccgacaa gctaattgct  3360
cgcaaaaagg attgggatcc taaaaaatat ggcggcttcg actcgcccac ggtcgcctac  3420
tctgtgctgg tcgtggcgaa ggtggagaag ggcaagtcca agaagctcaa gagcgtcaag  3480
gagctgctgg ggatcacgat catggagcgt agttcgtttg agaagaatcc catcgacttc  3540
ctggaggcta agggctacaa ggaggtcaaa aaggacctca tcattaagct gccgaagtac  3600
agcctcttcg agctggagaa cgggcggaaa cgtatgctcg cctccgctgg ggagttacaa  3660
aaggggaacg agctggcgct gccgtctaag tacgtcaact tcctgtacct ggcctcccac  3720
tacgagaagc tcaaggggtc gccggaggac aacgagcaga agcagctctt cgtagagcag  3780
cacaagcact acctggacga gatcatcgag cagatttcag agttctcaaa gcgggtcatc  3840
ctcgccgacg ccaacctgga caaggtgctc tcggcctaca acaagcaccg ggacaagccg  3900
atccgcgaac aggccgaaaa catcatccac ctgttcacgc tcaccaacct cggtgcccgg  3960
gcggccttca gtactttga cacgaccatc gaccggaagc gctatacctc gacgaaggag  4020
gtgctggacg ccaccctgat ccaccagtcc atcaccgggc tttacgagac ccggatcgac  4080
ctctcgcagc ta                                                       4092
```

SEQ ID NO: 64          moltype = DNA   length = 4101
FEATURE                Location/Qualifiers
source                 1..4101
                       mol_type = other DNA
                       organism = synthetic construct
SEQUENCE: 64

```
gacaagaagt atagtattgg actcgccatc ggaaccaact ctgtggggtg ggctgttatt  60
acagatgaat ataaggtgcc atccaaaaag tttaaagttc tgggcaatac tgatagacac  120
tcaatcaaga agaatctgat aggtgcactt ctgtttgata gtggagagac tgccgaggca  180
accagactta aaaggactgc aagaagaaga tataccagaa gaaagaatag gatttgctat  240
ttgcaggaaa tcttcagcaa cgaaatggcc aaggttgatg actcattttt ccataggtta  300
gaggagagtt ttcttgtgga ggaagataag aagcacgaaa gacacccaat tttcgggaat  360
atagtggacg aggtggctta tcatgagaag tatcccacta tctaccacct gagaaagaaa  420
cttgtggact caaccgataa ggctgatctt aggcttatat acttggccct tgcacatatg  480
atcaaattca ggggccattt tcttatcgaa ggcgatctta tcccgataa ctcagatgtg  540
gacaagctgt ttatacaact acaatcaac tcttcgagga gaatcccatt  600
aacgcctccg gcgtgatgc aaaagccata ctgtcagcca gactgagcaa aagtaggaga  660
ctggagaatc ttatagccca actgcccggt gaaaagaaga atgggctct cggaaatctg  720
atcgctcttt cattggggt gacacccaac tttaagagta actttgactt ggcagaagat  780
gcaaagttgc agctcagtaa agacacatat gacgatgacc ttgacaatct cttggcacaa  840
ataggggatc aatacgctga ccttttcctc gctgccaaga cgctactg  900
ttgtccgaca ttcttagggt taataccgaa attacaaagg cccctcttag tgcaagtatg  960
atcaaaaggt atgatgagca tcaccaagac cttacactgc tgaaggctct ggttagcag  1020
caactcccta aaaagtataa ggaaatattc ttcgaccaaa gtaagaacgg gtacgccggt  1080
tatattgatg ggggcgcaag tcaagaagaa ttttacaaat tcatcaagcc aattcttgaa  1140
aagatggacg ggactgagga attgctggtg aaactgaata gagagacct cttagaaaa  1200
cagaggacat ttgacaatgg gtccatccca caccagattc atctggggga actccacgca  1260
atattgagga gacaagaaga cttttaccca ttccttaagg ataatagaga gaaatcgaa  1320
aaaatcctga ctttcaggat tccttactat gttgggccac tggccagggg gaactcaaga  1380
ttcgcttgga tgacaaggaa gtcagaagaa accataaccc cttggaattt tgaagaggtg  1440
gttgataagg gggcatcagc ccagtcttc atagagaaa tgataaaaat tgataaaaat  1500
cttccaaatg agaaggtttt gccaaaacat agtctttgt acgagtactt tactgtttat  1560
aacgaattga ccaaggtgaa gtatgtgacc gagggaatga ggaagccagc attttttgtcc  1620
ggggagcaaa agaaagcaat cgttgatctt ctcttcaaga ccaacagaaa agtgaccgtg  1680
aaacaactga aggaagacta cttcaaaaag atagaatgtt tcgattcagt ggaaattagc  1740
ggtgttgaag acaggttcaa tgcttcattg ggtacttacc acgacctgtt gaagataatc  1800
```

```
aaagacaagg actttctcga taatgaggag aacgaagaca tcttggaaga cattgtgctt 1860
acactcactt tgtttgagga cagggaaatg attgaggaaa gactcaaaac ttacgctcat 1920
ttgtttgatg ataaggttat gaaacaacta aaaagaagaa ggtacaccgg ctggggaaga 1980
ttgagtagga aactgatcaa cggtattaga gataaacaat ccggaaagac tatcctcgat 2040
ttccttaaga gtgatggctt tgcaaatagg aattttatgc agctgattca tgacgactca 2100
cttaccttca aagaagacat ccaaaaagct caggtgtctg ggcaaggcga cagtctgcat 2160
gaacatatag ctaacttggc tgggagtccc gccatcaaga aggggatact tcaaacagtt 2220
aaagttgtgg acgaattggt gaaggtaatg ggaaggcaca agcctgaaaa tatagtgata 2280
gaaatggcaa gggaaaatca aacaacccag aagggacag agaacagtag ggaaaggatg 2340
aaaaggatag aagaggggat caaagagctt ggtagccaga tcctcaagga acatccagtg 2400
gagaataccc aacttcaaaa cgagaaactc tatttgtact acttgcagaa cggaagagat 2460
atgtatgtgg accaagagct tgatattaac aggctgagcg attatgacgt tgaccacata 2520
gtgccccaat cattcctcaa ggatgactct attgataata aggtgctgac aaggagtgac 2580
aagaatagag ggaaatccga caacgttcca tccgaggaag ttgtgaagaa gatgaagaac 2640
tactggaggc agttgctgaa cgctaagctc attacccaga ggaaattcga taacctgacc 2700
aaagcagaga gaggcgggct gagcgaactc gataaagcag gtttcatcaa gagacaactc 2760
gtggagacta ggcaaattac taagcacgtg gctcaaatac tcgacagcag gatgaacaca 2820
aagtacgacg agaacgacaa gctcattaga gaggttaagg ttattactct gaaaagtaaa 2880
ttggttagcg atttcagaaa ggatttccaa ttctataagg ttagagagat caacaattat 2940
catcatgcac atgatgccta tctgaatgct gtggttggta cagcccttat caagaagtac 3000
cctaagctag agagcgagtt tgtgtacgga gattataagg tgtatgatgt gaggaaaatg 3060
atcgctaaaa gtgagcaaga gattggaaag gctaccgcca aatacttctt ttattccaat 3120
attatgaatt tcttcaagac agaaatcacc ctggctaacg gcgagataag gaagaggccg 3180
cttatcgaaa ctaatgggga gacaggcgaa atagtgtggg acaaaggag ggatttcgca 3240
actgtgagga aggttttgag catgcctcag gtgaatatcg ttaagaaaac cgaagttcaa 3300
actggagggg tctctaagga aagcattctc cccaagagga actccgacaa gctgattgct 3360
agaaagaaag actgggaccc caagaagtat ggcgggattcg actcacccac tgtggcatat 3420
agcgttctcg tggtggcaaa ggttgaaaag ggtaaatcca aaaaactcaa atccgtgaag 3480
gaactccttg gcataactat tatggaaagg agtagctttg aaaagaatcc catcgacttt 3540
ctcgaagcta agggctataa ggaagttaag aaggacctta taatcaaact tccaaaatac 3600
tccctttttg agttggaaaa cggcagaaag agaatgttgg ccagtgccgg ggagcttcaa 3660
aagggcaacg aactggctct gcctagcaaa tatgtgaact ttttgtatct ggcatcacac 3720
tacgagaaac ttaaaggctc tcctgaggac aacgagcaaa aacagctctt tgttgaacag 3780
cataagcact acctcgacga gattattgag cagatcagcg agttctcaaa gagagttatt 3840
ctggctgacg ctaatcttga caaggttttg tccgcttaca acaaacacag ggataagcca 3900
atcagggagc aggcagaaaa cataatccat ctctttaccc tgacaaacct cggtgcccc 3960
gctgctttca agtattttga tactaccatt gacaggaaga gatatacttc cactaaggaa 4020
gtgctcgacg caaccctcat acaccaaagt atcacaggcc tctatgaaac taggatagat 4080
ttgtctcaac ttgggggcga t                                            4101
```

```
SEQ ID NO: 65          moltype = DNA  length = 4101
FEATURE                Location/Qualifiers
source                 1..4101
                       mol_type = other DNA
                       organism = synthetic construct
SEQUENCE: 65
gacaaaaagt attccatcgg gcttgctatc ggaaccaact ctgtggggtg ggcagttatt 60
accgacgaat acaaggtgcc cagcaagaag tttaaggttc tggggaacac agatagacat 120
agcataaaga aaaacctgat aggcgcactg ttgttcgact ccggggaaac agccgaagct 180
accaggctga agagaactgc aagaagaagg tacaccagaa gaaaaaacag aatatgttat 240
ctccaagaga ttttctctaa cgagatggcc aaggtgacg actcattctt tcacagactg 300
gaagaatctt tccttgtgga agaagataag aaacacgaga ggcaccctat tttttggcaat 360
atcgtggatg aggtggctta ccacgaaaaa taccctacaa tataccacct caggaaaaaa 420
ttggttgata gtacagacaa ggccgacctc aggctcatct atttggccct ggcccatatg 480
attaaattca gggggcactt tctcatcgag ggagatttga accccgacaa cagtgatgtt 540
gataagctct ttattcagct cgtgcagact tacaatcagt tgtttgagga aaaccccatt 600
aatgcttccg gggtggacgc caaggcaatc ctttctgcaa gactctcaaa gtcaaggaga 660
ctcgaaaatc tgatagcaca gcttccagga gagaagaaga cgggctctt tggaaacctg 720
atcgctctgt cactcggact cacacccaat ttcaaaagca attttgattt ggcagaggac 780
gctaagctgc aactcagtaa ggatacctac gacgatgact tggataatct gctcgcacaa 840
attggggacc agtatgcaga cctgtttctc gcagctaaga acttgagtga cgccatattg 900
ctcagtgaca tcctcagggt taataccgag attacaaaag ctccactctc tgcaagcatg 960
atcaagaggt atgacgagca ccatcaagac ctgacactcc ttaaggcgtt ggttaggcag 1020
caacttcctg aaaagtataa ggaaatcttc ttcgatcaaa gcaaaaacgg ctacgccgtg 1080
tatatagacg ggggagcatc ccaagaagaa ttttataagt tcataaaacc tatattggag 1140
aagatggacg ggacagagga attgctcgtg aaactgaaca gggaggatct cctcaggaag 1200
caaaggacct tcgacaatgg ctccatccca atcagattc acctcggcga actgcacgca 1260
atactgagaa gacaagagga cttttatcct ttcctgaagg acaacaggga gaaaatcgag 1320
aaaatcttga cattcagaat cccatactac gttgggcctc tggccagagg taacagtagg 1380
ttcgcctgga tgactaggaa atcagaggag actattacac cctggaactt tgaagaagtt 1440
gttgataagg gagcttcagc acaatcattc atcgaaagaa tgacaaactt tgacaaaaat 1500
ctgcctaatg agaaagtgct cccaaaacat tccctgctgt atgagtattt taccgtttat 1560
aacgagctta ccaaggtgaa atacgttact gaaggtatga aaagccagc ttttctttca 1620
ggggagcaaa gaaaggctat cgtggatctt ctctttaaga ccaacagaaa ggtaccgtg 1680
aagcagctta aggaagacta ctttaaaaag atcgagtgtt ttgactcagt ggaaataagc 1740
ggtgttgaag atagattcaa cgcatccttg ggaacttatc atgatcttct taagataatc 1800
aaggataaag actttctcga caacgaggaa aacgaagata tactggagga catagttctg 1860
acacttactt tgttcgagga tagggagatg atcgaggaaa gactgaaaac atatgctcac 1920
cttttcgacg acaaagttat gaaacaactc aagagaagga gatatacagg gtgggggaga 1980
```

-continued

```
ttgagcagga aactgattaa tggtatcaga gacaaacagt caggaaaaac aatactcgac  2040
tttttgaaat cagacgggtt cgcaaatagg aatttcatgc agcttataca cgacgattca  2100
cttactttta aagaggacat tcaaaaggct caagttagtg gacaaggtga ctccctccac  2160
gaacacatcg caaatctcgc tggcagccct gcaattaaga agggtatact ccagacagtt  2220
aaggttgttg acgagctggt taaagtgatg ggaagacaca aacccgagaa catagtgata  2280
gagatggcca gggaaaacca aaccactcaa aaagggcaga aaaattccag agagaggatg  2340
aaaaggattg aagaaggtat caaggagctg ggtagccaaa ttctgaaaga acatcctgtg  2400
gaaaacactc aactccagaa tgagaaactc tatctgtact atctgcaaaa tgggagagat  2460
atgtatgtgg accaggaact ggacataaac aggctctcag attacgatgt ggatcatatc  2520
gtgccacagt cctttcttaa ggatgatagc atcgacaata aggtgcttac caggtccgac  2580
aagaacaggg gaaagtcaga taacgtgcct tctgaagaag ttgttaaaaa gatgaagaac  2640
tactggagac agctgcttaa cgctaagctc ataacacaga ggaagtttga caacttgacc  2700
aaggccgaga gaggcggact ctcagaattg gataaggcag ggttcataaa aaggcagctg  2760
gtggaaacaa ggcagataac taaacatgtg gctcagatcc tcgatagtag gatgaataca  2820
aaatacgatg agaacgacaa gctcataagg gaggttaaag tgataactct gaaatccaaa  2880
ctggttagcg attttaggaa ggatttccag ttttacaaag ttagggagat caacaattat  2940
catcacgccc acgatgccta cttgaacgca gttgtgggta ctgcacttat caaaaagtac  3000
cctaagctgg aatccgagtt tgtttatgga gactataagg tgtacgacgt tagaaaaatg  3060
attgcaaagt cagagcagga gatagggaaa gccactgcaa aatatttctt ttatagcaat  3120
atcatgaatt tctttaagac agaaatcaca ctggccaatg gggaaataag gaagaggccc  3180
ctgatcgaaa ctaatggcga gacaggggag attgtgtggg ataaaggtag ggactttgca  3240
acagtgagga aagtgctgag catgccccaa gttaatatcg ttaaaaagac cgaggttcaa  3300
acaggggggct ttagtaagga aagcattttg cccaagagga atagtgacaa attgattgct  3360
aggaaaaaag attgggaccc caaaaagtat ggcggatttg atagccccac tgttgcttac  3420
tccgtgctcg tggttgcaaa ggtggagaag ggaaagagca agaaactgaa gtcagttaag  3480
gaactccttg gtatcactat catggaaaga agctcctttg agaagaaccc tattgacttc  3540
ctggaggcta aagggtacaa agaggttaag aaagacctta tcattaaatt gcccaaatat  3600
agtcttttcg agcttgaaaa cggaagaaag aggatgcttg catccgctgg cgaattgcaa  3660
aagggcaatg agcttgctct cccttccaag tatgtgaact tcctttatct tgcctcacac  3720
tatgaaaaac tcaaaggttc acccgaagac aacgaacaaa agcaactatt tgtggaacaa  3780
cacaagcact acctggacga aatcattgag caaatttctg agttttcaaa aagggtaatc  3840
ttggctgacg caaatctcga caaagttttg tcagcttaca acaaacatag agataagcca  3900
attagagagc aagctgagaa tatcatccat ctgtttaccc tgactaacct tggagcgcct  3960
gctgctttta aatatttcga caccacaatc gacaggaaga ggtacactag cactaaggaa  4020
gttctcgacg ccaccctcat ccaccagagt attacaggcc tgtacgagac aagaattgat  4080
ctttctcaac ttggtggtga c                                           4101
```

```
SEQ ID NO: 66          moltype = DNA  length = 4101
FEATURE                Location/Qualifiers
source                 1..4101
                       mol_type = other DNA
                       organism = synthetic construct
SEQUENCE: 66
gataagaagt actcaatcgg tctggcaatc ggaaccaact ctgtgggttg ggcagtgatt  60
acagatgagt ataaggtgcc aagcaaaaaa ttcaaggtgc tgggtaatac cgacagacac  120
agcattaaga agaatttgat tggagcactc ctctttgact caggggaaac agcagaggca  180
acaaggctga agaggacagc aaggcggagg tacacaaggc ggaaaaacag gatatgctac  240
ctccaggaaa tctttagcaa cgagatggct aaagtggatg atagcttttt ccatagactc  300
gaagaatcct tcttgttga agaggacaaa aagcatgaaa ggcatcccat cttcggcaat  360
atagttgatg aggttgcata ccatgagaag taccccacaa tctaccacct cagaaagaaa  420
cttgtggact ccacagataa agcagacctg aggctcatat acctcgcact cgcacacatg  480
atcaagttca gagggcactt tctcatcgaa ggtgacctga tccagataa ttcagatgtg  540
gataaactgt ttatacagct ggtgcaaaca tacaaccaac ttttcgagga aaacccaatc  600
aatgcctccg tgttgatgc aaaggccatc ctgtcagcaa gactcagcaa aagcaggcgg  660
ctcgaaaacc tcatcgccca gcttcccggt gaaaagacaa acgggctctt tggtaatctc  720
atcgcattga gccttggtct tactccaaac ttcaagagca attttgatct ggcagaggat  780
gctaaactgc aactctcaaa ggacacatat gacgatgacc ttgacaatct gttggcccag  840
atcgggggacc aatatgcaga cctcttcctg gccgcaaaga atctgtcaga tgcaatcctc  900
ttgtccgaca tactgagagt taacactgag atcacaaagg cacctctgtc cgcctccatg  960
attaagagat acgatgagca tcaccaggat ctgactttgc tcaaagccct cgttagacag  1020
cagttgccag aaaagtacaa agaaatattc tttgatcaat caaaaaacgg atatgcaggg  1080
tacatcgacg gtggggcaag ccaggaagag ttctacaaat catcaaaacc tatcctggaa  1140
aagatggatg gacagaaga gctgctggtt aagctgaata gggaagacct cctcagaaag  1200
cagaggacat ttgataacgg gagcatccct catcaaatcc acctcggtga actccatgct  1260
atcctgagaa ggcaggaaga cttttatcca ttttttgaagg acaataggga gaaaatcgaa  1320
aaaatcctga cattcagaat cccatactac gttggtcctc tggcaagagg taacagtagg  1380
ttcgcatgga tgacaaggaa aagcgaggag acaatcacac cctggaattt tgaggaagtt  1440
gttgacaagg gtgccagcgc acaatccttt atcgaaagaa tgacaaattt cgacaagaat  1500
ctgcctaacg aaaaggttct cccaaagcat tcactcctgt acgaatattt tacagtttat  1560
aacgaactga ctaaagttaa atacgttacc gagggtatga ggaagccagc attcctttcc  1620
ggggaacaga gaaaagctat tgtggacctc ctgttcaaga caaatagaaa agtgacagtt  1680
aagcaactca agaggattca cttcaaaaag atcgaatgtt ttgactctgt ggagatcagc  1740
ggggtggagg atagattcaa cgccagcctg gtacatatc atgatctcct gaaaatcatt  1800
aaagacaagg acttccttga caacgaggag aacgaggaca ttctggaaga cattgttctg  1860
accctcacac tctttgagga tagggagatg attgaggaa gactgaagac ctacgcccac  1920
ctctttgacg ataaagtgat gaaacagctc aagagaagaa ggtatacagg ttgggggaga  1980
ctgagcagga agttgatcaa tgggattagg gacaaacagt ccgggaaaac aatcctcgat  2040
tttctgaagt cagacggttt cgcaaacaga aatttatgc agctcattca cgatgacagc  2100
ttgacattca aggaagacat ccaaaaggct caagtgagcg gccaaggga tagcctccac  2160
```

-continued

```
gagcatattg caaatctggc aggttcacca gccatcaaaa agggcatact tcagacagtt    2220
aaggttgtgg acgaattggt taaagttatg ggcaggcata agccagagaa tatcgttatc    2280
gaaatggcaa gggagaacca aacaactcaa aaagggcaga aaaatagcag agagaggatg    2340
aaaagaatcg aggaagggat caaggaactt gggtcccaaa tcctcaagga gcacccagtt    2400
gaaaatactc aactgcaaaa cgagaagctc tatctctact atctccaaaa cgggagggat    2460
atgtatgttg accaggagct ggatattaac agactgtcag attatgatgt tgatcatatc    2520
gtgccccagt cattcctgaa ggacgattcc atcgacaaca aagttctcac aaggtccgat    2580
aaaaacaggg gcaagtccga taacgttcca agcgaagaag tggtgaaaaa gatgaaaaac    2640
tattggagac aacttctgaa tgcaaagttg attactcaga gaaagtttga caacctcaca    2700
aaagcagaaa gaggcgggct tagcgaactc gataaggcag ggtttatcaa aagcagctg     2760
gttgagacaa ggcagatcac aaaaacatgtg gcacagatcc ttgactcaag gatgaatacc    2820
aagtatgatg agaatgataa gttgatcagg gaggttaaag ttatcacact caaatccaaa    2880
ctggtgtcag acttcaggaa agactttcaa ttttataagg tgagggagat caataactac    2940
caccatgcac atgacgccta cctgaacgca gtggtgagca cagcattgat taaaaaatac    3000
cctaagctgg agtctgagtt tgtgtacggg gactacaagg tgtacgacgt gaggaaaatg    3060
atagccaagt ccgagcagga gatcgggaaa gcaacagcta agtatttctt ttacagtaat    3120
atcatgaatt tctttaaaac tgagattact ctggcaaacg gggagatcag gaaaagaccc    3180
ctcatcgaga ctaatggtga aacaggtgag atcgtttggg acaaggggag ggattttgct    3240
actgttagaa aagttctgag tatgccacaa gtgaatattg tgaaaaagac agaagttcag    3300
acaggtgggt tctccaaaga atccatcctg cccaagagaa attcagacaa gctcatcgca    3360
agaaagaagg actgggaccc taagaagtac ggaggatttg acagcccccac cgtggcctat    3420
tccgtgcttg ttgtggcaaa ggtggagaaa gggaagagca aaaaactgaa atccgtgaaa    3480
gaactgctgg gaattaccat catggaaaga agctcctttg agaagaaccc aatcgacttc    3540
ctggaagcaa aaggatataa ggaagtgaaa aaggacctca ttatcaagct cccaaaatac    3600
tcacttttcg agttggagaa cggtagaaag aggatgctgg caagcgcagg ggaacttcag    3660
aaaggcaatg agctggcatt gccatcaaag tatgtgaatt tcctctactt ggccagccat    3720
tacgagaaac ttaaaggtag cccagaagat aacgagcaaa aacagctctt tgtggaacag    3780
cataagcatt atctggatga gatcatagaa caaatctcag agtttttccaa gagagttatc    3840
ctcgcagatg caaacctgga taaggttctc tcagcctata ataagcatag agacaagcca    3900
attagagagc aagcagagaa cattatccac ttgttcactc ttacaaacct gggggccacca    3960
gccgccttca aatatttcga tacaacaata gacagaaaga ggtataccag caccaaagaa    4020
gttctcgacg ccacactgat ccatcaatca atcacaggcc tttacgaaac taggatcgac    4080
ttgtcacaac tgggtgggga t                                             4101
```

SEQ ID NO: 67          moltype = DNA   length = 3307
FEATURE                Location/Qualifiers
source                 1..3307
                       mol_type = other DNA
                       organism = synthetic construct
SEQUENCE: 67

```
gagcaaggac acctacgacg acgacttgga caacctattg gcccagatag gtgaccagta     60
tgcagacctc ttccttgcgg ccaagaactt gagtgacgct atactgctca gtgacatcct    120
gagggtgaac actgagatca ctaaggcccc tctctctgcc tcaatgatta agcgttacga    180
cgagcatcac caggatctca ccctgcttaa ggcccttgtt cggcagcagc tccctgagaa    240
gtacaaggag atatttttttg accagtctaa gaacggctac gccggttaca ttgacggtgg    300
ggcaagccag gaggagttct acaagttcat caagccgatc cttgagaaga tggacggcac    360
cgaggacgta cttgtcaagt tgaaccggga agacctgctc cggaaacagc gtacattcga    420
caacggcagc atccctcacc agatccacct gggcgaacta cacgccatcc tccgacgtca    480
ggaggacttc tatccattct tgaaagataa cagggaaaaa atcgaaaaaa tacttacgtt    540
tcgaatacct tactacgtgg ggcccccttgc tcggggaaac tccagattcg catggatgac    600
caggaagtca gaggagacca tcacaccctg gaactttgag gaggtggttg acaaaggtgc    660
ttctgcccag tccttcattg agcggatgac taacttcgac aagaacctgc ccaacgagaa    720
ggtgctgcca aagcacagcc tgctctacga atactttact gtgtacaatg agctgacgaa    780
ggtgaagtac gtgacagagg ggatgcggaa gcccgctttc ctgagcggcg agcaaaaaaa    840
agcaatcgtg gacctactgt tcaagaccaa ccgaaaggtg acagtgaagc agctcaagga    900
ggactacttc aaaaaaatcg agtgcttcga ctctgttgag ataagcggcg tggaggaccg    960
attcaacgcc tcattgggaa cctatcacga cctgctcaag atcattaagg acaaggactt   1020
cctggataat gaggagaatg aggacatcct ggaggatatt gtgctgaccc ttactctatt   1080
cgaggacagg gagatgatcg aggagcgact caagacctac gctcacctgt tcgacgacaa   1140
ggttatgaag caattgaagc gtaggcgata cacggggtgg ggaagactct cccgaaaact   1200
gataaacggc atcagggaca agcagtcagg aagacgatcc ttggacttcc tgaaatccga   1260
cgggttcgcc aaccgcaact tcatgcagct cattcacgac gactcactaa cgttcaaaga   1320
ggacattcag aaggctcaag tcagtggaca aggcgactcc ctgcacgagc acattgcaaa   1380
ccttgcgggc tcccccggcga ttaaaaaggg cattctccaa acggttaagg tggtggacga   1440
gctggtgaag gtgatgggcc gacacaagcc tgagaacatc gtgatcgaga tggccaggga   1500
gaaccagact acccagaagg gtcagaagaa ctctcgggaa cgtatgaagc gtattgagga   1560
ggggattaag gagttgggct ctcaaatcct caaggagcac cctgtgaga acactcagct   1620
ccaaaacgag aagctgtacc tgtactacct gcaaaacggg cgcgatatgt acgtggatca   1680
ggagttggac atcaacaggc ttagcgatta cgacgtggac cacatcgtgc cacagtcatt   1740
cttaaaggac gacagcatcg acaacaaggt tctgacgagg agcgacaaga tcgagggaa    1800
aagtgacaat gttccatccg aggaggtggt caagaaaatg aagaactatt ggcgtcagct   1860
tctgaacgcc aagctcatca cccagcggaa attcgacaac ctgactaagg ctgagcgagg   1920
cggactctcc gagcttgaca aggctggctt catcaagcgg cagttggtcg aaacccgaca   1980
gataacgaag cacgttgccc agatacttga ctcccgtatg aacaccaagt acgacgagga   2040
cgacaagctc atcagggagg tgaaggtcat tacccttaag tccaaactcg tcagcgactt   2100
tcgtaaggac ttccagttct acaaggtgcg cgagatcaat aactaccacc acgcacacga   2160
cgcctacctg aacgcagtgg ttggaaccgc gttgattaaa aagtaccccca agttggagtc   2220
ggagttcgtt tacgggggact acaaggtgta cgacgttcgg aagatgatcg ccaagtctga   2280
acaggagatc gggaaagcaa ccgccaagta tttcttctat agcaacatca tgaacttctt   2340
```

-continued

```
taaaaccgag atcacacttg ccaatggcga gatccgtaag aggccgctga tcgagacaaa   2400
tggggagact ggcgagatcg tgtgggacaa gggccgcgac ttcgcaaccg ttcggaaagt   2460
cttgtccatg cctcaagtca acatcgtcaa gaagactgag gtgcaaacag gcgggttctc   2520
gaaggagtcc atactgccca agaggaactc agacaagctc atagcacgca aaaaagactg   2580
ggatccaaag aaatacggcg ggttcgactc gccgacagtc gcatactccg tgttagtggt   2640
ggctaaagtg gaaaagggga agtccaagaa gctcaagtcc gtcaaggagt tgctcgggat   2700
caccattatg gaacggtcct cattcgagaa gaatcccatt gacttcctag aggcgaaggg   2760
ctacaaagag gtcaaaaagg acctaattat taagctcccc aagtattcac tcttcgaact   2820
tgaaaatggt cgtaagcgga tgttggcaag cgctggagag cttcagaagg ggaacgagct   2880
tgcactgcct tccaagtacg tgaacttcct gtacctcgcc tctcattacg agaagttgaa   2940
gggctcaccg gaggacaacg agcagaagca gttgttcgtg gagcagcaca agcactacct   3000
cgacgagatc attgagcaga taagtgagtt cagcaaacgg gtgatccttg ccgacgctaa   3060
cctggacaag gtgctgagcg cctacaacaa gcacagagac aagccgatcc gagagcaagc   3120
ggagaacatc atacacctgt tcaccctcac gaacctcggg gctcccgcag ccttcaaata   3180
ttttgacacg accatcgacc gtaaacgcta cactagcacg aaggaggtgc tggacgctac   3240
ccttatccac cagtccatca ccggcctgta cgagacgaga atcgacttgt cgcagctcgg   3300
tggtgac                                                             3307
```

SEQ ID NO: 68              moltype = DNA   length = 4101
FEATURE                    Location/Qualifiers
source                     1..4101
                           mol_type = other DNA
                           organism = synthetic construct
SEQUENCE: 68

```
gacaaaaaat actcaattgg tctggcaatt gggaccaaca gtgtcggatg ggccgtgatt   60
accgacgagt acaaggtgcc gtccaaaaaa ttcaaggtgc ttgggaacac cgaccgccac   120
tcgatcaaga aaaacctaat cggtgcgttg cttttcgaca gtggggagac cgccgaggca   180
acacgcttaa aacgcacagc taggaggaga tatacacggc gcaagaaccg aatatgctac   240
ttacaggaga tattctccaa tgagatggcg aaggtggacg actctttctt ccatcggctt   300
gaggaatcct tcctggtcga ggaggacaag aagcacgagc gacacccgat attcgggaac   360
atcgttgatg aggtggcgta ccacgagaag tacccaacga tataccactt acgcaagaag   420
ctcgtggact ctacggacaa ggccgacttg cgccttatct acttggcact ggcccacatg   480
attaagttcc gaggccactt ccttatcgag ggtgacctga accccgataa ctccgacgtg   540
gacaagtct tcatccaact cgtccagaca tacaaccagc tattcgagga gaatcctatc   600
aacgcctctg gggtggacgc taaagctatc ctctcagccc gcctgtcaaa gtcgaggagg   660
ttggagaacc taatcgccca gcttccaggc gagaagaaaa atgggctgtt cggaaacctt   720
atcgcactct cactgggcct aaccccgaac ttcaagtcca acttcgacct ggcagaggac   780
gcgaaattgc agttgtcgaa agacacctat gacgatgacc tggacaacct gttggcccag   840
ataggggacc agtacgccga cctgttccta gcggccaaga acctgtccga cgccatcttg   900
ctgtcggata tactgcgggt gaacaccgag atcactaaag cacctctctc cgccagcatg   960
attaagcgtt acgacgagca ccaccaagat ttgaccctgc taaaggcact tgtacggcag   1020
cagcttcccg agaagtacaa ggagatcttt ttcgaccaaa gcaagaacgg ctacgccggg   1080
tacatcgacg gaggtgccag ccaggaggag ttctacaagt tcattaagcc catcctggag   1140
aagatggacg ggactgagga actacttgtg aagctgaacc gggaagactt actacggaag   1200
cagcgtacct tcgacaacgg ttctatccca catcagatcc atcttgggga gttgcacgcg   1260
atcctgcgac gccaggagga cttttacccc ttcctgaaag acaaccgcga gaaaatcgag   1320
aagatactga ccttcagaat aaccttactac gtcggacccc ttgcgcgagg caactcaaga   1380
ttcgcgtgga tgaccaggaa atcagaggag accatcacac cctggaattt cgaggaggtg   1440
gttgacaagg tgcctccgc ccagtccttt atcgaacgaa tgaccaactt cgacaagaac   1500
ttgcccaacg agaaggtgct ccccaaacac agcctcctct acgaatattt cacagtgtac   1560
aacgagctta ctaaagttaa gtatgttact gagggcagg ggaaacccgc cttcctgtca   1620
ggcgagcaga agaaagctat tgtggacctc cttttcaaga ccaaccggaa ggtgacagtg   1680
aagcagctca aggaggacta cttcaagaag atagagtgct tcgacagcgt ggagatcagc   1740
ggggtggagg acagattcaa tgcctctctc ggaacatacc acgacttgct taagatcatc   1800
aaggacaagg acttcctcga caacgaggaa aacgaggata ttctggagga tattgttctg   1860
actcttaccc tgttcgagga ccgggagatg atcgaggagc gtctcaagac ctacgcccac   1920
ctgttcgacg acaaagttat gaagcagctc aagcgtcgga gatataccgg atggggccgt   1980
ctgtctcgga agctcatcaa cgggatcagg gacaagcagt cagggaagac gatcttagac   2040
ttccttaagt ctgacggctt cgccaacagg aacttcatgc agttgatcca cgacgacagc   2100
cttaccttca aggaggacat ccagaaggcc caagtgagtg gccagggtga cagcctccac   2160
gagcatattg ctaatcttgc gggttcccca gcgattaaaa agggcatact tcaaaccgtt   2220
aaggtggtgg acgagcttgt caaggtgatg gggcgcacaa gcccgagaa catcgtgatc   2280
gagatggcca gggagaacca gaccaccca aggggcaga agaatagccg agaacgcatg   2340
aagcgacatg gagggggat taaggagcta gggagccgac tcctcaagga acatcccgtc   2400
gagaacaccc agctccagaa cgagaagcta tacctctact acttgcaaaa cgggagggat   2460
atgtacgtgg atcaggagtt ggacattaac cgcctaagcg actacgacgt agatcacatc   2520
gtgcctcagt cattcctcaa agacgacagc attgacaaca aagtcttgac ccgatccgac   2580
aagaaccgag gaaaatccga caatgtgccc tcagaggagg tcgtcaagaa aatgaagaac   2640
tattggaggc agctacttaa cgccaaactc ataacccagc ggaagttcga caacctgaca   2700
aaggctgagc ggggtgggct cagcgagctt gacaaggctg gcttcatcaa gcggcagttg   2760
gtggagacaa gacagataac gaagcacgtg gctcagatcc tggactctcg catgaacacg   2820
aagtacgacg agaacgacaa attgatccgc gaggtcaagg ttattacgct caagagcaaa   2880
cttgtcagcg atttccgcaa ggacttccag ttctacaagg tgagggagat taacaactac   2940
caccatgcac atgatgccta cttgaacgca gtggtgggga ccgcgcttat taaaaagtac   3000
cctaagttgg agtcagagtt cgtttatggg gactacaagg tgtacgacgt ccggaagatg   3060
attgcaaagt ctgaacagga aatcgggaag gccaccgcca aatatttctt ctacagtaac   3120
attatgaatt tttttaagac tgaaattact ctcgcaaacg gcgagatcag gaagcgtccc   3180
ctcatcgaga caaacgggga gaccggggag atagtctggg acaaggggcg ggacttcgct   3240
acggtgagga aggtgctctc gatgccacaa gtgaacatcg tcaaaaagac agaggtgcag   3300
```

-continued

```
accggtggct tctcaaagga gtcaatcctg ccaaaacgta acagcgacaa gctcatcgcc   3360
cgcaagaaag actgggaccc taagaagtat ggtgggttcg actcaccgac ggtcgcatac   3420
tccgttctgg tcgtggcaaa ggtggaaaag ggcaagtcca aaaaactgaa atccgtgaag   3480
gagttgcttg gcattaccat catggaacgc agcagcttcg agaagaaccc cattgacttc   3540
ctggaggcta aagggtacaa ggaggtcaag aaagatttaa ttattaagct acctaagtac   3600
agcttgttcg agctggagaa cggccgaaaa cgaatgctcg catccgccgg ggaacttcaa   3660
aagggcaacg agcttgcgct gccctccaag tacgtgaact tcctgtactt ggcatcccac   3720
tacgagaaac tcaagggtag cccagaggac aacgagcaga agcagctatt cgtggagcag   3780
cacaagcact acctcgacga gataatcgag cagatcagtg agttcagtaa gcgggtgata   3840
ctcgcggacg ccaacttgga caaggtgctt agtgcctaca acaagcaccg tgacaagccc   3900
atccgagaac aggctgagaa catcatccac cttttcactc tgacaaacct cggtgctccc   3960
gccgccttca aatacttcga cactaccatc gacaggaagc gctacacatc tacgaaggaa   4020
gttcttgacg ctacgcttat tcatcagtct atcacagggc tgtacgagac aaggatcgac   4080
cttagccaac tcggcgggga t                                             4101
```

```
SEQ ID NO: 69          moltype = DNA  length = 14046
FEATURE                Location/Qualifiers
source                 1..14046
                       mol_type = genomic DNA
                       organism = Zea mays
```

SEQUENCE: 69
```
ttctttgaca tcctatttta acaaaaacaa gttagtacat aaatcgacaa taaaataata   60
aaatatgcaa taaatcata aaatatgcaa taaatcatg atccatactc gtcaatcgta   120
atcgtaatca aaatcaggat ctagttgctt tcgtcgattt aatggacgcc aagtagcttt   180
cttctttctc gtcactcgtt ttcttttgg aggaacctct acatcatttt gatcgcctaa   240
taaagattct tccaacattt cagtttgtac attaaacgtg cttgtaagtt cttcgtcttg   300
gaaaatctca gcagccccca cttcctgctc gatttgactt tcaacataac cagcatcacc   360
aggagcatat agtcgttcac gcggattaac tttgtacact accctccaat caaccaaacc   420
gttttttctta gatggatatg tcatataata cacctgctcg cattggtggg caaggattat   480
agtgtcgtga cctttaatc tatcgttgtg tttgacttcc accatgccat attgattttc   540
tcgcgttgta tttggagaaa accaatcaca atcgaagaac accactttga gttgtttatc   600
tccaaaaaac ttgtactcga ttatatcatt aatgactcca taataattag tcaccttccc   660
ttcatcatcg acagctctag ttacaactcc ggagtttgtc gtggctgcta gaggatgatc   720
atcttcgaac cttgtggaac ggaatctaaa accattgaca tcataccgac cataacgtct   780
gccagttact gctcctaggg ataattgtcg aaggtccggg tgtatattgt catttttatc   840
tacataatct cgaaaccaac acaagaaatt aagtccccca tcttttccct ctcgacgaat   900
ctggtcacgt tcacagccag agatgcaatt ttgagaatca aattccctgt tagtacaagg   960
aaacaaacct tttagtatca caacaaaaat tctagcggca atgactaaaa taaagtttac   1020
acttacagga gaaactgact catctcttcc atgttgttat acatgtaaag taaagcagtc   1080
ttccattcgt cgttggtgaa acagtatgtt gtgctgggtc ctacagtttt gcccctccat   1140
tgaaaaattt caatatcact aataggggc tcgtcgacat gataccgcaa cgtatgggca   1200
ttgacattgt gttcctctgc aaagtacagg cccgtgaacg atgctatctc tttgtatttg   1260
aattcttcag cgatgcaccc ttcaactcgt ctcttattac caaccattgc acgtagcttt   1320
tttagtgtcc tttcgatgtg atacatccat ctatattgca caggacctcc taccttagct   1380
tcgtatggta ggtgaacaag tagatgttgc atcggattga agaaacctgg tggaaatatt   1440
tttttcaagtt tgcataccaa aatcggtatt tcttgctcaa gcttctccat catctctttc   1500
tttattttctt tggcacaaag atgtctataa aagtagctta gctccgctaa tgctttccag   1560
acatcatttt ttacaaaacc acgaaacata acaggaagga gtctttccat tattatgtgg   1620
tagtcatgac tcttcaaccc agaaaacttg cccgtcttca aattcacaga ccttctaaag   1680
cccgcggcgt aaccatctgg gaactttaag ttttttcaacc atttcatcaa ttgtttcttc   1740
ctttttaggtt taatactgaa aggagcacgt ggcttcttct gattctctcc tatctccata   1800
gttggtcttc tacagattaa ggccaagtct ttccttgcct tagggttgtc ttttgttttg   1860
tcggtgatat tcatgcaagt gctgataatg cttttcaccca tatttcgttc ctggtgcatg   1920
acatcaatgt tatgcattag aatcaaggct ttcatataag ggagttccca tagaccacat   1980
ttgtgagtcc aattatgctc ggttccataa ccttcaaaac gatttccatg ttcgtttagt   2040
ttcaaatcat taagtctcgc gagaatctca ggaccactta gacgcttggg tggtcccctc   2100
gtcacaatcg tgtcctttttt aaaagcgttc ctatcgaacc tgaacgggtg atcctctggc   2160
aaaaaacatc tatggcaatc gaagtaacat atctttccac caaactttag tcgaaagcat   2220
aaagtgtctt caacgcatat aggacatgtc aaaatcccat gacaactcca tccagcaaag   2280
ataccataag ccataaaatc atgaatagac cataaaaacg cggctctcag gttgaacttc   2340
tgtttcttgt aacaatcgta cgcctcgact ccttcccaca aaattttcaa ttcttcaatc   2400
aggggtctca tcatcacatc gatctttgtt ccaggatgat ccggaccagg tattataaga   2460
cacaagaaaa taaattcata tttcatgcaa agagctggtg gaaggttgta tggaacagca   2520
aagacgggcc aacatgagta cgacgtagca gttagttgta atggtgagaa accatctgtt   2580
gccaaaccga agcggacatt ccgcacttca tcagcaaagc tggaatcaaa agcatctagt   2640
gccttccatg catctgtatc agctgggtgc accatgacat ttggattctc acgtaccct   2700
tctttgtgcc acctcatgtg tctggctgta ttttttggaga tgaacaaacg tttcaaccga   2760
ggtatgagag gcatgtaacg aagctgctta tgtgcaatct tcgtagtcac ggtcaaacca   2820
tcgtcgtttt caacctcaac gaatctacgc tcaccacata cagtacactt cttctcacct   2880
gcggtctcct tccagaaaag catacaatta ttttcacaga catcgatttt ttcgtagtcc   2940
ataccgaggc cagataacag ctttttagac tgatacatgt cctttggcat cttgtgattc   3000
tccgaagta catcactgat caagttcaaa agttccttgt aacagttgtt tgagaatgca   3060
aacttagact taatagccat aagtcgagtc acaaatacaa ggacagtcac ttttgtgtgc   3120
tcatgcaacg gctcttcggc agcttaagg agctcgaaga acttctgaac ctcaggtgta   3180
gctggatcct caaactcggt gggttgaccg gggttctccg aatcgacggt tagaaactca   3240
tggcgtacat cgtcaagcat ctcttccatc ctatcgtagt cctcctcttc atgtgactga   3300
acttccgata caatacgagg tgggtcctca ccgtggtgca cccacacctc atagcctggc   3360
atataaccgt tcttgcaaat atgtatcgac atagtcctcc tgtcaaggaa attaatgttc   3420
cgacacttgc tacaagggca cctaacatcg gttccagtct ctgaccgagc aaaagcatgg   3480
```

-continued

```
tcgagaaaag catcagtctt ggccacccac tcacttgata gagcacctct tttcttccaa  3540
ccttcataca tccatcgacg attctcctcc atactagata cgatacgtta acttaattag  3600
ataagtactg cacgtgcatt ccgtttttac gaagaaatca cgcccctaca tctgtaggaa  3660
aggataggtc ctaaacccac ccaggagtga ccgacgagac cgtgtttatg acaagacatg  3720
tggtcgtgcg aaatttcggc agcataaccc cgttgttctc caatcgcacg cctaaaaatg  3780
gtgcaattga agaacagaga ggttatgctg ccgaaactaa gcaggagcac atgcttttgt  3840
cataaacacg gactctgtcg gtcaccccga ggctgtccaa aaaagggaca attccggccc  3900
aacataacctc acatgcgtcg cttgtaaggt gtgttgggcc gaaacgggtg acgcctaggt  3960
ttcgtttgtt cacactacga tacactatga ttaactataa tcatcgtgca ttattaaata  4020
attaaactaa taaaccataa tacaatatta catacgaaat aatattgtta tagatgacaa  4080
atcatataaa atgaccttat ttccgagggc ataataatta ccctcggaaa ttaaaaatta  4140
aaattatcta aagtaccact aaataaagta aaacaaacta ctttaattaa ctaatcaaat  4200
tttgaccgtc ggacataaca aactaaacaa tcaaatgcat taatacatac aatttcaatc  4260
aaatacatta atacaaacat acaattctaa tcaaatacat taataaaagc atacaatttt  4320
aataaacaaa attgctaatt aagtatactc acttagcggg tgtggagagt cggccggcga  4380
tgggcgcacg ggcggcggcg ggcgcacggg gccgttggcc ggagcacggg gcggcggcga  4440
ccggcgaacg gggcggcggc gaccggcgaa cggggcggcg gcggcggcgg ccggagcacg  4500
ggcgtggcgg tggccggagc acgagctagg ggcggtggtg gccggagcac gggcgtggcg  4560
gtggtggccg gagcacggc gtggcggtgg ccggagcacg agcacgagc ggtggggcgg  4620
cggcgggcgc cggagcacga gcagtggggg cgggcggtac ggcgataggg cgggacggcg  4680
acgagcgtgg cggcgacgag cgtggcggcg acggcggctt ctcctcggac acggcggagg  4740
cgtgctcggc ggcggcagga tagaaacgcg cggtctcggg tgaaactgaa ggcgcgcggg  4800
tcggaaccgc gcgttaaaaa gccttatgtc cgacggctcg gtacgaggcc gtcggacata  4860
agctaatgtc cgacggccag ggggtcggcc gtcggacata aggtaatgtc cgacggtcag  4920
tctgccagcc gtcggttata tttttattt tcgacggccg ctgttggccg tcggacataa  4980
ccgtatgtcc gacggttgcc tacggcgcgt cggacataag acgaccgtcg gaattgtata  5040
gttttactgt agtgctccct cactatcttg ttctcgcctc gttttttctct ccctccgcga  5100
gcgccaaggc agcgcagcta cgagacaagc acacgtaata gtactagtgc gccgttgccc  5160
tgcctgcctg ccctgtgccc tgccttgcac cacaccacca ccaccgcaga tccggtctgg  5220
tccagtccgg cccggtccgc tactaaacaa accagccag cgcgcgcccc agcgagagga  5280
gaggaggagg ggccggggtc ggcacggcgg gcagaattgc ctctgctgcc tgcgcgctgc  5340
cctgccctgc cagagggatc ggagggagag cgatcagtca acaagcccag gaggaggagg  5400
aggaggaggg agagatccgc gtgccggccg gaggcgggct ccgggagatc gaccgagcga  5460
ccggcctcgg tcccggtgcg gtggtggatg gggatggcgc ccgccgggtg ggtgggcggg  5520
ctcgtggcgg agagcttctt cgtggcgtgc cccgcgcacg agtcccgcaa gaagaacgag  5580
cgcaacatct tctgcctcgc ctgctgcgcc agcatctgcc cgcactgcgc cccgcgcacc  5640
gccaccaccc gctcctccag gtgagtgcga gtctcgtcgt cgtcctcctc ctcgcccggc  5700
ctctcctctt ccttcctccg gcggccttcc cctctccctg ccaggctgcc atggcgtcgc  5760
gtggcatgca cctggccggg cgatctgctc agtttctact cctgctagct tcgcagcaat  5820
tctcgccgcc gctgtcccgc tccgctccgc ttcttgttgt tgttggatga acacaccacc  5880
tccccaccgc caccgccacc ggggggcagc tttttggggg ttattgctgg tggcctcggt  5940
tcttgtgcaa cggatgggaa cggcgggac gagtaccaat caatcgattt ctttatttga  6000
tttaattgtt tatttattat tcctcggcgt atatagcact agacgctact tcttcctata  6060
tactactact agagtagtac tacaagtgta gaggaggagg ggcatgggaa ttggatgtgt  6120
agtatctcgc ttttgttttg tcgcgtgctg tctcttcctt ccttccttcc ttggactaga  6180
tttggtcccg gctttagcct aaacaaaaaa atatttcccc cctaccattt ctcgcatgat  6240
ttgatttgat gcgtggtctc ttctcgtgtc gtccgtgcgc gggaaggaat caagggaaag  6300
gaaaggaaac caaaccccat ctcgctaatc gctctcctct ctctctctct ctcccttcct  6360
cgcaggcagg cagaggcagt acaggttgtt gcaaaacttg cacgtacttg attcctcgcg  6420
cgcgcagcgc cttgtcgcct tgcgaggttt ggtttggttg ggtcatgagc tcatccatcc  6480
attccctttt ccacccatgc atgcatgcat gcatgccact cccttgatta gggtttataa  6540
gccagcagga ggcgctgatt gagtcctaat ctgcgccact gtaacagcaa tcccaaccat  6600
gattttcgca cccgctccag gactccggag cagtgctact tcttcatcgc tataattaat  6660
ataattcgtc tgctccttcc tgcctgaccg gggtattaaa tcctgtgtat gtacgtagta  6720
ctaacaaaca aggacaaggc agtaaaaatt ctcgttacgg aacattatct actccgacct  6780
cccttgcatt tttttttgg aattagtacc cgggcgttca tcgcgacctg catgcaactg  6840
tttcctcaac gagctagcca ttacatgctt ttagttttt ataaaatata tatgcatgca  6900
tggcaaaact tttttccttttt taaattttcg ggagttaaag aggaggaggg tcgaaaattc  6960
aaatccccc acccgggca tgcaaaccct tcttcttttct ctccgtagct ttgtcttgta  7020
gctgcagcca tgcatttccc ccctactttc atgcagcagc aactaatcca tccggatatg  7080
ctggcgctgc gggagccgga gtctcgaacc caaatggcaa aaaaagctgc ggggggaggt  7140
tttaccgctg cctcttcatt ggaattccaa tccttgggat taggatcctc tgcggtaatc  7200
gccagcctcc tgctgcgctt ccgcttgctt ccccgtccat taataggcct ggttatccaa  7260
actgttttgc caagtatagc aacatttccc tgcccccgt cctgccgact tcttcctata  7320
actgataaag gaaaaaaaat cggttcgggc ctttgaatta gattttaccg tatgcgcccg  7380
cgcgcggtaa ctgcgcggcc tgtctttttt taccaaacag aggcatcgac gacgacactg  7440
ttgtcccccg acgacgaccc catctctccc tggtgcgtgc tacacgacca aacttctctc  7500
tccttacctt agggtggggt ggtttgtggg gtctcccagg ccatgataaa gatcaccact  7560
ggagtggtac tgctgcccgg ccggtcaaag catggggc atcgcgtggt gtgtggccca  7620
acccaaagtt gtaccctgct gctgctgtac cgcctgcgtt gttatcttag gccccgtttc  7680
aatctcacgg gataaacttt agcttcatgc taaactttag ctatatgaat tgaagtgcta  7740
aagtttagct ttaattacca ccattagctc tcatgtttag attataaatg ctaaaagta  7800
gctagaaaaa agctgctaaa gtttatctcg cgagattgga acacggcctt atcttagagt  7860
atgaaactgc ggttgtaaac atgtttagcg ccaactgcta tgtacgtgat caggtgcggc  7920
gctacgtgta ccatgacgtc gtccgcctcg cgcgacctaga gaagctcatc gactgctcct  7980
gtgtccaggt gattccctat ctatcgtcgt atctgtcttg cattagtgct tcgaatttg  8040
atggtgatgc tgatgatgag tacgttaatt atatagtagt aaaactcccc tctctctttg  8100
tgtgtgtgat gtgtgaccgc gcagacctac acaatcaaca gtgccaaggt gatcttcctg  8160
aagccgaggc cgcagtccag gcctttcaag ggctccggca acatctgcct cacgtgcgac  8220
```

-continued

```
aggatcctcc aggagccctt ccacttctgc tccctctcat gcaaggttgc attggtcagc  8280
tagctagcat catcgcatac gccatgcata tgcatcgtcg gattcggatc atatcgttca  8340
gtgcgtacgt ggatcatgtc atatgttatt acgcaggtgg accacgtgat gacgcaggga  8400
ggggacctgt ccaacatcct gcagcactac ggcgccggcg gtggcggtgg cggtggcacg  8460
gcggacccgg accgcctcgc gttcccgagg ttcgagaacc tccgcgtcgt cgacggctcg  8520
gacctcgacg acgacgtcca ggtcgtcacc ccagactcca ccctcgagga cccgaccaac  8580
aacgcgggcg gcgggtccag cgacaacggt actgacgacg ccagacggca ggtcgtcgtc  8640
catggcggcg gcgaggcggc caagcggaag aaaggggggcg gcttcttgcc ccagatcgtg  8700
ctgtcactcg gcggcggcgg cggcggcggc aacaggagga agggtgcccc ccacaggtcc  8760
cctctggcct aagcagcgct accttcatgc atgcgtcccc ctgctgctgc tcgttatata  8820
tcacaagtca caacacacgt agcgcgctgt ggttgcatgc agtgatgatg gtgtgggtgg  8880
tagctacagt attaattagt agtagcgtgt tataatagta tcttaatggt gattagcctc  8940
gtagagagac gacgacaagc tggtagctgg tcgatcggtt ttgcttgggg ggaaggtctt  9000
ggtggccttg tgatccgtct agcagctcgc taggaccaac catggccgcc gcgccatctc  9060
atgagacttt agagagagag agagagagag agggtcatgg gggaggtaga gggggggagg  9120
acggttgtaa aagcagttcc cattgttaca ggcaccaggt agtaactggt cagtggggcc  9180
cacttctgca ggcggtgggg cccatacgat cgaggtggct accaattttg tatttgatgt  9240
accaagggtt actcgcggtc tcgcgcatac aatttccaca cctatatatg ttatatataa  9300
atgataatat atctgaattc tgtcccagac taaacaggtt gttttcagca gtctgtatcc  9360
gttccatgtg ggctcaagtg attttcagct gcctgtttgg cgtgtcaagc agctgttgag  9420
acatgaggcc gagagctctc gcccagtctc gcccgtaggg atgaaagtag gatgggaaaa  9480
tcccgtaccg accgttatcg tataaccgaa tttgttagtt ttgtcccgat cgttttcgaa  9540
cccgacgtaa aaaacgaaaa cgggacgaaa acgggatata caaaacggta aacgaaaacg  9600
gaaacggtag agctgtttta ccgaccgttt aaccgggatc ccgttttttaa tcgggatgat  9660
cccgtttgt taccgtattt tgtaattcgg gatcacttca atatagacag ctataggcat  9720
cactttgagg cccagcccat ctaagaaaaa cctaacgcgc tgttctgctc ccaggcgtcg  9780
ccgtccacac tcctctctcc cagctcgctg ccgtagtgcc atcagctcgt cactcgcagg  9840
cgccggcgcg cagccgtccg ccctcctgct ctgtgcggct ttgcctctcc cagctcgcct  9900
cgccagtcgc caggccagag tgccatcgca gcttcccagg ctcccagctc gccagagtgc  9960
cggacgccac gccagcccgg tccggtctcc ggtcggcggt cggtccgatcg ccgctgctcc 10020
agctggctgc ccaggcgact agacgtccac gacggctcgg cgatcggcag gcagctcgct 10080
ccacctccac aggccacgac tccctctgct gctgctgtcc tccacggatc cactgctggc 10140
tgctgctccc tccacagaga atcgccttgc tacaccatgt gagcagtcct gcagtcctgc 10200
cgtgttagac gctagctgct agctcccagc cgtactccac cacgtttttgg tgcataagct 10260
gcgtgttgcc ttgctttta ctgttgttgt tttaattctg tggtgcataa ttctgttggt 10320
gcgtacttct attgggcgta ctttatatta tgtcatgtgt gctagtagac ttatatggct 10380
tcttatgtag ccaagagctc aatatttatc acttatgtgc tactaagatg tttggtttga 10440
tgaatcactc tatccaaaat gaagtggtgc atcatgggtc cattcctcaa atttggtggg 10500
atgacttcat tccacatatt agtactaaac aactaactat gaggaatgag gtggtgatgg 10560
attaactcac tccattccac aaaccaaaca aaaaagtgag gagtgagaag atgatgaact 10620
atatcgttcc tcaaaccaaa cactccatac attaaactat gtgtgctcca gatttatatg 10680
acttttttct atgtttaatt aagacttgtg tttacaattt tttatatttg tttttaagtt 10740
ttgaatatat gttttcatgg tgtgattta ccgaacaaaa ataccggttc ccgtccgatt 10800
tcggctttaa cccgaccgga tcgtatcggt tttcgcttac cgtatttatc ccgttcgttt 10860
tcgttaccga tatatcccgt tttcgttttc gtcccgcaag ttaaatatga aaatgaaaac 10920
ggtagaggta ttttaccgac cgttcccgac cgttttcatc cctactcgcc cgcgtgcatg 10980
gattgttgca tgcatgtgat gcgcgcgcgc acacgcctag cgctcccgtc caaactcccc 11040
agtcgtgttg ctgtgacctg ctggctgttt gatgcagttg tgattcgctt tgcaatggac 11100
cacggtctct gtcccatggt gtgtgtatct gtgtgtctga gtgtggagac gacagagact 11160
cgaaaagatg gtgtggtggc tgttcgatcc agggctcgct tgatgcctgt ttttttttcc 11220
acgagaact ctctattaga gaacagatgc atgggtcgtt ttttagcctc tctagaccag 11280
gatgtgaaag gtagaaaagc cattctcacg tgaggttaca gtacttgtag ctttccatta 11340
ctcatatact tgcaggaatt aatattggac actctttttc tactctcgct ctgttttaaa 11400
tcgcaagcta ttttttccact ttcttaaaaa tgtagcagct tttaccgagt acatctcggt 11460
acgtacctaa aaaaaagctt gtagtataag ctttcaaccg agtgtttata aggcttcgcc 11520
gagtgcttcc ggcactcggc gaagctattg attccggtag tgccgggttg aatttacttt 11580
tgtatcactg agcgtgcgaa gagaacagcg gtatttctgg catcgatcgg gcacccttcc 11640
tcggaatcat ggctttttga gagtgaccaa caggcagtgc gcgcggtctc ggaacctgaa 11700
aattgtttgg ttgtatcgaa tgacttgtca cggccactcg aggcaggcat gagacgctcc 11760
accggaccgc cacaccatgc atagtgacag atcatcaaaa ggtggtttta aaactcgaat 11820
ttttatctga ctatatagca aataaatcct tttgtacgct cagtttcata tatagacgaa 11880
attctcccac ctctcccatg catgcatgtc atcgatcatt cttgtttatc tggtgatgta 11940
tttaatgaag acagaaattc gagtgagatt tccagtggaa atagccttat tagtgtgcca 12000
tgaacgaagt tctgaagtcg aaaccagacg agagtccccca tgcacgatgc catggatatc 12060
gccagtacgt acaggacgtg cgccagcacg atgcaactgt cagcagacag cagccaaaac 12120
gcaattcttg tttcagctgg gtgggcaatt ccgaggtgtg ctaaataaaa gcatgatcca 12180
tgcatataga tgagcatgca gcccgcagcc cgacagcccg gcacgaggcc cggtttttttg 12240
gcccggccca agcacggcac ggcccgtctg gtttcgtgcc cgtgccggcc cggcccggta 12300
gaccaggccg tgcttgggct gccggatgcg cccgccgggc ggccccggcctag 12360
gaaaagcagg cacggagccg gcccggttcc aggcgagggg catatccggc cgcccctccc 12420
caccgcccgt tcagtccccc agtccctagt tccccacgcc acgcgatttg ctccgcagcc 12480
tccgccctcc gctcgtccgc tcgccgctcc ctccccattc tccgtcaacg ccgagccgtc 12540
gccactgccg ttgccggatc tccgtcgtcg accgacgaga tctcctctct gcctctctcc 12600
agtcttcgtc actcggtgac gcatcggctc tccattcccc aatctgtaac cctaatcccc 12660
tttccggctt tccctcacct ctccggtgac gcatcggctc tccactgccg gatctccgtc 12720
accggcgaca tctgcacgct tgttctgtgc ggctcaccct ctccggctct ccctcccaa 12780
tccctcgct cgtcgtcgtc gtcatcggtc gtcggcttgt cgcgcgtcgt cgtccctag 12840
accctcgtct ccggctccgg gctccggctt ggcaggtacg tgtacgtccc tctccggctc 12900
tccctcccca atccgacaaa ccctaaccct aatcccttgc ttggtaggtc gccggccgac 12960
```

```
tacgccgtgg tcgtgctggt gccgccagtg ccgttgaggt acggtgccga gaggggggcc    13020
gggcatggat gacgacgacg acaatggccg gtaccctaga accatcaacg acgagctcgt    13080
tgagttaggg cagcttcccg atgacgtcga cgacatggga gatgctgctg ctgccttatt    13140
cggtatcggt agcagtcatg gtgccggcga cctggagggg acagctgccg ggccggttcc    13200
ggttagtgat gctgctggct ctaacgaact tgattcattg acttcttcca gcactggtaa    13260
gcgtcgatct gctgtttggg atgacttcac tgaagtcact gaaaaccgta atggtaagaa    13320
ggtgcgcatt gctggtattt gcaaattttg caaggctcgg ttgagtgcta gttctaatgc    13380
tggcactgga catttgctta ggcaccagaa atcatgtaaa aagaagtctg atcatgctgc    13440
tatggttcaa actagactag ctttgaaccc tgatgggtct tttagaaact gggaatatga    13500
tcctcaggtg gctaggactg agctttgtcg tttgattgct agacttgatc ttcctttagg    13560
gatagctgac acagatgctt gggataatta cattcaacat gctcacaacc ctagatatgt    13620
tagggtatct aggtttacaa ctgctagaga cttggctaag ctatacaatg aaaagctaaa    13680
gaacttaaaa gatgatgttt ttcctggtgt gtcttctatt tgcttgactt ctgatatatg    13740
gtctggtaat gccaaggaag actacattac tgttgttgct cattttatta atgctgattg    13800
ggagttaaag aagtgtgtga taggcttaa attgatccaa gtgtctcata atggtgttaa    13860
cattgctgaa cgcattgctt gtgtgattca atactttggc atgattgata aagtgttctc    13920
tattaccttaa gataatgctt cttctaattc aactgccatg ctcacattgt cacctatgct    13980
tgctggttat ttgggtgctg atgttgatcc aacagatact agtaacaaaa catatagtgt    14040
gcttca                                                              14046

SEQ ID NO: 70               moltype = DNA  length = 1661
FEATURE                    Location/Qualifiers
source                     1..1661
                           mol_type = other DNA
                           organism = Zea mays
SEQUENCE: 70
caccaccacc accgcagatc cggtctggtc cagtccggcc cggtccgcta ctaaacaaac     60
cagcccagcg cgcgccccag cgagaggaga ggaggagggg ccggggtcgg cacggcgggc    120
agaattgcct ctgctgcctg cgcgctgccc tgccctgcca gagggatcgg agggagagcg    180
atcagtcaac aagcccagga ggaggaggag gaggagggag agatccggt gccggccgga    240
ggcgggctcc gggagatcga ccgagcgacc ggcctcggtc ccggtgcggt ggtggatggg    300
gatggcgccc gccgggtggg tgggcgggct cgtggcggag agcttcttcg tggcgtgccc    360
cgcgcacgag tcccgcaaga gaacgagcg caacatcttc tgcctcgcct gctgcgccag    420
catctgcccg cactgcgccc cgcgcaccgc caccacccgc tcctccagcg ccaactgcta    480
tgtacgtgat caggtgcggc gctacgtgta ccatgacgtc gtccgcctcg gcgacctaga    540
gaagctcatc gactgctcct gtgtccagac ctacacaatc aacagtgcca aggtgatctt    600
cctgaagccg aggccgcagt ccaggccttt caagggctcc ggcaacatct gcctcacgtg    660
cgacaggatc ctccaggagc ccttccactt ctgctccctc tcatgcaagg tggaccacgt    720
gatgacgcag ggaggggacc tgtccaacat cctgcagcac tacggcgccg gcggtggcgg    780
tggcggtggc acggcggacc cggaccgcct cgcgttcccg aggttcgaga acctccgcgt    840
cgtcgacggc tcggacctcg acgacgacgt ccaggtcgtc accccagact ccaccctcga    900
ggacccgacc aacaacgcgg gcggcgggtc cagcgacaac ggtactgacg acgccagacg    960
gcaggtcgtc gtccatggcg gcgggaggc ggccaagcgg aagaaagggg gcggcttctt    1020
gccccagatc gtgctgtcac tcggcggcgg cggcggcggc ggcaacagga ggaagggtgc    1080
cccccacagg tcccctctgg cctaagcagc gctaccttca tgcatgcgtc ccctgctgc    1140
tgctcgttat atatcacaag tcacaacaca cgtagcgcgc tgtggttgca tgcagtgatg    1200
atggtgtggg tggtagctac agtattaatt agtagtacgt tgttataata gtatcttaat    1260
ggtgattagc ctcgtagaga gacgacgaca agctggtagc tggtcgatcg gttttgcttg    1320
gggggaaggt cttggtggcc ttgtgatccg tctagcagct cgctaggacc aaccatggcc    1380
gccgcgccat ctcatgagac tttagagaga gagagagaga gagggtca tggggaggt    1440
agaggggga gagacggttg taaaagcagt tcccattgtt acaggcacca ggtagtaact    1500
ggtcagtggg gcccacttct gcaggcggtg gggcccatac gatcgaggtg gctaccaatt    1560
ttgtatttga tgtaccaagg gttactcgcg gtctcgcgca tacaatttcc acacctatat    1620
atgttatata taaatgataa tatatctgaa ttctgtccca g                      1661

SEQ ID NO: 71               moltype = AA  length = 269
FEATURE                    Location/Qualifiers
source                     1..269
                           mol_type = protein
                           organism = Zea mays
SEQUENCE: 71
MGMAPAGWVG GLVAESFFVA CPAHESRKKN ERNIFCLACC ASICPHCAPR TATTRSSSAN     60
CYVRDQVRRY VYHDVVRLGD LEKLIDCSCV QTYTINSAKV IFLKPRPQSR PFKGSGNICL    120
TCDRILQEPF HFCSLSCKVD HVMTQGGDLS NILQHYGAGG GGGGGGTADPD RLAFPRFENL    180
RVVDGSDLDD DVQVVTPDST LEDPTNNAGG GSSDNGTDDA RRQVVVHGGG EAAKRKKGGG    240
FLPQIVLSLG GGGGGGNRRK GAPHRSPLA                                     269

SEQ ID NO: 72               moltype = DNA  length = 223
FEATURE                    Location/Qualifiers
source                     1..223
                           mol_type = genomic DNA
                           organism = Zea mays
SEQUENCE: 72
gagtcccgca agaagaacga gcgcaacatc ttctgcctcg cctgctgcgc cagcatctgc     60
ccgcactgcg ccccgcgcac cgccaccacc cgctcctcca gcgccaactg ctatgtacgt    120
gatcaggtgc ggcgctacgt gtaccatgac gtcgtccgcc tcggcgacct agagaagctc    180
atcgactgct cctgtgtcca gacctacaca atcaacagtg cca                     223

SEQ ID NO: 73               moltype = DNA  length = 143
```

-continued

```
FEATURE                 Location/Qualifiers
source                  1..143
                        mol_type = genomic DNA
                        organism = Zea mays
SEQUENCE: 73
cctgctgcgc cagcatctgc ccgcactgcg ccccgcgcac cgccaccacc cgctcctcca   60
gcgccaactg ctatgtacgt gatcaggtgc ggcgctacgt gtaccatgac gtcgtccgcc   120
tcggcgacct agagaagctc atc                                           143

SEQ ID NO: 74           moltype = DNA   length = 103
FEATURE                 Location/Qualifiers
source                  1..103
                        mol_type = genomic DNA
                        organism = Zea mays
SEQUENCE: 74
ccgcactgcg ccccgcgcac cgccaccacc cgctcctcca gcgccaactg ctatgtacgt   60
gatcaggtgc ggcgctacgt gtaccatgac gtcgtccgcc tcg                     103

SEQ ID NO: 75           moltype = DNA   length = 63
FEATURE                 Location/Qualifiers
source                  1..63
                        mol_type = genomic DNA
                        organism = Zea mays
SEQUENCE: 75
cgccaccacc cgctcctcca gcgccaactg ctatgtacgt gatcaggtgc ggcgctacgt   60
gta                                                                 63

SEQ ID NO: 76           moltype = DNA   length = 224
FEATURE                 Location/Qualifiers
source                  1..224
                        mol_type = genomic DNA
                        organism = Zea mays
SEQUENCE: 76
atgtacgtga tcaggtgcgg cgctacgtgt accatgacgt cgtccgcctc ggcgacctag   60
agaagctcat cgactgctcc tgtgtccaga cctacacaat caacagtgcc aaggtgatct   120
tcctgaagcc gaggccgcag tccaggcctt caagggctc cggcaacatc tgcctcacgt    180
gcgacaggat cctccaggag cccttccact tctgctccct ctca                    224

SEQ ID NO: 77           moltype = DNA   length = 144
FEATURE                 Location/Qualifiers
source                  1..144
                        mol_type = genomic DNA
                        organism = Zea mays
SEQUENCE: 77
tcgtccgcct cggcgaccta gagaagctca tcgactgctc ctgtgtccag acctacacaa   60
tcaacagtgc caaggtgatc ttcctgaagc cgaggccgca gtccaggcct ttcaagggct   120
ccggcaacat ctgcctcacg tgcg                                          144

SEQ ID NO: 78           moltype = DNA   length = 104
FEATURE                 Location/Qualifiers
source                  1..104
                        mol_type = genomic DNA
                        organism = Zea mays
SEQUENCE: 78
agaagctcat cgactgctcc tgtgtccaga cctacacaat caacagtgcc aaggtgatct   60
tcctgaagcc gaggccgcag tccaggcctt tcaagggctc cggc                    104

SEQ ID NO: 79           moltype = DNA   length = 64
FEATURE                 Location/Qualifiers
source                  1..64
                        mol_type = genomic DNA
                        organism = Zea mays
SEQUENCE: 79
tgtgtccaga cctacacaat caacagtgcc aaggtgatct tcctgaagcc gaggccgcag   60
tcca                                                                64

SEQ ID NO: 80           moltype = DNA   length = 24
FEATURE                 Location/Qualifiers
source                  1..24
                        mol_type = genomic DNA
                        organism = Zea mays
SEQUENCE: 80
caacagtgcc aaggtgatct tcct                                          24

SEQ ID NO: 81           moltype = AA   length = 74
FEATURE                 Location/Qualifiers
source                  1..74
                        mol_type = protein
                        organism = Zea mays
```

```
SEQUENCE: 81
ESRKKNERNI FCLACCASIC PHCAPRTATT RSSSANCYVR DQVRRYVYHD VVRLGDLEKL   60
IDCSCVQTYT INSA                                                     74

SEQ ID NO: 82            moltype = AA   length = 34
FEATURE                  Location/Qualifiers
source                   1..34
                         mol_type = protein
                         organism = Zea mays
SEQUENCE: 82
PHCAPRTATT RSSSANCYVR DQVRRYVYHD VVRL                               34

SEQ ID NO: 83            moltype = AA   length = 20
FEATURE                  Location/Qualifiers
source                   1..20
                         mol_type = protein
                         organism = Zea mays
SEQUENCE: 83
ATTRSSSANC YVRDQVRRYV                                               20

SEQ ID NO: 84            moltype = AA   length = 74
FEATURE                  Location/Qualifiers
source                   1..74
                         mol_type = protein
                         organism = Zea mays
SEQUENCE: 84
VRDQVRRYVY HDVVRLGDLE KLIDCSCVQT YTINSAKVIF LKPRPQSRPF KGSGNICLTC   60
DRILQEPFHF CSLS                                                     74

SEQ ID NO: 85            moltype = AA   length = 31
FEATURE                  Location/Qualifiers
source                   1..31
                         mol_type = protein
                         organism = Zea mays
SEQUENCE: 85
LEKLIDCSCV QTYTINSAKV IFLKPRPQSR P                                  31

SEQ ID NO: 86            moltype = AA   length = 21
FEATURE                  Location/Qualifiers
source                   1..21
                         mol_type = protein
                         organism = Zea mays
SEQUENCE: 86
CVQTYTINSA KVIFLKPRPQ S                                             21

SEQ ID NO: 87            moltype = AA   length = 7
FEATURE                  Location/Qualifiers
source                   1..7
                         mol_type = protein
                         organism = Zea mays
SEQUENCE: 87
NSAKVIF                                                             7

SEQ ID NO: 88            moltype = DNA   length = 23
FEATURE                  Location/Qualifiers
source                   1..23
                         mol_type = other DNA
                         organism = synthetic construct
SEQUENCE: 88
gcgccaactg ctatgtacgt gat                                          23

SEQ ID NO: 89            moltype = DNA   length = 23
FEATURE                  Location/Qualifiers
source                   1..23
                         mol_type = other DNA
                         organism = synthetic construct
SEQUENCE: 89
ggaagatcac cttggcactg ttg                                          23

SEQ ID NO: 90            moltype = DNA   length = 23
FEATURE                  Location/Qualifiers
source                   1..23
                         mol_type = other DNA
                         organism = synthetic construct
SEQUENCE: 90
aggaagatca ccttggcact gtt                                          23

SEQ ID NO: 91            moltype = DNA   length = 14035
FEATURE                  Location/Qualifiers
```

```
source                   1..14035
                         mol_type = other DNA
                         organism = synthetic construct
SEQUENCE: 91
ttctttgaca tcctatttta acaaaaacaa gttagtacat aaatcgacaa taaaataata   60
aaatatgcaa taaaatcata aaatatgcaa taaaatcatg atccatactc gtcaatcgta  120
atcgtaatca aaatcaggat ctagttgctt tcgtcgattt aatggacgcc aagtagcttt  180
cttctttctc gtcactcgtt ttcttttttgg aggaacctct acatcatttt gatcgcctaa  240
taaagattct tccaacattt cagtttgtac attaaacgtg cttgtaagtt cttcgtcttg  300
gaaaatctca gcagcccca cttcctgctc gatttgactt tcaacataac cagcatcacc   360
aggagcatat agtcgttcac gcggattaac tttgtacact accctccaat caaccaaacc  420
gtttttctta gatggatatg tcatataata cacctgctcg cattggtggg caaggattat  480
agtgtcgtga cctttaatc tatcgttgtg tttgacttcc accatgccat attgatttc   540
tcgcgttgta tttgggagaaa accaatcaca atcgaagaac accactttga gttgtttatc  600
tccaaaaaac ttgtactcga ttatatcatt aatgactcca taataattag tcacctttccc  660
ttcatcatcg acagctctag ttacaactcc ggagtttgtc gtggctgcta gaggatgatc  720
atcttcgaac cttgtggaac ggaatctaaa accattgaca tcataccgac cataacgtct  780
gccagttact gctcctaggg ataattgtcg aaggtccggg tgtatattgt cattttttatc  840
tacataatct cgaaaccaac acaagaaatt aagtcccca tcttttccct ctcgacgaat  900
ctggtcacgt tcacagccag agatgcaatt ttgagaatca aattccctgt tagtacaagg  960
aaacaaacct tttagtatca caacaaaaat tctagcggca atgactaaaa taaagtttac 1020
acttacagga gaaactgact catctcttcc atgttgttat acatgtaaag taaagcagtc 1080
ttccattcgt cgttggtgaa acagtatgtt gtgctgggtc ctacagtttt gcccctccat 1140
tgaaaaattt caatatcact aatagggggc tcgtcgacat gataccgcaa cgtatgggca 1200
ttgacattgt gttcctctgc aaagtacagg cccgtgaacg atgctatctc tttgtatttg 1260
aattcttcag cgatgcaccc ttcaactcgt ctcttattac caaccattgc acgtagcttt 1320
tttagtgtcc tttcgatgtg atacatccat ctatattgca caggacctcc taccttagct 1380
tcgtatggta ggtgaacaag tagatgttgc atcggattga agaaacctgg tggaaatatt 1440
ttttcaagtt tgcataccaa aatcggtatt tcttgctcaa gcttctccat catctctttc 1500
tttatttctt tggcacaaag atgtctataa aagtagctta gctccgctaa tgctttccag 1560
acatcattt ttacaaaacc acgaaacata acaggaagga gtctttccat tattatgtgg 1620
tagtcatgac tcttcaaccc agaaaacttg cccgtcttca aattcacaga ccttctaaag 1680
cccgcggcgt aaccatctgg gaactttaag ttttttcaacc atttcatcaa ttgtttcttc 1740
cttttaggtt taatactgaa aggagcacgt ggcttcttct gattctctcc tatctccata 1800
gttggtcttc tacagattaa ggccaagtct ttccttgcct taggggttgtc ttttgttttg 1860
tcggtgatat tcatgcaagt gctgataatg ctttcaccca tatttcgttc ctggtgcatg 1920
acatcaatgt tatgcattag aatcaaggct ttcatataag ggagttccca tagaccacat 1980
ttgtgagtcc aattatgctc ggttccataa ccttcaaaac gatttccatg ttcgtttagt 2040
ttcaaatcat taagtctcgc gagaatctca ggaccactta gacgcttggg tggtccctc  2100
gtcacaatcg tgtcctttt aaaagcgttc ctatcgaacc tgaacgggtg atcctctggc 2160
aaaaaacatc tatggcaatc gaagtaacat atctttccac caaactttag tcgaaagcat 2220
aaagtgtctt caacgcatat aggacatgtc aaaatcccat gacaactcca tccagcaaag 2280
ataccataag ccataaaatc atgaatagac cataaaaacg cggctctcag gttgaacttc 2340
tgtttcttgt aacaatcgta cgcctcgact ccttcccaca aaattttcaa ttcttcaatc 2400
aggggtctca tcatcacatc gatctttgtt ccaggatgat ccggaccagg tattataaga 2460
cacaagaaaa taaattcata tttcatgcaa agagctggtg gaaggttgta tggaacagca 2520
aagacgggcc aacatgagta cgacgtagca gttagattga atggtgagaa accatctgtt 2580
gccaaaccga agcggacatt ccgcacttca tcagcaaagc tggaatcaaa agcatcagt  2640
gccttccatg catctgtatc agctgggtgc accatgacat ttggattctc acgtaccct  2700
tctttgtgcc acctcatgtg tctggctgta ttttggaga tgaacaaacg tttcaaccga 2760
ggtatgagag gcatgtaacg aagctgctta tgtgcaatct tcgtagtcac ggtcaaacca 2820
tcgtcgtttt caacctcaac gaatctacgc tcaccacata cagtacactt cttctcacct 2880
gcggtctcct tccagaaaag catacaatta ttttcacaga catcgatttt ttcgtagtcc 2940
ataccgaggc cagataacag ctttttagac tgatacatgt cctttggcat cttgtgattc 3000
tccggaagta catcactgat caagttcaaa agttccttgt aacagttgtt tgagaatgca 3060
aacttagact taatagccat aagtcgagtc acaaatacaa ggacagtcac ttttgtgtgc 3120
tcatgcaacg gctcttcggc agctttaagg agctcgaaga acttctgaac ctcaggtgta 3180
gctggatcct caaactcggt gggttgaccg gggttctccg aatcgacggt tagaaactca 3240
tggcgtacat cgtcaagcat ctcttccatc ctatcgtagt cctcctcttc atgtgactga 3300
acttccgata caatacgagg tgggtcctca ccgtggtgca cccacacctc atagcctggc 3360
atataaccgt tcttgcaaat atgtatcgac atagtcctcc tgtcaaggaa attaatgttc 3420
cgacacttgc tacaagggca cctaacatcg gttccagtct ctgaccgagc aaaagcatgg 3480
tcgagaaaag catcagtctt ggccacccac tcacttgata gagcacctct tttcttccaa 3540
ccttcataca tccatcgacg attctcctcc atactagata cgatacgtta acttaattag 3600
ataagtactg cacgtgcatt ccgttttttac gaagaaatca cgcccctaca tctgtaggaa 3660
aggataggtc ctaaacccac ccaggagtga ccgacgagac cgtgtttatg acaagacatg 3720
tggtcgtgcg aaatttcggc agcataaccc cgttgttctc caatcgcacg cctaaaaatg 3780
gtgcaattga agaacagaga ggttatgctg ccgaaactaa gcaggagcac atgctttttgt 3840
cataaacacg gactctgtcg gtcaccccga ggctgtccaa aaaagggaca attccggccc 3900
aacataccctc acatgcgtcg cttgtaaggt gtgttgggcc gaaacggtg acgcctaggt  3960
ttcgtttgtt cacactacga tacactatga ttaactataa tcatcgtgca ttattaaata 4020
attaaactaa taaaccataa tacaatatta catacgaaat aatattgtta tagatgacaa 4080
atcatataaa atgaccttat ttccgagggc ataataatta ccctcggaaa ttaaaaatta 4140
aaattatcta aagtaccact aaataaagta aaacaaatct ctttaattaa ctaatcaaat 4200
tttgaccgtc ggacataaca aactaaacaa tcaaatgcat taatacatac aatttcaatc 4260
aaatacatta atacaaacat acaattctaa tcaaatacat taataaaagc atacaatttt 4320
aataaacaaa attgctaatt aagtatactc acttagcggg tgtggagagt cggccggcga 4380
tgggcgcacg ggcggcggcg ggcgcacggg ccgttggcc ggagcacggg gcggcggcga 4440
ccggcgaacg gggcggcggc gaccggcgaa cggggcggcg gcggcggcgg ccggagcacg 4500
```

-continued

```
ggcgtggcgg  tggccggagc  acgagctagg  ggcggtggtg  gccggagcac  gggcgtggcg  4560
gtggtggccg  gagcacgggc  gtggcggtgg  ccggagcacg  agcacggagc  ggtggggcgg  4620
cggcgggcgc  cggagcacga  gcagtggggg  cgggcggtac  ggcgataggg  cgggacggcg  4680
acgagcgtgg  cggcgacgag  cgtggcggcg  acggcggctt  ctcctcggac  acggcggagg  4740
cgtgctcggc  ggcggcagga  tagaaacgcg  cggtctcggg  tgaaactgaa  ggcgcgcggg  4800
tcggaaccgc  gcgttaaaaa  gccttatgtc  cgacggctcg  gtacgaggcc  gtcggacata  4860
agctaatgtc  cgacggccag  ggggtcggcc  gtcggacata  aggtaatgtc  cgacggtcag  4920
tctgccagcc  gtcggttata  tttttttattt  tcgacggccg  ctgttggccg  tcggacataa  4980
ccgtatgtcc  gacggttgcc  tacgggccgt  cggacataag  acgaccgtcg  gaattgtata  5040
gtttactgt  agtgctccct  cactatcttg  ttctcgcctc  gtttttctct  ccctccgcga  5100
gcgccaaggc  agcgcagcta  cgagacaagc  acacgtaata  gtactagtgc  gccgttgccc  5160
tgcctgcctg  ccctgtgccc  tgccttgcac  cacaccacca  ccaccgcaga  tccggtctgg  5220
tccagtccgg  cccggtccgc  tactaaacaa  accagccag  cgcgcgcccc  agcgagagga  5280
gaggaggagg  ggccggggtc  ggcacggcgg  gcagaattgc  ctctgctgcc  tgcgcgctgc  5340
cctgccctgc  cagagggatc  ggagggagag  cgatcagtca  acaagcccag  gaggaggagg  5400
aggaggaggg  agagatccgc  gtgccggccg  gaggcgggct  ccgggagatc  gaccgagcga  5460
ccggcctcgg  tcccggtgcg  gtggtggatg  gggatggcgc  ccgccgggtg  ggtgggcggg  5520
ctcgtgggcg  agagcttctt  cgtggcgtgc  cccgcgcacg  agtcccgcaa  gaagaacgag  5580
cgcaacatct  tctgcctcgc  ctgctgcgcc  agcatctgcc  cgcactgcgc  cccgcgcacc  5640
gccaccaccc  gctcctccag  gtgagtgcga  gtctcgtcgt  cgtcctcctc  ctcgcccggc  5700
ctctcctctt  ccttcctccg  gcggccttcc  cctctccctg  ccaggctgcc  atggcgtcgc  5760
gtggcatgca  cctggccggg  cgatctgctc  agtttctact  cctgctagct  tcgcagcaat  5820
tctcgccgcc  gctgtcccgc  tccgctccgc  ttcttgttgt  tgttggatga  acacaccacc  5880
tccccaccgc  caccgccacc  gggggggcagc  ttttttggggg  ttattgctgg  tggcctcggt  5940
tcttgtgcaa  cggatgggaa  cggcggggac  gagtaccaat  caatcgattt  ctttatttga  6000
tttaattgtt  tatttattat  tcctcggcgt  atatagcact  agacgctact  tcttcctata  6060
tactactact  agagtagtac  tacaagtgta  gaggaggagg  ggcatgggaa  ttggatgtgt  6120
agtatctcgc  ttttgttttg  tcgcgtgctg  tctcttcctt  ccttccttcc  ttggactaga  6180
tttggtcccg  gctttagcct  aaacaaaaaa  atatttcccc  cctaccattt  ctcgcatgat  6240
ttgatttgat  gcgtggtctc  ttctcgtgtc  gtccgtgcgc  gggaaggaat  caagggaaag  6300
gaaaggaaac  caaacccat  ctcgctaatc  gctctcctct  ctctctctct  ctcccttcct  6360
cgcaggcagg  cagaggcagt  acaggttgtt  gcaaaacttg  cacgtacttg  attcctcgcg  6420
cgcgcagcgc  cttgtcgcct  tgcgaggttt  ggtttggttg  ggtcatgagc  tcatccatcc  6480
attccctttt  ccacccatgc  atgcatgcat  gcatgccact  cccttgatta  gggtttataa  6540
gccagcagga  ggcgctgatt  gagtcctaat  ctgcgccact  gtaacagcaa  tcccaaccat  6600
gattttcgca  cccgctccag  gactccggag  cagtgctact  tcttcatcgc  tataattaat  6660
ataattcgtc  tgctccttcc  tgcctgaccg  gggtattaaa  tcctgtgtat  gtacgtagta  6720
ctaacaaaca  aggacaaggc  agtaaaaatt  ctcgttacgg  aacattatct  actccgacct  6780
cccttgcatt  ttttttttgg  aattagtacc  cgggcgttca  tcgcgacctg  catgcaactg  6840
tttcctcaac  gagctagcca  ttacatgctt  ttagtttttt  ataaaatata  tatgcatgca  6900
tggcaaaact  ttttccttttt  taaattttcg  ggagttaaag  aggaggaggg  tcgaaaattc  6960
aaatccccc  accggggca  tgcaaaccct  tcttctttct  ctccgtagct  ttgtcttgta  7020
gctgcagca  tgcatttccc  ccctactttc  atgcagcagc  aactaatcca  tccggatatg  7080
ctggcgctgc  gggagccgga  gtctcgaacc  caaatggcaa  aaaaagctgc  ggggggaggt  7140
tttaccgctg  cctcttcatt  ggaattccaa  tccttgggat  taggatcctc  tgcggtaatc  7200
gccagcctcc  tgctgcgctt  ccgcttgctt  ccccgtccat  taataggcct  ggttatccaa  7260
actgtttgc  caagtatagc  aacatttccc  tgccccccgt  cctgccgact  gaacccgact  7320
actgataaag  gaaaaaaaat  cggttcgggc  ctttgaatta  gattttaccg  tatgcgcccg  7380
cgcgcggtaa  ctgcgcggcc  tgtctttttt  taccaaacag  aggcatcgac  gacgacactg  7440
ttgtcccccg  acgacgaccc  catctctccc  tggtgcgtgc  tacacgacca  aacttctctc  7500
tccttacctt  agggtggggt  ggttttgggg  gtctcccagg  ccatgataaa  gatcaccact  7560
ggagtggtac  tgctgcccgg  ccggtcaaag  catgggggcc  atcgcgtggt  gtgtggccca  7620
acccaaagtt  gtaccctgct  gctgctgtac  cgcctgcgtt  gttatcttag  gccccgtttc  7680
aatctcacgg  gataaacttt  agcttcatgc  taaactttag  ctatatgaat  tgaagtgcta  7740
aagtttagct  ttaattacca  ccattagctc  tcatgtttag  attataaatg  gctaaaagta  7800
gctagaaaaa  agctgctaaa  gtttatctcg  cgagattgga  acacggcctt  atcttagagt  7860
atgaaactgc  ggttgctaaac  atgtttagcg  ccaactgcta  aggtgcggcg  ctacgtgtac  7920
catgacgtcg  tccgcctcgg  cgacctagag  aagctcatcg  actgctcctg  tgtccaggtg  7980
attccctatc  tatcgtcgta  tctgtcttgc  attagtgctt  cgaattttga  tggtgatgct  8040
gatgatgagt  acgttaatta  tatagtagta  aaactcccct  ctctctttgt  gtgtgtgatg  8100
tgtgaccgcg  cagacctaca  caatcaacag  tgccaaggtg  atcttcctga  agccgaggcc  8160
gcagtccagg  cctttcaagg  gctccggcaa  catctgcctc  acgtgcgaca  ggatcctcca  8220
ggagcccttc  cacttctgct  ccctctcatg  caaggttgca  ttggtcagct  agctagcatc  8280
atcgcatacg  ccatgcatat  gcatcgtcgg  attcggatca  tatcgttcag  tgcgtacgtg  8340
gatcatgtca  tatgttatta  cgcaggtgga  ccacgtgatg  acgcagggag  gggacctgtc  8400
caacatcctg  cagcactacg  gcgccggcgg  tggcggtggc  ggtggcacgg  cggacccgga  8460
ccgcctcgcg  ttcccgaggt  tcgagaacct  ccgcgtcgtc  gacggctcgg  acctcgacga  8520
cgacgtccag  gtcgtcaccc  cagactccac  cctcgaggac  ccgaccaaca  acgcgggcgg  8580
cgggtccagc  gacaacggta  ctgacgacgc  cagacggacg  gtcgtcgtcc  atggcggcgg  8640
cgaggcggcc  aagcggaaga  aagggggcgg  cttcttgccc  cagatcgtgc  tgtcactcgg  8700
cggcggcggc  ggcggcggca  acaggaggaa  gggtgccccc  cacaggtccc  ctctggccta  8760
agcagcgcta  ccttcatgca  tgcgtccccc  tgctgctgct  cgttatatat  cacaagtcac  8820
aacacacgta  gcgcgctgtg  gttgcatgca  gtgatgatgg  tgtgggtggt  agctacagta  8880
ttaattagta  gtagcgtgtt  ataatagtat  cttaatggtg  attagcctcg  tagagagacg  8940
acgacaagct  ggtagctggt  cgatcggttt  tgcttgggg  gaaggtcttg  gtggccttgt  9000
gatccgtcta  gcagctcgct  aggaccaacc  atggccgccg  cgccatctca  tgagactttta  9060
gagagagaga  gagagagaga  gggtcatggg  ggaggtagag  gggggagaga  cggttgtaaa  9120
agcagttccc  attgttacag  gcaccaggta  gtaactggtc  agtggggccc  acttctgcag  9180
gcggtggggc  ccatacgatc  gaggtggcta  ccaattttgt  atttgatgta  ccaagggtta  9240
```

-continued

```
ctcgcggtct cgcgcataca atttccacac ctatatatgt tatatataaa tgataatata  9300
tctgaattct gtcccagact aaacaggttg ttttcagcag tctgtatccg ttccatgtgg  9360
gctcaagtga tttttcagctg cctgtttggc gtgtcaagca gctggttgaga catgaggccg  9420
agagctctcg cccagtctcg cccgtaggga tgaaagtagg atgggaaaat cccgtaccga  9480
ccgttatcgt ataaccgaat ttgttagttt tgtcccgatc gttttcgaac cgacgtaaa  9540
aaacgaaaac gggacgaaaa cgggatatac aaaacggtaa acggaaacgg aaacggtaga  9600
gctgttttac cgaccgttta accgggatcc cgttttttaat cgggatgatc ccgtttttgtt  9660
accgtatttt gtaattcggg atcacttcaa tatagacagc tataggcatc actttgaggc  9720
ccagcccatc taagaaaaac ctaacgcgct gttctgctcc caggcgtcgc cgtccacact  9780
cctctctccc agctcgctgc cgtagtgcca tcagctcgtc actcgcaggc gccggcgcgc  9840
agccgtccgc cctcctgctc tgtgcggctt tgcctctccc agctcgcctc gccagtcgcc  9900
aggccagagt gccatcgcag cttcccaggc tcccagctcg ccagagtgcc ggacgccacg  9960
ccagcccggt ccggtctccg gtcggcggtc ggtcgatcgc cgctgctcca gctggctgcc 10020
caggcgacta gacgtccacg acggctcggc gatcggcagg cagctcgctc cacctccaca 10080
ggccacgact ccctctgctg ctgctgtcct ccacggatcc actgctggct gctgctccct 10140
ccacagagaa tcgccttgct acaccatgtg agcagtcctg cagtcctgcc gtgttagacg 10200
ctagctgcta gctcccagcc gtactccacc acgtttggt gcataagctg cgtgttgcct 10260
tgcttttac tgttgttgtt ttaattctgt ggtgcataat tctgttggtg cgtacttcta 10320
ttgggcgtac tttatattat gtcatgtgtg ctagtagact tatatggctt cttatgtagc 10380
caagagctca atatttatca cttatgtgct actaagatgt ttggttttgat gaatcactct 10440
atccaaaatg aagtggtgca tcatgggtcc attcctcaaa tttggtggga tgacttcatt 10500
ccacatatta gtactaaaca actaactatg aggaatgagg tggtgatgga ttaactcact 10560
ccattccaca aaccaaacaa aaaagtgagg agtgagaaga tgatgaacta tatcgttcct 10620
caaaccaaac actccataca ttaaactatg tgtgctccag atttatatga cttttttcta 10680
tgtttaatta agacttgtgt ttacaatttt ttatatttgt ttttaagttt tgaatatatg 10740
ttttcatggt gtgattttac cgaacaaaaa taccggttcc cgtccgattt cggctttaac 10800
ccgaccggat cgtatcggtt ttcgcttacc gtatttatcc cgttcgtttt cgttaccgat 10860
atatcccgtt ttcgttttcg tcccgcaagt taaatatgaa aatgaaaacg gtagaggtat 10920
tttaccgacc gttcccgacc gttttcatcc ctactcgccc gcgtgcatgg attgttgcat 10980
gcatgtgatg cgcgcgcgca cacgcctagc gctcccgtcc aaactcccca gtcgtgttgc 11040
tgtgacctgc tggctgtttg atgcagttgt gattcgcttt gcaatggacc acggtctctg 11100
tcccatggtg tgtgtatctg tgtgtctgag tgtggagacg acagagactc gaaaagatgg 11160
tgtggtggct gttcgatcca gggctcgctt gatgcctgtt ttttttttcca cgagaatctc 11220
tctattagag aacagatgca tgggtcgttt tttagcctct ctagaccagg atgtgaaagg 11280
tagaaaagcc attctcacgt gaggttacag tacttgtagc tttccattac tcatatactt 11340
gcaggaatta atattggaca ctcttttttct actctcgctc tgtttaaat cgcaagctat 11400
ttttccactt tcttaaaaat gtagcagctt ttaccgagta catctcggta cgtacctaaa 11460
aaaaagcttg tagtataagc tttcaaccga gtgtttataa ggcttcgccg agtgcttccg 11520
gcactcgacg aagctattga ttccggtagt gccgggttga atttactttt gtatcactga 11580
gcgtgcgaag agaacagcgg tatttctggc atcgatcggg cacccttcct cggaatcatg 11640
gcttttttgag agtgaccaac aggcagtgcg cgcggtctcg gaacctgaaa attgtttggt 11700
tgtatcgaat gacttgtcac ggccactcga ggcaggcatg agacgctcca ccggaccgcc 11760
acaccatgca tagtgacaga tcatcaaaag gtggttttaa aactcgaatt tttatctgac 11820
tatatagcaa ataaatcctt ttgtacgctc agtttcatat atagacgaaa ttctcccacc 11880
tctcccatgc atgcatgtca tcgatcattc ttgtttatct ggtgatgtat ttaatgaaga 11940
cagaaattcg agtgagattt ccagtggaaa tagccttatt agtgtgccat gaacgaagtt 12000
ctgaagtcga aaccagacga gagtccccat gcacgatgcc atggatatcg ccagtacgta 12060
caggacgtgc gccagcacga tgcaactgtc agcagacagc agccaaaacg caattcttgt 12120
ttcagctggg tgggcaattc cgaggtgtgc taaataaaag catgatccat gcatatagat 12180
gagcatgcag cccgcagccc gacagcccgg cacgaggccc ggtttttttgg cccggcccaa 12240
gcacggcacg gcccgtctgg tttcgtgccc gtgccggccc ggcccggtag accaggccgt 12300
gcttgggctg ccggatgcgc ccgccgggcg gcacggcccg gcccgctagg aaaagcaggc 12360
acggagccgg cccggttcca ggcgaggggc atatccgccc gccctcccc accgccgtt  12420
cagtcccca gtccctagtt ccccacgcca cgcgatttgc tccgcagcct ccgccctccg 12480
ctcgtccgct cgccgctccc tccccattct ccgtcaacgc cgagccgtcg ccactgccgt 12540
tgccggatct ccgtcgtcga ccgacgagat ctcctctctg cctctctcca gtcttcgtca 12600
ctcggtgacg catcggctct ccattcccca atctgtaacc ctaatcccct ttccggcttt 12660
ccctcacctc tccggtgacg catcggctct ccactgccgg atctccgtca ccggcgacat 12720
ctgcacgctt gttctgtgcg gctcacccctc tccggctctc cctccccaat ccctcgctc 12780
gtcgtcgtcg tcatcggtcg tcggcttgtc gcgcgtcgtc gtccctaga ccctcgtctc 12840
cggctccggg ctccggcttg gcaggtacgt gtacgtccct ctccggctct ccctcccaa 12900
tccgacaaac cctaacccta atcccttgct tggtaggtcg ccggccgact acgccgtggt 12960
cgtgctggtg ccgccagtgc cgttgaggta cggtgccgag aggggggccg ggcatggatg 13020
acgacgacga caatggccgg taccctagaa ccatcaacga cgagctcgtt gagttagggc 13080
agcttcccga tgacgtcgac gacatgggag atgctgctgc tgccttattc ggtatcggta 13140
gcagtccatg tgccggcgac ctggagggga cagctgccgg gccggttccg gttagtgatg 13200
ctgctggctc taacgaactt gattcattga cttcttccag cactggtaag cgtcgatctg 13260
ctgtttggga tgacttcact gaagtcactg aaaaccgtaa tggtaagaag gtgcgcattg 13320
ctggtatttg caaattttgc aaggctcggt tgagtgctag ttctaatgct ggcactggac 13380
atttgcttag gcaccagaaa tcatgtaaaa agaagtctga tcatgctgct atggttcaaa 13440
ctagactagc tttgaaccct gatgggtctt ttagaaactg gaatatgat cctcaggtgg 13500
ctaggactga gctttgtcgt ttgattgcta gacttgatct tcctttaggg atagctgaca 13560
cagatgcttg ggataattac attcaacatg ctcacaaccc tagatatgtt agggtatcta 13620
gcttacaac tgctagagac ttggctaagc tatacaatga aaagctaaag aacttaaaag 13680
atgatgtttt tcctggtgtg tcttctattt gcttgacttc tgatatatgg tctggtaatg 13740
ccaaggaaga ctacattact gttgttgctc attttattaa tgctgattgg gagttaaaga 13800
agtgtgtgat aggctttaaa ttgatccaag tgtctcataa tggtgttaac attgctgaac 13860
gcattgcttg tgtgattcaa tactttggca tgattgataa agtgttctct attaccttag 13920
ataatgcttc ttctaattca actgccatgc tcacattgtc acctatgctt gctggttatt 13980
```

-continued

```
tgggtgctga tgttgatcca acagatacta gtaacaaaac atatagtgtg cttca        14035

SEQ ID NO: 92            moltype = DNA   length = 799
FEATURE                  Location/Qualifiers
source                   1..799
                         mol_type = other DNA
                         organism = synthetic construct
SEQUENCE: 92
atggggatgg cgcccgccgg gtgggtgggc gggctcgtgg cggagagctt cttcgtggcg        60
tgcccCgcgc acgagtCccg caagaagaac gagcgcaaca tcttctgcct cgcctgctgc       120
gccagcatct gcccgcactg cgcccCgcgc accgccacca cccgctcctc cagcgccaac       180
tgctaaggtg cggcgctacg tgtaccatga cgtcgtccgc ctcggcgacc tagagaagct       240
catcgactgc tcctgtgtcc agacctacac aatcaacagt gccaaggtga tcttcctgaa       300
gccgaggccg cagtccaggc ctttcaaggg ctccggcaac atctgcctca cgtgcgacag       360
gatcctccag gagcccttcc acttctgctc cctctcatgc aaggtggacc acgtgatgac       420
gcagggaggg gacctgtcca acatcctgca gcactacggc gccggcggtg gcggtggcgg       480
tggcacggcg gacccggacc gcctcgcgtt cccgaggttc gagaacctcc gcgtcgtcga       540
cggctcggac ctcgacgacg acgtccaggt cgtcaccca gactccaccc tcgaggaccc       600
gaccaacaac gcgggcggcg ggtccagcga caacggtact gacgacgcca gacggcaggt       660
cgtcgtccat ggcggcggcg aggcggccaa gcggaagaaa ggggccggct tcttgcccca       720
gatcgtgctg tcactcggcg gcggcggcgg cggcggcaac aggaggaagg gtgcccccca       780
caggtcccct ctggcctaa                                                   799

SEQ ID NO: 93            moltype = AA   length = 61
FEATURE                  Location/Qualifiers
source                   1..61
                         mol_type = protein
                         organism = synthetic construct
SEQUENCE: 93
MGMAPAGWVG GLVAESFFVA CPAHESRKKN ERNIFCLACC ASICPHCAPR TATTRSSSAN        60
C                                                                       61

SEQ ID NO: 94            moltype = DNA   length = 14022
FEATURE                  Location/Qualifiers
source                   1..14022
                         mol_type = other DNA
                         organism = synthetic construct
SEQUENCE: 94
ttctttgaca tcctatttta acaaaaacaa gttagtacat aaatcgacaa taaaataata        60
aaatatgcaa taaaatcata aaatatgcaa taaaatcatg atccatactc gtcaatcgta       120
atcgtaatca aaatcaggat ctagttgctt tcgtcgattt aatggacgcc aagtagcttt       180
cttctttctc gtcactcgtt ttcttttttgg aggaacctct acatcatttt gatcgcctaa      240
taaagattct tccaacattt cagtttgtac attaaacgtt cttgtaagtt cttcgtcttg       300
gaaaatctca gcagcccCca cttcctgctc gatttgactt tcaacataac cagcatcacc       360
aggagcatat agtcgttcac gcggattaac tttgtacact accctccaat caaccaaacc       420
gtttttctta gatggatatg tcatataata cacctgctcg cattggtggg caaggattat       480
agtgtcgtga cctttaatc tatcgttgtg tttgacttcc accatgccat attgattttc        540
tcgcgttgta tttggagaaa accaatcaca atcgaagaac accactttga gttgtttatc       600
tccaaaaaac ttgtactcga ttatatcatt aatgactcca taataattag tcaccttccc       660
ttcatcatcg acagctctag ttacaactcc ggagtttgtc gtggctgcta gaggatgatc       720
atcttcgaac cttgtggaac ggaatctaaa accattgaca tcataccgac cataacgtct      780
gccagttact gctcctaggg ataattgtcg aaggtccggg tgtatattgt catttttatc      840
tacataatct cgaaaccaac acaagaaatt aagtccccca tcttttccct ctcgacgaat      900
ctggtcacgt tcacagccag agatgcaatt ttgagaatca aattccctgt tagtacaagg      960
aaacaaacct tttagtatca caacaaaaat tctagcggca atgactaaaa taaagtttac     1020
acttacagga gaaactgact catctcttcc atgttgttat acatgtaaag taaagcagtc     1080
ttccattcgt cgttggtgaa acagtatgtt gtgctgggtc ctacagtttt gcccctccat     1140
tgaaaaattt caatatcact aatagggggc tcgtcgacat gataccgcaa cgtatgggca     1200
ttgacattgt gttcctctgc aaagtacagg cccgtgaacg atgctatctc tttgtatttg     1260
aattcttcag cgatgcaccc ttcaactcgt ctcttattac caaccattgc acgtagcttt     1320
tttagtgtcc tttcgatgtg atacatccat ctatattgca caggacctcc taccttagct     1380
tcgtatggta ggtgaacaag tagatgttgc atcggattga agaaacctgg tggaaatatt     1440
ttttcaagtt tgcataccaa aatcggtatt tcttgctcaa gcttctccat catctctttc     1500
tttattttctt tggcacaaag atgtctataa aagtagctta gctccgctaa tgcttttccag     1560
acatcatttt ttacaaaacc acgaaacata acaggaagga gtcttttccat tattatgtgg     1620
tagtcatgac tcttcaaccc agaaaacttg cccgtcttca aattcacaga ccttctaaag     1680
cccgcggcgt aaccatctgg gaactttaag ttttcaacc atttcatcaa ttgtttcttc      1740
cttttaggtt taatactgaa aggagcacgt ggcttcttct gattctctcc tatctccata     1800
gttggtcttc tacagattaa ggccaagtct ttccttgct tagggttgtc ttttgttttg      1860
tcggtgatat tcatgcaagt gctgataatg ctttcaccca tatttcgttc ctggtgcatg     1920
acatcaatgt tatgcattag aatcaaggct ttcatataag ggagttccca tagaccacat     1980
ttgtgagtcc aattatgctc ggttccataa ccttcaaaac gatttccatg ttcgtttagt     2040
ttcaaatcat taagtctcgc gagaatctca ggaccactta gacgcttggg tggtcccctc     2100
gtcacaatcg tgtccttttt aaaagcgttc tcatcgaacc tgaacgggtg atcctctggc     2160
aaaaaacatc tatggcaatc gaagtaacat atctttccac caaactttag tcgaaagcat     2220
aaagtgtctt caacgcatat aggacatgtc aaaatcccat gacaactcca tccagcaaag     2280
ataccataag cctataaatc atgaatagac cataaaaacg cggctctcag gttgaacttc     2340
tgtttcttgt aacaatcgta cgcctcgact ccttcccaca aaattttcaa ttcttcaatc     2400
aggggtctca tcatcacatc gatctttgtt ccaggatgat ccgaccagg tattatataga     2460
```

```
cacaagaaaa taaattcata tttcatgcaa agagctggtg gaaggttgta tggaacagca  2520
aagacgggcc aacatgagta cgacgtagca gttagattga atggtgagaa accatctgtt  2580
gccaaaccga agcggacatt ccgcacttca tcagcaaagc tggaatcaaa agcatctagt  2640
gccttccatg catctgtatc agctgggtgc accatgacat ttggattctc acgtacccct  2700
tctttgtgcc acctcatgtg tctggctgta tttttggaga tgaacaaacg tttcaaccga  2760
ggtatgagag gcatgtaacg aagctgctta tgtgcaatct tcgtagtcac ggtcaaacca  2820
tcgtcgtttt caacctcaac gaatctacgc tcaccacata cagtacactt cttctcacct  2880
gcggtctcct tccagaaaag catacaatta ttttcacaga catcgatttt ttcgtagtcc  2940
ataccgaggc cagataaacag cttttttagac tgatacatgt cctttggcat cttgtgattc  3000
tccggaagta catcactgat caagttcaaa agttccttgt aacagttgtt tgagaatgca  3060
aacttagact taatagccat aagtcgagtc acaaatacaa ggacagtcac ttttgtgtgc  3120
tcatgcaacg gctcttcggc agctttaagg agctcgaaga acttctgaac ctcaggtgta  3180
gctggatcct caaactcggt gggttgaccg gggttctccg aatcgacggt tagaaactca  3240
tggcgtacat cgtcaagcat ctcttccatc ctatcgtagt cctcctcttc atgtgactga  3300
acttccgata caatacgagg tgggtcctca ccgtggtcga cccacacctc atagcctggc  3360
atataaccgt tcttgcaaat atgtatcgac atagtcctcc tgtcaaggaa attaatgttc  3420
cgacacttgc tacaagggca cctaacatcg gttccagtct ctgaccgagc aaaagcatgg  3480
tcgagaaaag catcagtctt ggccacccac tcacttgata gagcacctct tttcttccaa  3540
ccttcataca tccatcgacg attctcctcc atactagata cgatacgtta acttaattag  3600
ataagtactg cacgtgcatt ccgtttttac gaagaaatca cgcccctaca tctgtaggaa  3660
aggataggtc ctaaacccac ccaggagtga ccgacgagac cgtgtttatg acaagacatg  3720
tggtcgtgcg aaatttcggc agcataaccc cgttgttctc caatcgcacg cctaaaaatg  3780
gtgcaattga agaacagaga ggttatgctg ccgaaactaa gcaggagcac atgcttttgt  3840
cataaacacg gactctgtcg gtcaccccga ggctgtccaa aaaagggaca attccggccc  3900
aacatacctc acatgcgtcg cttgtaaggt gtgttgggcc gaaacgggtg acgcctaggt  3960
ttcgtttgtt cacactacga tacactatga ttaactataa tcatcgtgca ttattaaata  4020
attaaactaa taaaccataa tacaatatta catcgaaat aatattgtta tagatgacaa  4080
atcatataaa atgaccttat ttccgagggc ataataatta ccctcggaaa ttaaaaatta  4140
aaattatcta aagtaccact aaataaagta aaacaaacta ctttaattaa ctaatcaaat  4200
tttgaccgtc ggacataaca aactaaacaa tcaaatgcat taatacatac aatttcaatc  4260
aaatacatta atacaaacat acaattctaa tcaaatacat taataaaagc atacaattt  4320
aataaacaaa attgctaatt aagtatactc acttagcggg tgtggagagt cggccggcga  4380
tgggcgcacg ggcggcggcg ggcgcacggg gccgttggcc ggagcacggg gcggcggcga  4440
ccggcgaacg ggggcggcggc gaccggcgaa cggggcggcg gcggcggcgg ccggagcacg  4500
ggcgtggcgg tggccggagc acgagctagg ggcggtggtg gccggagcac gggcgtggcg  4560
gtggtggccg gagcacgggc gtggcggtgg ccggagcacg agcacgagc ggtggggcgg  4620
cggcgggcgc cggagcacga gcagtggggg cgggcggtac ggcgataggg cgggacggcg  4680
acgagcgtgg cggcgacgag cgtggcggcg acggcggctt ctcctcggac acggcggagg  4740
cgtgctcggc ggcggcagga tagaaacgcg cggtctcggg tgaaactgaa ggcgcgcggg  4800
tcggaaccgc gcgttaaaaa gccttatgtc cgacggctcg gtacgaggcc gtcggacata  4860
agctaatgtc cgacggccag ggggtcggcc gtcggacata aggtaatgtc cgacggtcag  4920
tctgccagcc gtcggttata ttttttattt tcgacggccg ctgttggccg tcggacataa  4980
ccgtatgtcc gacggttgcc tacgggccgt cggacataag acgaccgtcg gaattgtata  5040
gttttactgt agtgctccct cactatcttg ttctcgcctc gttttttctct ccctccgcga  5100
gcgccaaggc agcgcagcta cgagacaagc acacgtaata gtactagtgc gccgttgccc  5160
tgcctgcctg ccctgtgccc tgccttgcac cacaccacca ccaccgcaga tccggtctgg  5220
tccagtccgg cccggtccgc tactaaacaa accagcccag cgccgccccc agcgagagga  5280
gaggaggagg ggccggggtc ggcacggcgg gcagaattgc ctctgctgcc tgcgcgctgc  5340
cctgccctgc cagagggatc ggagggagag cgatcagtca acaagcccag gaggaggagg  5400
aggaggaggg agagatccgc gtgccggccg gaggcgggct ccgggagatc gaccgagcga  5460
ccggcctcgg tcccggtgcg gtggtggatg gggatggcgc cgccgggtg ggtgggcggg  5520
ctcgtggcgg agagcttctt cgtggcgtgc cccgcgcacg agtcccgcaa gaagaacag  5580
cgcaacatct tctgcctcgc ctgctgcgcc agcatctgcc cgcactgcgc cccgcgcacc  5640
gccaccaccc gctcctccag gtgagtgcga gtctcgtcgt cgtcctcctc ctcgcccggc  5700
ctctcctctt ccttcctccg gcggccttcc cctctccctg ccaggctgcc atggcgtcgc  5760
gtggcatgca cctggccggg cgatctgctc agtttctact cctgctagct tcgcagcaat  5820
tctcgccgcc gctgtccgc tccgctccgc ttcttgttgt tgttggatga acacaccacc  5880
tccccaccgc caccgccacc gggggggcagc ttttttggggg ttattgctgg tggcctcggt  5940
tcttgtgcaa cggatgggaa cggcgggac gagtaccaat caatcgattt ctttatttga  6000
tttaattgtt tatttattat tcctcggcgt atatagcact agacgctact tcttcctata  6060
tactactact agagtagtac tacaagtgta gaggaggagg ggcatgggaa ttggatgtgt  6120
agtatctcgc ttttgttttg tcgcgtgctg tctcttcctt ccttccttcc ttggactaga  6180
tttggtcccg gctttagcct aaacaaaaaa atatttcccc cctaccattt ctcgcatgat  6240
ttgatttgat gcgtggtctc ttctcgtgtc gtccgtgcgg gggaaggaat caagggaaag  6300
gaaaggaaac caaaccccat ctcgctaatc gctctcctct ctctctctct ctcccttcct  6360
cgcaggcagg cagaggcagt acaggttgtt gcaaaacttg cacgtacttg attcctcgcg  6420
cgcgcagcgc cttgtcgcct tgcgaggttt ggtttggttg ggtcatgagc tcatccatcc  6480
attcccttttt ccacccatgc atgcatgcat gcatgccact ccttgatta gggtttataa  6540
gccagcagga ggcgctgatt gagtcctaat ctgcgccact gtaacagcaa tcccaaccat  6600
gattttcgca cccgctccag gactccggag cagtgctact tcttcatcgc tataattaat  6660
ataattcgtc tgctccttcc tgcctgaccg gggtattaaa tcctgtgtat gtacgtagta  6720
ctaacaaaca aggacaaggc agtaaaaatt ctcgttacgg aacattatct actccgacct  6780
cccttgcatt tttttttggg aattagtacc cgggcgttca tcgcgacctg catgcaactg  6840
tttcctcaac gagctagcca ttacatgctt ttagttttt ataaaatata tatgcatgca  6900
tggcaaaact ttttccttttt taaatttctg ggagttaaag aggaggaggg tcgaaaattc  6960
aaatccccc accggggca tgcaaaccct tcttctttct ctccgtagct ttgtcttgta  7020
gctgcagcca tgcatttccc ccctactttc atgcagcagc aactaatcca tccggatatg  7080
ctggcgctgc gggagccgga gtctcgaacc caaatggcaa aaaaagctgc ggggggaggt  7140
tttaccgctg cctcttcatt ggaattccaa tccttgggat taggatcctc tgcggtaatc  7200
```

-continued

```
gccagcctcc tgctgcgctt ccgcttgctt ccccgtccat taataggcct ggttatccaa    7260
actgttttgc caagtatagc aacatttccc tgccccccgt cctgccgact gaaccccgcc    7320
actgataaag gaaaaaaaat cggttcgggc ctttgaatta gattttaccg tatgcgcccg    7380
cgcgcggtaa ctgcgcggcc tgtctttttt taccaaacag aggcatcgac gacgacactg    7440
ttgtcccccg acgacgaccc catctctccc tggtgcgtgc tacacgacca aacttctctc    7500
tccttacctt agggtggggt ggtttttggg gtctcccagg ccatgataaa gatcaccact    7560
ggagtggtac tgctgcccgg ccggtcaaag catggggggcc atcgcgtggt gtgtggccca    7620
acccaaagtt gtaccctgct gctgctgtac cgcctgcgtt gttatcttag gccccgtttc    7680
aatctcacgg gataaacttt agcttcatgc taaacttag ctatatgaat tgaagtgcta    7740
aagtttagct ttaattacca ccattagctc tcatgtttag attataaatg gctaaaagta    7800
gctagaaaaa agctgctaaa gtttatctcg cgagattgga acacggcctt atcttagagt    7860
atgaaactgc ggttgtaaac atgtttagcg ccaactgcta tgtgtaccat gacgtcgtcc    7920
gcctcggcga cctagagaag ctcatcgact gctcctgtgt ccaggtgatt ccctatctat    7980
cgtcgtatct gtcttgcatt agtgcttcga attttgatgg tgatgctgat gatgagtacg    8040
ttaattatat agtagtaaaa ctccccctctc tctttgtgtg tgtgatgtgt gaccgcgcag    8100
acctacacaa tcaacagtgc caaggtgatc ttcctgaagc cgaggccgca gtccaggcct    8160
ttcaagggct ccggcaacat ctgcctcacg tgcgacagga tcctccagga gcccttccac    8220
ttctgctccc tctcatgcaa ggttgcattg gtcagctagc tagcatcatc gcatacgcca    8280
tgcatatgca tcgtcggatt cggatcatat cgttcagtgc gtacgtggat catgtcatat    8340
gttattacgc aggtcggacca cgtgatgacg cagggagggg acctgtccaa catcctgcag    8400
cactacggcg ccggcggtgg cggtggcggt ggcacggcgg acccggaccg cctcgcgttc    8460
ccgaggttcg agaacctccg cgtcgacgac ggctcggacc tcgacgacga cgtccaggtc    8520
gtcaccccag actccaccct cgaggacccg accaacaacg cgggcggcgg gtccagcgac    8580
aacggtactg acgacgccag acggcaggtc gtcgtccatg gcggcggcga ggcggccaag    8640
cggaagaaag ggggcggctt cttgccccag atcgtgctgt cactcggcgg cggcggcggc    8700
ggcggcaaca ggaggaaggg tgccccccac aggtcccctc tggcctaagc agcgctacct    8760
tcatgcatgc gtccccctgc tgctgctcgt tatatatcac aagtcacaac acacgtagcg    8820
cgctgtggtt gcatgcagtg atgatggtgt gggtggtagc tacagtatta attagtagta    8880
gcgtgttata atagtatctt aatggtgatt agcctcgtag agagacgacg acaagctggt    8940
agctggtcga tcggttttgc ttgggggggaa ggtcttggtg gccttgtgat ccgtctagca    9000
gctcgctagg accaaccatg gccgccgcgc catctcatga gactttagag agagagagag    9060
agagagaggg tcatggggga ggtagagggg ggagagacga ttgtaaaagc agttcccatt    9120
gttacaggca ccaggtagta actggtcagt ggggcccact tctgcaggcg gtggggccca    9180
tacgatcgag gtggctacca attttgtatt tgatgtacca agggttactc gcggtctcgc    9240
gcatacaatt tccacaccta tatatgttat atataaatga taatatatct gaattctgtc    9300
ccagactaaa caggttgttt tcagcagtct gtatccgttc catgtgggct caagtgattt    9360
tcagctgcct gtttggcgtg tcaagcagct gttgagacat gaggccgaga gctctcgccc    9420
agtctcgccc gtagggatga aagtaggatg ggaaaatccc gtaccgaccg ttatcgtata    9480
accgaatttg ttagttttgt cccgatcgtt ttcgaacccg acgtaaaaaa cgaaaacggg    9540
acgaaaacgg gatatacaaa acggtaaacg gaaacggaaa cggtagagct gtttttaccga   9600
ccgtttaacc gggatcccgt ttttaatcgg gatgatcccg ttttgttacc gtattttgta    9660
attcgggatc acttcaatat agacagctat aggcatcact ttgaggccca gcccatctaa    9720
gaaaaaccta acgcgctgtt ctgctcccag gcgtcgcccg ccacactcct ctctcccagc    9780
tcgctgccgt agtgccatca gctcgtcact cgcaggcgcc ggcgcgcagc cgtccgccct    9840
cctgctctgt gcggctttgc ctctcccagc tcgcctcgcc agtcgccagg ccagagtgcc    9900
atcgcagctt cccaggctcc cagctcgcca gagtgccgga cgccacgcca gcccggtccg    9960
gtctccggtc ggcggtcggt cgatcgccgc tgctccagct ggctgcccag gcgactagac    10020
gtccacgacg gctcggcgat cggcaggcag ctcgctccac ctccacaggc cacgactccc    10080
tctgctgctg ctgtcctcca cggatccact gctggctgct gctccctcca cagagaatcg    10140
ccttgctaca ccatgtgagc agtcctgcag tcctgccgtg ttagacgcta gctgctagct    10200
cccagccgca ctccaccacg tttggtgca taagctgcgt gttgccttgc tttttactgt     10260
tgttgtttta attctgtggt gcataaattct gttggtgcgt acttctattg ggcgtacttt    10320
atattatgtc atgtgtgcta gtagacttat atggcttctt atgtagccaa gagctcaata    10380
tttatcactt atgtgctact aagatgtttg gtttgatgaa tcactctatc caaaatgaag    10440
tggtgcatca tgggtccatt cctcaaattt ggtgggatga cttcattcca catattagta    10500
ctaaacaact aactatgagg aatgaggtgg tgatggatta actcactcca ttccacaaac    10560
caaacaaaaa agtgaggagt gagaagatga tgaactatat cgttcctcaa accaaacact    10620
ccatacatta aactatgtgt gctccagatt tatatgactt ttttctatgt ttaattaaga    10680
cttgtgttta caattttta tatttgtttt taagttttga atatatgttt tcatggtgtg    10740
attttaccga acaaaaatac cggttcccgt ccgatttcgg ctttaacccg accggatcgt    10800
atcggttttc gcttaccgta tttatcccgt tcgttttcgt taccgatata tcccgttttc    10860
gttttcgtcc cgcaagttaa atatgaaaat gaaacggta gaggtatttt accgaccgtt    10920
cccgaccgtt ttcatcccta ctcgcccgcg tgcatggatt gttgcatgca tgtgatgcgc    10980
gcgcgcacac ggctcggcgct ccccagtc cccgtccaaa ctccccagtc gttgctgtt gacctgctgg   11040
ctgtttgatg cagttgtgat tcgctttgca atggaccacg gtctctgtcc catggtgtgt    11100
gtatctgtgt gtctgagtgt ggagacgaca gagactcgaa aagatggtgt ggtggctgtt    11160
cgatccaggg ctcgcttgat gcctgttttt ttttccacga gaatctctct attagagaac    11220
agatgcatgg gtcgtttttt agcctctcta gaccaggatg tgaaaggtag aaaagccatt    11280
ctcacgtgag gttacagtac ttgtagcttt ccattactca tacttgca ggaattaata    11340
ttggacactc ttttttctact ctcgctctgt tttaaatcgc aagctatttt tccactttct    11400
taaaaatgta gcagctttta ccgagtacat ctcggtacgt acctaaaaaa aagcttgtag    11460
tataagcttt caaccgagtg tttataaggc ttcgccgagt gcttccggca ctcggcgaag    11520
ctattgattc cggtagtgcc gggttgaatt tacttttgta tcactgagcg tgcgaagaga    11580
acagcggtat ttctggcatc gatcgggcac ccttcctcgg aatcatgct ttttgagagt    11640
gaccaacagg cagtgcgcgc ggtctcggaa cctgaaaatt gtttggttgt atcgaatgac    11700
ttgtcacggc cactcgaggc aggcatgaga cgctccaccg gaccgccaca ccatgcatag    11760
tgacagatca tcaaaaggtg gttttaaaac tcgaatttt atctgactat atagcaaata    11820
aatccttttg tacgctcagt ttcatatata gacgaaattc tccaacctct cccatgacatg    11880
catgtcatcg atcattcttg tttatctggt gatgtatta atgaagacag aaattcgagt     11940
```

```
gagatttcca gtggaaatag ccttattagt gtgccatgaa cgaagttctg aagtcgaaac   12000
cagacgagag tccccatgca cgatgccatg gatatcgcca gtacgtacag gacgtgcgcc   12060
agcacgatgc aactgtcagc agacagcagc caaaacgcaa ttcttgtttc agctgggtgg   12120
gcaattccga ggtgtgctaa ataaaagcat gatccatgca tatagatgag catgcagccc   12180
gcagcccgac agcccggcac gaggcccggt tttttggccc ggcccaagca cggcacggcc   12240
cgtctggttt cgtgcccgtg ccggcccggc ccggtagacc aggccgtgct tgggctgccg   12300
gatgcgcccg ccgggcggca cggccccggcc cgctaggaaa agcaggcacg gagccggccc   12360
ggttccaggc gaggggcata tccgcccgcc cctccccacc gcccgttcag tcccccagtc   12420
cctagttccc cacgccacgc gatttgctcc gcagcctccg ccctccgctc gtccgctcgc   12480
cgctccctcc ccattctccg tcaacgccga gccgtcgcca ctgccgttgc cggatctccg   12540
tcgtcgaccg acgagatctc ctctctgcct ctctccagtc ttcgtcactc ggtgacgcat   12600
cggctctcca ttccccaatc tgtaaccceta atccccttte cggctttccc tcacctctcc   12660
ggtgacgcat cggctctcca ctgccggatc tccgtcaccg gcgacatctg cacgcttgtt   12720
ctgtgcggct caccctctcc ggctctccct ccccaatccc ctcgctcgtc gtcgtcgtca   12780
tcggtcgtcg gcttgtcgcg cgtcgtcgtc ccctagaccc tcgtctccgg ctccgggctc   12840
cggcttggca ggtacgtgta cgtccctctc cggctctccc tccccaatcc gacaaaccct   12900
aaccctaatc ccttgcttgg taggtcgccg gccgactacg ccgtggtcgt gctggtgccg   12960
ccagtgccgt tgaggtacgg tgccgagagg ggggccggcc atggatgacg acgacgacaa   13020
tggccggtac cctagaacca tcaacgacga gctcgttgag ttagggcagc ttcccgatga   13080
cgtcgacgac atgggagatg ctgctgctgc cttattcggt atcggtagca gtcatggtgc   13140
cggcgacctg gaggggacag ctgccgggcc ggttccggtt agtgatgctg ctggctctaa   13200
cgaacttgat tcattgactt cttccagcac tggtaagcgt gatctgctg tttgggatga   13260
cttcactgaa gtcactgaaa accgtaatgg taagaaggtg cgcattgctg gtatttgcaa   13320
attttgcaag gctcggttga gtgctagttc taatgctggc actggacatt tgcttaggca   13380
ccagaaatca tgtaaaaaga agtctgatca tgctgctatg gttcaaacta gactagcttt   13440
gaaccctgat gggtctttta gaaactggga atatgatcct caggtggcca ggactgagct   13500
ttgtcgtttg attgctagac ttgatcttcc tttaggggata gctgacacag atgcttggga   13560
taattacatt caacatgctc acaaccctag atatgttagg gtatctaggt ttacaactgc   13620
tagagacttg gctaagctat acaatgaaaa gctaaagaac ttaaaagatg atgttttttcc   13680
tggtgtgtct tctatttgct tgacttctga tatatggtct ggtaatgcca aggaagacta   13740
cattactgtt gttgctcatt ttattaatgc tgattgggag ttaaagaagt gtgtgatagg   13800
ctttaaattg atccaagtgt ctcataatgg tgttaacatt gctgaacgca ttgcttgtgt   13860
gattcaatac tttggcatga ttgataaagt gttctctatt accttagata atgcttcttc   13920
taattcaact gccatgctca cattgtcacc tatgcttgct ggttatttgg gtgctgatgt   13980
tgatccaaca gatactagta acaaaacata tagtgtgctt ca                     14022
```

SEQ ID NO: 95         moltype = DNA   length = 786
FEATURE               Location/Qualifiers
source                1..786
                      mol_type = other DNA
                      organism = synthetic construct SEQUENCE: 95
```
atggggatgg cgcccgccgg gtgggtgggc gggctcgtgg cggagagctt cttcgtggcg   60
tgccccgcgc acgagtcccg caagaagaac gagcgcaaca tcttctgcct cgcctgctgc   120
gccagcatct gcccgcactg cgcccccgcgc accgccacca cccgctcctc cagcgccaac   180
tgctatgtgt accatgacgt cgtccgcctc ggcgacctag agaagctcat cgactgctcc   240
tgtgtccaga cctacacaat caacagtgcc aaggtgatct tcctgaagcc gaggccgcag   300
tccaggcctt tcaagggctc cggcaacatc tgcctcacgt gcgacaggat cctccaggag   360
cccttccact tctgctccct ctcatgcaag gtggaccacg tgatgacgca gggaggggac   420
ctgtccaaca tcctgcagca ctacggcgcc ggcggtggcg gtggcggtgg cacggcggac   480
ccggaccgcc tcgcgttccc gaggttcgag aacctccgcg tcgtcgacgg ctcggacctc   540
gacgacgacg tccaggtcgt caccccagac tccaccctcg aggacccgac caacaacgcg   600
ggcggcgggt ccagcgacaa cggtactgac gacgccagac ggcaggtcgt cgtccatggc   660
ggcggcgagg cggccaagcg gaagaaaggg ggcggcttct tgccccagat cgtgctgtca   720
ctcggcggc gcggcggcgg cggcaacagg aggaagggtg ccccccacag gtcccctctg   780
gcctaa                                                              786
```

SEQ ID NO: 96         moltype = AA   length = 261
FEATURE               Location/Qualifiers
source                1..261
                      mol_type = protein
                      organism = synthetic construct SEQUENCE: 96
```
MGMAPAGWVG GLVAESFFVA CPAHESRKKN ERNIFCLACC ASICPHCAPR TATTRSSSAN   60
CYVYHDVVRL GDLEKLIDCS CVQTYTINSA KVIFLKPRPQ SRPFKGSGNI CLTCDRILQE   120
PPHFCSLSCK VDHVMTQGGD LSNILQHYGA GGGGGGGTAD PDRLAFPRFE NLRVVDGSDL   180
DDDVQVVTPD STLEDPTNNA GGGSSDNGTD DARRQVVVHG GGEAAKRKKG GGFLPQIVLS   240
LGGGGGGNR RKGAPHRSPL A                                             261
```

SEQ ID NO: 97         moltype = DNA   length = 14034
FEATURE               Location/Qualifiers
source                1..14034
                      mol_type = other DNA
                      organism = synthetic construct SEQUENCE: 97
```
ttctttgaca tcctatttta acaaaaacaa gttagtacat aaatcgacaa taaaataata   60
aaatatgcaa taaaatcata aaatatgcaa taaaatcatg atccatactc gtcaatcgta   120
atcgtaatca aaatcaggat ctagttgctt cgtcgattat aatggacgcc aagtagcttt   180
cttctttctc gtcactcgtt ttctttttgg aggaacctct acatcatttt gatcgcctaa   240
```

-continued

```
taaagattct tccaacattt cagtttgtac attaaacgtg cttgtaagtt cttcgtcttg    300
gaaaatctca gcagcccca cttcctgctc gatttgactt tcaacataac cagcatcacc    360
aggagcatat agtcgttcac gcggattaac tttgtacact accctccaat caaccaaacc    420
gttttttta gatggatatg tcatataata cacctgctcg cattggtggg caaggattat    480
agtgtcgtga cctttaatc tatcgttgtg tttgacttcc accatgccat attgattttc    540
tcgcgttgta tttggagaaa accaatcaca atcgaagaac accactttga gttgtttatc    600
tccaaaaaac ttgtactcga ttatatcatt aatgactcca taataattag tcaccttccc    660
ttcatcatcg acagctctag ttacaactcc ggagtttgtc gtggctgcta gaggatgatc    720
atcttcgaac cttgtggaac ggaatctaaa accattgaca tcataccgac cataacgtct    780
gccagttact gctcctaggg ataattgtcg aaggtccggg tgtatattgt cattttatc    840
tacataatct cgaaaccaac acaagaaatt aagtcccca tctttccct ctcgacgaat    900
ctggtcacgt tcacagccag agatgcaatt ttgagaatca aattccctgt tagtacaagg    960
aaacaaacct tttagtatca caacaaaaat tctagcggca atgactaaaa taaagtttac   1020
acttacagga gaaactgact catctcttcc atgttgttat acatgtaaag taaagcagtc   1080
ttccattcgt cgttggtgaa acagtatgtt gtgctgggtc ctacagtttt gcccctccat   1140
tgaaaaattt caatatcact aataggggc tcgtcgacat gataccgcaa cgtatgggca   1200
ttgacattgt gttcctctgc aaagtacagg cccgtgaacg atgctatctc tttgtatttg   1260
aattcttcag cgatgcaccc ttcaactcgt ctcttattac caaccattgc acgtagcttt   1320
tttagtgtcc tttcgatgtg atacatccat ctatattgca caggacctcc taccttagct   1380
tcgtatggta ggtgaacaag tagatgttgc atcggattga agaaacctgg tggaaatatt   1440
ttttcaagtt tgcataccaa aatcggtatt tcttgctcaa gcttctccat catctctttc   1500
tttatttctt tggcacaaag atgtctataa aagtagctta gctccgctaa tgctttccag   1560
acatcatttt ttacaaaacc acgaaacata acaggaagga gtctttccat tattatgtgg   1620
tagtcatgac tcttcaaccc agaaaacttg cccgtcttca aattcacaga ccttctaaag   1680
cccgcggcgt aaccatctgg gaactttaag ttttttcaacc atttcatcaa ttgtttcttc   1740
cttttaggtt taatactgaa aggagcacgt ggcttcttct gattctctcc tatctccata   1800
gttggtcttc tacagattaa ggccaagtct ttccttgcct tagggttgtc ttttgttttg   1860
tcggtgatat tcatgcaagt gctgataatg ctttcacccca tatttcgttc ctggtgcatg   1920
acatcaatgt tatgcattag aatcaaggct ttcatataag ggagttccca tagaccacat   1980
ttgtgagtcc aattatgctc ggttccataa ccttcaaaac gatttccatg ttcgtttagt   2040
ttcaaatcat taagtctcgc gagaatctca ggaccactta gacgcttggg tggtcccctc   2100
gtcacaatcg tgtcctttt aaaagcgttc ctatcgaacc tgaacgggtg atcctctggc   2160
aaaaaacatc tatggcaatc gaagtaacat atctttccac caaactttag tcgaaagcat   2220
aaagtgtctt caacgcatat aggacatgtc aaaatcccat gacaactcca tccagcaaag   2280
ataccataag ccataaaatc atgaatagac cataaaaacg cggctctcag gttgaacttc   2340
tgtttcttgt aacaatcgta cgcctcgact ccttcccaca aaattttcaa ttcttcaatc   2400
aggggtctca tcatcacatc gatctttgtt ccaggatgat ccggaccagg tattataaga   2460
cacaagaaaa taaattcata tttcatgcaa agagctggtg gaaggttgta tggaacagca   2520
aagacgggcc aacatgagta cgacgtagca gttagattga atggtgagaa accatctgtt   2580
gccaaaccga agcggacatt ccgcacttca tcagcaaagc tggaatcaaa agcatctagt   2640
gccttccatg catctgtatc agctgggtgc accatgacat ttggattctc acgtaccct    2700
tctttgtgcc acctcatgtg tctggctgta ttttggaga tgaacaaacg tttcaaccga   2760
ggtatgagag gcatgtaacg aagctgctta tgtgcaatct tcgtagtcac ggtcaaacca   2820
tcgtcgtttt caacctcaac gaatctacgc tcaccacata cagtacactt cttctcacct   2880
gcggtctcct tccagaaaag catacaatta ttttcacaga catcgatttt ttcgtagtcc   2940
ataccgagcc cagataacag cttttttagac tgatacatgt cctttggcat cttgtgattc   3000
tccggaagta catcactgat caagttcaaa agttccttgt aacagttgtt tgagaatgca   3060
aacttagact taatagccat aagtcgagtc acaaatacaa ggacagtcac ttttgtgtgc   3120
tcatgcaacg gctcttcggc agctttaagg agctcgaaga acttctgaac ctcaggtgta   3180
gctggatcct caaactcggt gggttgaccg gggtctccg aatcgacggt tagaaactca   3240
tggcgtacat cgtcaagcat ctcttccatc ctatcgtagt cctcctcttc atgtgactga   3300
acttccgata caatacgagg tgggtcctca ccgtggtgca cccacacctc atagcctggc   3360
atataaccgt tcttgcaaat atgtatcgac atagtcctcc tgtcaaggaa attaatgttc   3420
cgacacttgc tacaagggca cctaacatcg gttccagtct ctgaccgagc aaaagcatgg   3480
tcgagaaaag catcagtctt ggccacccac tcacttgata gagcacctct tttcttccaa   3540
ccttcataca tccatcgacg attctcctcc atactagata cgatacgtta acttaattag   3600
ataagtactg cacgtgcatt ccgttttac gaagaaatca cgcccctaca tctgtaggaa   3660
aggataggtc ctaaacccac ccaggagtga ccgacgagac cgtgtttatg acaagacatg   3720
tggtcgtgcg aaatttcggc agcataaccc cgttgttctc caatcgcacg cctaaaaatg   3780
gtgcaattga agaacagaga ggttatgctg ccgaaactaa gcaggagcac atgctttttg   3840
cataaacacg gactctgtcg gtcaccccga ggctgtccaa aaaagggaca attccggccc   3900
aacatacctc acatgcgtcg cttgtaaggt gtgttgggcc gaaacgggtg acgcctaggt   3960
ttcgtttgtt cacactacga tacactatga ttaactataa tcatcgtgca ttattaaata   4020
attaaactaa taaaccataa tacaatatta catacgaaat aatattgtta tagatgacaa   4080
atcatataaa atgaccttat ttccgagggc ataataattc ccctcggaaa ttaaaaatta   4140
aaattatcta aagtaccact aaataaagta aaacaaacta ctttaattaa ctaatcaaat   4200
tttgaccgtc ggacataaca aactaaacaa tcaaatgcat taatacatac aatttcaatc   4260
aaatacatta atacaaacat acaattctaa tcaaatacat taataaaagc atacaatttt   4320
aataaacaaa attgctaatt aagtatactc acttagcggg tgtggagagt cggccggcg   4380
tgggcgcacg ggcggcggcg ggcgcacggg gccgttggcc ggagcacggg gcggcggcga   4440
ccggcgaacg gggcggcggc gaccggcgaa cggggcggcg gcggcggcgg ccggagcacg   4500
ggcgtggcg tggccggagc acgagctagg ggcggtggtg gccggagcac gggcgtggcg   4560
gtggtggccg gagcacgggc gtggcggtgg ccggagcacg agcacggagc ggtggggcgg   4620
cggcgggcgc cggagcacga gcagtggggg cgggcggtga cggacgggcg   4680
acgagcgtgg cggcgacgag cgtggcggcg acgcggcgct tcctcggac acggcggagg   4740
cgtgctcggc ggcggcagga tagaaacgcg cggtctcggg tgaaactgaa ggcgcgcggg   4800
tcggaaccgc gcgttaaaaa gccttatgtc cgacggctcg gtacgaggcc gtcggacata   4860
agctaatgtc cgacggccag ggggtcggcc gtcggacata aggtaatgtc cgacggtcag   4920
tctgccagcc gtcggttata ttttttattt tcgacggccg ctgttggccg tcggacataa   4980
```

-continued

```
ccgtatgtcc gacggttgcc tacgggccgt cggacataag acgaccgtcg gaattgtata   5040
gttttactgt agtgctccct cactatcttg ttctcgcctc gttttttctct ccctccgcga   5100
gcgccaaggc agcgcagcta cgagacaagc acacgtaata gtactagtgc gccgttgccc   5160
tgcctgcctg ccctgtgccc tgccttgcac cacaccacca ccaccgcaga tccggtctgg   5220
tccagtccgg cccggtccgc tactaaacaa accagcccag cgcgcgcccc agcgagagga   5280
gaggaggagg ggccggggtc ggcacggcgg gcagaattgc ctctgctgcc tgcgcgctgc   5340
cctgccctgc cagagggatc ggagggagag cgatcagtca acaagcccag gaggaggagg   5400
aggaggaggg agagatccgc gtgccggccg gaggcgggct ccgggagatc gaccgagcga   5460
ccggcctcgg tcccggtgcg gtggtggatg gggatggcgc ccgccgggtg ggtgggcggg   5520
ctcgtggcgg agagcttctt cgtggcgtgc cccgcgcacg agtcccgcaa gaagaacgag   5580
cgcaacatct tctgcctcgc ctgctgcgcc agcatctgcc cgcactgcgc cccgcgcacc   5640
gccaccaccc gctcctccag gtgagtgcga gtctcgtcgt cgtcctcctc ctcgcccggc   5700
ctctcctctt ccttcctccg gcggccttcc cctctccctg ccaggctgcc atggcgtcgc   5760
gtggcatgca cctggccggg cgatctgctc agtttctact cctgctagct tcgcagcaat   5820
tctcgccgcc gctgtcccgc tccgctccgc ttcttgttgt tgttggatga acacaccacc   5880
tccccaccgc caccgccacc gggggggcagc tttttggggg ttattgctgg tggcctcggt   5940
tcttgtgcaa cggatgggaa cggcgggggac gagtaccaat caatcgattt ctttatttga   6000
tttaattgtt tatttattat tcctcggcgt atatagcact agacgctact tcttcctata   6060
tactactact agagtagtac tacaagtgta gaggaggagg ggcatgggaa ttggatgtgt   6120
agtatctcgc ttttgtttg tcgcgtgctg tctcttcctt ccttccttcc ttggactaga   6180
tttggtcccg gctttagcct aaacaaaaaa atatttcccc cctaccattt ctcgcatgat   6240
ttgatttgat gcgtggtctc ttctcgtgtc gtccgtgcgc gggaaggaat caagggaaag   6300
gaaaggaaac caaaccccat ctcgctaatc gctctcctct ctctctctct ctcccttcct   6360
cgcaggcagg cagaggcagt acaggttgtt gcaaaacttg cacgtacttg attcctcgcg   6420
cgcgcagcgc cttgtcgcct tgcgaggttt ggtttggttg ggtcatgagc tcatccatcc   6480
attcccctttt ccacccatgc atgcatgcat gcatgccact cccttgatta gggtttataa   6540
gccagcagga ggcgctgatt gagtcctaat ctgcgccact gtaacagcaa tcccaaccat   6600
gattttcgca cccgctccag gactccggag cagtgctact tcttcatcgc tataattaat   6660
ataattcgtc tgctccttcc tgcctgaccg gggtattaaa tcctgtgtat gtacgtagta   6720
ctaacaaaca aggacaaggc agtaaaaatt ctcgttacgg aacattatct actccgacct   6780
cccttgcatt tttttttttgg aattagtacc cgggcgttca tcgcgacctg catgcaactg   6840
tttcctcaac gagctagcca ttacatgctt ttagttttt ataaaatata tatgcatgca   6900
tggcaaaact ttttcctttt taaattttcg ggagttaaag aggaggaggg tcgaaaattc   6960
aaatccccc acccggggca tgcaaaccct tcttctttct ctccgtagct ttgtcttgta   7020
gctgcagcca tgcatttccc ccctactttc atgcagcagc aactaatcca tccggatatg   7080
ctggcgctgc gggagccgga gtctcgaacc caaatggcaa aaaaagctgc gggggggaggt   7140
tttaccgctg cctcttcatt ggaattccaa tccttgggat taggatcctc tgcggtaatc   7200
gccagcctcc tgctgcgctt ccgcttgctt ccccgtccat taataggcct ggttatccaa   7260
actgttttgc caagtatagc aacatttccc tgcccccgct cctgccgact gaaccccgcc   7320
actgataaag gaaaaaaaat cggttcgggc ctttgaatta gattttaccg tatgcgcccg   7380
cgcgcggtaa ctgcgcggcc tgtctttttt taccaaacag aggcatcgac gacgacactg   7440
ttgtcccccg acgacgaccc catctctccc tggtgcgtgc tacacgacca aacttctctc   7500
tccttacctt agggtggggt ggttttgggg gtctcccagg ccatgataaa gatcaccact   7560
ggagtggtac tgctgcccgg ccggtcaaag catggggggcc atcgcgtggt gtgtggccca   7620
acccaaagtt gtaccctgct gctgctgtac cgcctgcgtt gttatcttag gccccgtttc   7680
aatctcacgg gataaacttt agcttcatgc taaactttag ctatatgaat tgaagtgcta   7740
aagtttagct ttaattacca ccattagctc tcatgtttag attataaatg gctaaaagta   7800
gctagaaaaa agctgctaaa gtttatctcg cgagattgga acacggcctt atcttagagt   7860
atgaaactgc ggttgtaaac atgtttagcg ccaactgcta ggtgcggcgc tacgtgtacc   7920
atgacgtcgt ccgcctcggc gacctagaga agctcatcga ctgctcctgt gtccaggtga   7980
ttccctatct atcgtcgtat ctgtcttgca ttagtgcttc gaatttttgat ggtgatgctg   8040
atgatgagta cgttaattat atagtagtaa aactcccctc tctctttgtg tgtgtgatgt   8100
gtgaccgcgc agacctacac aatcaacagt gccaaggtga tcttcctgaa gccgaggccg   8160
cagtccaggc ctttcaaggg ctccggcaac atctgcctca cgtgcgacag gatcctccag   8220
gagcccttcc acttctgctc cctctcatgc aaggttgcat tggtcagcta gctagcatca   8280
tcgcatacgc catgcatatg catcgtcgga ttcggatcat atcgttcagt gcgtacgtgg   8340
atcatgtcat atgttattac gcaggtggac cacgtgatga cgcagggagg ggacctgtcc   8400
aacatcctgc agcactacgg cgccggcggt ggcggtggcg gtggcacggc ggacccggac   8460
cgcctcgcgt tcccgaggtt cgagaacctc cgcgtcgtcg acggctcgga cctcgacgac   8520
gacgtccagg tcgtcacccc agactccacc ctcgaggacc cgaccaacaa cgccggcgac   8580
gggtccagcg acaacggtac tgacgacgcc agacggcagg tcgtcgtcca tggcggcggc   8640
gaggcggcca agcggaagaa aggggggcggc ttcttgcccc agatcgtgct gtcactcggc   8700
ggcggcggcg gcggcggcaa caggaggaag ggtgcccccc acaggtcccc tctggcctaa   8760
gcagcgctac cttcatgcat gcgtccccct gctgctgctc gttatatatc acaagtcaca   8820
acacacgtag cgcgctgtgg ttgcatgcag tgatgatggt gtgggtggta gctacagtat   8880
taattagtag tagcgctgtta taatagtatc ttaatggtga ttagcctcgt agagagacga   8940
cgacaagctg gtagctggtc gatcggtttt gcttgggggg aagtcttgg tggccttgtg   9000
atccgtctag cagctcgcta ggaccaacca tggccgccgc gccatctcat gagactttag   9060
agagagagag agagagagag agagagggg ggtcatgggg gaggtagag ggttgtaaaa   9120
gcagttccca ttgttacagg caccaggtag taactggtca gtggggccca cttctgcagg   9180
cggtggggcc catacgatcg aggtggctac caattttgta tttgatgtac caagggttac   9240
tcgcggtctc gcgcatacaa tttccacacc tatatatgtt atatataaat gataatatat   9300
ctgaattctg tcccagacta aacaggttgt tttcagcagt ctgtatccgt tccatgtggg   9360
ctcaagtgat tttcagctgc ctgtttggcg tgtcaagcag ctgttgagac atgaggccga   9420
gagctctcgc ccagtctcgc ccgtagggat gaaagtagga tgggaaaatc ccgtaccgac   9480
cgttatcgta taaccgaatt tgttagtttt gtcccgatcg ttttcgaacc cgacgtaaaa   9540
aacgaaaacg ggacgaaaac gggatataca aaacggtaaa cggaaacgga aacggtagag   9600
ctgttttacc gaccgtttaa ccgggatccc gtttttaatc gggatgatcc cgttttgtta   9660
ccgtattttg taattcggga tcacttcaat atagacagct ataggcatca ctttgaggcc   9720
```

-continued

```
cagcccatct aagaaaaacc taacgcgctg ttctgctccc aggcgtcgcc gtccacactc   9780
ctctctccca gctcgctgcc gtagtgccat cagctcgtca ctcgcaggcg ccggcgcgca   9840
gccgtccgcc ctcctgctct gtgcggcttt gcctctccca gctcgcctcg ccagtcgcca   9900
ggccagagtg ccatcgcagc ttcccaggct cccagctcgc cagagtgccg gacgccacgc   9960
cagcccggtc cggtctccgg tcggcggtcg gtcgatcgcc gctgctccag ctggctgccc  10020
aggcgactag acgtccacga cggctcggcg atcggcaggc agctcgctcc acctccacag  10080
gccacgactc cctctgctgc tgctgtcctc cacggatcca ctgctggctg ctgctccctc  10140
cacagagaat cgccttgcta caccatgtga gcagtcctgc agtcctgccg tgttagacgc  10200
tagctgctag ctcccagccg tactccacca cgttttggtg cataagctgc gtgttgcctt  10260
gcttttact gttgttgttt taattctgtg gtgcataatt ctgttggtgc gtacttctat  10320
tgggcgtact ttatattatg tcatgtgtgc tagtagactt atatggcttc ttatgtagcc  10380
aagagctcaa tatttatcac ttatgtgcta ctaagatgtt tggtttgatg aatcactcta  10440
tccaaaatga agtggtgcat catgggtcca ttcctcaaat ttggtgggat gacttcattc  10500
cacatattag tactaaacaa ctaactatga ggaatgaggt ggtgatggat taactcactc  10560
cattccacaa accaaacaaa aaagtgagga gtgagaagat gatgaactat atcgttcctc  10620
aaaccaaaca ctccatacat taaactatgt gtgctccaga tttatatgac ttttttctat  10680
gtttaattaa gacttgtgtt tacaattttt tatatttgtt tttaagtttt gaatatatgt  10740
tttcatggtg tgattttacc gaacaaaaat accggttccc gtccgatttc ggctttaacc  10800
cgaccggatc gtatcggttt tcgcttaccg tatttatccc gttcgtttc gttaccgata  10860
tatcccgttt tcgttttcgt cccgcaagtt aaatatgaaa atgaaaacgg tagaggtatt  10920
ttaccgaccg ttcccgaccg ttttcatccc tactcgcccg cgtgcatgga ttgttgcatg  10980
catgtgatgc gcgcgcgcac acgcctagcg ctcccgtcca aactccccag tcgtgttgct  11040
gtgacctgct ggctgtttga tgcagttgtg attcgctttg caatggacca cggtctctgt  11100
cccatggtgt gtgtatctgt gtgtctgagt gtggagacga cagagactcg aaaagatggt  11160
gtggtggctg ttcgatccag ggctcgcttg atgcctgttt ttttttccac gagaatctct  11220
ctattagaga acagatgcat gggtcgtttt ttagcctctc tagaccagga tgtgaaaggt  11280
agaaaagcca ttctcacgtg aggttacagt acttgtagct ttccattact catatacttg  11340
caggaattaa tattggacac tcttttttcta ctctcgctct gttttaaatc gcaagctatt  11400
tttccacttt cttaaaaatg tagcagcttt taccgagtac atctcggtac gtacctaaaa  11460
aaaagcttgt agtataagct ttcaaccgag tgtttataag gcttcgccga gtgcttccgg  11520
cactcggcga agctattgat tccggtagtg ccgggttgaa tttacttttg tatcactgag  11580
cgtgcgaaga aacagcggt atttctggca tcgatcgggc acccttcctc ggaatcatgg  11640
cttttttgaga gtgaccaaca ggcagtgcgc gcggtctcgg aacctgaaaa ttgtttggtt  11700
gtatcgaatg acttgtcacg gccactcgag gcaggcatga gacgctccac cggaccgcca  11760
caccatgcat agtgacagat catcaaaagg tggtttaaa actcgaattt ttatctgact  11820
atatagcaaa taaatccttt tgtacgctca gtttccatata tagacgaaat tctcccacct  11880
ctcccatgca tgcatgtcat cgatcattct tgtttatctg gtgatgtatt taatgaagac  11940
agaaattcga gtgagatttc cagtggaaat agccttatta gtgtgccatg aacgaagttc  12000
tgaagtcgaa accagacgag agtccccatg cacgatgcca tggatatcgc cagtacgtac  12060
aggacgtgcg ccagcacgat gcaactgtca gcagacagca gccaaaacgc aattcttgtt  12120
tcagctgggt gggcaattcc gaggtgtgct aaataaaagc atgatccatg catatgaatg  12180
agcatgcagc ccgcagcccg acagcccggc acgaggcccg gttttttggc ccggcccaag  12240
cacggcacgg cccgtctggt ttcgtgcccg tgccggcccg gcccggtaga ccaggccgtg  12300
cttgggctgc cggatgcgcc cgccgggcgg cacggcccgg cccgctagga aaagcaggca  12360
cggagccggc ccggttccag gcgaggggca tatccgcccg cccctcccca ccgcccgttc  12420
agtccccag tccctagttc cccacgccac gcgatttgct ccgcagcctc cgccctccgc  12480
tcgtccgctc gccgctccct ccccattctc cgtcaacgcc cagccgtcgc cactgccgtt  12540
gccggatctc cgtcgtcgac cgacgagatc tcctctctgc ctctctccag tcttcgtcac  12600
tcggtgacgc atcggctctc cattcccaa tctgtaaccc taatcccctt tccggctttc  12660
cctcacctct ccggtgacgc atcggctctc cactgccgga tctccgtcac cggcgacatc  12720
tgcacgcttg ttctgtgcgg ctcaccctct ccggctctcc ctccccaatc cctcgctcg  12780
tcgtcgtcgt catcggtcgt cggcttgtcg cgcgtcgtcg tccctagac cctcgtctcc  12840
ggctccgggc tccggcttgg caggtacgtg tacgtccctc tccggctctc cctccccaat  12900
ccgacaaacc ctaaccctaa tcccttgctt ggtaggtcgc cggccgacta cgccgtggtc  12960
gtgctggtgc cgccagtgcc gttgaggtac ggtgccgaga gggggggccgg gcatggatga  13020
cgacgacgac aatggccggt accctagaac catcaacgac gagctcgttg agttagggca  13080
gcttcccgat gacgtcgacg acatgggaga tgctgctgct gccttattcg gtatcggtag  13140
cagtcatggt gccggcgacc tggaggggac agctgccggg ccggttccgg ttagtgatgc  13200
tgctggctct aacgaacttg attcattgac ttcttccagc actggtaagc gtcgatctgc  13260
tgtttgggat gacttcactg aagtcactga aaaccgtaat ggtaagaagg tgcgcattgc  13320
tggtatttgc aaattttgca aggctcggtt gagtgctagt tctaatgctg gcactggaca  13380
tttgcttagg caccagaaat catgtaaaaa gaagtctgat catgctgcta tggttcaaac  13440
tagactagct ttgaaccctg atgggtcttt tagaaactgg gaatatgatc ctcaggtggc  13500
taggactgag ctttgtcgtt tgattgctag acttgatctt cctttaggga tagctgacac  13560
agatgcttgg gataattaca ttcaacatgc tcacaaccct agatatgtta gggtatctag  13620
gtttacaact gctagagact tggctaagct atacaatgaa aagctaaaga acttaaaaga  13680
tgatgttttt cctggtgtgt cttctatttg cttgacttct gatatatggt ctggtaatgc  13740
caaggaagac tacattactg ttgttgctca ttttattaag gctgattggg agttaaagaa  13800
gtgtgtgata ggctttaaat tgatccaagt gtctcataat gtgttaaca ttgctgaacg  13860
cattgcttgt gtgattcaat actttggcat gattgataaa gtgttctcta ttaccttaga  13920
taatgcttct tctaattcaa ctgccatgct cacattgtca cctatgcttg ctggttattt  13980
gggtgctgat gttgatccaa cagatactag taacaaaaca tatagtgtgc ttca         14034
```

SEQ ID NO: 98          moltype = DNA   length = 798
FEATURE                Location/Qualifiers
source                 1..798
                       mol_type = other DNA
                       organism = synthetic construct
SEQUENCE: 98

-continued

```
atgggggatgg cgcccgccgg gtgggtgggc gggctcgtgg cggagagctt cttcgtggcg    60
tgccccgcgc acgagtcccg caagaagaac gagcgcaaca tcttctgcct cgcctgctgc   120
gccagcatct gcccgcactg cgccccgcgc accgccacca cccgctcctc cagcgccaac   180
tgctaggtgc ggcgctacgt gtaccatgac gtcgtccgcc tcggcgacct agagaagctc   240
atcgactgct cctgtgtcca gacctacaca atcaacagtg ccaaggtgat cttcctgaag   300
ccgaggccgc agtccaggcc tttcaagggc tccggcaaca tctgcctcac gtgcgacagg   360
atcctccagg agcccttcca cttctgctcc ctctcatgca aggtggacca cgtgatgacg   420
cagggagggg acctgtccaa catcctgcag cactacggcg ccggcggtgg cggtggcggt   480
ggcacggcgg acccggaccg cctcgcgttc ccgaggttcg agaacctccg cgtcgtcgac   540
ggctcggacc tcgacgacga cgtccaggtc gtcaccccag actccaccct cgaggacccg   600
accaacaacg cgggcggcgg gtccagcgac aacggtactg acgacgccag acggcaggtc   660
gtcgtccatg cgcggcggcga ggcggccaag cggaagaaag ggggcggctt cttgccccag   720
atcgtgctgt cactcggcgg cggcggcggc ggcggcaaca ggaggaaggg tgcccccac   780
aggtcccctc tggcctaa                                                  798
```

```
SEQ ID NO: 99          moltype = DNA   length = 14042
FEATURE                Location/Qualifiers
source                 1..14042
                       mol_type = other DNA
                       organism = synthetic construct
SEQUENCE: 99
ttcttTgaca tcctatttta acaaaaacaa gttagtacat aaatcgacaa taaaataata    60
aaatatgcaa taaaatcata aaatatgcaa taaaatcatg atccatactc gtcaatcgta   120
atcgtaatca aaatcaggat ctagttgctt tcgtcgattt aatggacgcc aagtagcttt   180
cttcttTctc gtcactcgtt ttcttttTgg aggaacctct acatcatttt gatcgcctaa   240
taaagattct tccaacattt cagtttgtac attaaacgtg cttgtaagtt cttcgtcttg   300
gaaaatctca gcagccccca cttcctgctc gatttgactt tcaacataac cagcatcacc   360
aggagcatat agtcgttcac gcggattaac tttgtacact accctccaat caaccaaacc   420
gttttTctta gatggatatg tcatataata cacctgctcg cattggtggg caaggattat   480
agtgtcgtga cctttTaatc tatcgttgtg tttgacttcc accatgccat attgattttc   540
tcgcgttgta tttggagaaa accaatcaca atcgaagaac accactttga gttgtttatc   600
tccaaaaaac ttgtactcga ttatatcatt aatgactcca taataattag tcaccttccc   660
ttcatcatcg acagctctag ttacaactcc ggagtttgtc gtggctgcta gaggatgatc   720
atcttcgaac cttgtggaac ggaatctaaa accattgaca tcataccgac cataacgtct   780
gccagttact gctcctaggg ataattgtcg aaggtccggg tgtatattgt catttTtatc   840
tacataatct cgaaaccaac acaagaaatt aagtccccca tctttTtccct ctcgacgaat   900
ctggtcacgt tcacagccag agatgcaatt ttgagaatca aattccctgt tagtacaagg   960
aaacaaacct tttagtatca caacaaaaat tctagcggca atgactaaaa taaagtttac  1020
acttacagga gaaactgact catctcttcc atgttgttat acatgtaaag taaagcagtc  1080
ttccattcgt cgttggtgaa acagtatgtt gtgctgggtc ctacagtttt gcccctccat  1140
tgaaaaattt caatatcact aataggggc tcgtcgacat gataccgcaa cgtatgggca  1200
ttgacattgt gttcctctgc aaagtacagg cccgtgaacg atgctatctc tttgtatttg  1260
aattcttcag cgatgcaccc ttcaactcgt ctcttattac caaccattgc acgtagcttt  1320
tttagtgtcc tttcgatgtg atacatccat ctatattgca caggacctcc taccttagct  1380
tcgtatggta ggtgaacaag tagatgttgc atcggattga agaaacctgg tggaaatatt  1440
ttttcaagtt tgcataccaa aatcggtatt tcttgctcaa gcttctccat catctctttc  1500
tttattTctt tggcacaaag atgtctataa aagtagctta gctccgctaa tgctttTccag  1560
acatcattTt ttacaaaacc acgaaacata acaggaagga gtctttTccat tattatgtgg  1620
tagtcatgac tcttcaaccc agaaaacttg cccgtcttca aattcacaga ccttctaaag  1680
cccgcggcgt aaccatctgg gaactttTaag ttttTtcaacc atttcatcaa ttgtttTcttc  1740
ctttTtaggtt taatactgaa aggagcacgt ggcttcttct gattctctcc tatctccata  1800
gttggtcttc tacagattaa ggccaagtct ttccttgcct tagggttgtc ttttTgttttTg  1860
tcggtgatat tcatgcaagt gctgataatg cttttcaccca tatttTcgttc ctggtgcatg  1920
acatcaatgt tatgcattag aatcaaggct ttcatataag ggagttccca tagaccacat  1980
ttgtgagtcc aattatgctc ggttccataa ccttcaaaac gatttccatg ttcgtttTagt  2040
ttcaaatcat taagtctcgc gagaatctca ggaccactta gacgcttggg tggtcccctc  2100
gtcacaatcg tgtcctttTt aaaagcgttc ctatcgaacc tgaacgggtg atcctctggc  2160
aaaaaacatc tatggcaatc gaagtaacat atctttccac caaacttTtag tcgaaagcat  2220
aaagtgtctt caacgcatat aggacatgtc aaaatcccat gacaactcca tccagcaaag  2280
ataccataag ccataaaatc atgaatagac cataaaaacg cggctctcag gttgaacttc  2340
tgtttTcttgt aacaatcgta cgcctcgact ccttccaca aaattTtTcaa ttcttcaatc  2400
aggggtctca tcatcacatc gatctttgtt ccaggatgat ccggaccagg tattataaga  2460
cacaagaaaa taaattcata tttcatgcaa agagctggtg gaaggttgta tggaacagca  2520
aagacgggcc aacatgagta cgacgtagca gttagtttga atgtgagaa accatctgtt  2580
gccaaaccga agcggacatt ccgcacttca tcagcaaagc tggaatcaaa agcatctagt  2640
gccttccatg catctgtatc agctgggtgc accatgacat ttggattctc acgtaccct  2700
tctttTgtgcc acctcatgtg tctggctgta ttttTtggaga tgaacaaacg tttcaaccga  2760
ggtatgagag gcatgtaacg aagctgctta tgtgcaatct tcgtagtcac ggtcaaacca  2820
tcgtcgtttTt caacctcaac gaatctacgc tcaccacata cagtacactt cttctcacct  2880
gcggtctcct tccagaaaag catacaatta tttTtcacaga catcgattTt ttcgtagtcc  2940
ataccgaggc cagataacag cttttttagac tgatacatgt cctttTggcat cttgtgattc  3000
tccggaagta catcactgat caagttcaaa agttccttgt aacagttgtt tgagaatgca  3060
aacttagact taatagccat aagtcgagtc acaaatacaa ggacagtcac ttttTgtgtgc  3120
tcatgcaacg gctcttcggc agcttTtaagg agctcgaaga acttctgaac ctcaggtgta  3180
gctggatcct caaactcggt gggttgaccg gggttctccg aatcgacggt tagaaactca  3240
tggcgtacat cgtcaagcat ctcttccatc ctatcgtagt cctcctcttc atgtgactga  3300
acttccgata caatacgagg tgggtcctca ccgtggtgca cccacacctc atagcctggc  3360
atataaccgt tcttgcaaat atgtatcgac atagtcctcc tgtcaaggaa attaatgttc  3420
cgacacttgc tacaagggca cctaacatcg gttccagtct ctgaccgagc aaaagcatgg  3480
```

-continued

```
tcgagaaaag catcagtctt ggccacccac tcacttgata gagcacctct tttcttccaa   3540
ccttcataca tccatcgacg attctcctcc atactagata cgatacgtta acttaattag   3600
ataagtactg cacgtgcatt ccgtttttac gaagaaatca cgcccctaca tctgtaggaa   3660
aggataggtc ctaaacccac ccaggagtga ccgacgagac cgtgtttatg acaagacatg   3720
tggtcgtgcg aaatttcggc agcataaccc cgttgttctc caatcgcacg cctaaaaatg   3780
gtgcaattga agaacagaga ggttatgctg ccgaaactaa gcaggagcac atgcttttgt   3840
cataaacacg gactctgtcg gtcaccccga ggctgtccaa aaaagggaca attccggccc   3900
aacatacctc acatgcgtcg cttgtaaggt gtgttgggcc gaaacgggtg acgcctaggt   3960
ttcgtttgtt cacactacga tacactatga ttaactataa tcatcgtgca ttattaaata   4020
attaaactaa taaaccataa tacaatatta catcgaaat aatattgtta tagatgacaa   4080
atcatataaa atgaccttat ttccgagggc ataataatta ccctcggaaa ttaaaaatta   4140
aaattatcta aagtaccact aaataaagta aaacaaacta ctttaattaa ctaatcaaat   4200
tttgaccgtc ggacataaca aactaaacaa tcaaatgcat taatacatac aatttcaatc   4260
aaatacatta atacaaacat acaattctaa tcaaatacat taataaaagc atacaatttt   4320
aataaacaaa attgctaatt aagtatactc acttagcggg tgtggagagt cggccggcga   4380
tgggcgcacg ggcggcggcg ggcgcacggg gccgttggcc ggagcacggg gcggcggcga   4440
ccggcgaacg gggcggcggc gaccggcgaa cggggcggcg gcggcggcgg ccggagcacg   4500
ggcgtggcgg tggccggagc acgagctagg ggcggtggtg gccggagcac gggcgtggcg   4560
gtggtggccg gagcacgggc gtggcggtgg ccggagcacg agcacgagc ggtggggcgg   4620
cggcgggcgc cggagcacga gcagtggggg cgggcggtac ggcgataggg cgggacggcg   4680
acgagcgtgg cggcgacgag cgtggcggcg acggcggctt ctcctcggac acggcggagg   4740
cgtgctcggc ggcggcagga tagaaacgcg cggtctcggg tgaaactgaa ggcgcgcggg   4800
tcggaaccgc gcgttaaaaa gccttatgtc cgacggctcg gtacgaggcc gtcggacata   4860
agctaatgtc cgacggccag ggggtcggcc gtcggacata aggtaatgtc cgacggtcag   4920
tctgccagcc gtcggttata tttttattt tcgacggccg ctgttggccg tcggacataa   4980
ccgtatgtcc gacggttgcc tacgggccgt cggacataag acgaccgtcg gaattgtata   5040
gttttactgt agtgctccct cactatcttg ttctcgcctc gtttttctct ccctccgcga   5100
gcgccaaggc agcgcagcta cgagacaagc acacgtaata gtactagtgc gccgttgccc   5160
tgcctgcctg ccctgtgccc tgccttgcac cacaccacca ccaccgcaga tccggtctgg   5220
tccagtccgg cccggtccgc tactaaacaa accagccag cgcgcgcccc agcgagagga   5280
gaggaggagg ggccggggtc ggcacggcgg gcagaattgc ctctgctgcc tgcgcgctgc   5340
cctgccctgc cagagggatc ggagggagag cgatcagtca acaagcccag gaggaggagg   5400
aggaggaggg agagatccgc gtgccggccg gaggcgggct ccgggagatc gaccgagcga   5460
ccggcctcgg tcccggtgcg gtggtggatg gggatggcgc ccgccgggtg ggtgggcggg   5520
ctcgtggcgg agagcttctt cgtggcgtgc cccgcgcacg agtcccgcaa gaagaacgag   5580
cgcaacatct tctgcctcgc ctgctgcgcc agcatctgcc cgcactgcgc cccgcgcacc   5640
gccaccaccc gctcctccag gtgagtgcga gtctcgtcgt cgtcctcctc ctcgcccggc   5700
ctctcctctt ccttcctccg gcggccttcc cctctccctg ccaggctgcc atggcgtcgc   5760
gtggcatgca cctggccggg cgatctgctc agtttctact cctgctagct tcgcagcaat   5820
tctcgccgcc gctgtcccgc tccgctccgc ttcttgttgt tgttggatga acacaccacc   5880
tccccaccgc caccgccacc gggggggcagc ttttttggggg ttattgctgg tggcctcggt   5940
tcttgtgcaa cggatgggaa cggcgggac gagtaccaat caatcgattt ctttatttga   6000
tttaattgtt tatttattat tcctcggcgt atatagcact agacgctact tcttcctata   6060
tactactact agagtagtac tacaagtgta gaggaggagg ggcatgggaa ttggatgtgt   6120
agtatctcgc ttttgttttg tcgcgtgctg tctcttcctt ccttccttcc ttggactaga   6180
tttggtcccg gctttagcct aaacaaaaaa atatttcccc cctaccattt ctcgcatgat   6240
ttgatttgat gcgtggtctc ttctcgtgtc gtccgtgcgc gggaaggaat caagggaaag   6300
gaaaggaaac caaaccccat ctcgctaatc gctctcctct ctctctctct ctcccttcct   6360
cgcaggcagg cagaggcagt acaggttgtt gcaaaacttg cacgtacttg attcctcgcg   6420
cgcgcagcgc cttgtcgcct tgcgaggttt ggtttggttg ggtcatgagc tcatccatcc   6480
attccctttt ccacccatgc atgcatgcat gcatgccact cccttgatta gggtttataa   6540
gccagcagga ggcgctgatt gagtcctaat ctgcgccact gtaacagcaa tcccaaccat   6600
gattttcgca cccgctccag gactccggag cagtgctact tcttcatcgc tataattaat   6660
ataattcgtc tgctccttcc tgcctgaccg gggtattaaa tcctgtgtat gtacgtagta   6720
ctaacaaaca aggacaaggc agtaaaaatt ctcgttacgg aacattatct actccgacct   6780
cccttgcatt tttttttttgg aattagtacc cgggcgttca tcgcgacctg catgcaactg   6840
tttcctcaac gagctagcca ttacatgctt ttagtttttt ataaaatata tatgcatgca   6900
tggcaaaact tttcctttt taaatttcg ggagttaaag aggaggaggg tcgaaaattc   6960
aaatcccccc acccggggca tgcaaaccct tcttctttct ctccgtagct ttgtcttgta   7020
gctgcagcca tgcatttccc ccctactttc atgcagcagc aactaatcca tccggatatg   7080
ctggcgctgc gggagccgga gtctcgaacc caaatggcaa aaaaagctgc gggggaggt   7140
tttaccgctg cctcttcatt ggaattccaa tccttgggat taggatcctc tgcggtaatc   7200
gccagcctcc tgctgcgctt ccgcttgctt ccccgtccat taataggcct ggttatccaa   7260
actgttttgc caagtatagc aacatttccc tgccccccgt cctgccgact gaacccgact   7320
actgataaag gaaaaaaaat cggttcgggc ctttgaatta gattttaccg tatgcgcccg   7380
cgcgcggtaa ctgcgcggcc tgtctttttt taccaaacag aggcatcgac gacgacactg   7440
ttgtcccccg acgacgaccc catctctccc tggtgcgtgc tacacgacca aacttctctc   7500
tccttacctt agggtggggt ggtttgtggg gtctcccagg ccatgataaa gatcaccact   7560
ggagtggtac tgctgcccgg ccggtcaaag catgggggcc atcgcgtggt gtgtggccca   7620
acccaaagtt gtaccctgct gctgctgtac cgcctgcgtt gttatcttag gccccgtttc   7680
aatctcacgg gataaacttt agcttcatgc taaacttta ctatatgaat tgaagtgcta   7740
aagtttagct ttaattacca ccattagctc tcatgtttag attataaatg ctaaaagta   7800
gctagaaaaa agctgctaaa gtttatctcg cgagattgga acacggcctt atcttagagt   7860
atgaaactgc ggttgtaaac atgtttagcg ccaactgcta tgtgatcagg tgcggcgtca   7920
cgtgtaccat gacgtcgtcc gcctcggcga cctagagaag ctcatcgact gctcctgtgt   7980
ccaggtgatt ccctatctat cgtcgtatct gtcttgcatt agtgcttcga attttgatgg   8040
tgatgctgat gatgagtacg ttaattatat agtagtaaaa ctccctctc tctttgtgtg   8100
tgtgatgtgt gaccgcgcag acctacacaa tcaacagtgc caaggtgatc ttcctgaagc   8160
cgaggccgca gtccaggcct ttcaagggct ccggcaacat ctgcctcacg tgcgacagga   8220
```

-continued

```
tcctccagga gcccttccac ttctgctccc tctcatgcaa ggttgcattg gtcagctagc  8280
tagcatcatc gcatacgcca tgcatatgca tcgtcggatt cggatcatat cgttcagtgc  8340
gtacgtggat catgtcatat gttattacgc aggtggacca cgtgatgacg cagggagggg  8400
acctgtccaa catcctgcag cactacggcg ccggcggtgg cggtggcggt ggcacggcgg  8460
acccggaccg cctcgcgttc ccgaggttcg agaacctccg cgtcgtcgac ggctcggacc  8520
tcgacgacga cgtccaggtc gtcaccccag actccaccct cgaggacccg accaacaacg  8580
cgggcggcgg gtccagcgac aacggtactg acgacgccag acggcaggtc gtcgtccatg  8640
gcggcggcga ggcggccaag cggaagaaag ggggcggctt cttgccccag atcgtgctgt  8700
cactcggcgg cggcggcggc ggcggcaaca ggaggaaggg tgccccccac aggtcccctc  8760
tggcctaagc agcgctacct tcatgcatgc gtccccctgc tgctgctcgt tatatatcac  8820
aagtcacaac acacgtagcg cgctgtggtt gcatgcagtg atgatggtgt gggtggtagc  8880
tacagtatta attagtagta gcgtgttata atagtatctt aatggtgatt agcctcgtag  8940
agagacgacg acaagctggt agctggtcga tcggtttttgc ttggggggaa ggtcttggtg  9000
gccttgtgat ccgtctagca gctcgctagg accaaccatg gccgccgcgc catctcatga  9060
gactttagag agagagagag agagagaggg tcatggggga ggtagagggg ggagagacgg  9120
ttgtaaaagc agttcccatt gttacaggca ccaggtagta actggtcagt ggggcccact  9180
tctgcaggcg gtgggggccca tacgatcgag gtggctacca attttgtatt tgatgtacca  9240
agggttactc gcggtctcgc gcatacaatt tccacaccta tatatgttat atataaatga  9300
taatatatct gaattctgtc ccagactaaa caggttgttt tcagcagtct gtatccgttc  9360
catgtgggct caagtgattt tcagctgcct gttttggcgtg tcaagcagct gttgagacat  9420
gaggccgaga gctctcgccc agtctcgccc gtagggatga aagtaggatg ggaaaatccc  9480
gtaccgaccg ttatcgtata accgaatttg ttagttttgt cccgatcgtt ttcgaacccg  9540
acgtaaaaaa cgaaaacggg acgaaaacgg gatatacaaa acggtaaacg gaaacggaaa  9600
cggtagagct gttttaccga ccgtttaacc gggatcccgt ttttaatcgg gatgatcccg  9660
ttttgttacc gtattttgta attcgggatc acttcaatat agacagctat aggcatcact  9720
ttgaggccca gcccatctaa gaaaaaccta acgcgctgtt ctgctcccag gcgtcgccgt  9780
ccacactcct ctctcccagc tcgctgccgt agtgccatca gctcgtcact cgcaggcgcc  9840
ggcgcgcagc cgtccgccct cctgctctgt gcggctttgc ctctcccagc tcgcctcgcc  9900
agtcgccagg ccagagtgcc atcgcagctt cccaggctcc cagctcgcca gagtgccgga  9960
cgccacgcca gcccggtccg gtctccggtc ggcggtcggt cgatcgccgc tgctccagct  10020
ggctgcccag gcgactagac gtccacgacg gctcggcgat cggcaggcag ctcgctccac  10080
ctccacaggc cacgactccc tctgctgctg ctgtcctcca cggatccact gctggctgct  10140
gctccctcca cagagaatcg ccttgctaca ccatgtgagc agtcctgcag tcctgccgtg  10200
ttagacgcga gctgctagct cccagccgta ctccaccacg ttttggtgca taagctgcgt  10260
gttgccttgc tttttactgt tgttgtttta attctgtggt gcataattct gttggtgcgt  10320
acttctattg ggcgtacttt atattatgtc atgtgtgcta gtagacttat atggcttctt  10380
atgtagccaa gagctcaata tttatcactt atgtgctact aagatgtttg gtttgatgaa  10440
tcactctatc caaaatgaag tggtgcatca tgggtccatt cctcaaattt ggtgggatga  10500
cttcattcca catattagta ctaaacaact aactatgagg aatgaggtgg tgatggatta  10560
actcactcca ttccacaaac caaacaaaaa agtgaggagt gagaagatga tgaactatat  10620
cgttcctcaa accaaacact ccatacatta aactatgtgt gctccagatt tatatgactt  10680
ttttctatgt ttaattaaga cttgtgttta caatttttta tatttgtttt taagtttttga  10740
atatatgttt tcatggtgtg attttaccga acaaaaatac cggttcccgt ccgatttcgg  10800
ctttaacccg accggatcgt atcggttttc gcttaccgta tttatcccgt tcgttttcgt  10860
taccgatata tcccgttttc gttttcgtcc cgcaagttaa atatgaaaat gaaaacggta  10920
gaggtatttt accgaccgtt cccgaccgtt ttcatcccta ctcgcccgcg tgcatggatt  10980
gttgcatgca tgtgatgcgc gcgcgcacac gcctagcgct cccgtccaaa ctccccagtc  11040
gtgttgctgt gacctgctgg cgtgtttgatg cagttgtgat tcgctttgca atggaccacg  11100
gtctctgtcc catggtgtgt gtatctgtgt gtctgagtgt ggagacgaca gagactcgaa  11160
aagatggtgt ggtggctgtt cgatccaggg ctcgcttgat gcctgttttt ttttccacga  11220
gaatctctct attagagaac agatgcatgg gtcgtttttt agcctctcta gaccaggatg  11280
tgaaaggtag aaaagccatt ctcacgtgag gttacagtac ttgtagcttt ccattactca  11340
tatacttgca ggaattaata ttggacactc tttttctact ctcgctctgt tttaaatcgc  11400
aagctatttt tccactttct taaaaatgta gcagctttta ccgagtacat ctcggtacgt  11460
acctaaaaaa aagcttgtag tataagcttt caaccgagtg tttataaggc ttcgccgagt  11520
gcttccggca ctcggcgaag ctattgattc cggtagtgcc gggttgaatt tacttttgta  11580
tcactgagcg tgcgaagaga acagcggtat ttctggcatc gatcgggcac ccttcctcgg  11640
aatcatggct ttttgagagt gaccaacagg cagtgcgcgc ggtctcggaa cctgaaaatt  11700
gtttggttgt atcgaatgac ttgtcacggc cactcgagag aggcatgaga cgctccaccg  11760
gaccgccaca ccatgcatag tgacagatca tcaaaaggtg gttttaaaac tcgaattttt  11820
atctgactat atagcaaata aatccttttg tacgctcagt ttcatatata gacgaaattc  11880
tcccacctct cccatgcatg catgtcatcg atcattcttg tttatctggt gatgtattta  11940
atgaagacag aaattcgagt gagatttcca gtggaaatag ccttattagt gtgccatgaa  12000
cgaagttctg aagtcgaaac cagacgagag tccccatgca cgatgccatg gatatcgcca  12060
gtacgtacag gacgtgcgcc agcacgatgc aactgtcagc agacagcagc caaaacgcaa  12120
ttcttgtttc agctgggtgg gcaattccga ggtgtgctaa ataaaagcat gatccatgca  12180
tatagatgag catgcagccc gcagcccgac agccggcac gaggcccggt tttttggccc  12240
ggcccaagca cggcacggcc cgtctggttt cgtgcccgtg ccggccggc ccggtagacc  12300
aggccgtgct tgggctgccg gatgcgcccg ccgggcggcg cgctaggaaa  12360
agcaggcacg gagccggccc ggttccaggc gaggggcata tccgcccgcc cctccccacc  12420
gcccgttcag tccccagtc cctagttccc cacgccacgc gatttgctcc gcagcctccg  12480
ccctccgctc gtccgctcgc cgctccctcc ccattctccg tcaacgccga gccgtcgcca  12540
ctgccgttgc cggatctccg tcgtcgaccg acgagatctc ctctctgcct ctctccagtc  12600
ttcgtcactc ggtgacgcat cggctctcca ttccccaatc tgtaacccta atccccttc  12660
cggctttccc tcacctctcc ggtgacgcat cggctctcca ctgccggatc tccgtcaccg  12720
gcgacatctg cacgcttgtt ctgtgcggct caccctctcc ggctctccct ccccaatccc  12780
ctcgctcgtc gtcgtcgtca tcggtcgtcg gcttgtcgcg cgtcgtcgtc ccctagaccc  12840
tcgtctccgg ctccgggctc cggcttggca ggtacggtgta cgtccctctc cggctctccc  12900
tccccaatcc gacaaaccct aacccctaatc ccttgcttgg taggtcgccg gccgactacg  12960
```

-continued

```
ccgtggtcgt gctggtgccg ccagtgccgt tgaggtacgg tgccgagagg ggggccgggc   13020
atggatgacg acgacgacaa tggccggtac cctagaacca tcaacgacga gctcgttgag   13080
ttagggcagc ttcccgatga cgtcgacgac atgggagatg ctgctgctgc cttattcggt   13140
atcggtagca gtcatggtgc cggcgacctg gaggggacag ctgccgggcc ggttccggtt   13200
agtgatgctg ctggcctaa cgaacttgat tcattgatct cttccagcac tggtaagcgt   13260
cgatctgctg tttgggatga cttcactgaa gtcactgaaa accgtaatgg taagaaggtg   13320
cgcattgctg gtatttgcaa attttgcaag gctcggttga gtgctagttc taatgctggc   13380
actggacatt tgcttaggca ccagaaatca tgtaaaaaga agtctgatca tgctgctatg   13440
gttcaaacta gactagcttt gaaccctgat gggtctttta gaaactggga atatgatcct   13500
caggtggcta ggactgagct ttgtcgtttg attgctagac ttgatcttcc tttagggata   13560
gctgacacag atgcttggga taattacatt caacatgctc acaaccctag atatgttagg   13620
gtatctaggt ttacaactgc tagagacttg gctaagctat acaatgaaaa gctaaagaac   13680
ttaaaagatg atgtttttcc tggtgtgtct tctatttgct tgacttctga tatatggtct   13740
ggtaatgcca aggaagacta cattactgtt gttgctcatt ttattaatgc tgattgggag   13800
ttaaagaagt gtgtgatagg cttttaaattg atccaagtgt ctcataatgg tgttaacatt   13860
gctgaacgca ttgcttgtgt gattcaatac tttggcatga ttgataaagt gttctctatt   13920
acctttagata atgcttcttc taattcaact gccatgctca cattgtcacc tatgcttgct   13980
ggttatttgg gtgctgatgt tgatccaaca gatactagta acaaaacata tagtgtgctt   14040
ca                                                                   14042

SEQ ID NO: 100          moltype = DNA   length = 806
FEATURE                 Location/Qualifiers
source                  1..806
                        mol_type = other DNA
                        organism = synthetic construct
SEQUENCE: 100
atggggatgg cgcccgccgg gtggtgggc gggctcgtgg cggagagctt cttcgtggcg    60
tgccccgcgc acgagtcccg caagaagaac gagcgcaaca tcttctgcct cgcctgctgc   120
gccagcatct gcccgcactg cgcccgcgc accgccacca cccgctcctc cagcgccaac    180
tgctatgtga tcaggtgcgg cgctacgtgt accatgacgt cgtccgcctc ggcgacctag   240
agaagctcat cgactgctcc tgtgtccaga cctacacaat caacagtgcc aaggtgatct   300
tcctgaagcc gaggccgcag tccaggcctt tcaagggctc cggcaacatc tgcctcacgt   360
gcgacaggat cctccaggag cccttccact tctgctccct ctcatgcaag gtggaccacg   420
tgatgacgca gggagggggac ctgtccaaca tcctgcagca ctacggcgcc ggcggtggcg   480
gtggcggtgg cacggcggac ccggaccgcc tcgcgttccc gaggttcgag aacctccgcg   540
tcgtcgacgg ctcggacctc gacgacgacg tccaggtcgt caccccagac tccaccctcg   600
aggacccgac caacaacgcg ggcggcgggt ccagcgacaa cggtactgac gacgccagac   660
ggcaggtcgt cgtccatggc ggcggcgagg cggccaagcg gaagaaaggg ggcggcttct   720
tgccccagat cgtgctgtca ctcggcggcg gcggcggcg cggcaacagg aggaagggtg    780
cccccacag gtcccctctg gcctaa                                         806

SEQ ID NO: 101          moltype = AA   length = 79
FEATURE                 Location/Qualifiers
source                  1..79
                        mol_type = protein
                        organism = synthetic construct
SEQUENCE: 101
MGMAPAGWVG GLVAESFFVA CPAHESRKKN ERNIFCLACC ASICPHCAPR TATTRSSSAN   60
CYVIRCGATC TMTSSASAT                                                 79

SEQ ID NO: 102          moltype = DNA   length = 14021
FEATURE                 Location/Qualifiers
source                  1..14021
                        mol_type = other DNA
                        organism = synthetic construct
SEQUENCE: 102
ttctttgaca tcctatttta acaaaaacaa gttagtacat aaatcgacaa taaaataata    60
aaatatgcaa taaaatcata aaatatgcaa taaaatcatg atccatactc gtcaatcgta   120
atcgtaatca aaatcaggat ctagttgctt tcgtcgattt aatggacgcc aagtagcttt   180
cttcttctc gtcactcgtt ttctttttgg aggaacctct acatcatttt gatcgcctaa   240
taaagattct tccaacattt cagtttgtac attaaacgtg cttgtaagtt cttcgtcttg   300
gaaaatctca gcagccccca cttcctgctc gatttgactt tcaacataac cagcatcacc   360
aggagcatat agtcgttcac gcggattaac tttgtacact accctccaat caaccaaacc   420
gttttctta gatggatatg tcatataata cacctgctcg cattggtggg caaggattat   480
agtgtcgtga ccttttaatc tatcgttgtg tttgacttcc accatgccat attgattttc   540
tcgcgttgta tttggagaaa accaatcaca atcgaagaac accactttga gttgtttatc   600
tccaaaaaac ttgtactcga ttatatcatt aatgactcca taataattag tcaccttccc   660
ttcatcatcg acagctctag ttacaactcc ggagtttgtc gtggctgcta gaggatgatc   720
atcttcgaac cttgtggaac ggaatctaaa accattgaca tcataccgac cataacgtct   780
gccagttact gctcctaggg ataattgtcg aaggtccggg tgtatattgt cattttttatc   840
tacataatct cgaaaccaac acaagaaatt aagtcccca tctttccct ctcgacgaat   900
ctggtcacgt tcacagccag agatgcaatt ttgagaatca aattccctgt tagtacaagg   960
aaacaaacct tttagtatca caacaaaaat tctagcggca atgactaaaa taaagtttac   1020
acttacagga gaaactgact catctcttcc atgttgttat acatgtaaag taaagcagtc   1080
ttccattcgt cgttggtgaa acagtatgtt gtgctgggtc ctacagtttt gcccctccat   1140
tgaaaaattt caatatcact aatagggggc tcgtcgacat gataccgcaa cgtatgggca   1200
ttgacattgt gttcctctgc aaagtacagg cccgtgaacg atgctatctc tttgtatttg   1260
aattcttcag cgatgcaccc ttcaactcgt ctcttattac caaccattgc acgtagcttt   1320
tttagtgtcc tttcgatgtg atacatccat ctatattgca caggacctcc tacottagct   1380
```

```
tcgtatggta ggtgaacaag tagatgttgc atcggattga agaaacctgg tggaaatatt   1440
ttttcaagtt tgcataccaa aatcggtatt tcttgctcaa gcttctccat catctctttc   1500
tttatttctt tggcacaaag atgtctataa aagtagctta gctccgctaa tgctttccag   1560
acatcatttt ttacaaaacc acgaaacata acaggaagga gtctttccat tattatgtgg   1620
tagtcatgac tcttcaaccc agaaaacttg cccgtcttca aattcacaga ccttctaaag   1680
cccgcggcgt aaccatctgg gaactttaag tttttcaacc atttcatcaa ttgtttcttc   1740
cttttaggtt taatactgaa aggagcacgt ggcttcttct gattctctcc tatctccata   1800
gttggtcttc tacagattaa ggccaagtct ttccttgcct tagggttgtc ttttgttttg   1860
tcggtgatat tcatgcaagt gctgataatg ctttcaccca tatttcgttc ctggtgcatg   1920
acatcaatgt tatgcattag aatcaaggct ttcatataag ggagttccca tagaccacat   1980
ttgtgagtcc aattatgctc ggttccataa ccttcaaaac gatttccatg ttcgtttagt   2040
ttcaaatcat taagtctcgc gagaatctca ggaccactta gacgcttggg tggtcccctc   2100
gtcacaatcg tgtccttttt aaaagcgttc ctatcgaacc tgaacgggtg atcctctggc   2160
aaaaaacatc tatggcaatc gaagtaacat atctttccac caaactttag tcgaaagcat   2220
aaagtgtctt caacgcatat aggacatgtc aaaatcccat gacaactcca tccagcaaag   2280
ataccataag ccataaaatc atgaatagac cataaaaacg cggctctcag gttgaacttc   2340
tgtttcttgt aacaatcgta cgcctcgact ccttcccaca aaattttcaa ttcttcaatc   2400
aggggtctca tcatcacatc gatctttgtt ccaggatgat ccggaccagg tattataaga   2460
cacaagaaaa taaattcata tttcatgcaa agagctggtg gaaggttgta tggaacagca   2520
aagacgggcc aacatgagta cgacgtagca gttagattga atggtgagaa accatctgtt   2580
gccaaaccga agcggacatt ccgcacttca tcagcaaagc tggaatcaaa agcatctagt   2640
gccttccatg catctgtatc agctgggtgc accatgacat ttggattctc acgtacccct   2700
tctttgtgcc acctcatgtg tctggctgta tttttggaga tgaacaaacg tttcaaccga   2760
ggtatgagag gcatgtaacg aagctgctta tgtgcaatct tcgtagtcac ggtcaaacca   2820
tcgtcgtttt caacctcaac gaatctacgc tcaccacata cagtacactt cttctcacct   2880
gcggtctcct tccagaaaag catacaatta tttttcacaga catcgatttt ttcgtagtcc   2940
ataccgaggc cagataacag ctttttagac tgatacatgt cctttggcat cttgtgattc   3000
tccggaagta catcactgat caagttcaaa agttccttgt aacagttgtt tgagaatgca   3060
aacttagact taatagccat aagtcgagtc acaaatacaa ggacagtcac ttttgtgtgc   3120
tcatgcaacg gctcttcggc agctttaagg agctcgaaga acttctgaac ctcaggtgta   3180
gctggatcct caaactcggt gggttgaccg gggttctccg aatcgacggt tagaaactca   3240
tggcgtacat cgtcaagcat ctcttccatc ctatcgtagt cctcctcttc atgtgactga   3300
acttccgata caatacgagg tgggtcctca ccgtggtgca cccacacctc atagcctggc   3360
atataaccgt tcttgcaaat atgtatcgac atagtcctcc tgtcaaggaa attaatgttc   3420
cgacacttgc tacaagggca cctaacatcg gttccagtct ctgaccgagc aaaagcatgg   3480
tcgagaaaag catcagtctt ggccacccac tcacttgata gagcacctct tttcttccaa   3540
ccttcataca tccatcgacg attctcctcc atactagata cgatacgtta acttaattag   3600
ataagtactg cacgtgcatt ccgttttac gaagaaatca cgcccctaca tctgtaggaa   3660
aggataggtc ctaaacccac ccaggagtga ccgacgaagc cgtgtttatg acaagacatg   3720
tggtcgtgcg aaatttcggc agcataaccc cgttgttctc caatcgcacg cctaaaaatg   3780
gtgcaattga agaacagaga ggttatgctc ccgaaactaa gcaggagcac atgcttttgt   3840
cataaacacg gactctgtcg gtcaccccga ggctgtccaa aaaagggaca attccggccc   3900
aacatacctc acatgcgtcg cttgtaaggt gtgttgggcc gaaacgggtg acgcctaggt   3960
ttcgtttgtt cacactacga tacactatga ttaactataa tcatcgtgca ttattaaata   4020
attaaactaa taaaccataa tacaatatta catacgaaat aatattgtta tagatgacaa   4080
atcatataaa atgaccttat ttccgagggc ataataatta ccctcggaaa ttaaaaatta   4140
aaattatcta aagtaccact aaataaagta aaacaaacta ctttaattaa ctaatcaaat   4200
tttgaccgtc ggacataaca aactaaacaa tcaaatgcat taatacatac aatttcaatc   4260
aaatacatta atacaaacat acaattctaa tcaaatacat taataaaagc atacaatttt   4320
aataaacaaa attgctaatt aagtatactc acttagcggg tgtggagagt cggccggcga   4380
tgggcgcacg ggcggcggcg ggcgcacggg gccgttggcg ggagcacggg gcggcggcga   4440
ccggcgaacg gggcggcggc gaccggccgaa cggggcggcg gcggcggcgg ccggagcacg   4500
ggcgtggcgg tggccggagc acgagctagg ggcggtggtg gccggagcac gggcgtggcg   4560
gtggtggccg gagcacgggc gtggcggtgg ccggagcacg agcacggagc ggtggggcgg   4620
cggcgggcgc cggagcacga gcagtggggg gggcggtac ggcgataggg cgggacggcg   4680
acgagcgtgg cggcgacgag cgtggcggcg acggcggctt ctcctcggac acggcggagg   4740
cgtgctcggc ggcggcagga tagaaacgcg cggtctcggg tgaaactgaa ggcgcgcggg   4800
tcggaaccgc gcgttaaaaa gccttatgtc cgacggctcg gtacgaggcc gtcggacata   4860
agctaatgtc cgacggccag ggggtcggcc gtcggacata aggtaatgtc cgacggtcag   4920
tctgccagcc gtcggttata ttttttattt tcgacggccg ctgttggccg tcggacataa   4980
ccgtatgtcc gacggttgcc tacgggccgt cggacataag acgaccgtcg gaattgtata   5040
gtttttactgt agtgctccct cactatcttg ttctcgcctc gttttttctct ccctccgcga   5100
gcgccaaggc agcgcagcta cgagacaagc acacgtaata gtactagtgc gccgttgccc   5160
tgcctgcctg ccctgtgccc tgccttgcac cacaccacca ccaccgcaga tccggtcgg   5220
tccagtccgg cccggtccgc tactaaacaa accagcccag cgcgcgcccc agcgagagga   5280
gaggaggagg ggcggggtc ggcacggcgg gcagaattgc ctctgctgcc tgcgcgctgc   5340
cctgccctgc cagagggatc ggaggagag cgatcagtca acaagcccag gaggaggagg   5400
aggaggaggg agagatccgc gtgccggccg gaggcgggct ccgggagatc gaccgagcga   5460
ccggcctcgg tcccggtgcg gtggtggatg gggatggcgc cgccgggtg ggtgggcggg   5520
ctcgtggcgg agagcttctt cgtggcgtgc cccgcgcacg agtcccgcaa gaagaacgag   5580
cgcaacatct tctgcctcgc ctgctgcgcc agcatctgcc cgcactgcgc cccgcgcacc   5640
gccaccaccc gctcctccag gtgagtgcga gtctcgtcgt cgtcctcctc ctcgcccggc   5700
ctctcctctt ccttcctccg gcggccttcc cctctccctg ccaggctgcc atggcgtcgc   5760
gtggcatgca cctggccggg cgatctgctc agtttctact cctgctagct tcgcagcaat   5820
tctcgccgcc gctgtccgc tccgctccgc ttcttgttgt tgttggatga acacaccacc   5880
tccccaccgc caccgccacc ggggggcagc ttttttgggg ttattgctgg tggcctcggt   5940
tcttgtgcaa cggatgggaa cggcgggac gagtaccaat caatcgattt ctttatttga   6000
tttaattgtt tatttattat tcctcggcgt atatagcact agacgctact tcttcctata   6060
tactactact agagtagtac tacaagtgta gaggaggagg ggcatgggaa ttggatgtgt   6120
```

-continued

```
agtatctcgc ttttgttttg tcgcgtgctg tctcttcctt ccttccttcc ttggactaga   6180
tttggtcccg gctttagcct aaacaaaaaa atatttcccc cctaccattt ctcgcatgat   6240
ttgatttgat gcgtggtctc ttctcgtgtc gtccgtgcgc gggaaggaat caagggaaag   6300
gaaaggaaac caaaccccat ctcgctaatc gctctcctct ctctctctct ctcccttcct   6360
cgcaggcagg cagaggcagt acaggttgtt gcaaaacttg cacgtacttg attcctcgcg   6420
cgcgcagcgc cttgtcgcct tgcgaggttt ggtttggttg ggtcatgagc tcatccatcc   6480
attccctttt ccacccatgc atgcatgcat gcatgccact cccttgatta gggtttataa   6540
gccagcagga ggcgctgatt gagtcctaat ctgcgccact gtaacagcaa tcccaaccat   6600
gattttcgca cccgctccag gactccggag cagtgctact tcttcatcgc tataattaat   6660
ataattcgtc tgctccttcc tgcctgaccg gggtattaaa tcctgtgtat gtacgtagta   6720
ctaacaaaca aggacaaggc agtaaaaatt ctcgttacgg aacattatct actccgacct   6780
cccttgcatt ttttttttgg aattagtacc cgggcgttca tcgcgacctg catgcaactg   6840
tttcctcaac gagctagcca ttacatgctt ttagtttttt ataaaatata tatgcatgca   6900
tggcaaaact ttttcctttt taaattttcg ggagttaaag aggaggaggg tcgaaaattc   6960
aaatcccccc acccggggca tgcaaaccct tcttctttct ctccgtagct ttgtcttgta   7020
gctgcagcca tgcatttccc ccctactttc atgcagcagc aactaatcca tccggatatg   7080
ctggcgctgg gggagccgga gtctcgaacc caaatggcaa aaaaagctgc gggggggaggt   7140
tttaccgctg cctcttcatt ggaattccaa tccttgggat taggatcctc tgcggtaatc   7200
gccagcctcc tgctgcgctt ccgcttgctt ccccgtccat taataggcct ggttatccaa   7260
actgtttttgc caagtatagc aacatttccc tgccccccgt cctgccgact gaaccccgcc   7320
actgataaag gaaaaaaaat cggttcgggc ctttgaatta gattttaccg tatgcgcccg   7380
cgcgcggtaa ctgcgcggcc tgtctttttt taccaaacag aggcatcgac gacgacactg   7440
ttgtcccccg acgacgaccc catctctccc tggtgcgtgc tacacgacca aacttctctc   7500
tccttacctt agggtggggt ggttttgggg gtctcccagg ccatgataaa gatcaccact   7560
ggagtggtac tgctgcccgg ccggtcaaag catgggggcc atcgcgtggt gtgtggccca   7620
acccaaagtt gtaccctgct gctgctgtac cgcctgcgtt gttatcttag gccccgtttc   7680
aatctcacgg gataaacttt agcttcatgc taaactttag ctatatgaat tgaagtgcta   7740
aagtttagct ttaattacca ccattagctc tcatgtttag attataaatg gctaaaagta   7800
gctagaaaaa agctgctaaa gtttatctcg cgagattgga acacggcctt atcttagagt   7860
atgaaactgc ggttgtaaac atgttcaggt gcggcgctac gtgtaccatg acgtcgtccg   7920
cctcggcgac ctagagaagc tcatcgactg ctcctgtgtc caggtgattc cctatctatc   7980
gtcgtatctg tcttgcatta gtgcttcgaa ttttgatggt gatgctgatg atgagtacgt   8040
taattatata gtagtaaaac tcccctctct ctttgtgtgt gtgatgtgtg accgcgcaga   8100
cctacacaat caacagtgcc aaggtgatct tcctgaagcc gaggccgcag tccaggcctt   8160
tcaagggctc cggcaacatc tgcctcacgt gcgacaggat cctccaggag cccttccact   8220
tctgctccct ctcatgcaag gttgcattgg tcagctagct agcatcatcg catacgccat   8280
gcatatgcat cgtcggattc ggatcatatc gttcagtgcg tacgtggatc atgtcatatg   8340
ttattacgca ggtggaccac gtgatgacgc agggaggga cctgtccaac atcctgcagc   8400
actacggcgc cggcggtggc ggtggcggtg gcacggcgga cccggaccgc ctcgcgttcc   8460
cgaggttcga gaacctccgc gtcgtcgacg gctcggacct cgacgacgac gtccaggtcg   8520
tcaccccaga ctccaccctc gaggacccga ccaacaacgc gggcggcggg tccagcgaca   8580
acggtactga cgacgccaga cggcaggtcg tcgtccatgg cggcggcgag gcggccaagc   8640
ggaagaaagg gggcggcttc ttgccccaga tcgtgctgtc actcggcggc ggcgtcggcg   8700
gcggcaacag gaggaagggt gccccccaca ggtcccctct ggcctaagca gcgctacctt   8760
catgcatgcg tcccctgct gctgctcgtt atatatcaca agtcacaaca cacgtagcgc   8820
gctgtggttg catgcagtga tgatggtgtg ggtggtagtc acagtattaa ttagtagtag   8880
cgtgttataa tagtatctta atggtgatta gcctcgtaga gagacgacga caagctggta   8940
gctggtcgat cggttttgct tggggggaag gtcttggtgg ccttgtgatc cgtctagcag   9000
ctcgctagga ccaaccatgg ccgccgcgcc atctcatgag actttagaga gagagagaga   9060
gagagaggg catgggggag gtagaggggg gagagacggt tgtaaaagca gttcccattg   9120
ttacaggcac caggtagtaa ctggtcagtg gggcccactt ctgcaggcgg tggggcccat   9180
acgatcgagg tggctaccaa ttttgtattt gatgtaccaa gggttactcg cggtctcgcg   9240
catacaattt ccacacctat atatgttata tataaatgat aatatatctg aattctgtcc   9300
cagactaaac aggttgtttt cagcagtctg tatccgttcc atgtgggctc aagtgatttt   9360
cagctgcctg tttggcgtgt caagcagctg ttgagacatg aggccgagag ctctcgccca   9420
gtctcgcccg tagggatgaa agtaggatgg gaaaatcccg taccgaccgt tatcgtataa   9480
ccgaatttgt tagttttgtc ccgatcgttt tcgaacccga cgtaaaaaac gaaaacggga   9540
cgaaacggga atatacaaaa cggtaaacgg aaacggaaac ggtagagctg ttttaccgac   9600
cgtttaaccg ggatcccgtt tttaatcggg atgatcccgt tttgttaccg tattttgtaa   9660
ttcgggatca cttcaatata gacagctata ggcatcactt tgaggcccag cccatctaag   9720
aaaaacctaa cgcgctgttc tgctcccagg cgtcgccgtc cacactcctc tctcccagct   9780
cgctgccgta gtgccatcag ctcgtcactc gcaggcgccg gcgcgcagcc gtccgccctc   9840
ctgctctgtg cggctttgcc tctcccagct cgcctcgcca gtcgccaggc cagagtgcca   9900
tcgcagcttc ccaggctccc agctcgccag agtgccggac gcacgccag cccggtccgg   9960
tctccggtcg gcggtcggtc gatcgccgct gctccagctg gctgccagg cgactagacg  10020
tccacgacgg ctcggcgatc ggcaggcagc tcgtccacc tccacaggcc acgactccct  10080
ctgctgctgc tgtcctccac ggatccactg ctggctgctg ctccctccac agagaatcgc  10140
cttgctacac catgtgagca gtcctgcagt cctgccgtgt tagacgctag ctgctagctc  10200
ccagccgtac tccaccacgt tttggtgcat aagctgcgtg ttgccttgct ttttactgtt  10260
gttgttttaa ttctgtggtg cataattctg ttggtgcgta cttctattgg gcgtacttta  10320
tattatgtca tgtgtgctag tagacttata tggcttctta tgtagccaag agctcaatat  10380
ttatcactta tgtgctacta agatgtttgg tttgatgaat cactctatcc aaaatgaagt  10440
ggtgcatcat gggtccattc ctcaaatttg gtgggatgac ttcattccac atattagtac  10500
taaacaacta actatgagga atgaggtggt gatggattaa ctcactccat tccacaaacc  10560
aaacaaaaaa gtgaggagtg agaagatgat gaactatatc gttcctcaaa ccaaacactc  10620
catacattaa actatgtgtg ctccagattt atatgacttt tttctatgtt taattaagac  10680
ttgtgtttac aattttttat atttgttttt aagtttgaa tatatgtttt catggtgtga  10740
ttttaccgaa caaaaatacc ggttcccgtc cgatttcggc tttaacccga ccggatcgta  10800
tcggtttttcg cttaccgtat ttatcccgtt cgttttcgtt accgatatat cccgttttcg  10860
```

-continued

```
ttttcgtccc gcaagttaaa tatgaaaatg aaaacggtag aggtattta  ccgaccgttc  10920
ccgaccgttt tcatccctac tcgcccgcgt gcatggattg ttgcatgcat gtgatgcgcg  10980
cgcgcacacg cctagcgctc ccgtccaaac tccccagtcg tgttgctgtg acctgctggc  11040
tgtttgatgc agttgtgatt cgctttgcaa tggaccacgg tctctgtccc atggtgtgtg  11100
tatctgtgtg tctgagtgtg gagacgacag agactcgaaa agatggtgtg gtggctgttc  11160
gatccagggc tcgcttgatg cctgtttttt tttccacgag aatctctcta ttagagaaca  11220
gatgcatggg tcgttttta  gcctctctag accaggatgt gaaaggtaga aaagccattc  11280
tcacgtgagg ttacagtact tgtagctttc cattactcat atacttgcag gaattaatat  11340
tggacactct ttttctactc tcgctctgtt ttaaatcgca agctatttt  ccactttctt  11400
aaaaatgtag cagctttac  cgagtacatc tcggtacgta cctaaaaaaa agcttgtagt  11460
ataagctttc aaccgagtgt ttataaggct tcgccgagtg cttccggcac tcggcgaagc  11520
tattgattcc ggtagtgccg ggttgaattt acttttgtat cactgagcgt gcgaagagaa  11580
cagcggtatt tctggcatcg atcgggcacc cttcctcgga atcatggctt tttgagagtg  11640
accaacaggc agtgcgcgcg gtctcggaac ctgaaaattg tttggttgta tcgaatgact  11700
tgtcacggca actcgaggca ggcatgagac gctccaccgg accgccacac catgcatagt  11760
gacagatcat caaaaggtgg ttttaaaact cgaattttta tctgactata tagcaaataa  11820
atccttttgt acgctcagtt tcatatatag acgaaattct cccacctctc ccatgcatgc  11880
atgtcatcga tcattcttgt ttatctggtg atgtatttaa tgaagacaga aattcgagtg  11940
agatttccag tggaaatagc cttattagtg tgccatgaac gaagttctga agtcgaaacc  12000
agacgagagt ccccatgcac gatgccatgg atatcgccag tacgtacagg acgtgcgcca  12060
gcacgatgca actgtcagca gacagcagcc aaaacgcaat tcttgtttca gctgggtggg  12120
caattccgag gtgtgctaaa taaaagcatg atccatgcat atagatgagc atgcagcccg  12180
cagcccgaca gcccggcacg aggcccggtt ttttggcccg gcccaagcac ggcacggccc  12240
gtctggtttc gtgcccgtgc cggcccggcc cggtagacca ggccgtgctt gggctgccgg  12300
atgcgcccgc cgggcggcac ggcccggccc gctaggaaaa gcaggcacgg agccggcccg  12360
gttccaggcg aggggcatat ccgcccgccc ctccccaccg ccgttcagt  ccccagtcc   12420
ctagttcccc acgccacgcg atttgctccg cagcctccgc cctccgctcg tccgctcgcc  12480
gctccctccc cattctccgt caacgccgag ccgtcgccac tgccgttgcc ggatctccgt  12540
cgtcgaccga cgagatctcc tctctgcctc tctccagtct tcgtcactcg gtgacgcatc  12600
ggctctccat tccccaatct gtaaccctaa tccccttttcc ggctttccct cacctctccg  12660
gtgacgcatc ggctctccac tgccggatct ccgtcaccgg cgacatctgc acgcttgttc  12720
tgtgcggctc accctctccg gctctccctc cccaatcccc tcgctcgtcg tcgtcgtcat  12780
cggtcgtcgg cttgtcgcgc gtcgtcgtcc cctagaccct cgtctccggc tccgggctcc  12840
ggcttggcag gtacgtgtac gtccctctcc ggctctccct ccccaatccg acaaaccctca  12900
accctaatcc cttgcttggt aggtcgccgg ccgactacgc cgtggtcgtg ctggtgccgc  12960
cagtgccgtt gaggtacggt gccgagaggg gggccgggca tggatgacga cgacgacaat  13020
ggccggtacc ctagaaccat caacgacgag ctcgttgagt tagggcagct tcccgatgac  13080
gtcgacgaca tgggagatgc tgctgctgcc ttattcggta tcggtagcag tcatggtgcc  13140
ggcgacctgg aggggacagc tgccgggccg gttccggtta gtgatgctgc tggctctaac  13200
gaacttgatt cattgacttc ttccagcact ggtaagcgtc gatctgctgt ttgggatgac  13260
ttcactgaag tcactgaaaa ccgtaatggt aagaaggtgc gcattgctgg tatttgcaaa  13320
ttttgcaagg ctcggttgag tgctagttct aatgctggca ctggacattt gcttaggcac  13380
cagaaatcat gtaaaaagaa gtctgatcat gctgctatgg ttcaaactag actagctttg  13440
aaccctgatg ggtcttttag aaactgggaa tatgatcctc aggtggctag gactgagctt  13500
tgtcgtttga ttgctagact tgatcttcct ttagggatag ctgacacaga tgcttgggat  13560
aattacattc aacatgctca caaccctaga tatgttaggg tatctaggtt tacaactgct  13620
agagactgg  ctaagctata caatgaaaag ctaaagaact aaaagatga  tgttttttcct  13680
ggtgtgtctt ctatttgctt gacttctgat atatggtctg gtaatgccaa ggaagactac  13740
attactgttg ttgctcattt tattaatgct gattgggagt taaagaagtg tgtgataggc  13800
tttaaattga tccaagtgtc tcataatggt gttaacattg ctgaacgcat tgcttgtgtg  13860
attcaatact ttggcatgat tgataaagtg ttctctatta ccttagataa tgcttcttct  13920
aattcaactg ccatgctcac attgtcacct atgcttgctg gttatttggg tgctgatgtt  13980
gatccaacag atactagtaa caaaacatat agtgtgcttc a                      14021
```

SEQ ID NO: 103          moltype = DNA  length = 710
FEATURE                 Location/Qualifiers
source                  1..710
                        mol_type = other DNA
                        organism = synthetic construct
SEQUENCE: 103
```
atggggatgg cgcccgccgg gtgggtgggc gggctcgtgg cggagagctt cttcgtggcg  60
tgccccgcgc acgagtcccg caagaagaac gagcgcaaca tcttctgcct cgcctgctgc  120
gccagcatct gcccgcactg cgccccgcgc accgccacca cccgctcctc cagacctaca  180
caatcaacag tgccaaggtg atcttcctga agccgaggcc gcagtccagg cctttcaagg  240
gctccggcaa catctgcctc acgtgcgaca ggatcctcca ggagcccttc cacttctgct  300
ccctctcatg caaggtggac cacgtgatga cgcaggagg  ggacctgtcc aacatcctgc  360
agcactacgc cgccggcgt  ggcggtggcg gtggcacggc ggaccgggac cgcctcgcgt  420
tcccgaggtt cgagaacctc cgcgtcgtcg acggctcgga cctcgacgac gacgtccagg  480
tcgtcacccc agactccacc ctcgaggacc cgaccaacaa cgtgcggcgg ggtccagcg  540
acaacggtac tgacgacgcc agacggcagg tcgtcgtcca tggcggcggc gaggcggcca  600
agcggaagaa aggggggcggc ttcttgcccc agatcgtgct gtcactcggc ggcggcggcg  660
gcggcggcaa caggaggaag ggtgcccccc acaggtcccc tctggcctaa              710
```

SEQ ID NO: 104          moltype = AA  length = 66
FEATURE                 Location/Qualifiers
source                  1..66
                        mol_type = protein
                        organism = synthetic construct
SEQUENCE: 104

-continued

```
MGMAPAGWVG GLVAESFFVA CPAHESRKKN ERNIFCLACC ASICPHCAPR TATTRSSRPT     60
QSTVPR                                                               66

SEQ ID NO: 105          moltype = DNA   length = 14040
FEATURE                 Location/Qualifiers
source                  1..14040
                        mol_type = other DNA
                        organism = synthetic construct
SEQUENCE: 105
ttctttgaca tcctatttta acaaaaacaa gttagtacat aaatcgacaa taaaataata     60
aaatatgcaa taaaatcata aaatatgcaa taaaatcatg atccatactc gtcaatcgta    120
atcgtaatca aaatcaggat ctagttgctt tcgtcgattt aatggacgcc aagtagcttt    180
cttctttctc gtcactcgtt ttctttttgg aggaacctct acatcatttt gatcgcctaa    240
taaagattct tccaacattt cagtttgtac attaaacgtg cttgtaagtt cttcgtcttg    300
gaaaatctca gcagcccca cttcctgctc gatttgactt tcaacataac cagcatcacc    360
aggagcatat agtcgttcac gcggattaac tttgtacact accctccaat caaccaaacc    420
gttttttctta gatggatatg tcatataata cacctgctcg cattggtggg caaggattat    480
agtgtcgtga ccttttaatc tatcgttgtg tttgacttcc accatgccat attgattttc    540
tcgcgttgta tttggagaaa accaatcaca atcgaagaac accactttga gttgtttatc    600
tccaaaaaac ttgtactcga ttatatcatt aatgactcca taataattag tcaccttccc    660
ttcatcatcg acagctctag ttacaactcc ggagtttgtc gtggctgcta gaggatgatc    720
atcttcgaac cttgtggaac ggaatctaaa accattgaca tcataccgac cataacgtct    780
gccagttact gctcctaggg ataattgtcg aaggtccggg tgtatattgt cattttatc    840
tacataatct cgaaaccaac acaagaaatt aagtccccca tctttccct ctcgacgaat    900
ctggtcacgt tcacagccag agatgcaatt ttgagaatca aattccctgt tagtacaagg    960
aaacaaacct tttagtatca caacaaaaat tctagcggca atgactaaaa taaagtttac   1020
acttacagga gaaactgact catctcttcc atgttgttat acatgtaaag taaagcagtc   1080
ttccattcgt cgttggtgaa acagtatgtt gtgctgggtc ctacagtttt gcccctccat   1140
tgaaaaattt caatatcact aatagggggc tcgtcgacat gataccgcaa cgtatgggca   1200
ttgacattgt gttcctctgc aaagtacagg cccgtgaacg atgctatctc tttgtatttg   1260
aattcttcag cgatgcaccc ttcaactcgt ctcttattac caaccattgc acgtagcttt   1320
tttagtgtcc tttcgatgtg atacatccat ctatattgca caggacctcc taccttagct   1380
tcgtatggta ggtgaacaag tagatgttgc atcggattga agaaacctgg tggaaatatt   1440
ttttcaagtt tgcataccaa aatcggtatt tcttgctcaa gcttctccat catctctttc   1500
tttattctt tggcacaaag atgtctataa aagtagctta gctccgctaa tgctttccag   1560
acatcatttt ttacaaaacc acgaaacata acaggaagga gtcttccat tattatgtgg   1620
tagtcatgac tcttcaaccc agaaaacttg cccgtcttca aattcacaga ccttctaaag   1680
cccgcggcgt aaccatctgg gaactttaag tttttcaacc atttcatcaa ttgtttcttc   1740
cttttaggtt taatactgaa aggagcacgt ggcttcttct gattctctcc tatctccata   1800
gttggtcttc tacagattaa ggccaagtct ttccttgcct tagggttgtc ttttgttttg   1860
tcggtgatat tcatgcaagt gctgataatg ctttcaccca tatttcgttc ctggtgcatg   1920
acatcaatgt tatgcattag aatcaaggct ttcatataag ggagttccca tagaccacat   1980
ttgtgagtcc aattatgctc ggttccataa ccttcaaaac gattccatg ttcgtttagt   2040
ttcaaatcat taagtctcgc gagaatctca ggaccactta gacgcttggg tggtcccctc   2100
gtcacaatcg tgtccttttt aaaagcgttc ctatcgaacc tgaacgggtg atcctctggc   2160
aaaaaacatc tatggcaatc gaagtaacat atctttccac caaactttag tcgaaagcat   2220
aaagtgtctt caacgcatat aggacatgtc aaaatcccat gacaactcca tccagcaaag   2280
ataccataag ccataaaatc atgaatagac cataaaaacg cggctctcag gttgaacttc   2340
tgtttcttgt aacaatcgta cgcctcgact ccttccaca aaattttcaa ttcttcaatc   2400
aggggtctca tcatcacatc gatctttgtt ccaggatgat ccggaccagg tattataaga   2460
cacaagaaaa taaattcata tttcatgcaa agagctggtg gaaggttgta tggaacagca   2520
aagacgggcc aacatgagta cgacgtagca gttagattga atggtgagaa accatctgtt   2580
gccaaaccga agcggacatt ccgcacttca tcagcaaagc tggaatcaaa agcatctagt   2640
gccttccatg catctgtatc agctgggtgc accatgacat ttggattctc acgtaccct   2700
tctttgtgcc acctcatgtg tctggctgta ttttgtggaga tgaacaaacg tttcaaccga   2760
ggtatgagag gcatgtaacg aagctgctta tgtgcaatct tcgtagtcac ggtcaaacca   2820
tcgtcgtttt caacctcaac gaatctacgc tcaccacata cagtacactt cttctcacct   2880
gcggtctcct tccagaaaag catacaatta ttttcacaga catcgatttt ttcgtagtcc   2940
ataccgaggc cagataacag cttttttagac tgatacatgt cctttggcat cttgtgattc   3000
tccggaagta catcactgat caagttcaaa agttccttgt aacagttgtt tgagaatgca   3060
aacttagact taatagccat aagtcgagtc acaaatacaa ggacagtcac ttttgtgtgc   3120
tcatgcaacg gctcttcggc agctttaagg agctcgaaga acttctgaac ctcaggtgta   3180
gctggatcct caaactcggt gggttgaccg gggttctccg aatcgacggt tagaaactca   3240
tggcgtacat cgtcaagcat ctcttccatc ctatcgtagt cctcctcttc atgtgactga   3300
acttccgata caatacgagg tgggtcctca ccgtggtgca cccacacctc atagcctggc   3360
atataaccgt tcttgcaaat atgtatcgac atagtcctcc tgtcaggaa attaatgttc   3420
cgacacttgc tacaagggca cctaacatcg gttccagtct ctgaccgagc aaaagcatgg   3480
tcgagaaaag catcagtctt ggccacccac tcacttgata gagcacctct tttcttccaa   3540
ccttcataca tccatcgacg attctcctcc atactagata cgatacgtta acttaattag   3600
ataagtactg cacgtgcatt ccgtttttac gaagaaatca cgcccctaca tctgtaggaa   3660
aggataggtc ctaaacccac ccaggagtga ccgacgagac cgtgtttatg acaagacatg   3720
tggtcgtgcg aaatttcggc agcataaccc cgttgttctc caatcgcacg cctaaaaatg   3780
gtgcaattga agaacagaga ggttatgctg ccgaaactaa gcaggagcac atgctttttgt   3840
cataaacacg gactctgtcg gtcaccccga ggctgtccaa aaaaggggaca attccggacc   3900
aacataccte acatgcgtcg cttgtaaggt gtgttgggcc gaaacgggtg acgcctaggt   3960
ttcgtttgtt cacactacga tacactatga ttaactataa tcatcgtgca ttattaaata   4020
attaaactaa taaaccataa tacaatatta catcgaaat aatattgtta tagatgacaa   4080
atcatataaa atgaccttat ttccgagggc ataataatta ccctcggaaa ttaaaaatta   4140
aaattatcta aagtaccact aaataaagta aaacaaacta ctttaattaa ctaatcaaat   4200
```

-continued

```
tttgaccgtc ggacataaca aactaaacaa tcaaatgcat taatacatac aattttcaatc  4260
aaatacatta atacaaacat acaattctaa tcaaatacat taataaaagc atacaatttt   4320
aataaacaaa attgctaatt aagtatactc acttagcggg tgtggagagt cggccggcga    4380
tgggcgcacg ggcggcggcg ggcgcacggg gccgttggcc ggagcacggg gcggcggcga    4440
ccggcgaacg gggcggcggc gaccggcgaa cggggcgggg gcggcgggcg ccggagcacg    4500
ggcgtggcgg tggccggagc acgagctagg ggcggtggtg gccggagcac gggcgtggcg    4560
gtggtggccg gagcacgggc gtggcggtgg ccggagcacg agcacggagc ggtggggcgg    4620
cggcgggcgc cggagcacga gcagtggggg cgggcggtac ggcgataggg cgggacggcg    4680
acgagcgtgg cggcgacgag cgtggcggcg acggcggctt ctcctcggac acggcggagg    4740
cgtgctcggc ggcggcagga tagaaacgcg cggtctcggg tgaaactgaa ggcgcgcggg    4800
tcggaaccgc gcgttaaaaa gccttatgtc cgacggctcg gtacgaggcc gtcggacata    4860
agctaatgtc cgacggccag ggggtcggcc gtcggacata aggtaatgtc cgacggtcag    4920
tctgccagcc gtcggttata ttttttattt tcgacggccg ctgttggccg tcggacataa    4980
ccgtatgtcc gacggttgcc tacgggccgt cggacataag acgaccgtcg gaattgtata    5040
gttttactgt agtgctccct cactatcttg ttctcgcctc gtttttctct ccctccgcga    5100
gcgccaaggc agcgcagcta cgagacaagc acacgtaata gtactagtgc gccgttgccc    5160
tgcctgcctg ccctgtgccc tgccttgcac cacaccacca ccaccgcaga tccggtctgg    5220
tccagtccgg cccggtccgc tactaaacaa accagcccag cgcgcgcccc agcgagagga    5280
gaggaggagg ggccggggtc ggcacggcgg gcagaattgc ctctgctgcc tgcgcgctgc    5340
cctgccctgc cagagggatc ggagggagag cgatcagtca acaagcccag gaggaggagg    5400
aggaggaggg agagatccgc gtgccggccg gaggcgggct ccgggagatc gaccgagcga    5460
ccggcctcgg tcccggtgcg gtggtggatg gggatggcgc ggtgccgggtg ggtgggcggg    5520
ctcgtggcgg agagcttctt cgtggcgtgc cccgcgcacg agtcccgcaa gaagaacgag    5580
cgcaacatct tctgcctcgc ctgctgcgcc agcatctgcc cgcactgcgc cccgcgcacc    5640
gccaccaccc gctcctccag gtgagtgcga gtctcgtcgt cgtcctcctc ctcgcccggc    5700
ctctcctctt ccttcctccg gcggccttcc cctctccctg ccaggctgcc atggcgtcga    5760
gtggcatgca cctggccggg cgatctgctc agtttctact cctgctagct tcgcagcaat    5820
tctcgccgcc gctgtcccgc tccgctccgc ttcttgttgt tgttggatga acacaccacc    5880
tccccaccgc caccgccacc ggggggcagc ttttttgggg ttattgctgg tggcctcggt    5940
tcttgtgcaa cggatgggaa cggcggggac gagtaccaat caatcgattt ctttatttga    6000
tttaattgtt tatttattat tcctcggcgt atatagcact agacgctact tcttcctata    6060
tactactact agagtagtac tacaagtgta gaggaggagg ggcatgggaa ttggatgtgt    6120
agtatctcgc ttttgtttttg tcgcgtgctg tctcttcctt ccttccttcc ttggactaga    6180
tttggtcccg gctttagcct aaacaaaaaa atatttcccc cctaccattt ctcgcatgat    6240
ttgatttgat gcgtggtctc ttctcgtgtc gtccgtgcgc gggaaggaat caagggaaag    6300
gaaaggaaac caaaccccat ctcgctaatc gctctcctct ctctctctct ctcccttcct    6360
cgcaggcagg cagaggcagt acaggttgtt gcaaaacttg cacgtacttg attcctcgcg    6420
cgcgcagcgc cttgtcgcct tgcgaggttt ggtttggttg ggtcatgagc tcatccatcc    6480
attcccttt ccacccatgc atgcatgcat gcatgccacc ccttgatta gggtttataa      6540
gccagcagga ggcgctgatt gagtcctaat ctgcgccact gtaacagcaa tcccaaccat    6600
gattttcgca cccgctccag gactccggag cagtgctact tcttcatcgc tataattaat    6660
ataattcgtc tgctccttcc tgcctgaccg gggtattaaa tcctgtgtat gtacgtagta    6720
ctaacaaaca aggacaaggc agtaaaaatt ctcgttacgg aacattatct actccgaccct   6780
cccttgcatt tttttttttgg aattagtacc cgggcgttca tcgcgacctg catgcaactg    6840
tttcctcaac gagctagcca ttacatgctt ttagtttttt ataaaatata tatgcatgca    6900
tggcaaaact ttttccttttt taaattttcg ggagttaaag aggaggaggg tcgaaaattc    6960
aaatcccccc acccggggca tgcaaaccct tcttctttct ctccgtagct ttgtcttgta    7020
gctgcagcca tgcatttccc ccctactttc atgcagcagc aactaatcca tccggatatg    7080
ctggcgctgc gggagccgga gtctcgaacc caaatggcaa aaaaagctgc gggggggaggt    7140
tttaccgctg cctcttcatt ggaattccaa tccttgggat taggatcctc tgcggtaatc    7200
gccagcctcc tgctgcgctt ccgcttgctt ccccgtccat taataggcct ggttatccaa    7260
actgtttttgc caagtatagc aacatttccc tgccccccgt cctgccgact gaaccccgcc    7320
actgataaag gaaaaaaaat cggttcgggc ctttgaatta gattttaccg tatgcgcccg    7380
cgcgcggtaa ctgcgcggcc tgtctttttt taccaaacag aggcatcgac gacgacactg    7440
ttgtcccccg acgacgaccc catctctccc tggtgcgtgc tacacgacca aacttctctc    7500
tccttacctt agggtggggt ggtttttgggg gtctcccagg ccatgataaa gatcaccact    7560
ggagtggtac tgctgcccgg ccggtcaaag catggggggcc atcgcgtggt gtgtggccca    7620
acccaaagtt gtaccctgct gctgctgtac cgcctgcgtt gttatcttag gccccgtttc    7680
aatctcacgg gataaacttt agcttcatgc taaacttttag ctatatgaat tgaagtgcta    7740
aagtttagct ttaattacca ccattagctc tcatgtttag attataaatg gctaaaagta    7800
gctagaaaaa agctgctaaa gtttatctcg cgagattgga acacggcctt atcttagagt    7860
atgaaactgc ggttgtaaac atgtttagcg ccaactgcta tgatcaggtg cggcgctacg    7920
tgtaccatga cgtcgtccgc ctcggcgacc tagagaagct catcgactgc tcctgtgtcc    7980
aggtgattcc ctatctatcg tcgtatctgt cttgcattag tgcttcgaat tttgatggtg    8040
atgctgatga tgagtacgtt aattatatag tagtaaaact cccctctctc tttgtgtgtg    8100
tgatgtgtga ccgcgcagac ctacacaatc aacagtgcca aggtgatctt cctgaagccg    8160
aggccgcagt ccaggccttt caagggctcc ggcaacatct gcctcacgtg cgacaggatc    8220
ctccaggagc ccttccactt ctgctccctc tcatgcaagg ttgcattggt cagctagcta    8280
gcatcatcgc atacgccatg catatgcatc gtcggattcg gatcatatcg ttcagtgcgt    8340
acgtggatca tgtcatatgt tattacgcag gtggaccacg tgatgacgca gggaggggac    8400
ctgtccaaca tcctgcagca ctacggcgcc ggcggtggcg gtggcggtgg cacggcggac    8460
ccggaccgcc tcgcgttccc gaggttcgag aacctccgcg tcgtcgacgg ctcggacctc    8520
gacgacgacg tccaggtcgt caccccagac tccaccctcg aggacccgac caacaacgcg    8580
ggcggcgggt ccagcgacaa cggtactgac gacgccaggc ggcaggtcgt cgtccatggc    8640
ggcggcgagg cggccaagcg gaagaaaggg ggcggcttct tgcccagat cgtgctgtca      8700
ctcggcggcg gcgcggcggg cggcaacagg aggaagggtg cccccacag gtcccctctg      8760
gcctaagcag cgctaccttc atgcatgcgt ccccctgctg ctgctcgtta tatatcacaa    8820
gtcacaacac acgtagcgcg ctgtggttgc atgcagtgat gatggtgtgg gtggtagcta    8880
cagtattaat tagtagtagc gtgttataat agtatcttaa tggtgattag cctcgtagag    8940
```

-continued

```
agacgacgac aagctggtag ctggtcgatc ggttttgctt gggggggaagg tcttggtggc  9000
cttgtgatcc gtctagcagc tcgctaggac caaccatggc cgccgcgcca tctcatgaga  9060
cttttagagag agagagagag agagagggtc atggggggagg tagagggggg agagacggtt  9120
gtaaaagcag ttcccattgt tacaggcacc aggtagtaac tggtcagtgg ggcccacttc  9180
tgcaggcggt ggggcccata cgatcgaggt ggctaccaat tttgtatttg atgtaccaag  9240
ggttactcgc ggtctcgcgc atacaatttc cacacctata tatgttatat ataaatgata  9300
atatatctga attctgtccc agactaaaca ggttgttttc agcagtctgt atccgttcca  9360
tgtgggctca agtgattttc agctgcctgt ttggcgtgtc aagcagctgt tgagacatga  9420
ggccgagagc tctcgcccag tctcgcccgt agggatgaaa gtaggatggg aaaatcccgt  9480
accgaccgtt atcgtataac cgaatttgtt agttttgtcc cgatcgtttt cgaacccgac  9540
gtaaaaaacg aaaacgggac gaaaacggga tatacaaaac ggtaaacgga aacgaaacg   9600
gtagagctgt tttaccgacc gtttaaccgg gatcccgttt ttaatcggga tgatcccgtt  9660
ttgttaccgt attttgtaat tcgggatcac ttcaatatag acagctatag gcatcacttt  9720
gaggcccagc ccatctaaga aaaacctaac gcgctgttct gctcccaggc gtcgccgtcc  9780
acactcctct ctcccagctc gctgccgtag tgccatcagc tcgtcactcg caggcgccgg  9840
cgcgcagccg tccgccctcc tgctctgtgc ggctttgcct ctcccagctc gcctcgccag  9900
tcgccaggcc agagtgccat cgcagcttcc caggctccca gctcgccaga gtgccggacg  9960
ccacgccagc ccggtccggt ctccggtcgg cggtcggtcg atcgccgctg ctccagctgg  10020
ctgcccaggc gactagacgt ccacgacggc tcggcgatcg gcaggcagct cgctccacct  10080
ccacaggcca cgactccctc tgctgctgct gtcctccacg gatccactgc tggctgctgc  10140
tccctccaca gagaatcgcc ttgctacacc atgtgagcag tcctgcagtc ctgccgtgtt  10200
agacgctagc tgctagctcc cagccgtact ccaccacgtt ttggtgcata agctgcgtgt  10260
tgccttgctt tttactgttg ttgttttaat tctgtggtgc ataattctgt tggtgcgtac  10320
ttctattggg cgtactttat attatgtcat gtgtgctagt agacttatat ggcttcttat  10380
gtagccaaga gctcaatatt tatcacttat gtgctactaa gatgtttggt ttgatgaatc  10440
actctatcca aaatgaagtg gtgtcatcatg ggtccattcc tcaaatttgg tgggatgact  10500
tcattccaca tattagtact aaacaactaa ctatgaggaa tgaggtggtg atggattaac  10560
tcactccatt ccacaaacca aacaaaaaag tgaggagtga gaagatgatg aactatatcg  10620
ttcctcaaac caaacactcc atacattaaa ctatgtgtgc tccagattta tatgactttt  10680
ttctatgttt aattaagact tgtgtttaca atttttttata tttgtttttta agttttgaat  10740
atatgttttc atggtgtgat tttaccgaac aaaaataccg gttcccgtcc gatttcggct  10800
ttaacccgac cggatcgtat cggttttcgc ttaccgtatt tatcccgttc gttttcgtta  10860
ccgatatatc ccgttttcgt tttcgtcccg caagttaaat atgaaaatga aaacggtaga  10920
ggtattttac cgaccgttcc cgaccgtttt catccctact cgcccgcgtg catggattgt  10980
tgcatgcatg tgatgcgcgc gcgcacacgc ctagcgctcc cgtccaaact ccccagtcgt  11040
gttgctgtga cctgctggct gtttgatgca gttgtgattc gctttgcaat ggaccacggt  11100
ctctgtccca tggtgtgtgt atctgtgtgt ctgagtgtgg agacgacaga gactcgaaaa  11160
gatggtgtgg tggctgttcg atccagggct cgcttgatgc ctgtttttttt ttccacgaga  11220
atctcctcat tagagaacag atgcatgggt cgtttttttag cctctctaga ccaggatgtg  11280
aaaggtagaa aagccattct cacgtgaggt tacagtactt gtagctttcc attactcata  11340
tacttgcagg aattaatatt ggacactctt tttctactct cgctctgttt taaatcgcaa  11400
gctatttttc cactttctta aaaatgtagc agcttttacc gagtacatct cggtacgtac  11460
ctaaaaaaaa gcttgtagta taagctttca accgagtgtt tataaggctt cgccgagtgc  11520
ttccggcact cggcgaagct attgattccg gtagtgccgg gttgaattta cttttgtatc  11580
actgagcgtg cgaagagaac agcggtattt ctggcatcga tcgggcaccc ttcctcggaa  11640
tcatggcttt ttgagagtga ccaacaggca gtgcgcgcgg tctcggaacc tgaaaattgt  11700
ttggttgtat cgaatgactt gtcacggcca ctcgaggcag gcatgagacg ctccaccgga  11760
ccgccacacc atgcatagtg acagatcatc aaaaggtggt tttaaaactc gaattttttat  11820
ctgactatat agcaaataaa tccttttgta cgctcagttt catatatagga cgaaattctc  11880
ccacctctcc catgcatgca tgtcatcgat cattcttgtt tatctggtga tgtatttaat  11940
gaagacagaa attcgagtga gatttccagt ggaaatagcc ttattagtgc gccatgaacg  12000
aagttctgaa gtcgaaacca gacgagagtc cccatgcacg atgccatgga tatcgccagt  12060
acgtacagga cgtcgccag cacgatgcaa ctgtcagcag acagcagcca aaacgcaatt  12120
cttgtttcag ctgggtgggc aattccgagg tgtgctaaat aaaagcatga tccatgcata  12180
tagatgagca tgcagcccgc agcccgacag cccggcacga ggccggtt tttgccccgg  12240
cccaagcacg gcacggcccg tctggtttcg tgcccgtgcc ggcccggccc ggtagaccag  12300
gccgtgcttg ggctgccgga tgcgcccgcc gggcggcacg gcccggcccg ctaggaaaag  12360
caggcacgga gccggcccgg ttccaggcga ggggcatatc cgcccgcccc tccccaccgc  12420
ccgttcagtc ccccagtccc tagttcccca cgccacgcga tttgctccgc agcctccgcc  12480
ctccgctcgt ccgctcgccg ctccctcccc attctccgtc aacgccgagc cgtcgccact  12540
gccgttgccg gatctccgtc gtcgaccgac gagatctcct ctctgcctct ctccagtctt  12600
cgtcactcgg tgacgcatcg gctctccatt ccccaatctg taaccctaat cccctttccg  12660
gctttccctc acctctccgg tgacgcatcg gctctccact gccggatctc cgtcaccggc  12720
gacatctgca cgcttgttct gtgcggctca ccctctccgg ctctccctcc ccaatccct   12780
cgctcgtcgt cgtcgtcatc ggtcgtcggc ttgtcgcgcg tcgtcgtccc ctagaccctc  12840
gtctccggct ccgggctccg gcttggcagg tacgtgtacg tccctctccg gctctccctc  12900
cccaatccga caaaccctaa ccctaatccc ttgcttggta ggtcgccggc cgactacgcc  12960
gtggtcgtgc tggtgccgcc agtgccgttg aggtacggtg ccgagagggg ggccgggcat  13020
ggatgacgac gacgacaatg gccggtaccc tagaaccatc aacgacgacg tcgttgagtt  13080
agggcagctt cccgatgacg tcgacgacat gggagatgct gctgctgcct tattcggtat  13140
cggtagcagt catggtgccg gcgacctgga ggggacagct gccgggccgg ttccggttag  13200
tgatgctgct ggctctaacg aacttgattc attgacttct tccagcactg gtaagcgtcg  13260
atctgctgtt tgggatgact tcactgaagt cactgaaaac cgtaatggta agaaggtgcg  13320
cattgctggt atttgcaaat tttgcaaggc tcggttgagt gctagttcta atgctggcac  13380
tggacatttg cttaggcacc agaaaatcatg taaaaagaag tctgatcatg ctgctatggt  13440
tcaaactaga ctagctttga accctgatgg gtctttttaga aactgggaat atgatcctca  13500
ggtggctagg actgagcttt gtcgtttgat tgctagactt gatcttcctt tagggatagc  13560
tgacacagat gcttgggata attacattca acatgctcac aaccctagat atgttagggt  13620
atctaggttt acaactgcta gagacttggc taagctatac aatgaaaagc taaagaactt  13680
```

```
aaaagatgat gtttttcctg gtgtgtcttc tatttgcttg acttctgata tatggtctgg  13740
taatgccaag gaagactaca ttactgttgt tgctcatttt attaatgctg attgggagtt  13800
aaagaagtgt gtgataggct ttaaattgat ccaagtgtct cataatggtg ttaacattgc  13860
tgaacgcatt gcttgtgtga ttcaatactt tggcatgatt gataaagtgt tctctattac  13920
cttagataat gcttcttcta attcaactgc catgctcaca ttgtcaccta tgcttgctgg  13980
ttatttgggt gctgatgttg atccaacaga tactagtaac aaaacatata gtgtgcttca  14040

SEQ ID NO: 106            moltype = DNA   length = 360
FEATURE                  Location/Qualifiers
source                   1..360
                         mol_type = other DNA
                         organism = synthetic construct
SEQUENCE: 106
atggggatgg cgcccgccgg gtgggtgggc gggctcgtgg cggagagctt cttcgtggcg  60
tgccccgcgc acgagtcccg caagaagaac gagcgcaaca tcttctgcct cgcctgctgc  120
gccagcatct gcccgcactg cgccccgcgc accgccacca cccgctcctc cagcgccaac  180
tgctatgatc aggtgcggcg ctacgtgtac catgacgtcg tccgcctcgg cgacctagag  240
aagctcatcg actgctcctg tgtccagacc tacacaatca acagtgccaa ggtgatcttc  300
ctgaagccga ggccgcagtc caggcctttc aagggctccg gcaacatctg cctcacgtgc  360

SEQ ID NO: 107            moltype = AA   length = 267
FEATURE                  Location/Qualifiers
source                   1..267
                         mol_type = protein
                         organism = synthetic construct
SEQUENCE: 107
MGMAPAGWVG GLVAESFFVA CPAHESRKKN ERNIFCLACC ASICPHCAPR TATTRSSSAN  60
CYDQVRRYVY HDVVRLGDLE KLIDCSCVQT YTINSAKVIF LKPRPQSRPF KGSGNICLTC  120
DRILQEPFHF CSLSCKVDHV MTQGGDLSNI LQHYGAGGGG GGGTADPDRL AFPRFENLRV  180
VDGSDLDDDV QVVTPDSTLE DPTNNAGGGS SDNGTDDARR QVVVHGGGEA AKRKKGGGFL  240
PQIVLSLGGG GGGGNRRKGA PHRSPLA                                      267

SEQ ID NO: 108            moltype = DNA   length = 14018
FEATURE                  Location/Qualifiers
source                   1..14018
                         mol_type = other DNA
                         organism = synthetic construct
SEQUENCE: 108
ttctttgaca tcctatttta acaaaaacaa gttagtacat aaatcgacaa taaaataata  60
aaatatgcaa taaaatcata aaatatgcaa taaaatcatg atccatactc gtcaatcgta  120
atcgtaatca aaatcaggat ctagttgctt tcgtcgattt aatggacgcc aagtagcttt  180
cttctttctc gtcactcgtt ttcttttgg aggaacctct acatcatttt gatcgcctaa  240
taaagattct tccaacattt cagtttgtac attaaacgtg cttgtaagtt cttcgtcttg  300
gaaaatctca gcagccccca cttcctgctc gatttgactt tcaacataac cagcatcacc  360
aggagcatat agtcgttcac gcggattaac tttgtacact accctccaat caaccaaacc  420
gttttttctta gatggatatg tcatataata cacctgctcg cattggtggg caaggattat  480
agtgtcgtga cctttaatc tatcgttgtg tttgacttcc accatgccat attgattttc  540
tcgcgttgta tttggagaaa accaatcaca atcgaagaac accactttga gttgtttatc  600
tccaaaaaac ttgtactcga ttatatcatt aatgactcca taataattag tcaccttccc  660
ttcatcatcg acagctctag ttacaactcc ggagtttgtc gtggctgcta gaggatgatc  720
atcttcgaac cttgtggaac ggaatctaaa accattgaca tcataccgac cataacgtct  780
gccagttact gctcctaggg ataattgtcg aaggtccggg tgtatattgt cattttatc  840
tacataatct cgaaaccaac acaagaaatt aagtcccca tcttttccct ctcgacgaat  900
ctggtcacgt tcacagccag agatgcaatt ttgagaatca aattccctgt tagtacaagg  960
aaacaaacct tttagtatca caacaaaaat tctagcggca atgactaaaa taaagtttac  1020
acttacagga gaaactgact catctcttcc atgttgttat acatgtaaag taaagcagtc  1080
ttccattcgt cgttggtgaa acagtatgtt gtgctgggtc ctacagtttt gcccctccat  1140
tgaaaaattt caatatcact aatagggggc tcgtcgacat gataccgcaa cgtatgggca  1200
ttgacattgt gttcctctgc aaagtacagg cccgtgaacg atgctatctc tttgtatttg  1260
aattcttcag cgatgcaccc ttcaactcgt ctcttattac caaccattgc acgtagcttt  1320
tttagtgtcc tttcgatgtg atacatccat ctatattgca caggacctcc taccttagct  1380
tcgtatggta ggtgaacaag tagatgttgc atcggattga agaaacctgg tggaaatatt  1440
ttttcaagtt tgcataccaa aatcggtatt tcttgctcaa gcttctccat catctctttc  1500
tttatttctt tggcacaaag atgtctataa aagtagctta gctccgctaa tgctttccag  1560
acatcatttt ttacaaaacc acgaaacata acaggaagga gtcttccat tattatgtgg  1620
tagtcatgac tcttcaaccc agaaaacttg cccgtcttca aattcacaga ccttctaaag  1680
cccgcggcgt aaccatctgg gaactttaag tttttcaacc atttcatcaa ttgtttcttc  1740
cttttaggtt taatactgaa aggagcacgt ggcttcttct gattctctcc tatctccata  1800
gttggtcttc tacagattaa ggccaagtct ttccttgct tagggttgtc ttttgttttg  1860
tcggtgatat tcatgcaagt gctgataatg ctttcaccca tatttcgttc ctggtcgatg  1920
acatcaatgt tatgcattag aatcaaggct ttcatataag ggagttccca tagaccacat  1980
ttgtgagtcc aattatgctc ggttccataa ccttcaaaac gatttccatg ttcgtttagt  2040
ttcaaatcat taagtctcgc gagaatctca ggaccactta gacgcttggg tggtcccctc  2100
gtcacaatcg tgtcctttt aaaagcgttc ctatcgaacc tgaacgggtg atcctctggc  2160
aaaaaacatc tatggcaatc gaagtaacat atctttccac caaactttag tcgaaagcat  2220
aaagtgtctt caacgcatat aggacatgtc aaaatcccat gacaactcca tccagcaaag  2280
ataccataag ccataaaatc atgaatagac cataaaaacg cggctctcag gttgaacttc  2340
tgtttcttgt aacaatcgta cgcctcgact ccttcccaca aaattttcaa ttcttcaatc  2400
aggggtctca tcatcacatc gatctttgtt ccaggatgat ccgaccagg tattataaga  2460
```

-continued

```
cacaagaaaa taaattcata tttcatgcaa agagctggtg gaaggttgta tggaacagca   2520
aagacgggcc aacatgagta cgacgtagca gttagattga atggtgagaa accatctgtt   2580
gccaaaccga agcggacatt ccgcacttca tcagcaaagc tggaatcaaa agcatctagt   2640
gccttccatg catctgtatc agctgggtgc accatgacat ttggattctc acgtacccct   2700
tctttgtgcc acctcatgtg tctggctgta tttttggaga tgaacaaacg tttcaaccga   2760
ggtatgagag gcatgtaacg aagctgctta tgtgcaatct tcgtagtcac ggtcaaacca   2820
tcgtcgtttt caacctcaac gaatctacgc tcaccacata cagtacactt cttctcacct   2880
gcggtctcct tccagaaaag catacaatta ttttcacaga catcgatttt ttcgtagtcc   2940
ataccgaggc cagataacag cttttttagac tgatacatgt cctttggcat cttgtgattc   3000
tccggaagta catcactgat caagttcaaa agttccttgt aacagttgtt tgagaatgca   3060
aacttagact taatagccat aagtcgagtc acaaatacaa ggacagtcac ttttgtgtgc   3120
tcatgcaacg gctcttcggc agctttaagg agctcgaaga acttctgaac ctcaggtgta   3180
gctggatcct caaactcggt gggttgaccg gggttctccg aatcgacggt tagaaactca   3240
tggcgtacat cgtcaagcat ctcttccatc ctatcgtagt cctcctcttc atgtgactga   3300
acttccgata caatacgagg tgggtcctca ccgtggtgca cccacacctc atagcctggc   3360
atataaccgt tcttgcaaat atgtatcgac atagtcctcc tgtcaaggaa attaatgttc   3420
cgacacttgc tacaagggca cctaacatcg gttccagtct ctgaccgagc aaaagcatgg   3480
tcgagaaaag catcagtctt ggccacccac tcacttgata gagcacctct tttcttccaa   3540
ccttcataca tccatcgacg attctcctcc atactagata cgatacgtta acttaattag   3600
ataagtactg cacgtgcatt ccgttttttac gaagaaatca cgcccctaca tctgtaggaa   3660
aggataggtc ctaaacccac ccaggagtga ccgacgagac cgtgtttatg acaagacatg   3720
tggtcgtgcg aaatttcggc agcataaccc cgttgttctc caatcgcacg cctaaaaatg   3780
gtgcaattga agaacagaga ggttatgctg ccgaaactaa gcaggagcac atgcttttgt   3840
cataaacacg gactctgtcg gtcaccccga ggctgtccaa aaaagggaca attccggccc   3900
aacataccatc acatgcgtcg cttgtaaggt gtgttgggcc gaaacgggtg acgcctaggt   3960
ttcgtttgtt cacactacga tacactatga ttaactataa tcatcgtgca ttattaaata   4020
attaaactaa taaaccataa tacaatatta catcgaaat aatattgtta tagatgacaa   4080
atcatataaa atgaccttat ttccgagggc ataataatta ccctcggaaa ttaaaaatta   4140
aaaattatcta aagtaccact aaataaagta aaacaaacta ctttaattaa ctaatcaaat   4200
tttgaccgtc ggacataaca aactaaacaa tcaaatgcat taatacatac aatttcaatc   4260
aaatacatta atacaaacat acaattctaa tcaaatacat taataaaagc atacaatttt   4320
aataaacaaa attgctaatt aagtatactc acttagcggg tgtggagagt cggccggcga   4380
tgggcgcacg ggcggcggcg ggcgcacggg gccgttggcc ggagcacggg gcggcggcga   4440
ccggcgaacg gggcggcggc gaccggcgaa cggggcggcg gcggcggcgg ccggagcacg   4500
ggcgtggcgg tggccggagc acgagctagg ggcggtggtg gccggagcac gggcgtggcg   4560
gtggtggccg gagcacggc gtggcggtgg ccggagcacg agcacgagc ggtggggcgg   4620
cggcgggcgc cggagcacga gcagtggggg cgggcggtac ggcgataggg cgggacggcg   4680
acgagcgtgg cggcgacgag cgtggcggcg acggcggctt ctcctcggac acggcggagg   4740
cgtgctcggc ggcggcagga tagaaacgcg cggtctcggg tgaaactgaa ggcgcgcggg   4800
tcggaaccgc gcgttaaaaa gccttatgtc cgacggctcg gtacgaggcc gtcggacata   4860
agctaatgtc cgacggccag ggggtcggcc gtcggacata aggtaatgtc cgacggtcag   4920
tctgccagcc gtcggttata tttttattt tcgacggccg ctgttggccg tcggacataa   4980
ccgtatgtcc gacggttgcc tacgggccgt cggacataag acgaccgtcg gaattgtata   5040
gttttactgt agtgctccct cactatcttg ttctcgcctc gtttttctct ccctccgcga   5100
gcgccaaggc agcgcagcta cgagacaagc acacgtaata gtactagtgc gccgttgccc   5160
tgcctgcctg ccctgtgccc tgccttgcac cacaccacca ccaccgcaga tccggtctgg   5220
tccagtccgg cccggtccgc tactaaacaa accagcccag cgccgcgcccc agcgagagga   5280
gaggaggagg ggccgggtc ggcacggcgg gcagaattgc ctctgctgcc tgcgcgctgc   5340
cctgccctgc cagagggatc ggaggagag cgatcagtca acaagcccag gaggaggagg   5400
aggaggaggg agagatccgc gtgccggccg gaggcgggct ccgggagatc gaccgagcga   5460
ccggcctcgg tcccggtgcg gtggtggatg gggatggcgc cgccgggtg ggtgggcggg   5520
ctcgtggcgg agagcttctt cgtggcgtgc cccgcgcacg agtcccgcaa gaagaacgag   5580
cgcaacatct tctgcctcgc ctgctgcgcc agcatctgcc cgcactgcgc cccgcgcacc   5640
gccaccaccc gctcctccag gtgagtgcga gtctcgtcgt cgtcctcctc ctcgcccggc   5700
ctctcctctt ccttcctccg gcggccttcc cctctccctg ccaggctgcc atggcgtcgc   5760
gtggcatgca cctggccggg cgatctgctc agtttctact cctgctagct tcgcagcaat   5820
tctcgccgcc gctgtcccgc tccgctccgc ttcttgttgt tgttggatga acacaccacc   5880
tccccaccgc caccgccacc gggggggcagc ttttttggggg ttattgctgg tggcctcggt   5940
tcttgtgcaa cggatgggaa cggcggggac gagtaccaat caatcgattt ctttatttga   6000
tttaattgtt tatttattat tcctcggcgt atatagcact agacgctact tcttcctata   6060
tactactact agagtagtac tacaagtgta gaggaggagg ggcatgggaa ttggatgtgt   6120
agtatctcgc ttttgtttttg tcgcgtgctg tctcttcctt ccttccttcc ttggactaga   6180
tttggtcccg gctttagcct aaacaaaaaa atatttcccc cctaccattt ctcgcatgat   6240
ttgatttgat gcgtggtctc ttctcgtgtc gtccgtgcgg gggaaggaat caagggaaag   6300
gaaaggaaac caaacccat ctcgctaatc gctctcctct ctctctctct ctcccttcct   6360
cgcaggcagg cagaggcagt acaggttgtt gcaaaacttg cacgtacttg attcctcgcg   6420
cgcgcagcgc cttgtcgcct tgcgaggttt ggtttggttg ggtcatgagc tcatccatcc   6480
attccctttt ccacccatgc atgcatgcat gcatgccact ccctgatta gggtttataa   6540
gccagcagga ggcgctgatt gagtcctaat ctgcgccact gtaacagcaa tcccaaccat   6600
gattttcgca cccgctccag gactccggag cagtgctact tcttcatcgc tataattaat   6660
ataattcgtc tgctccttcc tgcctgaccg gggtattaaa tcctgtgtat gtacgtagta   6720
ctaacaaaca aggacaaggc agtaaaaatt ctcgttacgg aacattatct actccgacct   6780
cccttgcatt tttttttttgg aattagtacc cgggcgttca tcgcgacctg catgcaactg   6840
tttcctcaac gagctagcca ttacatgctt ttagtttttt ataaaatata tatgcatgca   6900
tggcaaaact ttttccttttt taaatttctg ggagttaaag aggaggaggg tcgaaaattc   6960
aaatcccccc acccgggca tgcaaaccct tcttcttttct ctccgtagct ttgtcttgta   7020
gctgcagcca tgcatttccc ccctactttc atgcagcagc aactaatcca tccggatatg   7080
ctggcgctgc gggagccgga gtctcgaacc caaatggcaa aaaaagctgc ggggggaggt   7140
tttaccgctg cctcttcatt ggaattccaa tccttgggat taggatcctc tgcggtaatc   7200
```

```
gccagcctcc tgctgcgctt ccgcttgctt cccgtccat taataggcct ggttatccaa      7260
actgttttgc caagtatagc aacatttccc tgcccccgt cctgccgact gaaccccgcc      7320
actgataaag gaaaaaaaat cggttcgggc ctttgaatta gattttaccg tatgcgcccg      7380
cgcgcggtaa ctgcgcggcc tgtctttttt taccaaacag aggcatcgac gacgacactg      7440
ttgtcccccg acgacgaccc catctctccc tggtgcgtgc tacacgacca aacttctctc      7500
tccttacctt agggtggggt ggttttgggg gtctcccagg ccatgataaa gatcaccact      7560
ggagtggtac tgctgcccgg ccggtcaaag catgggggcc atcgcgtggt gtgtggccca      7620
acccaaagtt gtaccctgct gctgctgtac cgcctgcgtt gttatcttag gccccgtttc      7680
aatctcacgg gataaacttt agcttcatgc taaactttag ctatatgaat tgaagtgcta      7740
aagtttagct ttaattacca ccattagctc tcatgtttag attataaatg gctaaaagta      7800
gctagaaaaa agctgctaaa gtttatctcg cgagattgga acacggcctt atcttagagt      7860
atgaaactgc ggttgtaaac atgtttagcg ccaactgcta tgtacgtgat caggtgcggc      7920
gctacgtgta ccatgacgtc gtccgcctcg gcgacctaga gaagctcatc gactgctcct      7980
gtgtccaggt gattccctat ctatcgtcgt atctgtcttg cattagtgct tcgaattttg      8040
atggtgatgc tgatgatgag tacgttaatt atatagtagt aaaactcccc tctctctttg      8100
tgtgtgtgat gtgtgaccgc gtgatcttcc tgaagccgag gccgcagtcc aggcctttca      8160
agggctccgg caacatctgc ctcacgtgcg acaggatcct ccaggagccc ttccacttct      8220
gctccctctc atgcaaggtt gcattggtca gctagctagc atcatcgcat acgccatgca      8280
tatgcatcgt cggattcgga tcatatcgtt cagtgcgtac gtggatcatg tcatatgtta      8340
ttacgcaggt ggaccacgtg atgacgcagg gaggggacct gtccaacatc ctgcagcact      8400
acggcgccgg cggtggcggt ggcggtggca cggcggaccc ggaccgcctc gcgttcccga      8460
ggttcgagaa cctccgcgtc gtcgacggct cggacctcga cggacctgca caggtcgtca      8520
ccccagactc caccctcgag gacccgacca acaacgcggg cggcgggtcc agcgacaacg      8580
gtactgacga cgccagacgg caggtcgtcg tccatggcgg cggcggaggcg gccaagcgga      8640
agaaaggggg cggcttcttg ccccagatcg tgctgtcact cggcggcggc ggcggcggcg      8700
gcaacaggag gaagggtgcc ccccacaggt cccctctggc ctaagcagcg ctaccttcat      8760
gcatgcgtcc ccctgctgct gctcgttata tatcacaagt cacaacacac gtagcgcgct      8820
gtggttgcat gcagtgatga tggtgtgggt ggtagctaca gtattaatta gtagtagcgt      8880
gttataatag tatcttaatg gtgattagcc tcgtagagag acgacgacaa gctggtagct      8940
ggtcgatcgg tttgcttgg ggggaaggtc ttggtgcct tgtgatccgt ctagcagctc      9000
gctaggacca accatggccg ccgcgccatc tcatgagact ttagagagag agagagagag      9060
agagggtcat gggggaggta gagggggggag agacggttgt aaaagcagtt cccattgtta      9120
caggcaccag gtagtaactg gtcagtgggg cccacttctg caggcggtgg ggcccatacg      9180
atcgaggtgg ctaccaattt tgtatttgat gtaccaaggg ttactcgcgg tctcgcgcat      9240
acaatttcca cacctatata tgttatatat aaatgataat atatctgaat tctgtcccag      9300
actaaacagg ttgtttttcag cagtctgtat ccgttccatg tgggctcaag tgattttcag      9360
ctgcctgttt ggcgtgtcaa gcagctgttg agacatgagg ccgagagctc tcgcccagtc      9420
tcgcccgtag ggatgaaagt aggatgggaa aatcccgtac cgaccgttat cgtataaccg      9480
aatttgttag ttttgtcccg atcgtttcg aacccgacgt aaaaaacgaa aacgggacga      9540
aaacgggata tacaaaacgg taaacggaaa cggaaacggt agagctgttt taccgaccgt      9600
ttaaccggga tcccgttttt aatcgggatg atcccgtttt gttaccgtat tttgtaattc      9660
gggatcactt caatatagac agctataggc atcactttga ggcccagccc atctaagaaa      9720
aacctaacgc gctgttctgc tcccaggcgt cgccgtccac actcctctct cccagctcgc      9780
tgccgtagtg ccatcagctc gtcactcgca ggcgccggcg cgcagccgtc cgccctcctg      9840
ctctgtgcgg ctttgcctct cccagctcgc ctcgccagtc gccaggccag agtgccatcg      9900
cagcttccca ggctcccagc tcgccagagt gccgacgcc acgccagccc ggtccggtct      9960
ccggtcggcg gtcggtcgat cgccgctgct ccagctggct gcccaggcga ctagacgtcc     10020
acgacggctc ggcgatcggc aggcagctcg ctccacctcc acaggccacg actccctctg     10080
ctgctgctgt cctccacgga tccactgctg gctgctgctc cctccacaga gaatcgcctt     10140
gctacaccat gtgagcagtc ctgcagtcct gccgtgttag acgctagctg ctagctccca     10200
gccgtactcc accacgtttt ggtgcataag ctgcgtgttg ccttgctttt tactgttgtt     10260
gttttaattc tgtggtgcat aattctgttg gtgcgtactt ctattgggcg tactttatat     10320
tatgtcatgt gtgctagtag acttatatgg cttcttatgt agccaagagc tcaatattta     10380
tcacttatgt gctactaaga tgtttggttt gatgaatcac tctatccaaa atgaagtggt     10440
gcatcatggg tccattcctc aaatttggtg ggatgacttc attccacata ttagtactaa     10500
acaactaact atgaggaatg aggtggtgat ggattaactc actccattcc acaaaccaaa     10560
caaaaaagtg aggagtgaga agatgatgaa ctatatcgtt cctcaaacca aacactccat     10620
acattaaact atgtgtgctc cagatttata tgactttttt ctatgtttaa ttaagacttg     10680
tgtttacaat ttttttatatt tgttttttaag ttttgaatat atgtttttcat ggtgtgattt     10740
taccgaacaa aaataccggt tcccgtccga tttcggcttt aacccgaccg gatcgtatcg     10800
gttttcgctt accgtattta tcccgttcgt tttcgttacc gatatatccc gttttcgttt     10860
tcgtcccgca agttaaatat gaaaatgaaa acggtagagg tattttaccg accgttcccg     10920
accgttttca tccctactcg cccgcgtgca tggattgttg catgcatgtg atgcgcgcgc     10980
gcacacgcct agcgctcccg tccaaactcc ccagtcgtgt tgctgtgacc tgctgagcgt     11040
ttgatgcagt tgtgattcgc tttgcaatgg accacggtct ctgtcccatg gtgtgtgtat     11100
ctgtgtgtct gagtgtggag acgacagaga ctcgaaaaga tggtgtgggt gctgttcgat     11160
ccagggctcg cttgatgcct gttttttttt ccacgagaat ctctctatta gagaacagat     11220
gcatgggtcg tttttttagcc tctctagacc aggatgtgaa aggtagaaaa gccattctca     11280
cgtgaggtta cagtacttgt agctttccat tactcatata cttgcaggaa ttaatattgg     11340
acactctttt tctactctcg ctctgtttta aatcgcaagc tatttttcca ctttcttaaa     11400
aatgtagcag cttttaccga gtacatctcg gtacgtacct aaaaaaaagc ttgtagtata     11460
agctttcaac cgagtgttta taaggcttcg ccgagtgctt ccggcactcg gcgaagctat     11520
tgattccggt agtgccgggt tgaatttact tttgtatcac tgagcgtgcg aagagaacag     11580
cggtatttct ggcatcgatc gggcacccct cctcggaatc atggctttt gagagtgacc     11640
aacaggcagt gcgcgcggtc tcggaacctg aaaattgttt ggttgtatcg aatgacttgt     11700
cacggccact cgaggcaggc atgagacgct ccaccggacc gccacaccat gcatagtgac     11760
agatcatcaa aaggtggttt taaaactcga atttttatct gactatatag caaataaatc     11820
cttttgtacg ctcagtttca tatatagacg aaattctccc acctctccca tgcatgcatg     11880
tcatcgatca ttcttgttta tctggtgatg tatttaatga agacagaaat tcgagtgaga     11940
```

-continued

```
tttccagtgg aaatagcctt attagtgtgc catgaacgaa gttctgaagt cgaaaccaga   12000
cgagagtccc catgcacgat gccatggata tcgccagtac gtacaggacg tgcgccagca   12060
cgatgcaact gtcagcagac agcagccaaa acgcaattct tgtttcagct gggtgggcaa   12120
ttccgaggtg tgctaaataa aagcatgatc catgcatata gatgagcatg cagcccgcag   12180
cccgacagcc cggcacgagg cccggttttt tggcccggcc caagcacggc acggcccgtc   12240
tggtttcgtg cccgtgccgg cccggcccgg tagaccaggc cgtgcttggg ctgccggatg   12300
cgcccgccgg gcggcacggc ccggcccgct aggaaaagca ggcacggagc cggcccggtt   12360
ccaggcgagg ggcatatccg cccgcccctc cccaccgccc gttcagtccc ccagtcccta   12420
gttccccacg ccacgcgatt tgctccgcag cctccgccct ccgctcgtcc gctcgccgct   12480
ccctccccat tctccgtcaa cgccgagccg tcgccactgc cgttgccgga tctccgtcgt   12540
cgaccgacga gatctcctct ctgcctctct ccagtcttcg tcactcggtg acgcatcggc   12600
tctccattcc ccaatctgta accctaatcc ccttttccggc tttccctcac ctctccggtg   12660
acgcatcggc tctccactgc cggatctccg tcaccggcga catctgcacg cttgtttctgt   12720
gcggctcacc ctctccggct ctccctcccc aatcccctcg ctcgtcgtcg tcgtcatcgg   12780
tcgtcggctt gtcgcgcgtc gtcgtcccct agaccctcgt ctccggctcc gggctccggc   12840
ttggcaggta cgtgtacgtc cctctccggc tctccctccc caatccgaca aaccctaacc   12900
ctaatccctt gcttggtagg tcgccggccg actacgccgt ggtcgtgctg gtgccgccag   12960
tgccgttgag gtacggtgcc gagagggggg ccgggcatgg atgacgacga cgacaatggc   13020
cggtacccta gaaccatcaa cgacgagctc gttgagttag ggcagcttcc cgatgacgtc   13080
gacgacatgg gagatgctgc tgctgcctta ttcggtatcg gtagcagtca tggtgccggc   13140
gacctggagg ggacagctgc cgggccggtt ccggttagtg atgctgctgg ctctaacgaa   13200
cttgattcat tgacttcttc cagcactggt aagcgtcgat gtctgtttg ggatgacttc   13260
actgaagtca ctgaaaaccg taatggtaag aaggtgcgca ttgctggtat ttgcaaattt   13320
tgcaaggctc ggttgagtgc tagttctaat gctggcactg gacatttgct taggcaccag   13380
aaatcatgta aaaagaagtc tgatcatgct gctatggttc aaactagact agctttgaac   13440
cctgatgggt cttttagaaa ctgggaatat gatcctcagg tggctaggac tgagctttgt   13500
cgtttgattg ctagacttga tcttccttta gggatagctg acacagatgc ttgggataat   13560
tacattcaac atgctcacaa ccctagatat gttagggtat ctaggtttac aactgctaga   13620
gacttggcta agctatacaa tgaaaagcta aagaacttaa aagatgatgt ttttcctggt   13680
gtgtcttcta tttgcttgac ttctgatata tggtctggta atgccaagga agactacatt   13740
actgttgttg ctcatttttat taatgctgat tgggagttaa agaagtgtgt gataggcttt   13800
aaattgatcc aagtgtctca taatggtgtt aacattgctg aacgcattgc ttgtgtgatt   13860
caatactttg gcatgattga taaagtgttc tctattacct tagataatgc ttcttctaat   13920
tcaactgcca tgctcacatt gtcacctatg cttgctggtt atttgggtgc tgatgttgat   13980
ccaacagata ctagtaacaa aacatatagt gtgcttca                           14018
```

```
SEQ ID NO: 109          moltype = DNA   length = 669
FEATURE                 Location/Qualifiers
source                  1..669
                        mol_type = other DNA
                        organism = synthetic construct
SEQUENCE: 109
atgggatgg cgcccgccgg gtgggtgggc gggctcgtgg cggagagctt cttcgtggcg     60
tgccccgcgc acgagtcccg caagaagaac gagcgcaaca tcttctgcct cgcctgctgc   120
gccagcatct gccccgcactg cgccccgcgc accgccacca cccgctcctc cagcgccaac   180
tgctatgtac gtgatcaggt gcggcgctac gtgtaccatg acgtcgtccg cctcggcgac   240
ctagagaagc tcatcgactg ctcctgtgtc caggtgatgc agggggaggg              300
gacctgtcca acatcctgca gcactacggc gccggcggtg gcggtggcgg tggcacggcg   360
gaccccggacc gcctcgcgtt cccgaggttc gagaacctcc gcgtcgtcga cggctcggac   420
ctcgacgacg acgtccaggt cgtcacccca gactccaccc tcgaggaccc gaccaacaac   480
gcgggcgacg ggtccagcga caacggtact gacgacgcca gacggcaggt cgtcgtccat   540
ggcggcggcg aggcggccaa gcggaagaaa ggggggcggct tcttgccccca gatcgtgctg   600
tcactcggcg gcggcggcgg cggcggcaac aggaggaagg gtgcccccca caggtcccct   660
ctggcctaa                                                           669
```

```
SEQ ID NO: 110          moltype = AA   length = 222
FEATURE                 Location/Qualifiers
source                  1..222
                        mol_type = protein
                        organism = synthetic construct
SEQUENCE: 110
MGMAPAGWVG GLVAESFFVA CPAHESRKKN ERNIFCLACC ASICPHCAPR TATTRSSSAN    60
CYVRDQVRRY VYHDVVRLGD LEKLIDCSCV QVDHVMTQGG DLSNILQHYG AGGGGGGTA    120
DPDRLAFPRF ENLRVVDGSD LDDDVQVVTP DSTLEDPTNN AGGGSSDNGT DDARRQVVVH   180
GGGEAAKRKK GGGFLPQIVL SLGGGGGGGN RRKGAPHRSP LA                      222
```

```
SEQ ID NO: 111          moltype = DNA   length = 14040
FEATURE                 Location/Qualifiers
source                  1..14040
                        mol_type = other DNA
                        organism = synthetic construct
SEQUENCE: 111
ttctttgaca tcctatttta acaaaaacaa gttagtacat aaatcgacaa taaaataata    60
aaatatgcaa taaaatcata aaatatgcaa taaaatcatg atccatactc gtcaatcgta   120
atcgtaatca aaatcaggat ctagttgctt tcgtcgattt aatggacgcc aagtagcttt   180
cttctttctc gtcactcgtt ttcttttttgg aggaacctct acatcatttt gatcgcctaa   240
taaagattct tccaacattt cagtttgtac attaaacgtg cttgtaagtt cttcgtcttg   300
gaaaatctca gcagccccca cttcctgctc gatttgactt tcaacataac cagcatcacc   360
aggagcatat agtcgttcac gcggattaac tttgtacact accctccaat caaccaaacc   420
```

-continued

```
gtttttctta gatggatatg tcatataata cacctgctcg cattggtggg caaggattat   480
agtgtcgtga ccttttaatc tatcgttgtg tttgacttcc accatgccat attgattttc   540
tcgcgttgta tttggagaaa accaatcaca atcgaagaac accactttga gttgtttatc   600
tccaaaaaac ttgtactcga ttatatcatt aatgactcca taataattag tcaccttccc   660
ttcatcatcg acagctctag ttacaactcc ggagtttgtc gtggctgcta gaggatgatc   720
atcttcgaac cttgtggaac ggaatctaaa accattgaca tcataccgac cataacgtct   780
gccagttact gctcctaggg ataattgtcg aaggtccggg tgtatattgt cattttttatc   840
tacataatct cgaaaccaac acaagaaatt aagtcccccca tcttttcccct ctcgacgaat   900
ctggtcacgt tcacagccag agatgcaatt ttgagaatca aattccctgt tagtacaagg   960
aaacaaacct tttagtatca caacaaaaat tctagcggca atgactaaaa taaagtttac   1020
acttacagga gaaactgact catctcttcc atgttgttat acatgtaaag taaagcagtc   1080
ttccattcgt cgttggtgaa acagtatgtt gtgctgggtc ctacagtttt gcccctccat   1140
tgaaaaattt caatatcact aatagggggc tcgtcgacat gataccgcaa cgtatgggca   1200
ttgacattgt gttcctctgc aaagtacagg cccgtgaacg atgctatctc tttgtatttg   1260
aattcttcag cgatgcaccc ttcaactcgt ctcttattac caaccattgc acgtagcttc   1320
tttagtgtcc tttcgatgtg atacatccat ctatattgca caggacctcc taccttagct   1380
tcgtatggta ggtgaacaag tagatgttgc atcggattga agaaacctgg tggaaatatt   1440
ttttcaagtt tgcataccaa aatcggtatt tcttgctcaa gcttctccat catctctttc   1500
tttatttctt tggcacaaag atgtctataa aagtagctta gctccgctaa tgctttccag   1560
acatcatttt ttacaaaacc acgaaacata acaggaagga gtctttccat tattatgtgg   1620
tagtcatgac tcttcaaccc agaaaacttg cccgtcttca aattcacaga ccttctaaag   1680
cccgcggcgt aaccatctgg gaactttaag tttttcaacc atttcatcaa tgttttcttc   1740
cttttaggtt taatactgaa aggagcacgt ggcttcttct gattctctcc tatctccata   1800
gttggtcttc tacagattaa ggccaagtct ttccttgcct tagggttgtc ttttgtttttg   1860
tcggtgatat tcatgcaagt gctgataatg ctttcaccca tatttcgttc ctggtgcatg   1920
acatcaatgt tatgcattag aatcaaggct ttcatataag ggagttccca tagaccacat   1980
ttgtgagtcc aattatgctc ggttccataa ccttcaaaac gatttccatg ttcgtttagt   2040
ttcaaatcat taagtctcgc gagaatctca ggaccactta gacgcttggg tggtcccctc   2100
gtcacaatcg tgtcctttt aaaagcgttc ctatcgaacc tgaacgggtg atcctctggc   2160
aaaaaacatc tatggcaatc gaagtaacat atctttccac caaactttag tcgaaagcat   2220
aaagtgtctt caacgcatat aggacatgtc aaaatcccat gacaactcca tccagcaaag   2280
ataccataag ccataaaatc atgaatagac cataaaaacg cggctctcag gttgaacttc   2340
tgtttcttgt aacaatcgta cgcctcgact ccttcccaca aaattttcaa ttcttcaatc   2400
aggggtctca tcatcacatc gatctttgtt ccaggatgat ccggaccagg tattataaga   2460
cacaagaaaa taaattcata tttcatgcaa agagctggtg gaaggttgta tggaacagca   2520
aagacgggcc aacatgagta cgacgtagca gttagattga atggtgagaa accatctgtt   2580
gccaaaccga agcggacatt ccgcacttca tcagcaaagc tggaatcaaa agcatctagt   2640
gccttccatg catctgtatc agctgggtgc accatgacat ttggattctc acgtacccct   2700
tctttgtgcc acctcatgtg tctggctgta ttttggatga tgaacaaacg tttcaaccga   2760
ggtatgagag gcatgtaacg aagctgctta tgtgcaatct tcgtagtcac ggtcaaacca   2820
tcgtcgtttt caacctcaac gaatctacgc tcaccacata cagtacactt cttctcacct   2880
gcggtctcct tccagaaaag catacaatta ttttcacaga catcgatttt ttcgtagtcc   2940
ataccgaggc cagataacag ctttttagac tgatacatgt cctttggcat cttgtgattc   3000
tccggaagta catcactgat caagttcaaa agttccttgt aacagttgtt tgagaatgca   3060
aacttagact taatagccat aagtcgagtc acaaatacaa ggacagtcac ttttgtgtgc   3120
tcatgcaacg gctcttcggc agctttaagg agctcgaaga acttctgaac ctcaggtgta   3180
gctggatcct caaactcggt gggttgaccg gggttctccg aatcgacggt tagaaactca   3240
tggcgtacat cgtcaagcat ctcttccatc ctatcgtagt cctcctcttc atgtgactga   3300
acttccgata caatacgagg tgggtcctca ccgtggtgca cccacacctc atagcctggc   3360
atataaccgt tcttgcaaat atgtatcgac atagtcctcc tgtcaaggaa attaatgttc   3420
cgcacacttgc tacaagggca cctaacatcg gttccagtct ctgaccgagc aaaagcatgg   3480
tcgagaaaag catcagtctt ggccacccac tcacttgata gagcacctct tttcttccaa   3540
ccttcataca tccatcgacg attctcctcc atactagata cgatacgtta acttaattag   3600
ataagtactg cacgtgcatt ccgttttttac gaagaaatca cgcccctaca tctgtaggaa   3660
aggataggtc ctaaacccac ccaggagtga ccgacgaagc cgtgtttatg acaagacatg   3720
tggtcgtgcg aaatttcggc agcataaccc cgttgttctc caatcgcacg cctaaaaatg   3780
gtgcaattga agaacagaga ggttatgctg ccgaaactaa gcaggagcac atgctttttgt   3840
cataaacacg gactctgtcg gtcaccccga ggctgtccaa aaaagggaca attccggccc   3900
aacatacctc acatgcgtcg cttgtaaggt gtgttgggcc gaaacgggtg acgcctaggt   3960
ttcgtttgtt cacactacga tacactatga ttaactataa tcatcgtgca ttattaaata   4020
attaaactaa taaaccataa tacaatatta catacgaaat aatattgtta tagatgacaa   4080
atcatataaa atgaccttat ttccgagggc ataataatta ccctcggaaa ttaaaaatta   4140
aaattatcta aagtaccact aaataaagta aaacaaacta ctttaattaa ctaatcaaat   4200
tttgaccgtc ggacataaca aactaaacaa tcaaatgcat taatacatac aatttcaatc   4260
aaatacatta atacaaacat acaattctaa tcaaatacat taataaaagc atacaatttt   4320
aataaacaaa attgctaatt aagtatactc acttagcggg tgtggagagt cggccggcga   4380
tgggcgcacg ggcggcggcg ggcgcacggg gccgttggcc ggagcacggg gcggcggcga   4440
ccggcgaacg gggcggcggc gaccggcgaa cggggcggcgg gcggcggcgg ccggagcacg   4500
ggcgtggcgg tggccggagc acgagctagg ggcggtggtg gccggagcac gggccgtggcg   4560
gtggtggccg gagcacgggc gtggcggtgg ccggagcacg agcacggagc ggtggggcgg   4620
cggcggcgc cggagcacga gcagtggggg cgggcggtac ggcgataggg cgggacggcg   4680
acgagcgtgg cggcgacgag cgtggcggcg acggcggctt ctcctcggac acggcggagg   4740
cgtgctcggc ggcggcagga tagaaacgcg cggtctcggg tgaaactgaa ggcgcgcggg   4800
tcggaaccgg gcgttaaaaa gccttatgtc cgacggctcg gtacgaggcc gtcggacata   4860
agctaatgtc cgacggccag ggggtcggcc gtcggacata aggtaatgtc cgacggtcag   4920
tctgccagcc gtcggttata tttttttattt tcgacggccg ctgttggccg tcggacataa   4980
ccgtatgtcc gacggttgcc tacgggccgt cggacataag acgaccgtcg gaattgtata   5040
gttttactgt agtgctccct cactatcttg ttctcgcctc gttttttctct ccctccgcga   5100
gcgccaaggc agcgcagcta cgagacaagc acacgtaata gtactagtgc gccgttgccc   5160
```

-continued

```
tgcctgcctg ccctgtgccc tgccttgcac cacaccacca ccaccgcaga tccggtctgg    5220
tccagtccgg cccggtccgc tactaaacaa accagcccag cgcgcgcccc agcgagagga    5280
gaggaggagg ggccggggtc ggcacggcgg gcagaattgc ctctgctgcc tgcgcgctgc    5340
cctgccctgc cagagggatc ggaggagag cgatcagtca acaagcccag gaggaggagg    5400
aggaggaggg agagatccgc gtgccggccg gaggcgggct ccgggagatc gaccgagcga    5460
ccggcctcgg tcccggtgcg gtggtggatg gggatggcgc ccgccgggtg ggtgggcggg    5520
ctcgtggcgg agagcttctt cgtggcgtgc cccgcgcacg agtcccgcaa gaagaacgag    5580
cgcaacatct tctgcctcgc ctgctgcgcc agcatctgcc cgcactgcgc cccgcgcacc    5640
gccaccaccc gctcctccag gtgagtgcga gtctcgtcgt cgtcctcctc ctcgcccggc    5700
ctctcctctt ccttcctccg gcggccttcc cctctccctg ccaggctgcc atggcgtcgc    5760
gtggcatgca cctggccggg cgatctgctc agtttctact cctgctagct tcgcagcaat    5820
tctcgccgcc gctgtcccgc tccgctccgc ttcttgttgt tgttggatga acacaccacc    5880
tccccaccgc caccgccacc gggggggcagc ttttttgggg ttattgctgg tggcctcggt    5940
tcttgtgcaa cggatgggaa cggcgggac gagtaccaac caatcgattt ctttatttga    6000
tttaattgtt tatttattat tcctcggcgt atatagcact agacgctact tcttcctata    6060
tactactact agagtagtac tacaagtgta gaggaggagg ggcatgggaa ttggatgtgt    6120
agtatctcgc ttttgttttg tcgcgtgctg tctcttcctt ccttccttcc ttggactaga    6180
tttggtcccg gctttagcct aaacaaaaaa atatttcccc cctaccattt ctcgcatgat    6240
ttgatttgat gcgtggtctc ttctcgtgtc gtccgtgcgc gggaaggaat caagggaaag    6300
gaaaggaaac caaaccccat ctcgctaatc gctctcctct ctctctctct ctcccttcct    6360
cgcaggcagg cagaggcagt acaggttgtt gcaaaacttg cacgtacttg attcctcgcg    6420
cgcgcagcgc cttgtcgcct tgcgaggttt ggtttggttg ggtcatgagc tcatccatcc    6480
attcccttt ccacccatgc atgcatgcat gcatgccact cccttgatta gggtttataa    6540
gccagcagga ggcgctgatt gagtcctaat ctgcgccact gtaacagcaa tcccaaccat    6600
gattttcgca cccgctccag gactccggag cagtgctact tcttcatcgc tataattaat    6660
ataattcgtc tgctccttcc tgcctgaccg gggtattaaa tcctgtgtat gtacgtagta    6720
ctaacaaaca aggacaaggc agtaaaaatt ctcgttacgg aacattatct actccgacct    6780
cccttgcatt tttttttgg aattagtacc cgggcgttca tcgcgacctg catgcaactg    6840
tttcctcaac gagctagcca ttacatgctt ttagtttttt ataaaatata tatgcatgca    6900
tggcaaaact ttttccttt taaattttcg ggagttaaag aggaggaggg tcgaaaattc    6960
aaatcccccc acccgggca tgcaaaccct tcttctttct ctccgtagct ttgtcttgta    7020
gctgcagcca tgcatttccc ccctacttc atgcagcagc aactaatcca tccggatatg    7080
ctggcgctgc gggagccgga gtctcgaacc caaatggcaa aaaaagctgc ggggggaggt    7140
tttaccgctg cctcttcatt ggaattccaa tccttgggat taggatcctc tgcggtaatc    7200
gccagcctcc tgctgcgctt ccgcttgctt ccccgtccat taataggcct ggttatccaa    7260
actgtttgc caagtatagc aacatttccc tgcccccgt cctgccgact gaaccccgcc    7320
actgataaag gaaaaaaat cggttcgggc ctttgaatta gattttaccg tatgcgcccg    7380
cgcgcggtaa ctgcgcggcc tgtctttttt taccaaacag aggcatcgac gacgacactg    7440
ttgtccccg acgacgaccc catctctccc tggtgcgtgc tacacgacca aacttctctc    7500
tccttacctt agggtggggt ggttttgggg gtctcccagg ccatgataaa gatcaccact    7560
ggagtggtac tgctgcccgg ccggtcaaag catggggcc atcgcgtggt gtgtggccca    7620
acccaaagtt gtaccctgct gctgctgtac cgcctgcgtt gttatcttag gccccgtttc    7680
aatctcacgg gataaacttt agcttcatgc taaactttag ctatatgaat tgaagtgcta    7740
aagtttagct ttaattacca ccattagctc tcatgtttag attataaatg gctaaaagta    7800
gctagaaaaa agctgctaaa gtttatctcg cgagattgga acacggcctt atcttagagt    7860
atgaaactgc ggttgtaaac atgtttagcg ccaactgcta tgtacgtgat caggtgcggc    7920
gctacgtgta ccatgacgtc gtccgcctcg gcgacctaga gaagctcatc gactgctcct    7980
gtgtccaggt gattccctat ctatcgtcgt atctgtcttg cattagtgct tcgaatttg    8040
atggtgatgc tgatgatgag tacgttaatt atatagtagt aaaactcccc tctctctttg    8100
tgtgtgtgat gtgtgaccgc gcagacctac acaatcaaca aggtgatctt cctgaagccg    8160
aggccgcagt ccaggccttt caagggctcc ggcaacatct gcctcacgtg cgacaggatc    8220
ctccaggagc ccttccactt ctgctccctc tcatgcaagg ttgcattggt cagctagcta    8280
gcatcatcgc atacgccatg catatgcatc gtcggattcg gatcatatcg ttcagtgcgt    8340
acgtggatca tgtcatatgt tattacgcag gtggaccacg tgatgacgca gggaggggac    8400
ctgtccaaca tcctgcagca ctacggcgcc ggcggtggcg gtggcggtgg cacggcggac    8460
ccggaccgcc tcgcgttccc gaggttcgag aacctccgcg tcgtcgacgg ctcggacctc    8520
gacgacgacg tccaggtcgt caccccagac tccaccctcg aggacccgac caacaacgcg    8580
ggcggcgggt ccagcgacaa cggtactgac gacgccagac ggcaggtcgt cgtccatggc    8640
ggcggcgagg cggccaagcg gaagaaaggg ggcggcttct tgccccagat cgtgctgtca    8700
ctcggcggcg gcggcggcag aggaagggtg ccccccacag gtccccctctg    8760
gcctaagcag cgctaccttc atgcatgcgt cccctgctg ctgctcgtta tatatcacaa    8820
gtcacaacac acgtagcgcg ctgtggttgc atgcagtgat gatggtgtgg gtggtagcta    8880
cagtattaat tagtagtagc gtgttataat agtatcttaa tggtgattag cctcgtagag    8940
agacgacgac aagctggtag ctggtcgatc ggttttgct gggggggaagg tcttggtggc    9000
cttgtgatcc gtctagcagc tcgctaggac caaccatggc cgccgcgcca tctcatgaga    9060
ctttagagag agagagag agagagggtc atggggggag tagaggggg agagacggtt    9120
gtaaaagcag ttcccattgt tacaggcacc aggtagtaac tggtcagtgg ggcccacttc    9180
tgcaggcggt ggggcccata cgatcgaggt ggctaccaat tttgtatttg atgtaccaag    9240
ggttactcgc ggtctcgcgc atacaatttc cacacctata tatgttatat ataaatgata    9300
atatatctga attctgtccc agactaaaca ggttgtttc agcagtctgt atccgttcca    9360
tgtgggctca agtgattttc agctgcctgt ttggcgtgtc aagcagctgt tgagacatga    9420
ggccgagagc tctcgcccag tctcgcccgt agggatgaaa gtaggatggg aaaatcccgt    9480
accgaccgtt atcgtataac cgaatttgtt agttttgtcc cgatcgtttt cgaacccgac    9540
gtaaaaaacg aaaacgggac gaaaacggga tatacaaaac ggtaaacgga aacggaaacg    9600
gtagagctgt tttaccgacc gtttaaccgg gatcccgttt ttaatcggga tgatcccgtt    9660
ttgttaccgt attttgtaat tcgggatcac ttcaatatag acagctatag gcatcacttt    9720
gaggcccagc ccatctaaga aaaacctaac gcgctgttct gctcccaggc gtcgccgtcc    9780
acactcctct ctcccagctc gctgccgtag tgccatcagc tcgtcactcg caggcgccgg    9840
cgcgcagccg tccgccctcc tgctctgtgc ggctttgcct ctcccagctc gcctcgccag    9900
```

-continued

```
tcgccaggcc agagtgccat cgcagcttcc caggctccca gctcgccaga gtgccggacg  9960
ccacgccagc ccggtccggt ctccggtcgg cggtcggtcg atcgccgctg ctccagctgg  10020
ctgcccaggc gactagacgt ccacgacggc tcggcgatcg gcaggcagct cgctccacct  10080
ccacaggcca cgactccctc tgctgctgct gtcctccacg gatccactgc tggctgctgc  10140
tccctccaca gagaatcgcc ttgctacacc atgtgagcag tcctgcagtc ctgccgtgtt  10200
agacgctagc tgctagctcc cagccgtact ccaccacgtt ttggtgcata agctgcgtgt  10260
tgccttgctt tttactgttg ttgtttttaat tctgtggtgc ataattctgt tggtgcgtac  10320
ttctattggg cgtactttat attatgtcat gtgtgctagt agacttatat ggcttcttat  10380
gtagccaaga gctcaatatt tatcacttat gtgctactaa gatgtttggt ttgatgaatc  10440
actctatcca aaatgaagtg gtgcatcatg ggtccattcc tcaaatttgg tgggatgact  10500
tcattccaca tattagtact aaacaactaa ctatgaggaa tgaggtggtg atggattaac  10560
tcactccatt ccacaaacca aacaaaaaag tgaggagtga gaagatgatg aactatatcg  10620
ttcctcaaac caaacactcc atacattaaa ctatgtgtgc tccagattta tatgactttt  10680
ttctatgttt aattaagact tgtgtttaca attttttata tttgtttta agttttgaat  10740
atatgttttc atggtgtgat tttaccgaac aaaaataccg gttcccgtcc gatttcggct  10800
ttaacccgac cggatcgtat cggttttcgc ttaccgtatt tatcccgttc gttttcgtta  10860
ccgatatatc ccgttttcgt tttcgtcccg caagttaaat atgaaaatga aaacggtaga  10920
ggtattttac cgaccgttcc cgaccgtttt catccctact cgcccgcgtg catggattgt  10980
tgcatgcatg tgatgcgcgc gcgcacacgc ctagcgctcc cgtccaaact ccccagtcgt  11040
gttgctgtga cctgctggct gtttgatgca gttgtgattc gctttgcaat ggaccacggt  11100
ctctgtccca tggtgtgtgt atctgtgtgt ctgagtgtgg agacgacaga gactcgaaaa  11160
gatggtgtgg tggctgttcg atccagggct cgcttgatgc ctgttttttt ttccacgaga  11220
atctctctat tagagaacag atgcatgggt cgttttttag cctctctaga ccaggatgtg  11280
aaaggtagaa aagccattct cacgtgaggt tacagtactt gtagctttcc attactcata  11340
tacttgcagg aattaatatt ggacactctt tttctactct cgctctgttt taaatcgcaa  11400
gctattttc cactttctta aaaatgtagc agcttttacc gagtacatct cggtacgtac  11460
ctaaaaaaaa gcttgtagta taagctttca accgagtgtt tataaggctt cgccgagtgc  11520
ttccggccact cggcgaagct attgattccg gtagtgccgg gttgaattta cttttgtatc  11580
actgagccgt cgaagagaac agcggtattt ctggcatcga tcgggcaccc ttcctcggaa  11640
tcatggcttt ttgagagtga ccaacaggca gtgcgcgcgg tctcggaacc tgaaaattgt  11700
ttggttgtat cgaatgactt gtcacggcca ctcgaggcag gcatgagacg ctccaccgga  11760
ccgccacacc atgcatagtg acagatcatc aaaaggtggt tttaaaactc gaattttat   11820
ctgactatat agcaaataaa tccttttgta cgctcagttt catatataga cgaaattctc   11880
ccacctctcc catgcatgca tgtcatcgat cattcttgtt tatctggtga tgtatttaat  11940
gaagacagaa attcgagtga gatttccagt ggaaatagcc ttattagtgt gccatgaacg  12000
aagttctgaa gtcgaaacca gacgagagtc cccatgcacg atgccatgga tatcgccagt  12060
acgtacagga cgtgcgccag cacgatgcaa ctgtcagcag acagcagcca aaacgcaatt  12120
cttgtttcag ctgggtgggc aattccgagg tgtgctaaat aaaagcatga tccatgcata  12180
tagatgagca tgcagcccgc agcccgacag cccggcacga ggcccggttt tttgccccgg  12240
cccaagcacg gcacggcccg tctggtttcg tgcccgtgcc ggcccggccc ggtagaccag  12300
gccgtgcttg ggctgccgga tgcgcccgcc gggcggcacg gcccggcccg ctaggaaaag  12360
caggcacgga gccggcccgg ttccaggcga ggggcatatc cgcccgcccc tccccaccgc  12420
ccgttcagtc ccccagtccc tagttcccca cgccacgcga tttgctccgc agcctccgcc  12480
ctccgctcgt ccgctcgccg ctccctcccc attctccgtc aacgccgagc cgtcgccact  12540
gccgttgccg gatctccgtc gtcgaccgac gagatctcct ctctgcctct ctccagtctt  12600
cgtcactcgg tgacgcatcg gctctccatt ccccaatctg taaccctaat cccctttccg  12660
gctttccctc acctctccgg tgacgcatcg gctctccact gcgggatctc cgtcaccggc  12720
gacatctgca cgcttgttct gtgcggctca ccctctccgg ctctccctcc ccaatcccct  12780
cgctcgtcgt cgtcgtcatc ggtcgtcggc ttgtcgcgcg tcgtcgtccc ctagaccctc  12840
gtctccggct ccgggctccg gcttggcagg tacgtgtacg tccctctccg gctctccctc  12900
cccaatccga caaaccctaa ccctaatccc ttgcttggta ggtcgccggc cgactacgcc  12960
gtggtcgtgc tggtgccgcc agtgccgttg aggtacggtg ccgagagggg ggccgggcat  13020
ggatgacgac gacgacaatg gccggtaccc tagaaccatc aacgacgagc tcgttgagtt  13080
agggcagctt cccgatgacg tcgacgacat gggagatgct gctgctgcct tattcggtat  13140
cggtagcagt catggtgccg gcgacctgga ggggacagct gccgggccgg ttccggttag  13200
tgatgctgct ggctctaacg aacttgattc attgacttct tccagcactg gtaagcgtcg  13260
atctgctgtt tgggatgact tcactgaagt cactgaaaac cgtaatggta agaaggtgcg  13320
cattgctggt atttgcaaat tttgcaaggc tcggttgagt gctagttcta atgctggcac  13380
tggacatttg cttaggcacc agaaatcatg taaaaagaag tctgatcatg ctgctatggt  13440
tcaaactaga ctagctttga accctgatgg gtcttttaga aactgggaat atgatcctca  13500
ggtggctagg actgagcttt gtcgtttgat tgctagactt gatcttcctt tagggatagc  13560
tgacacagat gcttgggata attacattca acatgctcac aaccctagat atgttagggt  13620
atctaggttt acaactgcta gagacttggc taagctatac aatgaaaagc taaagaactt  13680
aaaagatgat gtttttcctg gtgtgtcttc tatttgctct acttctgata tatggtcctg  13740
taatgccaag gaagactaca ttactgttgt tgctcatttt attaatgctg attgggagtt  13800
aaagaagtgt gtgataggct ttaaattgat ccaagtgtct cataatggtg ttaacattgc  13860
tgaacgcatt gcttgtgtga ttcaatactt tggcatgatt gataaagtgt tctctattac  13920
cttagataat gcttcttcta attcaactgc catgctcaca ttgtcaccta tgcttgctgg  13980
ttatttgggt gctgatgttg atccaacaga tactagtaac aaaacatata gtgtgcttca  14040
```

```
SEQ ID NO: 112        moltype = DNA  length = 804
FEATURE                Location/Qualifiers
source                 1..804
                       mol_type = other DNA
                       organism = synthetic construct
SEQUENCE: 112
atggggatgg cgcccgccgg gtgggtgggc gggctcgtgg cggagagctt cttcgtggcg  60
tgccccgcgc acgagtcccg caagaagaac gagcgcaaca tcttctgcct cgcctgctgc  120
gccagcatct gcccgcactg cgccccgcgc accgccacca cccgctcctc cagcgccaac  180
```

```
tgctatgtac gtgatcaggt gcggcgctac gtgtaccatg acgtcgtccg cctcggcgac   240
ctagagaagc tcatcgactg ctcctgtgtc cagacctaca caatcaacaa ggtgatcttc   300
ctgaagccga ggccgcagtc caggcctttc aagggctccg gcaacatctg cctcacgtgc   360
gacaggatcc tccaggagcc cttccacttc tgctccctct catgcaaggt ggaccacgtg   420
atgacgcagg gaggggacct gtccaacatc ctgcagcact acggcgccgg cggtggcggt   480
ggcggtggca cggcggaccc ggaccgcctc gcgttcccga ggttcgagaa cctccgcgtc   540
gtcgacggct cggacctcga cgacgacgtc caggtcgtca ccccagactc caccctcgag   600
gacccgacca caacgcgggg cggcgggtcc agcgacaacg gtactgacga cgccagacgg   660
caggtcgtcg tccatggcgg cggcgaggcg gccaagcgga agaaagggg cggcttcttg   720
ccccagatcg tgctgtcact cggcggcggc ggcggcggcg gcaacaggag gaagggtgcc   780
ccccacaggt ccctctggc ctaa                                          804

SEQ ID NO: 113            moltype = AA   length = 267
FEATURE                   Location/Qualifiers
source                    1..267
                          mol_type = protein
                          organism = synthetic construct
SEQUENCE: 113
MGMAPAGWVG GLVAESFFVA CPAHESRKKN ERNIFCLACC ASICPHCAPR TATTRSSSAN   60
CYVRDQVRRY VYHDVVRLGD LEKLIDCSCV QTYTINKVIF LKPRPQSRPF KGSGNICLTC   120
DRILQEPFHF CSLSCKVDHV MTQGGDLSNI LQHYGAGGGG GGGTADPDRL AFPRFENLRV   180
VDGSDLDDDV QVVTPDSTLE DPTNNAGGGS SDNGTDDARR QVVVHGGGEA AKRKKGGGFL   240
PQIVLSLGGG GGGGNRRKGA PHRSPLA                                      267

SEQ ID NO: 114            moltype = DNA   length = 11
FEATURE                   Location/Qualifiers
source                    1..11
                          mol_type = genomic DNA
                          organism = Zea mays
SEQUENCE: 114
tgtacgtgat c                                                       11

SEQ ID NO: 115            moltype = DNA   length = 24
FEATURE                   Location/Qualifiers
source                    1..24
                          mol_type = genomic DNA
                          organism = Zea mays
SEQUENCE: 115
tacgtgatca ggtgcggcgc tacg                                         24

SEQ ID NO: 116            moltype = AA   length = 8
FEATURE                   Location/Qualifiers
source                    1..8
                          mol_type = protein
                          organism = Zea mays
SEQUENCE: 116
RDQVRRYV                                                            8

SEQ ID NO: 117            moltype = DNA   length = 12
FEATURE                   Location/Qualifiers
source                    1..12
                          mol_type = genomic DNA
                          organism = Zea mays
SEQUENCE: 117
atgtacgtga tc                                                      12

SEQ ID NO: 118            moltype = DNA   length = 25
FEATURE                   Location/Qualifiers
source                    1..25
                          mol_type = genomic DNA
                          organism = Zea mays
SEQUENCE: 118
ttagcgccaa ctgctatgta cgtga                                        25

SEQ ID NO: 119            moltype = DNA   length = 28
FEATURE                   Location/Qualifiers
source                    1..28
                          mol_type = genomic DNA
                          organism = Zea mays
```

-continued

```
SEQUENCE: 119
gcagacctac acaatcaaca gtgccaag                                        28

SEQ ID NO: 120        moltype = AA  length = 47
FEATURE               Location/Qualifiers
source                1..47
                      mol_type = protein
                      organism = Zea mays
SEQUENCE: 120
TYTINSAKVI FLKPRPQSRP FKGSGNICLT CDRILQEPFH FCSLSCK                   47
```